(12) United States Patent
Lee et al.

(10) Patent No.: US 11,337,964 B2
(45) Date of Patent: May 24, 2022

(54) ISOINDOLINE DERIVATIVE, PHARMACEUTICAL COMPOSITION AND USE THEREOF

(71) Applicant: Kangpu Biopharmaceuticals, Ltd., Shanghai (CN)

(72) Inventors: Wen-Cherng Lee, Shanghai (CN); Baisong Liao, Shanghai (CN); Lei Zhang, Shanghai (CN)

(73) Assignee: Kangpu Biopharmaceuticals, Ltd., Shanghai (CN)

( * ) Notice: Subject to any disclaimer, the term of this patent is extended or adjusted under 35 U.S.C. 154(b) by 0 days.

(21) Appl. No.: 16/488,794

(22) PCT Filed: Feb. 27, 2018

(86) PCT No.: PCT/CN2018/077324
§ 371 (c)(1),
(2) Date: Aug. 26, 2019

(87) PCT Pub. No.: WO2018/157779
PCT Pub. Date: Sep. 7, 2018

(65) Prior Publication Data
US 2020/0061033 A1   Feb. 27, 2020

(30) Foreign Application Priority Data

Feb. 28, 2017 (CN) .......................... 201710112364.2
Aug. 22, 2017 (CN) .......................... 201710725987.7

(51) Int. Cl.
| | |
|---|---|
| C07D 401/06 | (2006.01) |
| A61K 31/437 | (2006.01) |
| A61K 31/4035 | (2006.01) |
| A61K 31/4439 | (2006.01) |
| A61K 45/06 | (2006.01) |
| C07D 209/48 | (2006.01) |
| C07D 471/04 | (2006.01) |

(52) U.S. Cl.
CPC ........ *A61K 31/437* (2013.01); *A61K 31/4035* (2013.01); *A61K 31/4439* (2013.01); *A61K 45/06* (2013.01); *C07D 209/48* (2013.01); *C07D 401/06* (2013.01); *C07D 471/04* (2013.01)

(58) Field of Classification Search
CPC .................................................. C07D 401/06
See application file for complete search history.

(56) References Cited

U.S. PATENT DOCUMENTS

2010/0204227 A1   8/2010   Muller et al.

FOREIGN PATENT DOCUMENTS

| AU | 2006200033 A1 | 2/2006 |
|---|---|---|
| CN | 1802353 A | 7/2006 |
| CN | 103402980 A | 11/2013 |
| JP | 2006-519851 A | 8/2006 |
| WO | 00/25777 A1 | 5/2000 |
| WO | 2004/060313 A2 | 7/2004 |
| WO | 2004/080423 A2 | 9/2004 |
| WO | 2006/018182 A1 | 2/2006 |
| WO | 2010/147922 A1 | 12/2010 |
| WO | 2012/015986 A2 | 2/2012 |
| WO | 2012/096884 A1 | 7/2012 |
| WO | 2012/097116 A2 | 7/2012 |

OTHER PUBLICATIONS

Banker et al., Prodrugs, Modern Pharmaceutics, 3rd edition, Revised and Expanded, pp. 451 and 596.*
Jordan "Tamoxifen . . . " Nature Rev. v.2, p. 205-213 (2003).*
Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Balant ed in Wolff et al. Burger's Medicinal Chemistry and Drug Discovery. 5th ed. vol. 1: Principles and Practice, pp. 949-982, 1996.*
Bundgaard, Design of Prodrugs, Chapter 1, p. 1, 1985.*
Silverman, Prodrugs and Drug Delivery Systems, The Organic Chemistry of Drug Design and Drug action, Chapter 8, pp. 352-400, 1992.*
Hulikal, Deuterium Labeled Compounds in Drug Discovery Process, Abstract, 2010.*

(Continued)

*Primary Examiner* — Patricia L Morris
(74) *Attorney, Agent, or Firm* — Morgan, Lewis & Bockius LLP

(57) ABSTRACT

Disclosed are a novel isoindoline derivative, a pharmaceutical composition and use thereof. The compound of formula I, or the pharmaceutically acceptable salt, solvate, polymorph, co-crystal, stereoisomer, isotopic compound, metabolite or prodrug thereof disclosed in the invention can regulate the generation and/or activity of PDE4 and/or TNF-α so as to effectively treat cancer and inflammatory diseases.

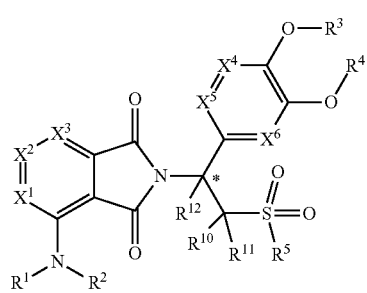

Formula I

16 Claims, No Drawings

(56) References Cited

OTHER PUBLICATIONS

Pimlott, PubMed Abstract (Nucl Med Commun. 26(3): 183-8), 2005.*
International Search Report issued in corresponding International Patent Application No. PCT/CN2018/077324 dated Jun. 5, 2018.
Partial Extended European Search Report issued in corresponding European Patent Application No. 18761354.2 dated Oct. 25, 2019.
Office Action issued in counterpart Japanese Patent Application No. 2019-547071 dated Jan. 5, 2021.

* cited by examiner

ISOINDOLINE DERIVATIVE, PHARMACEUTICAL COMPOSITION AND USE THEREOF

FIELD OF THE INVENTION

Provided are a novel isoindoline derivative, a pharmaceutical composition and a use thereof.

BACKGROUND OF THE INVENTION

Cyclic adenosine-3', 5'-monophosphate (cAMP) plays an important role as secondary messenger in cells. The intracellular hydrolysis of cAMP to adenosine-5'-monophosphate (AMP) is associated with many inflammatory diseases, including but not limited to psoriasis, allergic rhinitis, shock, hereditary allergic dermatitis, Crohn's disease, adult respiratory distress syndrome (ARDS), eosinophilic granuloma, allergic conjunctivitis, osteoarthritis and ulcerative colitis. Cyclic nucleotide phosphodiesterase (PDE) is an important factor controlling the level of cAMP. It is known that there are 11 members in PDE family. Although PDE1, PDE2, PDE3, PDE4 and PDE7 all use cAMP as a substrate, only PDE4 and PDE7 are highly selective for the hydrolysis of cAMP. Therefore, PDE inhibitors, especially PDE4 inhibitors, are considered as cAMP enhancers. Immune cells contain PDE3 and PDE4, of which PDE4 is ubiquitous in human monocytes. Therefore, inhibition of PDE4 is the goal of therapeutic interventions in various disease processes. Studies have shown that the administration of PDE4 inhibitors restores memory in animal models, including those of Alzheimer's disease. PDE4 has been shown to be the major regulator of circular AMP in airway smooth muscle and inflammatory cells. PDE4 inhibitors can be used to treat various diseases, including allergic and inflammatory diseases, diabetes, central nervous system diseases, pain and so on.

Tumor necrosis factor-α (TNF-α) is a kind of proinflammatory cytokine, which plays an important role in immune homeostasis, inflammation, and host defense. TNF-α has been proved to be one of the major mediators of inflammation. Uncontrolled activity of TNF-α or overproduction of TNF-α is associated with the pathology of various diseases, including but not limited to cancers and inflammatory diseases. The dysregulation of TNF-α can also lead to autoimmune diseases, toxic shock syndrome, cachexia, arthritis, psoriasis, HIV infection and AIDS, nervous system diseases and central nervous system diseases, sepsis, congestive heart failure, transplant rejection and virus infections. Thus, reducing the level of TNF-α, or regulating the activity of TNF-α is a promising strategy in treating many immunological, inflammatory and malignant diseases (e.g., cancers and inflammation).

Thus, compounds capable of inhibiting PDE4 and/or TNF-α can treat a variety of diseases. For example, Apremilast is a small molecule PDE4 inhibitor and immunomodulator that inhibits PDE4 and TNF-α, and was approved by FDA for the treatment of psoriatic arthritis and plaque psoriasis. However, Apremilast has central nervous system side effects and gastrointestinal side effects such as headache, nausea and vomiting and gastric secretion. Therefore, it is clinically urgent to continue looking for performance-optimized PDE4 inhibitors.

Content of the Invention

The invention provides a compound of formula I, or the pharmaceutically acceptable salt, solvate, polymorph, co-crystal, stereoisomer, isotope compound, metabolite or prodrug thereof:

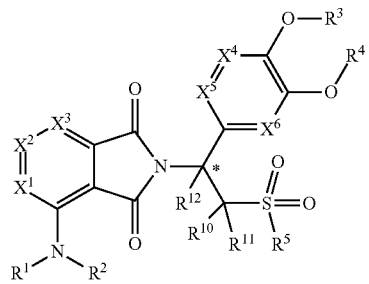

Formula I wherein, the carbon atom labelled by * is an asymmetric center;

$R^1$ and $R^2$ are independently H, D, substituted or unsubstituted $(C_1-C_6)$alkyl, substituted or unsubstituted $(C_3-C_6)$cycloalkyl, $R^6$—$S(O)_2$— or $R^6$—$C(O)$—; or, $R^1$ and $R^2$ and the nitrogen atom to which they are attached together form a 5-7 membered heterocycle containing N;

$R^6$ is substituted or unsubstituted $(C_3-C_6)$cycloalkyl; or $(C_1-C_6)$alkyl, which is optionally substituted with one or more groups selected from D, halogen, hydroxyl, amino, $(C_1-C_6)$alkyl amino and $(C_1-C_6)$alkoxy or benzyloxy;

$X^1$, $X^2$, $X^3$, $X^4$, $X^5$ and $X^6$ are independently CH, CD, $CR^7$ or N;

$R^7$ is halogen or cyano;

$R^3$ and $R^4$ are independently H, substituted or unsubstituted $(C_1-C_6)$alkyl, substituted or unsubstituted $(C_3-C_6)$cycloalkyl, or, substituted or unsubstituted $(C_1-C_6)$alkyl-$(C_3-C_6)$cycloalkyl; or, $R^3$ and $R^4$ and the oxygen atom to which they are attached together form a 5-7 membered heterocycle containing O;

$R^5$ is substituted or unsubstituted $(C_1-C_6)$alkyl;

$R^{10}$, $R^{11}$ and $R^{12}$ are independently H or D;

The substituent in substituted $(C_1-C_6)$alkyl, substituted $(C_3-C_6)$cycloalkyl, or, substituted $(C_1-C_6)$alkyl-$(C_3-C_6)$cycloalkyl is one or more (e.g. 1-6, preferably, 1-5) selected from the group consisting of: D, halogen, hydroxyl, amino, $(C_1-C_6)$alkyl amino and $(C_1-C_6)$alkoxy, benzyloxy; when there are a plurality of substituents, the substituents are the same or different; provided that, one of $X^1$, $X^2$, $X^3$, $X^4$, $X^5$ and $X^6$ is N; or, at least one of $X^1$, $X^2$, $X^3$, $X^4$, $X^5$ and $X^6$ is $CR^7$.

Preferably, the asymmetric center refers to (S)-configured carbon, (R)-configured carbon or a racemate, more preferably, (S)-configured carbon.

In a preferred embodiment, the $(C_1-C_6)$alkyl in the substituted or unsubstituted $(C_1-C_6)$alkyl, the substituted or unsubstituted $(C_1-C_6)$alkyl-$(C_3-C_6)$cycloalkyl or the $(C_1-C_6)$alkyl amino is preferably a $(C_1-C_4)$alkyl. The $(C_1-C_4)$alkyl is preferably methyl, ethyl, isopropyl, n-propyl, n-butyl, isobutyl or tert-butyl. The substituted $(C_1-C_6)$alkyl in the substituted or unsubstituted $(C_1-C_6)$alkyl or substituted or unsubstituted $(C_1-C_6)$alkyl-$(C_3-C_6)$cycloalkyl is preferably substituted with one or more halogen or D. In a preferred embodiment, the substituted $(C_1-C_6)$alkyl is preferably $CD_3$, $CH_2D$, $CHD_2$, $C_2D_5$, $CH_2CD_3$ or $CHF_2$.

In a preferred embodiment, the $(C_1-C_6)$alkoxy is preferably a $(C_1-C_4)$alkoxy. The $(C_1-C_4)$alkoxy is preferably methoxy, ethoxy, isopropoxy, n-propoxy, n-butoxy, isobutoxy or tert-butoxy.

In a preferred embodiment, the $(C_3-C_6)$cycloalkyl in the substituted or unsubstituted $(C_3-C_6)$cycloalkyl and the substituted or unsubstituted $(C_1\text{-}C_6)$alkyl-$(C_3\text{-}C_6)$cycloalkyl is preferably cyclopropyl, cyclobutyl, cyclopentyl or cyclohexyl.

In a preferred embodiment, the halogen is preferably fluorine, chlorine, bromine or iodine, more preferably, fluorine, chlorine or bromine.

In a preferred embodiment, $(C_1\text{-}C_6)$alkyl amino is

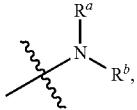

wherein, one of $R^a$ and $R^b$ is H, the other is $(C_1\text{-}C_6)$alkyl; or $R^a$ and $R^b$ are independently $(C_1\text{-}C_6)$alkyl.

In a preferred embodiment, when $R^1$ and $R^2$ and the nitrogen atom to which they are attached together form a 5-7 membered heterocycle containing N, the 5-7 membered heterocycle containing N is preferably selected from

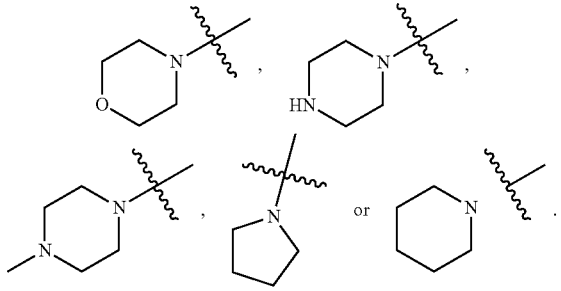

In a preferred embodiment, when $R^3$ and $R^4$ and the oxygen atom to which they are attached together form a 5-7 membered heterocycle containing O, the 5-7 membered heterocycle containing O is preferably or O

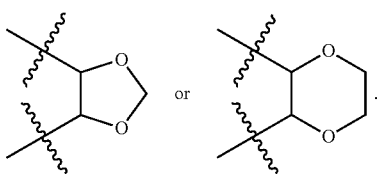 [SMILES: *C1OCOC1* ; *C1OCCOC1*]

In a preferred embodiment, $X^1$ is N, $X^2$, $X^3$, $X^4$, $X^5$ and $X^6$ are independently CH, CD or $CR^7$;

In a preferred embodiment, $X^2$ is N, $X^1$, $X^3$, $X^4$, $X^5$ and $X^6$ are independently CH, CD or $CR^7$;

In a preferred embodiment, $X^3$ is N, $X^1$, $X^2$, $X^4$, $X^5$ and $X^6$ are independently CH, CD or $CR^7$;

In a preferred embodiment, $X^4$ is N, $X^1$, $X^2$, $X^3$, $X^5$ and $X^6$ are independently CH, CD or $CR^7$;

In a preferred embodiment, $X^5$ is N, $X^1$, $X^2$, $X^3$, $X^4$ and $X^6$ are independently CH, CD or $CR^7$;

In a preferred embodiment, $X^6$ is N, $X^1$, $X^2$, $X^3$, $X^4$ and $X^5$ are independently CH, CD or $CR^7$.

In a preferred embodiment, $X^6$ is N, $X^1$, $X^2$, $X^3$ are independently CH, CD or $CR^7$, $X^4$, $X^5$ are independently CH, CD;

In a preferred embodiment, $X^6$ is N, $X^1$ is $CR^7$, $X^2$, $X^3$, $X^4$ and $X^5$ are independently CH or CD. In a further embodiment, $X^6$ is N, $X^1$ is $CR^7$, $X^2$, $X^3$, $X^4$ and $X^5$ are CH.

In a preferred embodiment, $X^6$ is N, $X^2$ is $CR^7$, $X^1$, $X^3$, $X^4$ and $X^5$ are independently CH or CD. In a further embodiment, $X^6$ is N, $X^2$ is $CR^7$, $X^1$, $X^3$, $X^4$ and $X^5$ is CH.

In a preferred embodiment, $X^6$ is N, $X^3$ is $CR^7$, $X^1$, $X^2$, $X^4$ and $X^5$ are independently CH or CD. In a further embodiment, $X^6$ is N, $X^3$ is $CR^7$, $X^1$, $X^2$, $X^4$ and $X^5$ is CH.

In a preferred embodiment, one of $R^1$ and $R^2$ is H or D, the other is $R^6$—S(O)$_2$— or $R^6$—C(O)—. In a further embodiment, one of $R^1$ and $R^2$ is H, the other is $R^6$—C(O)—.

In a preferred embodiment, $R^6$ is $(C_3\text{-}C_6)$cycloalkyl; or $(C_1\text{-}C_4)$alkyl, which is optionally substituted with one or more substituents selected from D, halogen, hydroxyl, amino, $(C_1\text{-}C_4)$alkyl amino, $(C_1\text{-}C_4)$alkoxy, benzyloxy. Preferably, $R^6$ is $(C_3\text{-}C_6)$cycloalkyl; or $(C_1\text{-}C_4)$alkyl, which is optionally substituted with one or more substituents selected from $(C_1\text{-}C_4)$alkoxy, benzyloxy. Further preferably, $R^6$ is cyclopropyl, methyl, ethyl, hydroxymethyl, benzyloxymethyl, methoxymethyl, isobutyl, dimethylaminomethyl, isopropyl, $CD_3$ or $C_2D_5$.

In a preferred embodiment, $R^7$ is fluorine, chlorine, bromine or cyano.

In a preferred embodiment, $R^3$ and $R^4$ are independently hydrogen, substituted or unsubstituted $(C_1\text{-}C_6)$alkyl. The substituted $(C_1\text{-}C_6)$alkyl may be a $(C_1\text{-}C_6)$alkyl substituted with one or more halogen or D. Preferably, $R^3$ and $R^4$ are independently H, methyl, ethyl, propyl, isopropyl, $CD_3$, $CH_2D$, $CHD_2$, $C_2D_5$, $CH_2CD_3$ or $CHF_2$.

In a preferred embodiment, $R^5$ is substituted or unsubstituted $(C_1\text{-}C_6)$alkyl. In a more preferably embodiment, $R^5$ is methyl, ethyl, propyl, isopropyl, $CD_3$, $CH_2D$, $CHD_2$, $C_2D_5$, or $CH_2CD_3$.

In a preferred embodiment, $X^3$ is $CR^7$, $X^1$, $X^2$, $X^4$, $X^5$ and $X^6$ are independently CH or CD; $R^7$ is fluorine, chlorine or cyano.

In a preferred embodiment, $X^2$ is $CR^7$, $X^1$, $X^3$, $X^4$, $X^5$ and $X^6$ are independently CH or CD; $R^7$ is fluorine, chlorine or cyano.

In a preferred embodiment, $X^1$ is $CR^7$, $X^2$, $X^3$, $X^4$, $X^5$ and $X^6$ are independently CH or CD; $R^7$ is fluorine, chlorine or cyano.

In a preferred embodiment, $X^3$ is $CR^7$, $X^1$, $X^2$, $X^4$, $X^5$ and $X^6$ are independently CH or CD; $R^7$ is fluorine, chlorine or cyano; one of $R^3$ and $R^4$ is substituted $(C_1\text{-}C_6)$alkyl, substituted $(C_3\text{-}C_6)$cycloalkyl or substituted $(C_1\text{-}C_6)$alkyl-$(C_3\text{-}C_6)$cycloalkyl. Preferably, one of $R^3$ and $R^4$ is $(C_1\text{-}C_6)$alkyl substituted with one or more halogen or D. More preferably, one of $R^3$ and $R^4$ is $CD_3$ or $CHF_2$.

In a preferred embodiment, $X^2$ is $CR^7$, $X^1$, $X^3$, $X^4$, $X^5$ and $X^6$ are independently CH or CD; $R^7$ is fluorine, chlorine or cyano; one of $R^3$ and $R^4$ is substituted $(C_1\text{-}C_6)$alkyl, substituted $(C_3\text{-}C_6)$cycloalkyl or substituted $(C_1\text{-}C_6)$alkyl-$(C_3\text{-}C_6)$cycloalkyl. Preferably, one of $R^3$ and $R^4$ is $(C_1\text{-}C_6)$alkyl substituted with one or more halogen or D. More preferably, one of $R^3$ and $R^4$ is $CD_3$ or $CHF_2$.

In a preferred embodiment, $X^1$ is $CR^7$, $X^2$, $X^3$, $X^4$, $X^5$ and $X^6$ are independently CH or CD; $R^7$ is fluorine, chlorine or cyano; one of $R^3$ and $R^4$ is substituted $(C_1\text{-}C_6)$alkyl, substituted $(C_3\text{-}C_6)$cycloalkyl or substituted $(C_1\text{-}C_6)$alkyl-$(C_3\text{-}C_6)$cycloalkyl. Preferably, one of $R^3$ and $R^4$ is $(C_1\text{-}C_6)$alkyl substituted with one or more halogen or D. More preferably, one of $R^3$ and $R^4$ is $CD_3$ or $CHF_2$.

In a preferred embodiment, $X^3$ is $CR^7$, $X^1$, $X^2$, $X^4$, $X^5$ and $X^6$ are independently CH or CD; $R^7$ is fluorine, chlorine or cyano; one of $R^3$ and $R^4$ is $CH_3$, $CD_3$, $C_2H_5$, $C_2D_5$, $CH_2CD_3$ or $CHF_2$, the other is $CD_3$ or $CHF_2$.

In a preferred embodiment, $X^3$ is $CR^7$, $X^1$, $X^2$, $X^4$, $X^5$ and $X^6$ are independently CH or CD; $R^7$ is fluorine, chlorine or cyano; $R^3$ is $CD_3$ or $CHF_2$, $R^4$ is $CH_3$, $CD_3$, $C_2H_5$, $C_2D_5$ or $CH_2CD_3$.
In a preferred embodiment, the compound of formula I is selected from the following compounds:
101
102
103
104
-continued
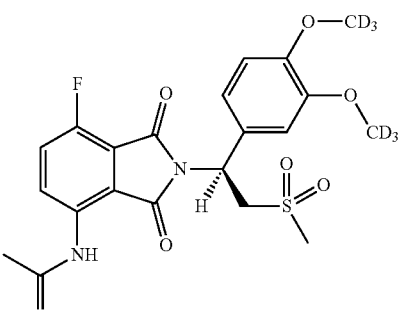
105
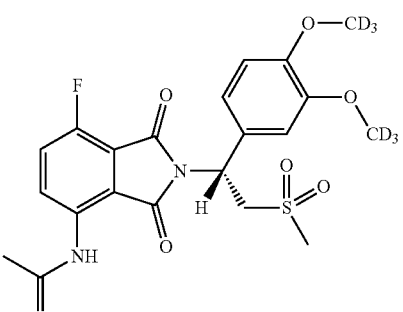
106
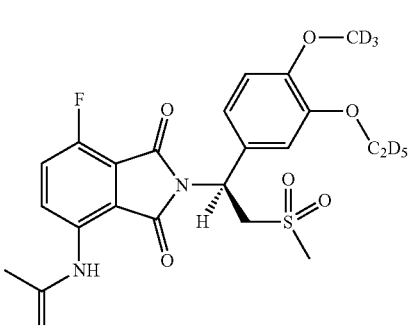
107
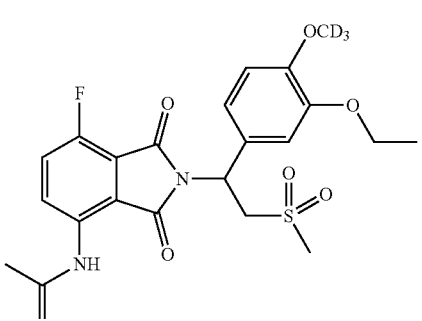
108
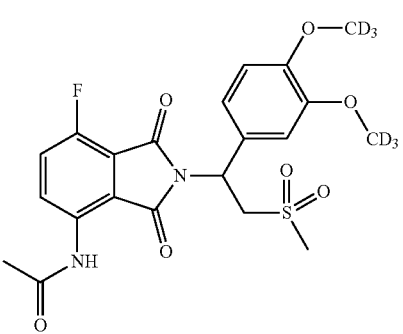
109

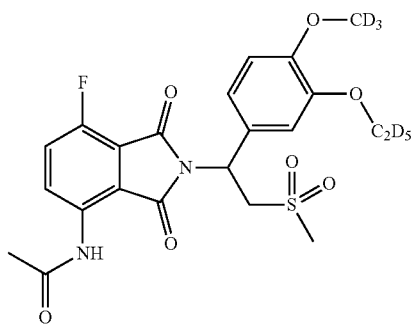
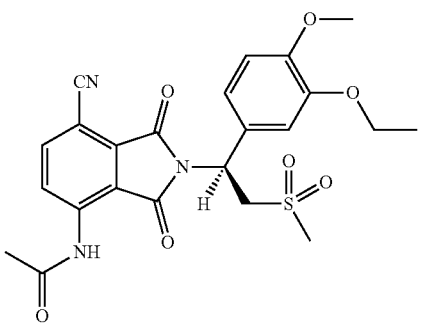

120 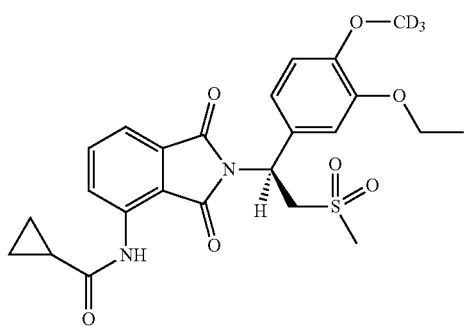
121 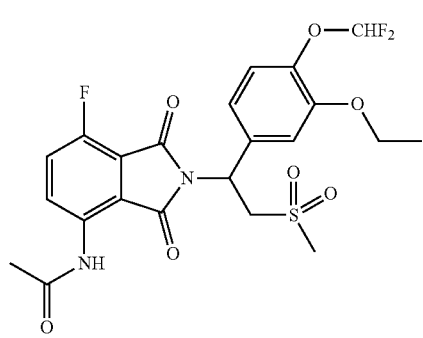
122 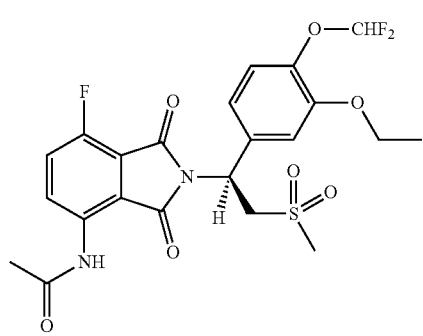
201 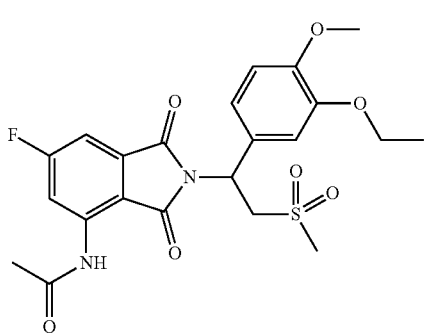
202 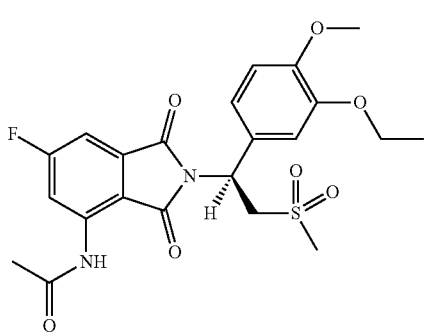
203 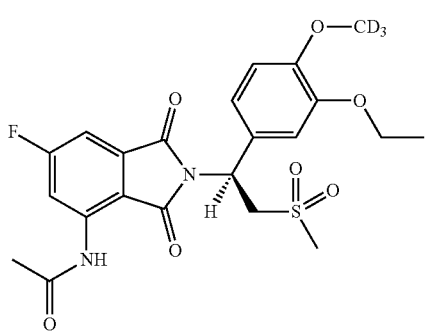
204 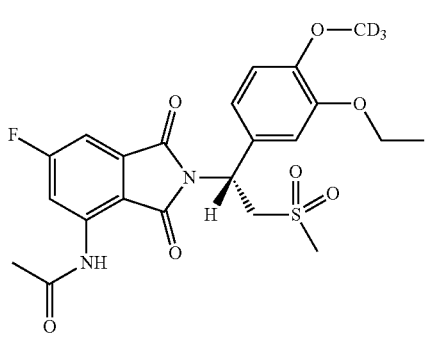
205 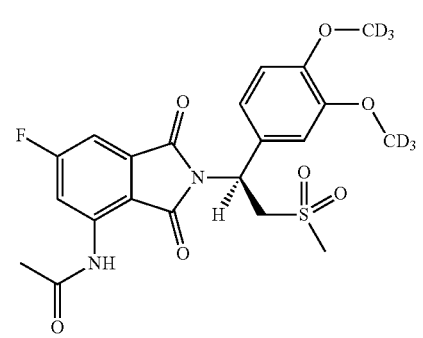
206 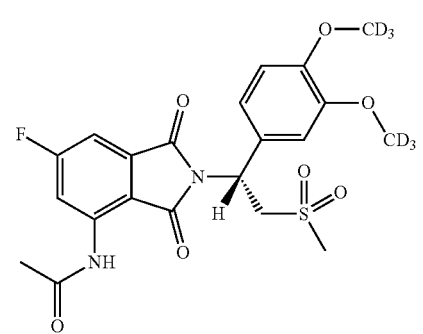
207 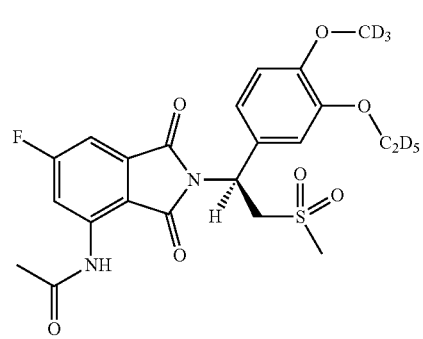

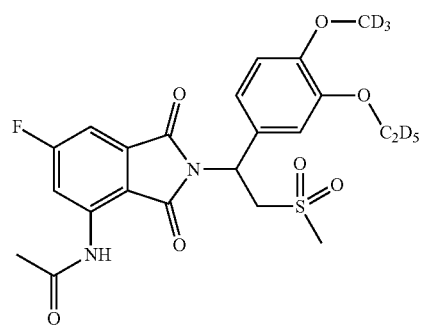 208
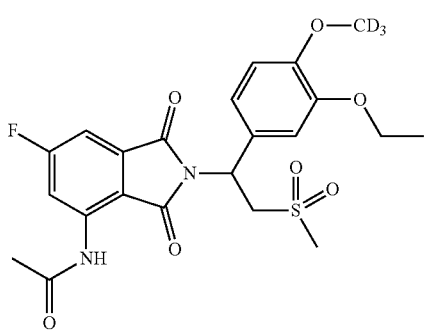 209
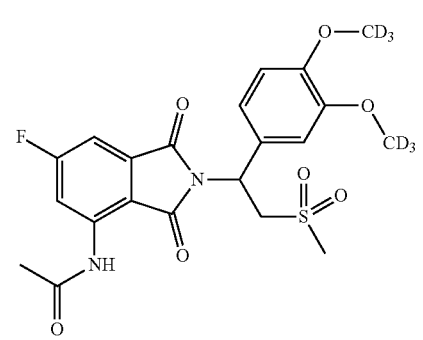 210
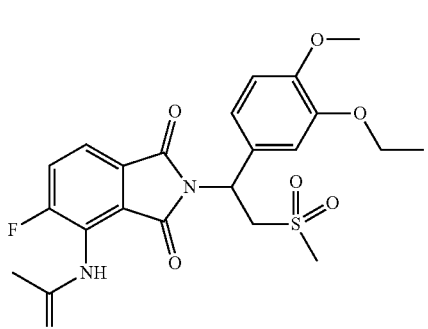 301
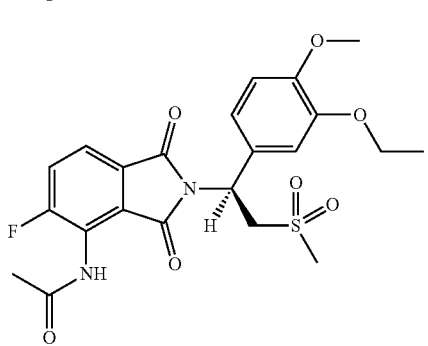 302
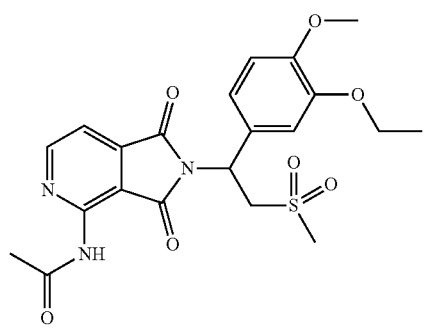 401
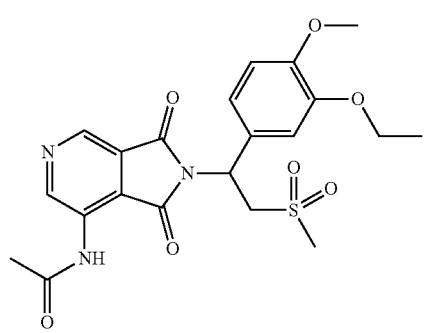 501
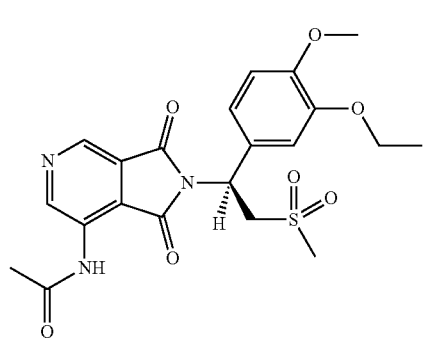 502
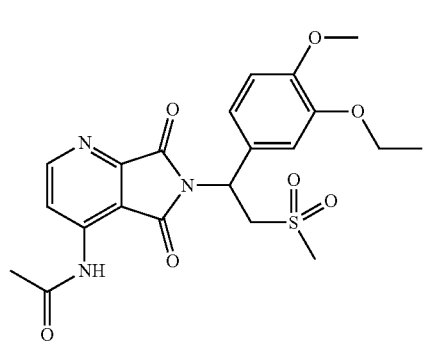 601
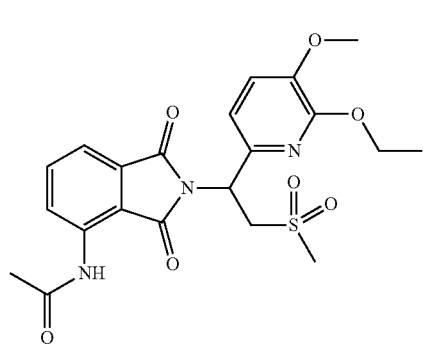 701

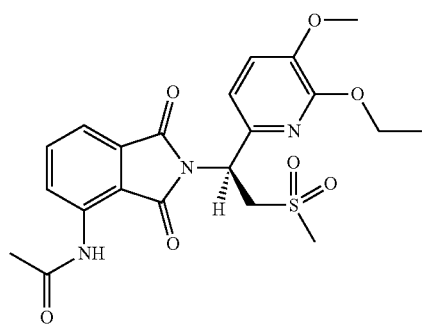
702
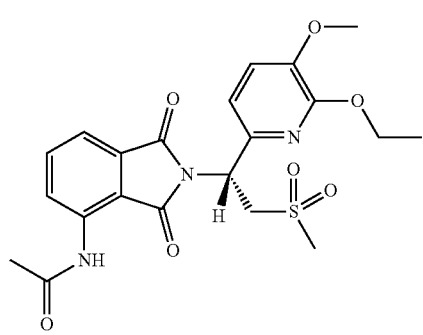
703
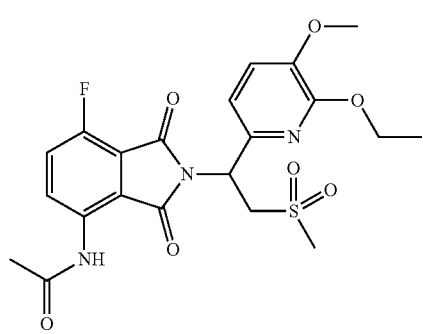
704
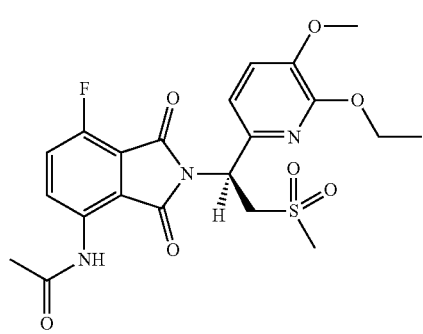
705
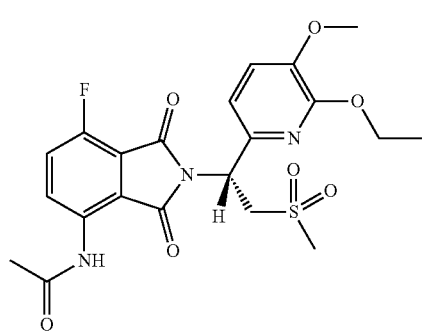
706
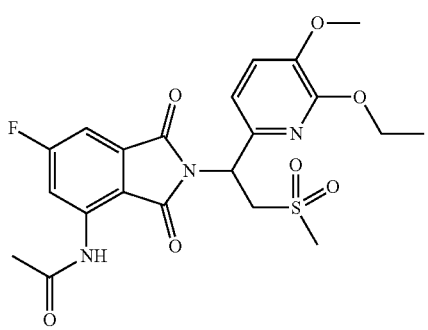
707
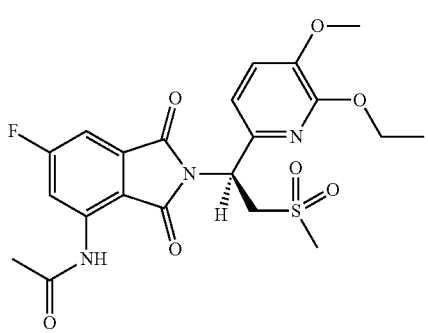
708
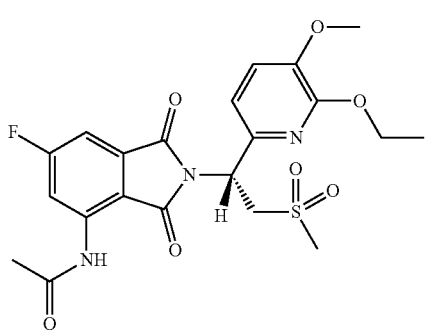
709
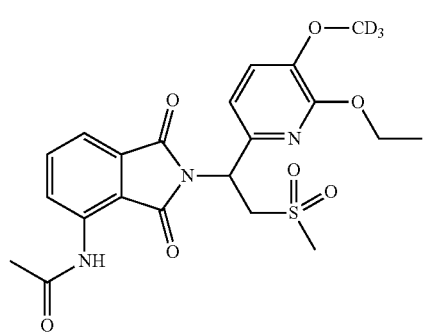
710
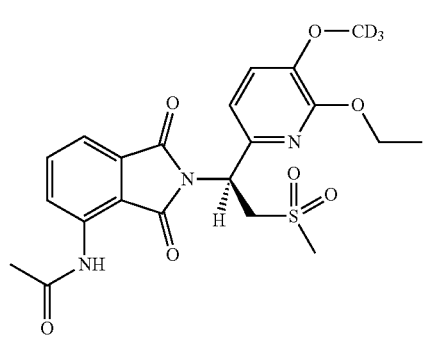
711

712 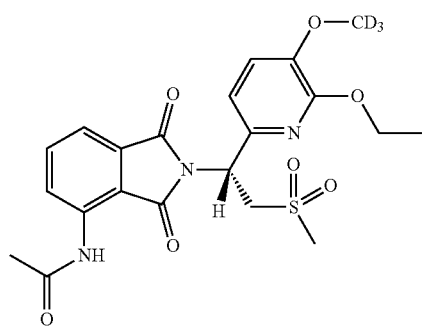
713 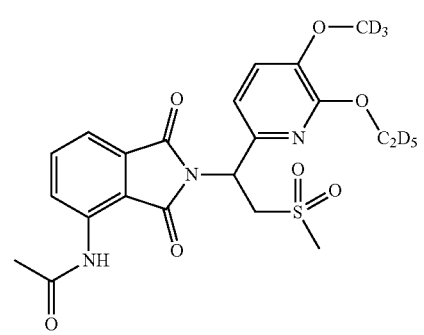
714 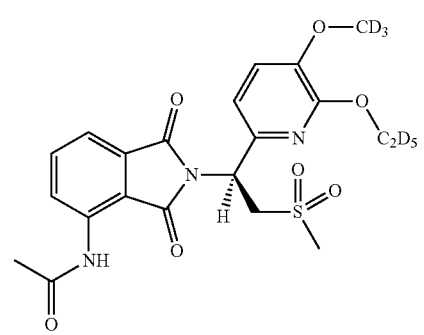
715 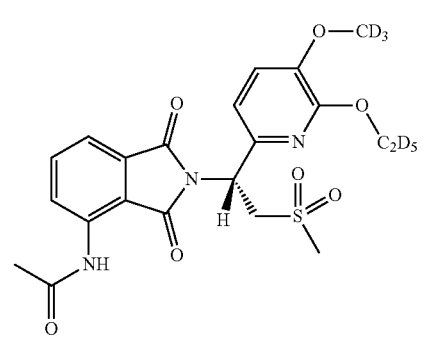
716 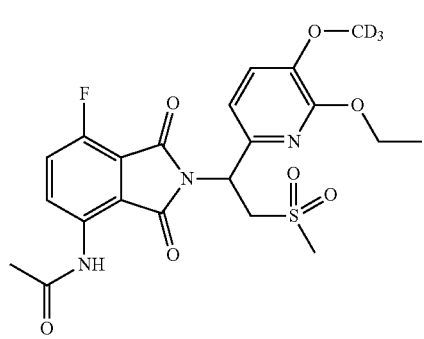
717 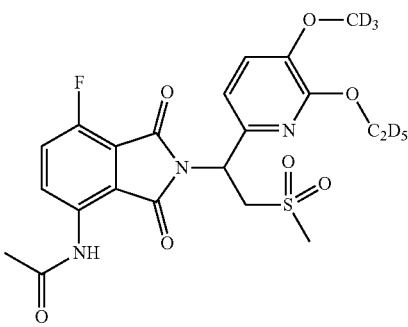
718 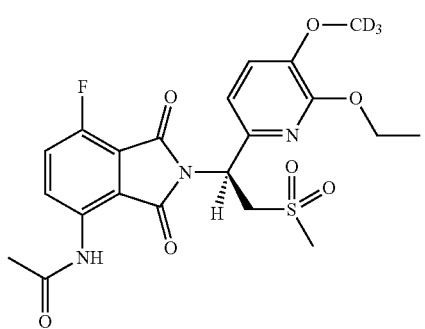
719 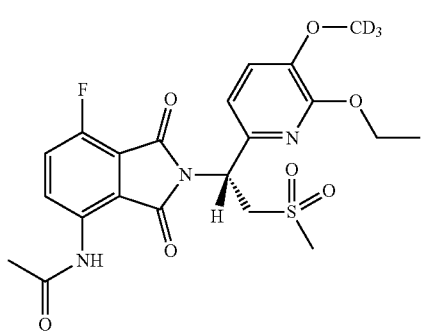
720 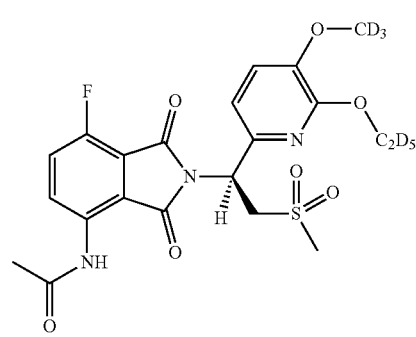
721 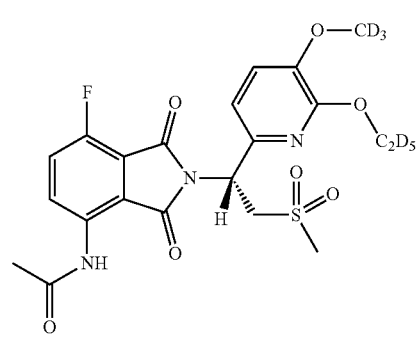

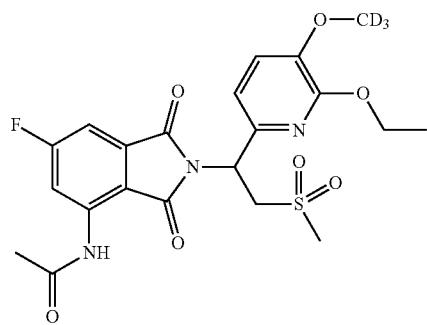
722
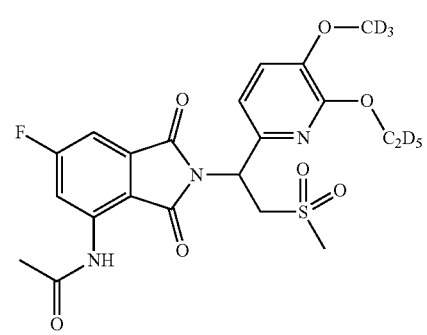
723
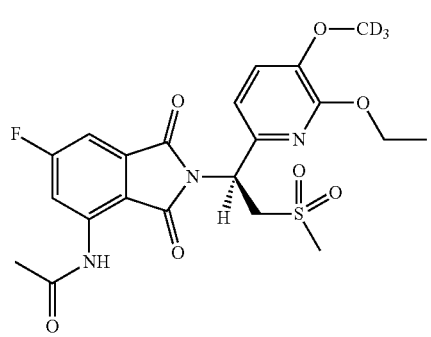
724
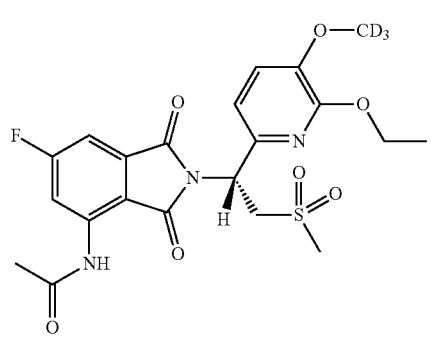
725
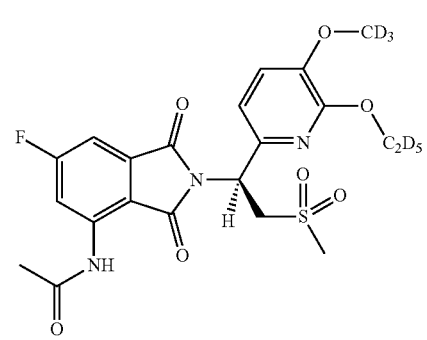
726
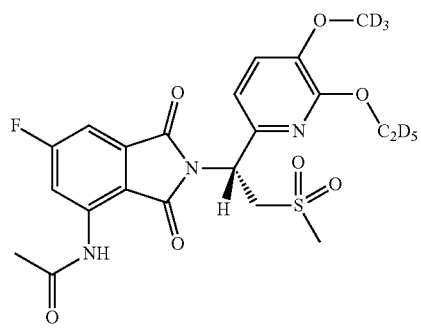
727
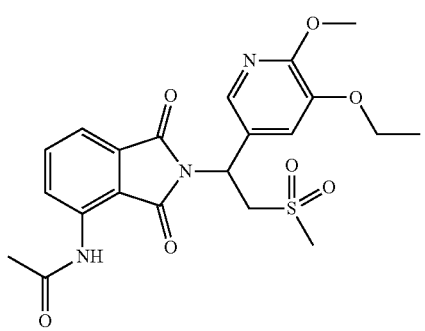
801
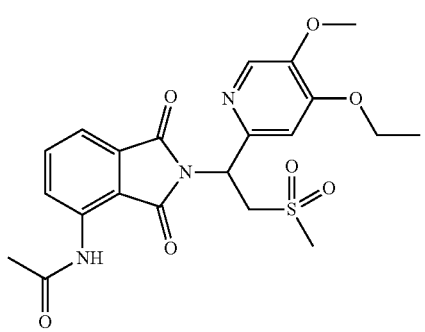
901
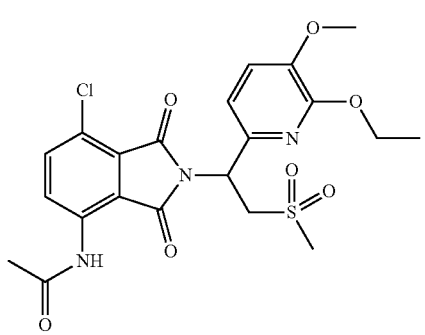
728
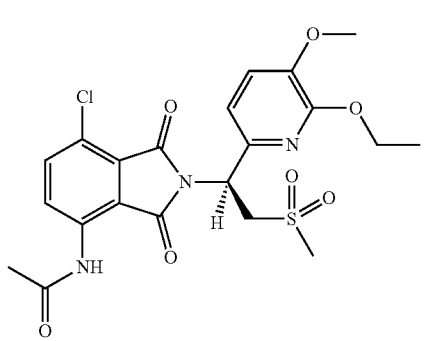
729

| | |
|---|---|
| 730 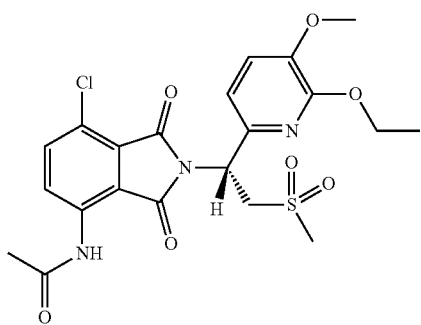 | 735 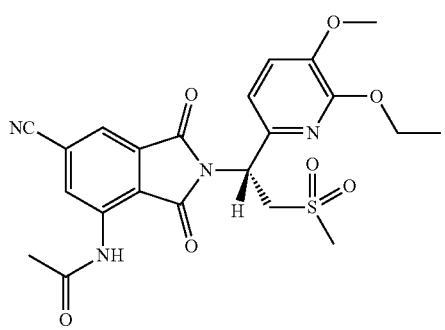 |
| 731 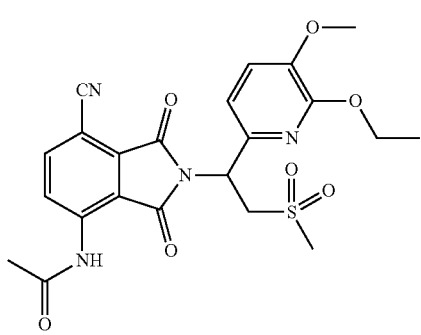 | 736 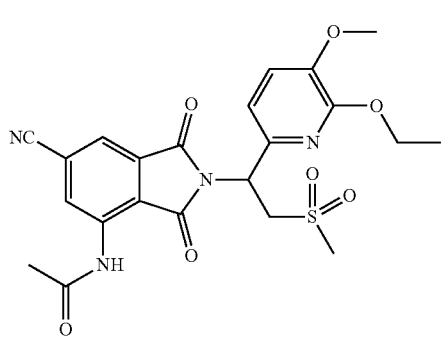 |
| 732 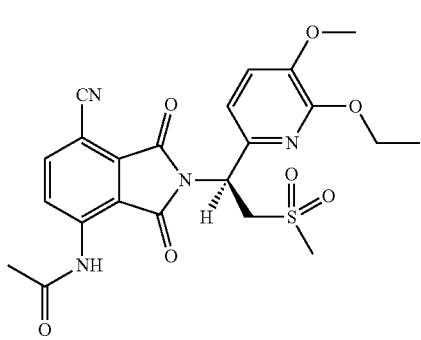 | 737 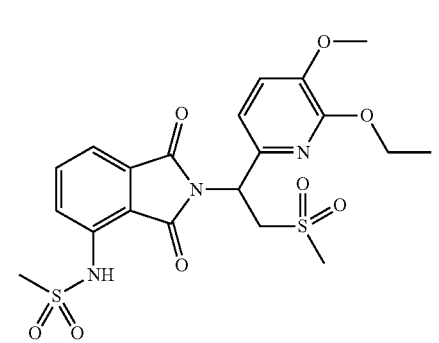 |
| 733 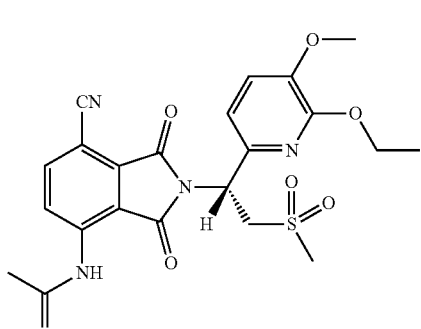 | 738 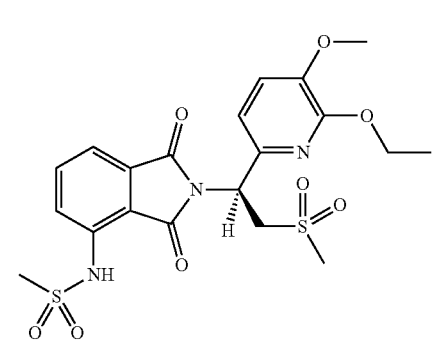 |
| 734 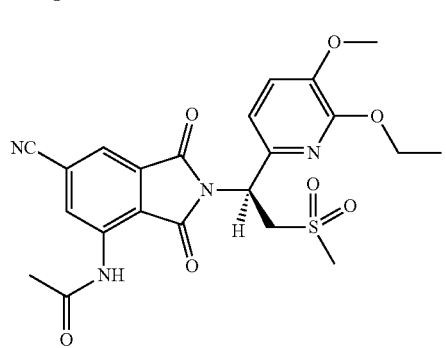 | 739 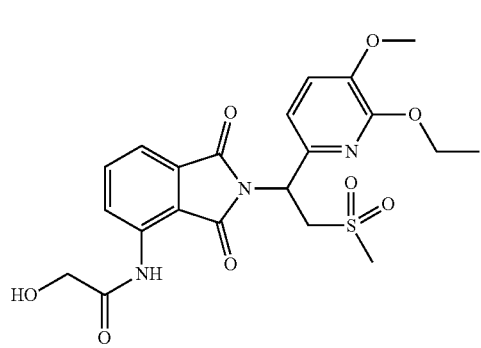 |

-continued
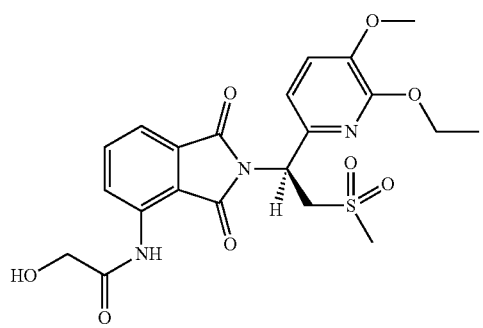
740
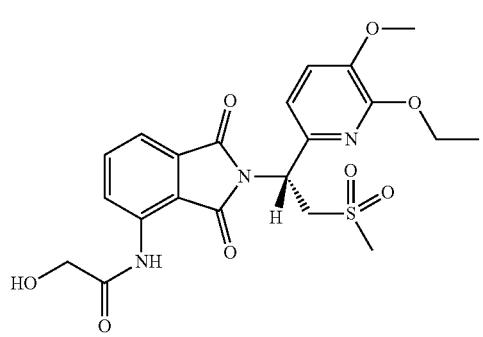
741
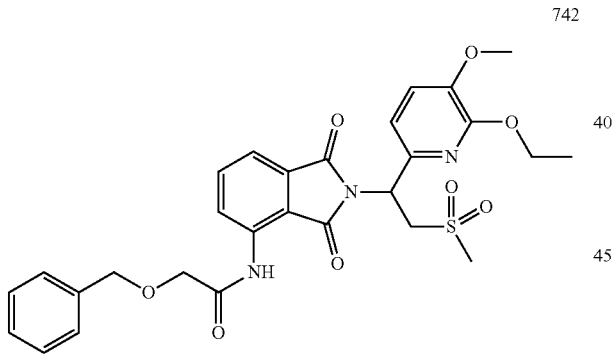
742
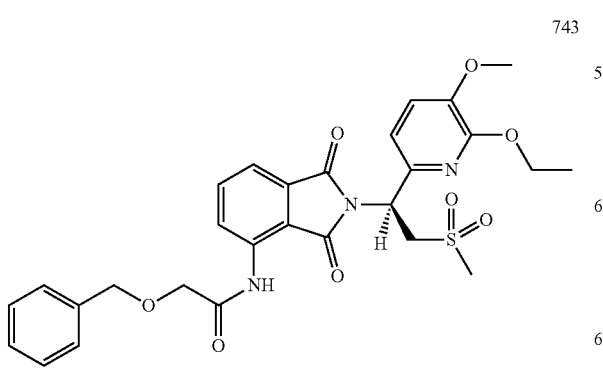
743
-continued
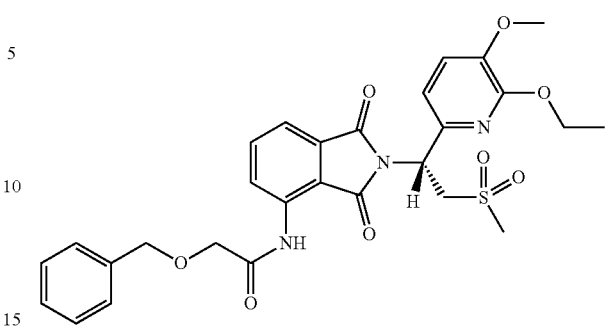
744
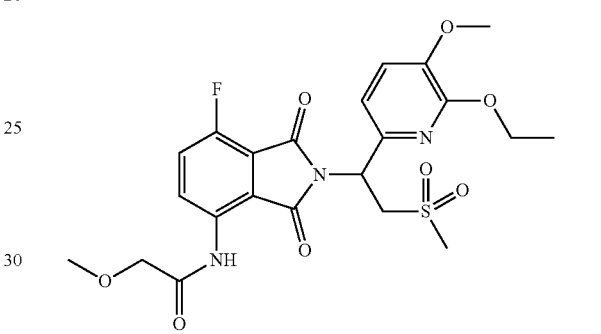
745
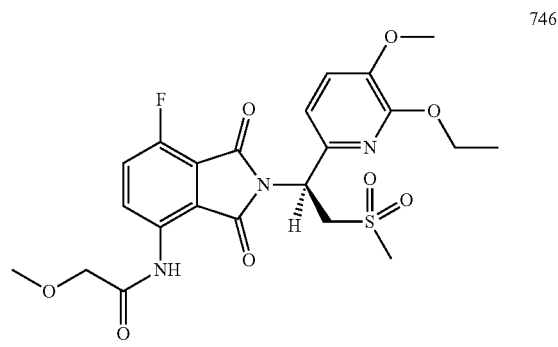
746
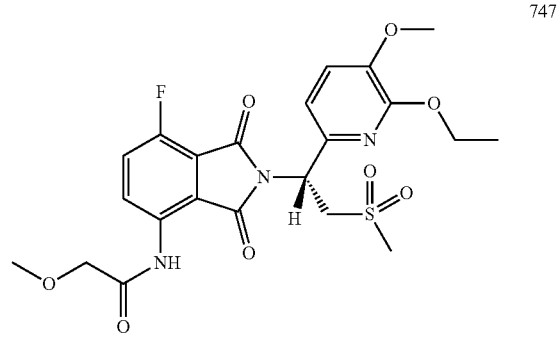
747

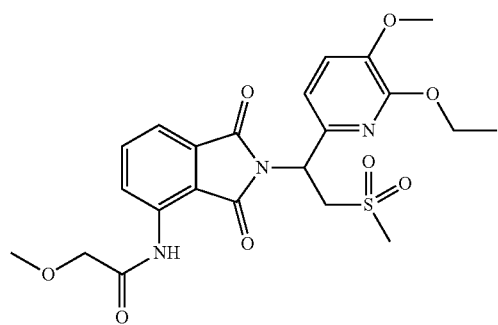
748
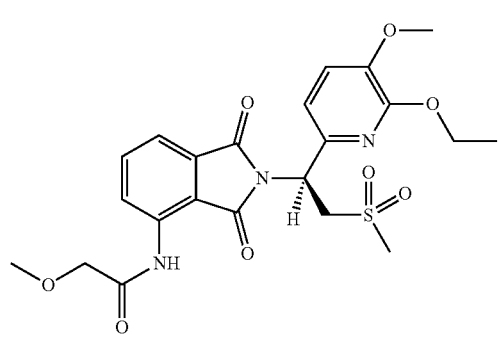
749
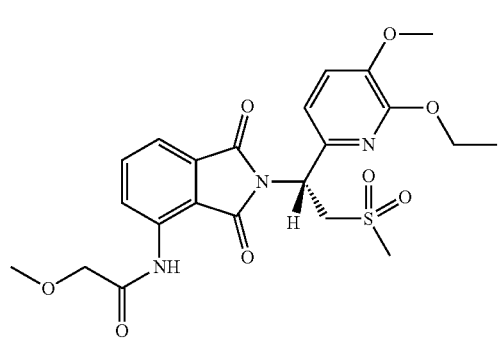
750
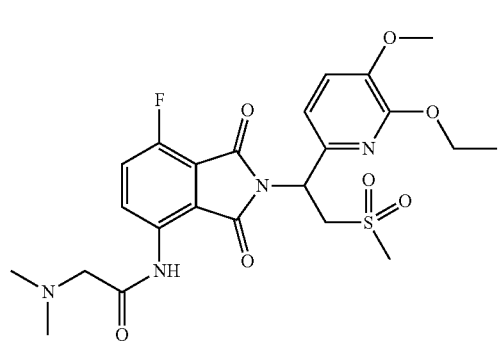
751
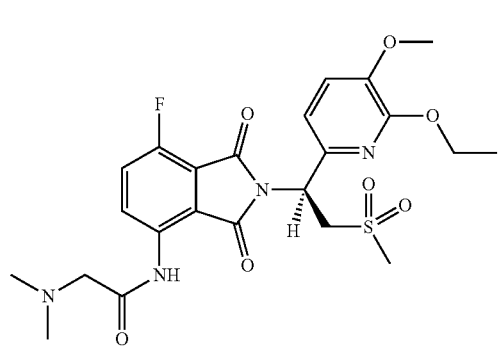
752
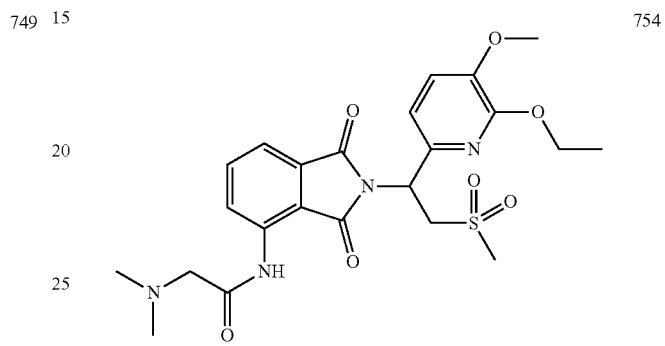
753
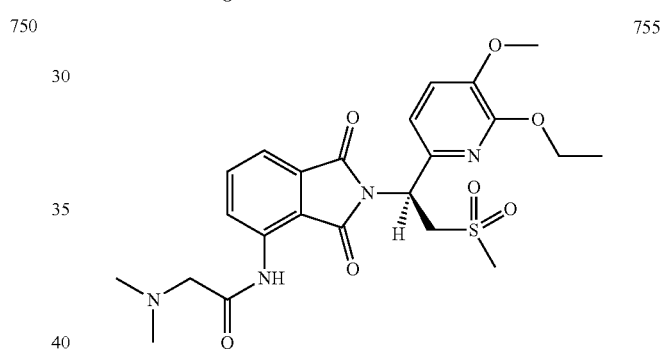
754
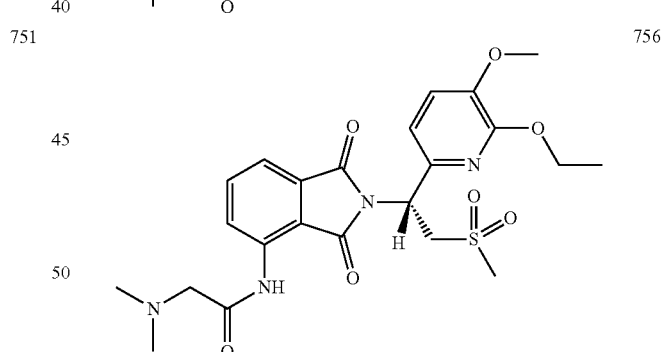
755
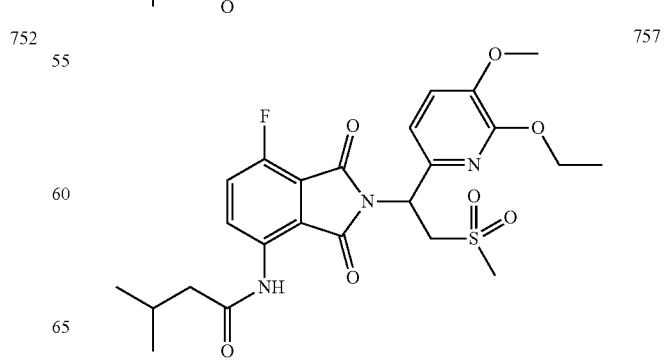
756
757

758 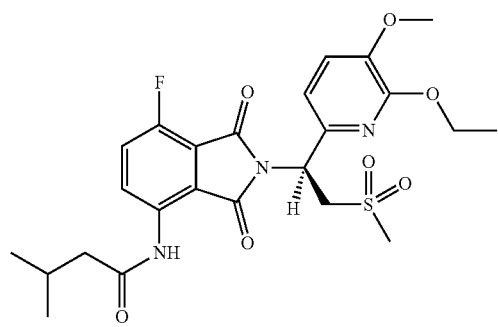
763 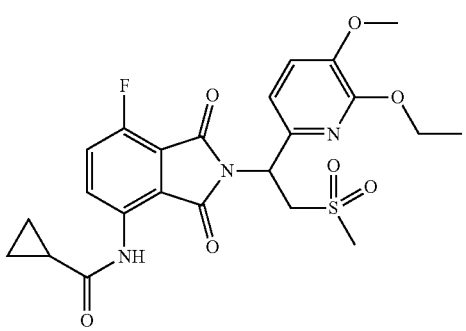
759 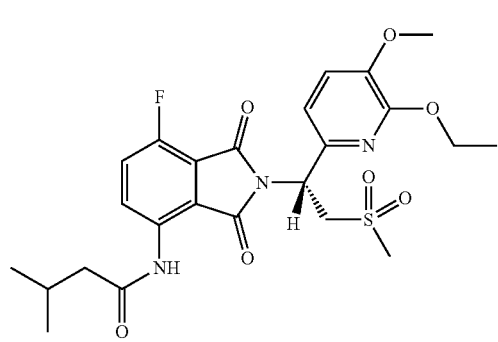
764 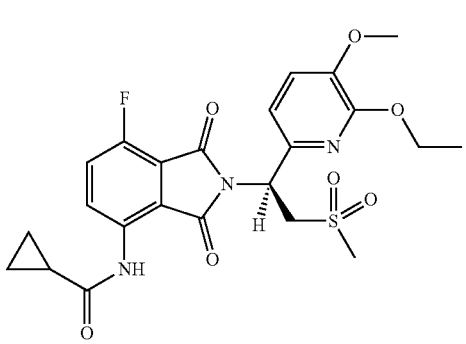
760 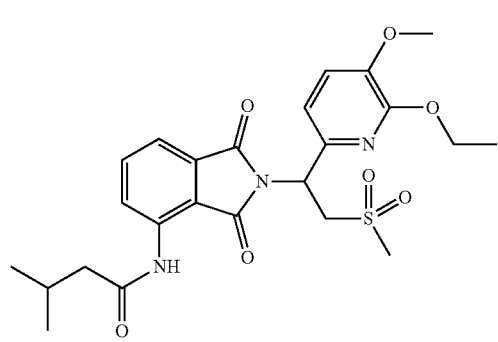
765 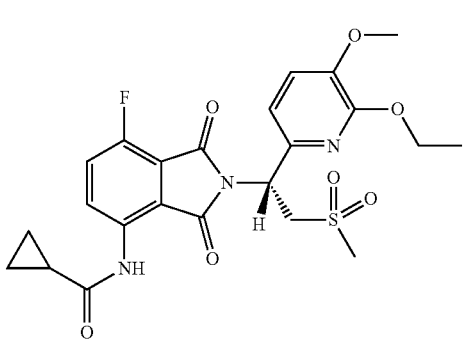
761 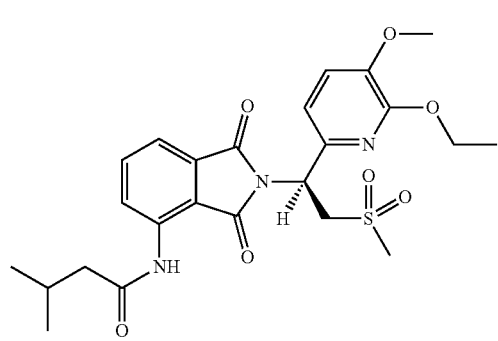
766 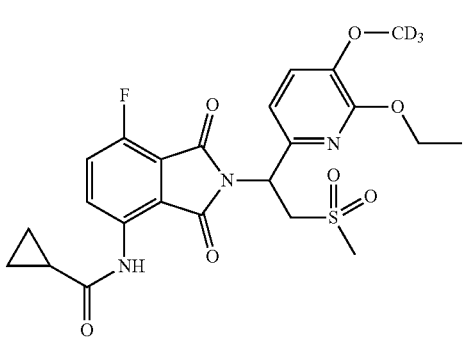
762 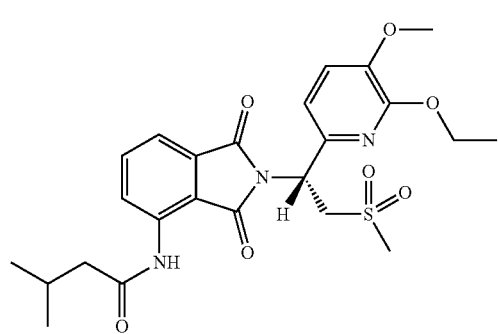
767 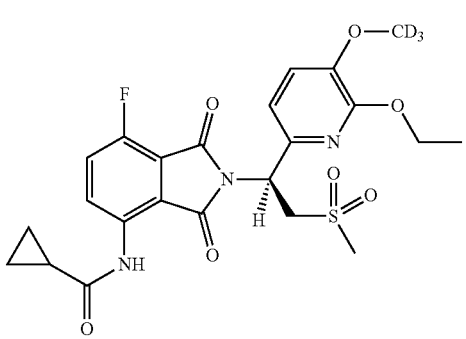

-continued

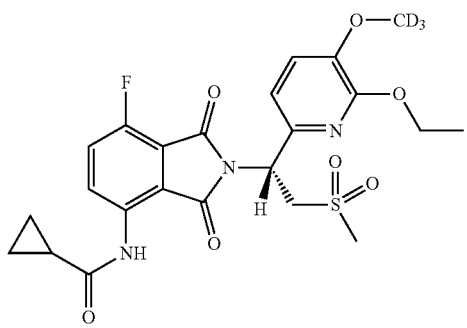
768

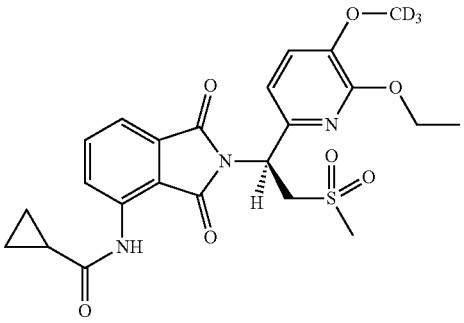
773

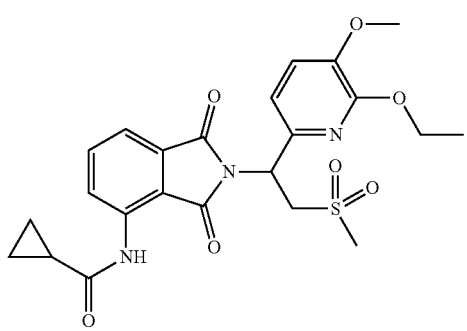
769

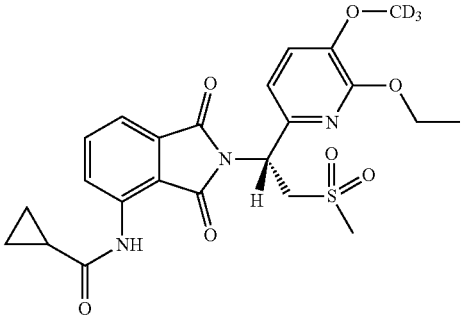
774

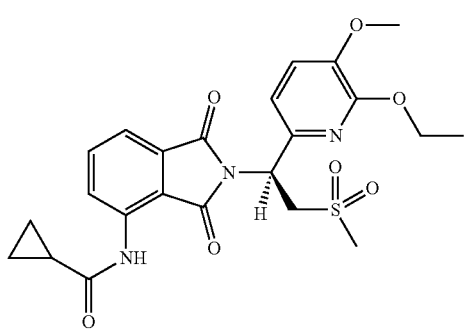
770

The invention further provides a method of preparing the compound of formula I, which is selected from method A or method B: method A, including the following steps: the compound of formula I-A and the compound of formula I-B are reacted as follows to prepare the compound of formula I;

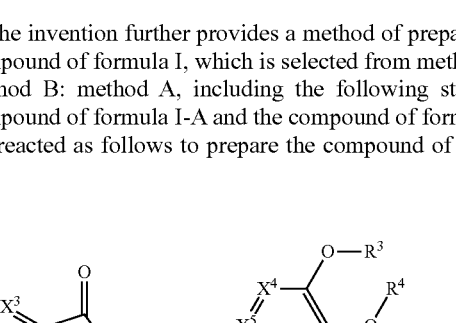

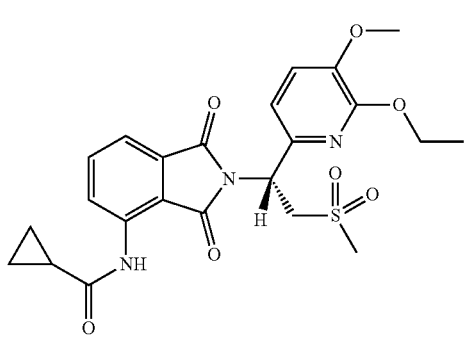
771

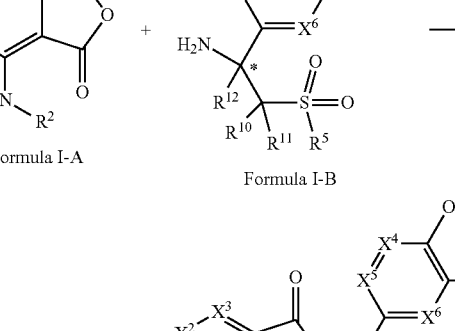

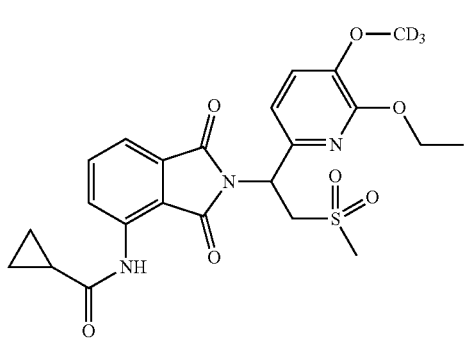
772

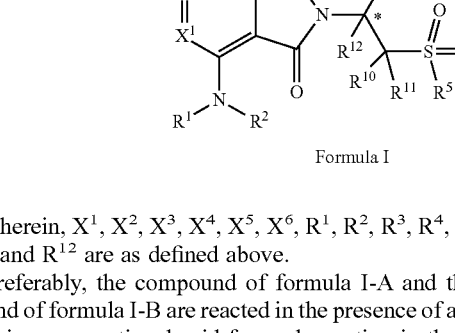

wherein, $X^1$, $X^2$, $X^3$, $X^4$, $X^5$, $X^6$, $R^1$, $R^2$, $R^3$, $R^4$, $R^5$, $R^{10}$, $R^{11}$ and $R^{12}$ are as defined above.

Preferably, the compound of formula I-A and the compound of formula I-B are reacted in the presence of acid. The acid is a conventional acid for such reaction in the field of organic synthesis, and is preferably, acetic acid.

In the preparation method of the compound of formula I, the reaction conditions may be the conventional conditions for such reaction in the field of organic synthesis. In the reaction, the amount of acid may not be specifically limited, as long as it does not affect the reaction. The amount of compound of formula I-A and compound of formula I-B may be selected according to the conventional amount of such reaction in the field of organic synthesis. The reaction temperature may be the conventional temperature for such reaction in this field, preferably, 10° C.-120° C.

method B, including the following steps: the compound of formula I-3 and the compound of formula I-4 are reacted as follows to prepare the compound of formula I;

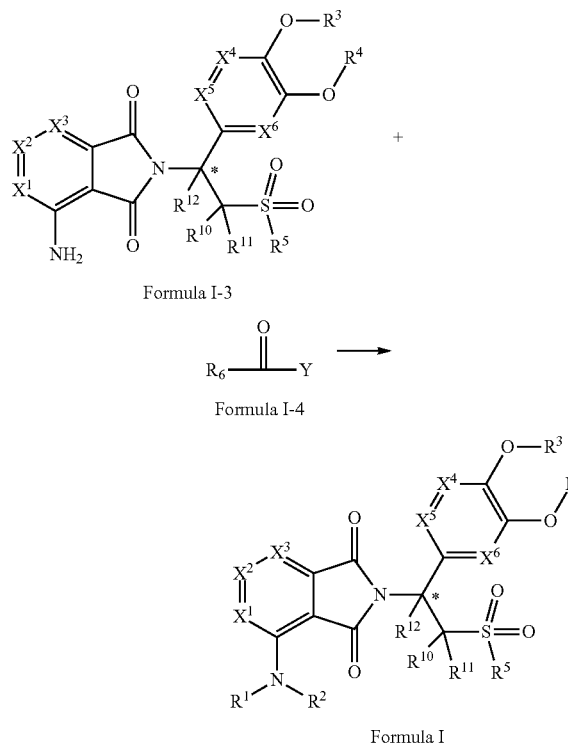

Formula I wherein $X^1$, $X^2$, $X^3$, $X^4$, $X^5$, $X^6$, $R^1$, $R^2$, $R^3$, $R^4$, $R^5$, $R^{10}$, $R^{11}$ and $R^{12}$ are as defined above; Y is a leaving group, such as halogen.

In another embodiment of the method B, the compound of f Formula I-4 may be replaced by the compound of formula I-4' ($R^6$—S(O)$_2$—Y) to prepare the compound of formula I, wherein the groups are as defined above.

The preparation methods of the compound of formula I may also be obtained by referring to the conventional methods of such kind of compounds in the field of organic synthesis. The conditions and steps involved in the chemical reactions may be carried out by referring to the conventional conditions and steps of such reactions in organic synthesis, and the compounds obtained by the above-mentioned methods may also be further modified in the peripheral positions to get other target compounds of the invention.

The invention also provides an intermediate compound for the synthesis of the compound of formula I, such as compounds of formula I-3,

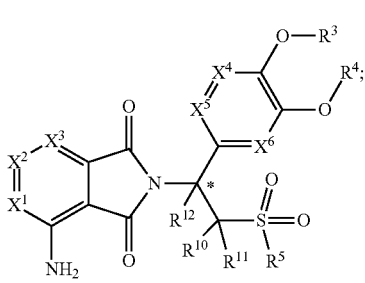

Formula I-3 wherein, $X^1$, $X^2$, $X^3$, $X^4$, $X^5$, $X^6 R^1$, $R^2$, $R^3$, $R^4$, $R^5$, $R^{10}$, $R^{11}$ and $R^{12}$ are as defined above.

The invention also provides a pharmaceutical composition, which comprises one or more of the compound of formula I, the pharmaceutically acceptable salt, solvate, polymorph, co-crystal, stereoisomer, isotope compound, metabolite and prodrug thereof, and one or more pharmaceutical excipients. The pharmaceutical composition may further comprise other therapeutic agent with pharmacological activity. The other therapeutic agent may include but not limited to anti-angiogenesis drugs, immunomodulators, immunotherapeutic drugs, chemotherapeutic drugs, hormone compounds, anti-tumor drugs or anti-inflammatory drugs.

The pharmaceutically acceptable excipient can be those widely used in drug manufacture field. The excipient is mainly used to provide a safe, stable and functionalized pharmaceutical composition, and can also provide a method which makes the active ingredients dissolved at a desired rate after the subject receives administration or promotes the effective absorption of the active ingredients after the subject is administered with the composition. The excipient can be an inert filler, or provide a certain function, such as stabilizing the overall pH value of the composition or preventing the degradation of the active ingredients of the composition. The pharmaceutically acceptable excipient may comprise one or more of the following excipients: binder, suspending agent, emulsifier, diluent, filler, granulating agent, adhesive, disintegrating agent, lubricant, anti-adhesive agent, glidant, wetting agent, gelling agent, absorption retarder, dissolution inhibitor, reinforcing agent, adsorbent, buffer, chelating agent, preservative, colorant, flavoring agent and sweetening agent.

The pharmaceutical composition of the invention can be prepared based on the contents disclosed herein according to any method known by one skilled in the art. For example, the pharmaceutical composition can be prepared by mixing one or more of the compound of formula I, or the pharmaceutically acceptable salt, solvate, polymorph, co-crystal, stereoisomer, isotopic compound, metabolite and prodrug thereof, with one or more pharmaceutically acceptable excipients, based on common preparation technology for medicaments. The technologies include but not limited to conventional mixing, dissolving, granulating, emulsifying, levigating, wrapping, embedding or freeze-dry process.

The pharmaceutical composition according to the invention may be formulated for administration in any route, including injection (intravenous), mucosal, oral administration (solid and liquid preparation), inhalation, ocular administration, rectal administration, topical or parenteral (infusion, injection, implantation, subcutaneous, vein, artery, intramuscular) administration. The pharmaceutical composition of the invention can also be controlled release or delayed release dosage forms. Examples of solid oral preparation include but not limited to powder, capsule, caplet, soft capsule or tablet. Examples of liquid preparation for oral or mucosal administration include but not limited to suspension, emulsion, elixir and solution. Examples of topical preparation include but not limited to emulsion, gel, ointment, cream, patch, paste, foam, lotion, drops or serum preparation. Examples of preparation for parenteral administration include but not limited to injection solution, dry preparation which can be dissolved or suspended in a pharmaceutically acceptable carrier, injectable suspension and injectable emulsion. Examples of other suitable preparations of the pharmaceutical composition include but not limited to eye drops and other ophthalmic preparations; aerosol, such as nasal spray or inhalation; liquid dosage forms suitable for parenteral administration; suppository and pastille.

The therapeutic or prophylactic amount of one or more of the compound of formula I, or the pharmaceutically acceptable salt, solvate, polymorph, co-crystal, stereoisomer, isotopic compound, metabolite and prodrug thereof, any pharmaceutical composition or preparation thereof etc., may be administered to a subject over a period (drug delivery cycle), followed by a period free of the compound (non-drug delivery cycle). The drug delivery cycle and non-drug delivery cycle can be repeated for required times. The required length and times of the drug delivery cycle and non-drug delivery cycle depend on the type and/or severity of the disease, disorder or condition being treated or prevented, and the gender, age, weight of the subject, and other parameters (e.g., the subject's biological, physical and physiological conditions, etc.). One skilled in the art can sufficiently determine a suitable length and times for the drug delivery cycle and non-drug delivery cycle based on the contents disclosed herein.

The invention further provided a method for regulating the generation or activity of PDE4 or TNF-α, which comprises administering to a subject in need a therapeutically effective amount of one or more of the compound of formula I, or the pharmaceutically acceptable salt, solvate, polymorph, co-crystal, stereoisomer, isotopic compound, metabolite and prodrug thereof, or the pharmaceutical composition thereof.

The invention further provided a use of the one or more of the compound of formula I, the pharmaceutically acceptable salt, solvate, polymorph, co-crystal, stereoisomer, isotopic compound, metabolite and prodrug thereof in the manufacture of a medicament for regulating the generation or activity of PDE4 and/or TNF-α.

The invention further provided the compound of formula I, or the pharmaceutically acceptable salt, solvate, polymorph, co-crystal, stereoisomer, isotopic compound, metabolite and prodrug thereof for use in regulating the generation or activity of PDE4 and/or TNF-α.

In an embodiment, when the term "regulate" is used to describe the activity or generation of a specific molecule, it refers to inhibiting the activity or generation of the molecule. In another embodiment, when the term "regulate" is used to describe the activity or generation of a specific molecule, it refers to increasing or enhancing the activity or generation of the molecule. However, in another embodiment, when the term "regulate" is used to describe the activity or generation of a specific molecule, it refers to decreasing or increasing the activity or generation of the molecule.

In another aspect, provided is a method of treating or preventing a disease, disorder or condition caused by abnormal generation or regulation of PDE4 and/or TNF-α comprising administering to a subject a therapeutically or prophylactically effective amount of the compound of formula I, the pharmaceutically acceptable salt, solvate, stereoisomer, isotopic compound, metabolite or prodrug thereof, or the pharmaceutical composition thereof.

The invention further provided a use of the one or more of the compound of formula I, the pharmaceutically acceptable salt, solvate, polymorph, co-crystal, stereoisomer, isotopic compound, metabolite and prodrug thereof in the manufacture of a medicament for treating or preventing a disease, disorder or condition related to abnormal generation or regulation of PDE4 and/or TNF-α.

The invention further provided the compound of formula I, the pharmaceutically acceptable salt, solvate, polymorph, co-crystal, stereoisomer, isotopic compound, metabolite and prodrug thereof for use in treating or preventing a disease, disorder or condition related to abnormal generation or regulation of PDE4 and/or TNF-α.

According to the method or use of the invention, examples of the disease, disorder or condition related to abnormal generation or regulation of PDE4 and/or TNF-α include but not limited to cancers, inflammatory diseases, diseases and disorders associated with undesired angiogenesis, pains, macular degeneration (MD) syndrome, skin diseases, keratosis, respiratory system disease (such as asthma or COPD), immunodeficiency diseases, central nervous system (CNS) diseases, autoimmune diseases, atherosclerosis, heredity, allergy, viruses, sleep disorders and associated syndrome. Well-known examples of the disease, disorder or condition in the field include but not limited to those described in PCT patent publications WO2012015986 and WO2006018182 and US patent publication US20100204227.

In an embodiment, examples of the disease, disorder or condition related to abnormal generation or regulation of PDE4 and/or TNF-α are psoriatic arthritis and plaque psoriasis.

The method of treating or preventing a disease, disorder or condition of the invention comprises administering one or more of the compound of formula I, the pharmaceutically acceptable salt, solvate, stereoisomer, isotopic compound, metabolite and prodrug thereof to a subject by any suitable means, such as injection, mucosal, oral, inhalation, ocular, rectal, long-acting implant, liposome, emulsion or sustained release method.

One skilled in the art understands that the therapeutically effective or prophylactically effective amount of the compound of the invention may vary with factors for a specific subject, such as age, diet, health, etc., the severity, complication and type of the disease, disorder or condition to be treated or prevented, and the preparation used etc. Based on the disclosures of the invention, one skilled in the art can easily determine therapeutically effective or prophylactically effective amount of the compound to be administered to the subject, so as to induce the desired biological or medical response in the subject.

The present application cites or describes a variety of publications, articles and patents, the purpose of citing or describing these references or incorporating these references by their entireties or discussing these references is to illustrate the background of the invention rather than admission that the contents of these references contribute to a part of the prior art of the invention.

Unless otherwise defined, the technical and scientific terms used herein have the same meanings as those commonly understood by one skilled in the art. Otherwise, certain terms used herein have the meanings specified in the present description. All the patents, published applications and publications cited herein are incorporated herein by reference, just like elaborating in detail herein. It should be noted that, unless otherwise indicated explicitly in the context, the singular form used herein and in the attached claims encompass the plural meaning.

Unless otherwise specifically defined, the ratios (including percentages) or parts used herein are by weight.

When used in conjunction with a numerical variable, the terms "about" and "approximately" generally mean that the value of that variable and all values of that variable are within experimental error (for example, within a 95% confidence interval for the mean) or ±10% of the specified value or wider.

The expressions "comprising", "including", "having", and the like, are meant to be open, and do not exclude additional unenumerated elements, steps, or components. The expression "consisting of" excludes any element, step or ingredient that is not specified. The expression "consisting essentially of" means that the scope is limited to the specified elements, steps or components, and the optionally existed elements, steps or components that do not substantially affect the basic and novel characteristics of the claimed subject matter. It should be understood that the expression "comprising" encompasses the expression "consisting essentially of" and "consisting of."

The term "substituted" or "substitute" means that any one or more hydrogen atoms on a particular atom are replaced by a substituent as long as the valence state of the particular atom is normal and the substituted compound is stable.

As used herein, when the specific salt, composition, and excipient etc. are referred to as "pharmaceutically acceptable", it means that the salt, composition, or excipient etc. are generally non-toxic, safe, and suitable for administration to a subject, preferably mammalian, more preferably human.

The term "pharmaceutically acceptable salt" used herein refers to a pharmaceutically acceptable organic or inorganic salt. Examples of the salt include but are not limited to, sulfate, citrate, acetate, oxalate, chloride, bromide, iodide, nitrate, hydrosulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzosulfonate, p-toluenesulfonate, and embonate (i.e. 1-1-methylene-bis(2-hydroxyl-3-naphthoate)). The compounds of the invention may be used to form pharmaceutically acceptable salts with various amino acids. Suitable alkali salt includes but is not limited to, aluminum salt, calcium salt, lithium salt, magnesium salt, potassium salt, sodium salt, zinc salt, bismuth salt and diethanolamine salt.

As used herein, the term "metabolite" refers to an active substance produced by a drug molecule which has gone through chemical structure changes in vivo, the active substance is generally a derivative of the aforementioned drug molecule, and also can be chemically modified.

As used herein and unless otherwise specified, the term "polymorph" refers to one or more kinds of crystal structure formed by different arrangements of molecules in the lattice space when crystallizing.

As used herein, the term "co-crystal" refers to a multi-component system comprising one or more API (active pharmaceutical ingredient) molecules and one or more object (or ligand) molecules. In the co-crystal, API molecules and object (or ligand) molecules exist as solids at room temperature when they are used in their pure form alone (in order to distinguish co-crystal from solvate or hydrate). From this particular definition, salts in which significant or complete proton exchange occurs between API molecules and guest molecules are excluded. In the co-crystal, API and ligands interact through hydrogen bonds and other possible non-covalent interactions. It is noted that the co-crystal itself may form solvates, including hydrates.

As used herein, the term "solvate" refers to a crystal form of the compound of formula I, or the pharmaceutically acceptable salt, polymorph, co-crystal, stereoisomer, isotopic compound, metabolite or prodrug thereof, which further has one or more solvent molecules incorporated into the crystal structure. The solvate may include a stoichiometric amount or a non-stoichiometric amount of solvent, and the solvent molecule in the solvent may exist in an ordered or non-ordered arrangement. The solvate containing a non-stoichiometric amount of solvent molecules may be formed by losing at least one solvent molecule (but not all) from the solvate. In a particular embodiment, a solvate refers to a hydrate, which means the crystal of the compound further includes water molecule, and the water molecule is used as a solvent.

As used herein and unless otherwise specified, the term "prodrug" refers to a derivative of the compound comprising a biologically reactive functional group, the biological reactive functional group can be cleaved from the compound or react in other ways to give the compound under biological conditions (in vivo or in vitro). Usually, the prodrug is inactive, or at least has lower activity than the compound, which makes the compound exhibit its activity after it is cleaved from the biologically reactive functional group. The biologically reactive functional group can be hydrolyzed or oxidized under biological conditions to give the compound. For instance, the prodrug may contain a biologically hydrolysable group. Examples of the biologically hydrolysable group include but not limited to a biologically hydrolysable phosphate, a biologically hydrolysable ester, a biologically hydrolysable amide, a biologically hydrolysable carbonic ester, a biologically hydrolysable carbamate and a biologically hydrolysable ureide.

The compound of formula I in the invention, the pharmaceutically acceptable salt, solvate, polymorph, co-crystal, stereoisomer, isotopic compound, metabolite or prodrug thereof, can contain one or more asymmetric centers ("stereoisomer"). As used herein, the term "stereoisomer" refers to all stereoisomers including enantiomer, diastereoisomer, epimer, endo-exo isomer, atropisomer, regioisomer, cis- and trans-isomer. The "stereoisomer" herein also includes "pure stereoisomer" and "enriched stereoisomer" or "racemic isomer" of the various aforementioned stereoisomers. These stereoisomers can be prepared according to an asymmetric synthesis process, or separated, purified and enriched by a chiral separation process (including but not limited to thin layer chromatography, rotating chromatography, column chromatography, gas chromatography, high pressure liquid chromatography, etc.), as well as obtained by chiral separation by means of bonding (chemical binding etc.) or salifying (physical binding etc.) with other chiral compound(s). The term "pure stereoisomer" herein refers to that the mass content of a stereoisomer of the compound is no less than 95% relative to other stereoisomers of the compound. The term "enriched stereoisomer" herein refers to that the mass content of a stereoisomer of the compound is no less than 50% relative to other stereoisomers of the compound. The term "racemic isomer" herein refers to that the mass content of a stereoisomer of the compound is equal to that of another stereoisomer of the compound.

The term "isotopic compound" used herein refers to that there is one or more atomic isotopes with natural or non-natural abundance contained in the compound of formula I, or the pharmaceutically acceptable salt, solvate, polymorph, co-crystal, stereoisomer, metabolite or prodrug thereof. Atomic isotopes with non-natural abundance include, but are not limited to, deuterium ($^2$H or D), tritium ($^3$H or T), iodine-125 ($^{125}$I), phosphorus-32 ($^{32}$P), carbon-13 ($^{13}$C) or carbon-14 ($^{14}$C). The aforementioned isotopic compound can also be used as a therapeutic or diagnostic agent (i.e., internal developing agent) or research tool. All the isotopic variants of the compound of the invention, whether or not radioactive, are included in the scope of the invention.

The term "isotope enriched" used herein refers to that there is one or more atomic isotopes with non-natural abundance contained in the compound of formula I, or the pharmaceutically acceptable salt, solvate, polymorph, co-crystal, stereoisomer, isotopic compound, metabolite or prodrug thereof. The term "isotope enriched" also refers to that the compound of formula I, or the pharmaceutically acceptable salt, solvate, polymorph, co-crystal, stereoisomer, isotopic compound, metabolite or prodrug compound thereof, contains at least one isotopic atom with non-natural abundance.

As used herein, the term "patient" or "subject" refers to any animal to be treated or have been treated with the compound or the composition according to an embodiment of the invention, mammalian is preferable, and human is the most preferable. The term "mammalian" used herein includes any mammals. Examples of mammal include but are not limited to cattle, horse, sheep, pig, cat, dog, mice, rat, rabbit, guinea pig, monkey, human, etc., human is the most preferable. The terms "subject" and "patient" are used interchangeably herein.

In an embodiment, the terms "treat" and "treating" refers to an improvement, prevention or reversal of a disease or disorder or at least one of identifiable symptoms thereof, such as treating cancer by reducing or stabilizing the symptoms of cancer or a disease. In another embodiment, "treat" or "treating" refers to an improvement, prevention or reversal of at least one measurable body parameter of a disease or disorder which is being treated, the disease or disorder may not be identified in mammal. However, in another embodiment, the term "treat" or "treating" refers to slow the progress of a disease or disorder, in physical, such as stabilizing identifiable symptoms, or in physiological, such as stabilizing physical parameters, or in both. In another embodiment, the term "treat" or "treating" refers to delaying the onset of a disease or disorder.

In some embodiments, the compound is administered for a prevention purpose. As used herein, "prevent" or "preventing" refers to a reduction in a risk of given disease or symptom. In a preferred mode of embodiment, the designated compound is administered to a subject for a prevention purpose, such as the subject with family history or tendency of cancer or autoimmune disease.

As used herein, "therapeutically effective amount" refers to an amount of the compound or the composition that can cause a biological or medical response (which is sought by researchers, veterinarians, physicians, or other clinicians) for a tissue system, an animal or a person, where may include relieving symptoms of the disease or symptom which is being treated. In a preferred embodiment, the therapeutically effective amount is an amount which is enough to effectively treat, improvably treat or prevent the disease, disorder or condition related to abnormal generation or regulation of PDE4 and/or TNF-α.

The term "prophylactically effective amount" refers to an amount of an active compound or agent (sought by researchers, veterinarians, physicians or other clinicians), that can inhibit the onset of a disease in a subject. A prophylactically effective amount of a compound refers to an amount of a therapeutic agent used alone or in combination with other active compound, which can provide a therapeutic benefit for treating or preventing the disease, disorder or condition.

Unless otherwise specified, the singular form of the term used herein, "a" or "an", also includes a plural meaning.

Unless otherwise specified, the term "or" or "and" used herein refers to "and/or".

Unless otherwise specified, the " ⁓ " or " ▬ " in the specific group herein refers to a connection position.

The term "optional" or "optionally" means the event or circumstance described subsequent thereto may or may not happen. This term encompasses the cases that the event or circumstance may or may not happen. For example, "optional substitution" or "optionally substituted" encompasses the cases that being unsubstituted or substituted.

The term "$C_m$-$C_n$" or "$C_{m-n}$" used herein refers to m-n carbon atoms in the part. For example, "$C_1$-$C_6$ alkyl" refers to an alkyl with 1-6 carbon atoms. The range of numbers herein covers the integers in a given range and the sub-ranges formed by these integers. For example, "$C_{1-6}$" or "$C_1$-$C_6$" means that the group may have 1, 2, 3, 4, 5 or 6 carbon atoms. Correspondingly, "$C_{1-6}$ alkyl" covers "$C_{2-5}$", "$C_{1-4}$", "$C_{2-4}$" and $C_1$, $C_2$, $C_3$, $C_4$, $C_5$, $C_6$, etc.

The term "one or more" or "at least one" used herein refers to 1, 2, 3, 4, 5, 6, 7, 8, 9 or more.

Unless otherwise specified, the term "hetero" refers to a heteroatom or a heteroatom group (i.e., an atomic group containing heteroatoms), i.e., an atom other than carbon and hydrogen, or an atomic group containing these atoms. Preferably, heteroatoms are independently selected from oxygen, nitrogen, sulfur, etc. In the embodiment in which there are two or more heteroatoms, the two or more heteroatoms may be the same to each other, or part or all of the two or more heteroatoms may be different from each other.

The term "alkyl", when used alone or in combination with other terms, refers to saturated aliphatic hydrocarbon groups consisting of straight or branched chains of carbon and hydrogen atoms, which are linked to the rest of the molecule by a single bond. "Alkyl" includes, for example, $C_1$-$C_6$ alkyl. Non-restrictive examples include, but are not limited to, methyl, ethyl, propyl, isopropyl, n-butyl, isobutyl, sec-butyl, tert-butyl, pentyl, hexyl, etc. The alkyl groups described herein may be optionally substituted.

The term "alkoxy", when used alone or in combination with other terms, refers to the "alkyl" described above, which is connected to the rest of the molecule by "—O—", wherein alkyl is defined as above. "Alkoxy" includes, for example, $C_1$-$C_6$ alkoxy. The alkoxy described herein may be optionally substituted.

The term "$C_3$-$C_6$ cycloalkyl", when used alone or in combination with other terms, refers to a saturated monovalent hydrocarbon ring containing 3, 4, 5 or 6 carbon atoms ("$C_3$-$C_6$ cycloalkyl"), examples of which are cyclopropyl, cyclobutyl, cyclopentyl or cyclohexyl, etc. The $C_3$-$C_6$ cycloalkyl described herein may be optionally substituted.

The term "($C_1$-$C_6$)alkyl amino" refers to

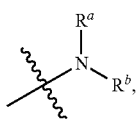

wherein one of $R^a$ and $R^b$ is H, the other is $(C_1-C_6)$alkyl; or $R^a$ and $R^b$ are independently $(C_1-C_6)$alkyl.

The term "heterocycle" or "heterocyclyl" refers to a group of saturated or unsaturated monocyclic or polycyclic systems in which one or more ring atoms are heteroatoms selected from N, O, S and the rest are C. Herein, when there are more than one heteroatom, heteroatoms can be the same or different from each other. "5-7 membered heterocycle" refers to heterocycles containing 5-7 ring atoms, wherein, one or more, preferably, 1 or 2 ring atoms are independently selected from O, N and S, and the rest ring atoms are C. The heterocycle or heterocyclyl described herein may be optionally substituted.

Accordingly, the term "5-7 membered heterocycle containing N" refers to the above-mentioned "5-7 membered heterocycle", wherein at least one heteroatom is N. The example is

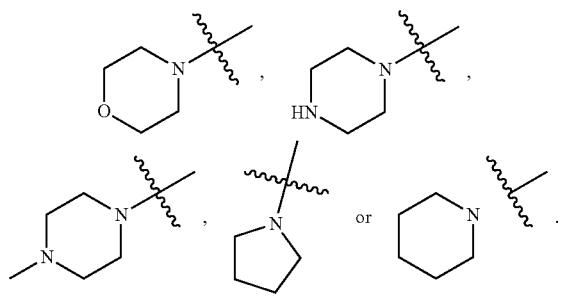

Similarly, the term "5-7 membered heterocycle containing O" refers to the above-mentioned "5-7 membered heterocycle", wherein at least one heteroatom is O. The example is

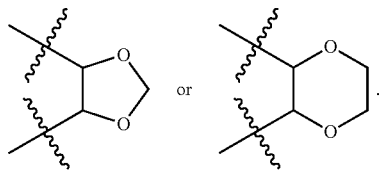 [SMILES: *C1OCOC1* ; *C1OCCOC1*]

The term "halo" or "halogen" refers to fluorine, chlorine, bromine or iodine.

The term "hydroxyl" refers to —OH.

The term "cyano" refers to —CN.

The term "amino" refers to —NH$_2$. The amino described herein may be optionally substituted, for example, be substituted with one or more $C_{1-6}$ alkyl.

The term "substituted" used herein refers to the optional substitution of one or more hydrogen of a designated atom by a given group, provided that the normal valence of the designated atom in the current situation is not exceeded and that the substitution forms a stable compound. Combinations of substituents and/or variables are permitted only when such combinations form stable compounds. Herein, examples of substituents include but are not limited to deuterium (D), benzyloxy, alkyl amine, $C_{1-6}$ alkyl, halogen, $C_{1-6}$ alkoxy, halogenated $C_{1-6}$ alkyl, halogenated $C_{1-6}$ alkoxy, heterocyclyl, nitro, cyano, hydroxyl, carboxyl, amino, sulfonyl, $C_3-C_6$ cycloalkyl, etc.

Deuterium (D or $^2$H) is a stable non-radioactive isotope of hydrogen, its atomic weight is 2.0144. Hydrogen exists in the form of an isotopic mixture of H (hydrogen or protium), D ($^2$H or deuterium) and T ($^3$H or tritium) in natural, where the deuterium abundance is 0.0156%. According to the common technical knowledge in the field, of all the compounds whose structures contain natural hydrogen atoms, the hydrogen atom actually represents a mixture of H, D and T. Therefore, if a compound contains a deuterium whose abundance greater than its natural abundance 0.0156% at any position, these compounds should be considered to be non-natural or deuterium enriched, and thus these compounds are novel compared with its non-enriched analogues.

In the invention, "deuterium enriched" compound refers to a compound of formula I, or the pharmaceutically acceptable salt, solvate, polymorph, co-crystal, stereoisomer, isotopic compound, metabolite or prodrug thereof, where the deuterium abundance is greater than its natural abundance at any relevant position. Therefore, in the "deuterium enriched" compound, the deuterium abundance at any of the relevant positions is likely between more than 0.0156% and 100%. The deuterium enriched position is represented by D, whereas the non-deuterium enriched position is represented by H. According to the common technical knowledge in the field, the symbol H may be elided at the non-deuterium enriched position. An example of a process for preparing a deuterium enriched compound is replacing the hydrogen with the deuterium, or employing deuterium-enriched starting material to synthesize the compound.

In the invention, the percentage of the deuterium in the enriched deuterium or the deuterium abundance refers to molar percentage.

In the invention, non-deuterium enriched refers to the hydrogen in natural, which is in the form of a mixture of isotopes H (hydrogen or protium), D ($^2$H or deuterium) and T ($^3$H or tritium).

Each preferred conditions aforementioned can be combined in any way without departing from the common knowledge in the art and thereby forming various preferred embodiments of the invention.

The reagents and starting materials used herein are all commercially available.

The positive effects of the invention are that the compound of formula I can regulate the generation and/or activity of PDE4 and/or TNF-α so as to effectively treat cancer and inflammatory diseases. In addition, the compound of the invention has lower toxicity and good safety.

DETAILED DESCRIPTION OF THE EMBODIMENTS

The invention will be further illustrated by the following examples, but it should not be constructed that the invention is limited to the scope of the examples. The experimental methods that are not specified in details in the following examples are those according to conventional methods and conditions, or according to the product manuals.

In the following examples, overnight means 10-16 hours, preferably 12 hours. Reflux refers to the reflux temperature of a solvent at atmospheric pressure.

Example 1 Synthesis of Compound 101

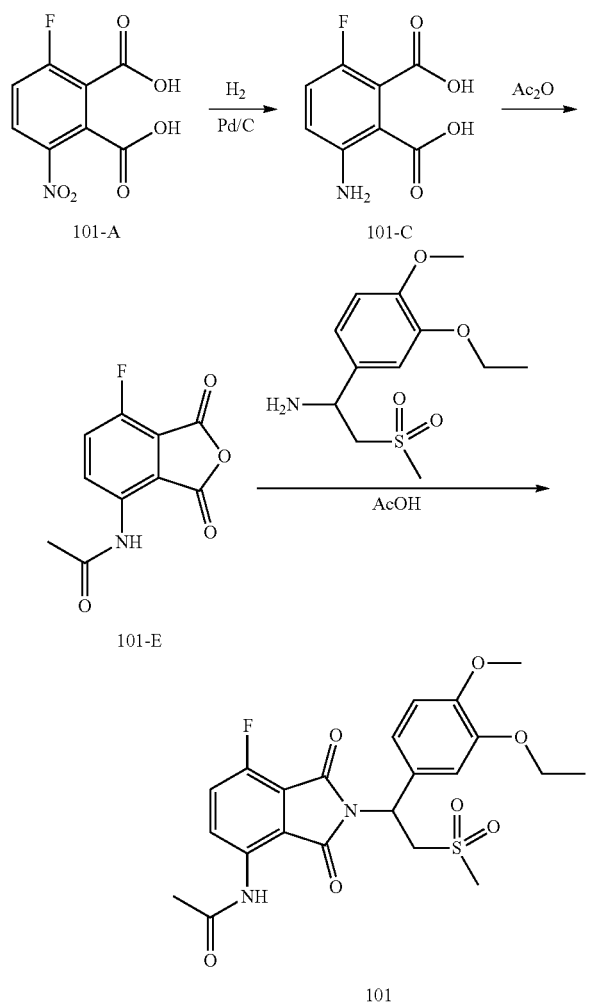

Step 1. Synthesis of Compound 101-C

To a solution of compound 101-A (3-fluoro-6-nitrophthalic acid) (1.9 g, 8.3 mmol) in MeOH (50 mL) was added Pd/C (200 mg, 10%, 50% water). The mixture was stirred at 25° C. overnight under $H_2$ (50 psi). After the reaction is finished, the mixture was filtered through a Celite pad, and the filtrate was concentrated to afford compound 101-C (3-amino-6-fluorophthalic acid) (1.6 g, yield: 97%) as a yellow solid. $^1$H NMR (300 MHz, DMSO-$d_6$) δ 7.09 (t, J=9.0 Hz, 1H), 6.74 (dd, J=6.0, 5.1 Hz, 1H).

Step 2. Synthesis of Compound 101-E

A solution of 101-C (500 mg, 2.5 mmol) in $Ac_2O$ (8 mL) was stirred at 25° C. overnight.

Then the solvent was evaporated to give compound 101-E [N-(7-fluoro-1,3-dioxo-1,3-dihydro isobenzofuran-4-yl)acetamide] (320 mg, yield: 57%) as a yellow solid. $^1$H NMR (300 MHz, DMSO-$d_6$) δ 9.94 (s, 1H), 8.34 (dd, J=9.3, 3.9 Hz, 1H), 7.79 (t, J=9.0 Hz, 1H), 2.16 (s, 3H).

Step 3. Synthesis of Compound 101

A solution of 101-E (380 mg, 1.7 mmol), 1-(3-ethoxy-4-methoxyphenyl)-2-(methylsulfonyl)ethanamine (CAS No. 253168-94-4) (465 mg, 1.7 mmol) in AcOH (10 mL) was stirred at 100° C. overnight. The reaction mixture was evaporated and purified by prep-HPLC ($NH_4HCO_3$/$CH_3CN$ system) and then freeze-dried to get 101 (N-(2-(1-(3-ethoxy-4-methoxyphenyl)-2-(methylsulfonyl)ethyl)-7-fluoro-1,3-dioxoisoindolin-4-yl)acetamide)) (412 mg, yield: 51%) as a yellow solid.

$^1$H NMR (300 MHz, DMSO-$d_6$) δ 9.74 (s, 1H), 8.37-8.42 (m, 1H), 7.64 (t, J=9.0 Hz, 1H), 7.04 (s, 1H), 6.90-6.99 (m, 2H), 5.74 (dd, J=10.2, 4.5 Hz, 1H), 4.11-4.33 (m, 2H), 4.04-3.97 (m, 2H), 3.72 (s, 3H), 2.99 (s, 3H), 2.15 (s, 3H), 1.30 (t, J=6.6 Hz, 3H). MS: 477 ([M−1]$^+$).

Synthesis of Starting Material 101-A

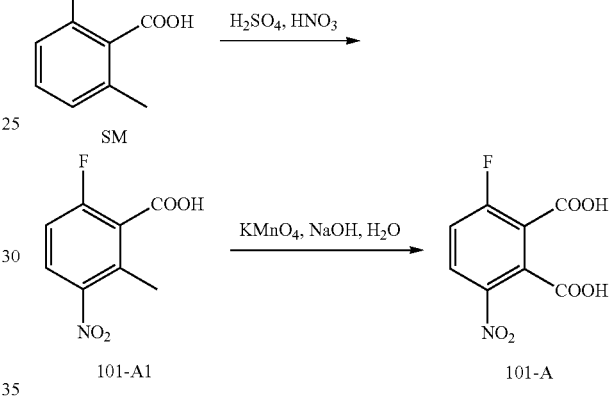

To a solution of 2-fluoro-6-methylbenzoic acid (CAS No. 90259-27-1) (14 g, 90.9 mmol) in 110 mL conc.$H_2SO_4$ was added dropwise fuming $HNO_3$ (5 mL) in 20 mL of conc.$H_2SO_4$ at −15° C. Then the mixture was stirred at 0° C. for 2 hours. The mixture was poured into crack-ice under stirring. The resulting solid was collected and dissolved in EtOAc (200 mL), washed with water (100 mL*2), dried over $Na_2SO_4$, filtered and concentrated to dry to give compound 101-A1 (6-fluoro-2-methyl-3-nitrobenzoic acid) (15.3 g, yield: 85%) as white solid. $^1$H NMR (300 MHz, $CDCl_3$) δ 8.01 (s, 1H), 7.18 (s, 1H), 2.63 (s, 3H).

To a solution of compound 101-A1 (6-fluoro-2-methyl-3-nitrobenzoic acid) (13.6 g, 68 mmol) in 150 mL $H_2O$ was added NaOH (8.2 g, 205 mmol), the solution was stirred at 80° C. for 3 hours. KMnO4 (86 g, 547 mmol) was added portion wise during 3 hours. Then the mixture was stirred at 80° C. for another 30 minutes. The solution was filtered and washed with hot water (80 mL*3). Cooled with ice-water and acidified with 2N HCl to pH=1. Extracted with EtOAc (200 mL*5), the combined EtOAc phase was washed with water (300 mL*2), brine (300 mL), dried over $Na_2SO_4$, filtrated and concentrated to dryness to give product 101-A (3-fluoro-6-nitrophthalic acid) (4.5 g, yield: 29%) as white solid. $^1$H NMR (300 MHz, DMSO) δ 8.28-8.24 (m, 1H), 7.8 (t, J=9.0 Hz, 1H).

Example 2 Synthesis of Compound 102

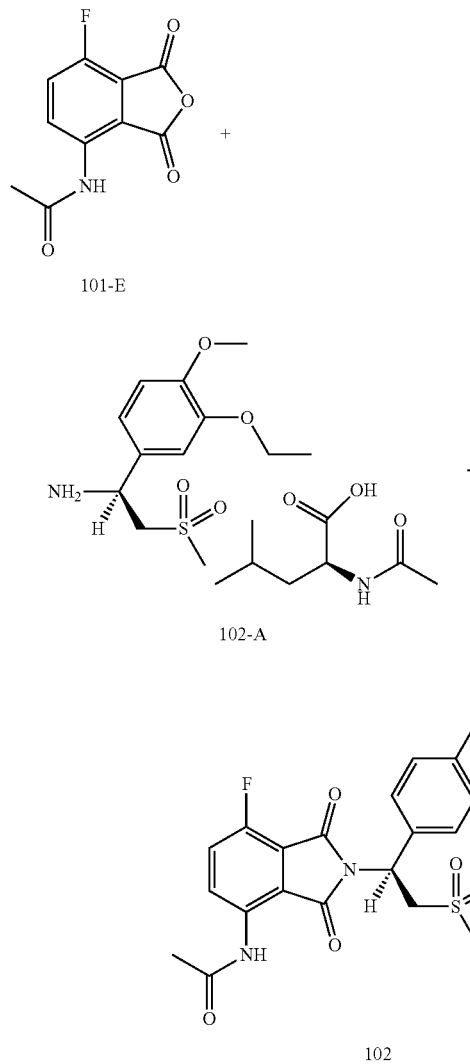

Example 3 Synthesis of Compound 103

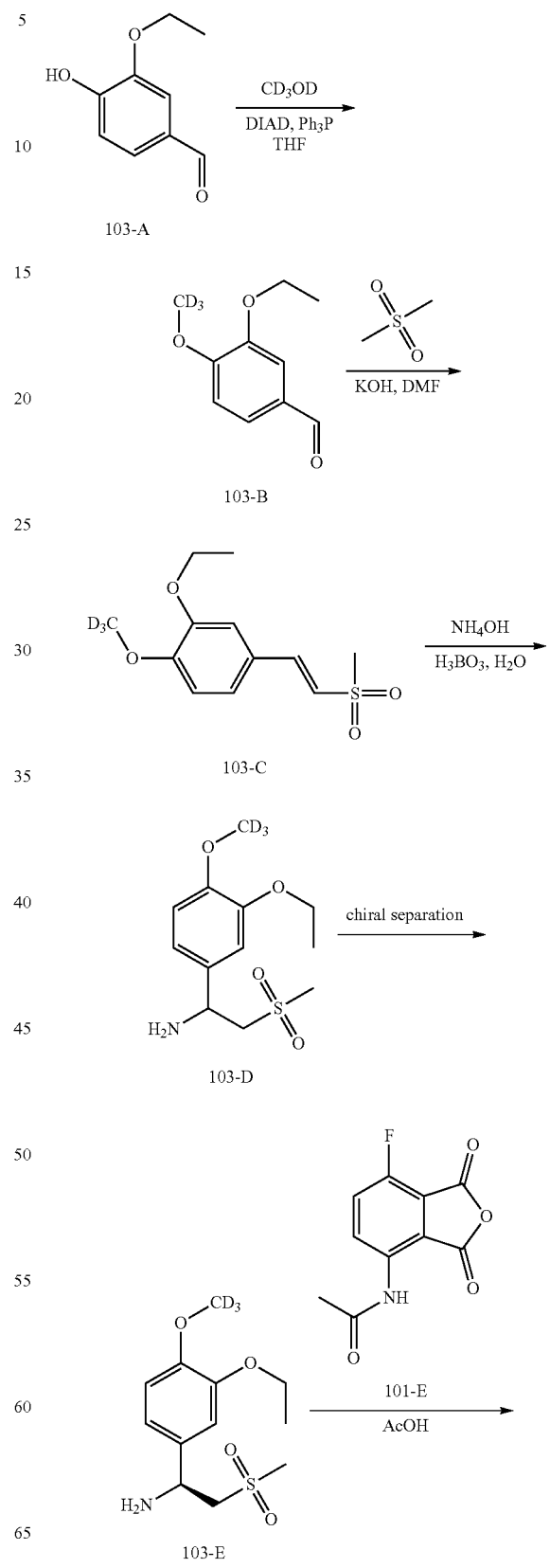

To a solution of 102-A ((S)-1-(3-ethoxy-4-methoxyphenyl)-2-(methylsulfonyl) ethanamine (S)-2-acetamido-4-methylpentanoate) (CAS No. 608141-43-1) (300 mg, 0.67 mmol) in AcOH (15 mL) was added 101-E (N-(7-fluoro-1,3-dioxo-1,3-dihydroisobenzofuran-4-yl)acetamide) (157 mg, 0.7 mmol) and reacted at 120° C. for overnight. The reaction mixture was evaporated to dryness via rotary evaporation, purified by prep-HPLC and freeze-dried to get compound 102 ((S)—N-(2-(1-(3-ethoxy-4-methoxyphenyl)-2-(methylsulfonyl)ethyl)-7-fluoro-1,3-dioxoisoindolin-4-yl)acetamide)) (197 mg, yield: 61%) as a yellow solid.

$^1$H NMR (400 MHz, DMSO-$d_6$) δ 9.73 (s, 1H), 8.41-8.44 (m, 1H), 7.65 (t, J=9.2 Hz, 1H), 7.06 (d, J=2.0 Hz, 1H), 6.93-7.01 (m, 2H), 5.76 (dd, J=10.4, 4.4 Hz, 1H), 4.31 (dd, J=14.4, 10.4 Hz, 1H), 4.16 (dd, J=14.4, 4.4 Hz, 1H), 4.02 (q, J=7.2 Hz, 2H), 3.74 (s, 3H), 3.02 (s, 3H), 2.17 (s, 3H), 1.32 (t, J=7.2 Hz, 3H). LC-MS: 496 ([M+18]$^+$).

-continued

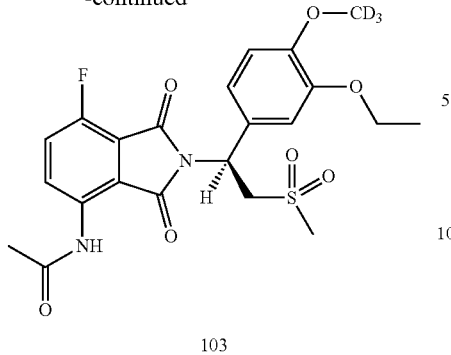

103

Step 1. Synthesis of Compound 103-B

To a solution of compound 103-A (3-ethoxy-4-hydroxybenzaldehyde, CAS No. 121-32-4) (10.1 g, 60.77 mmol), CD$_3$OD (2.4 g, 66.9 mmol) and Ph$_3$P (19.12 g, 73 mmol) in THF (250 mL) was slowly added DIAD (14.75 g, 73 mmol) at 0° C. Then the mixture was stirred at 30° C. for 2 hours. The solvent was removed by evaporation and the residue was purified by column chromatography on silica gel eluted with PE:EtOAc (4:1) to give the product 103-B (3-ethoxy-4-d$_3$-methoxybenzaldehyde) as colorless oil (11 g, 99%).

$^1$H NMR (300 MHz, CDCl$_3$) δ 9.85 (s, 1H), 7.41-7.46 (m, 2H), 6.98 (d, J=8.1 Hz, 1H), 4.18 (q, J=6.9 Hz, 2H), 1.50 (t, J=6.9 Hz, 3H).

Step 2. Synthesis of Compound 103-C

A solution of dimethyl sulfone (14.1 g, 150.3 mmol), KOH (5.05 g, 90.1 mmol) in DMF (150 mL) was stirred for 15 minutes at 30° C. Compound 103-B (11 g, 60.1 mmol) was added to the mixture slowly. The mixture was stirred for 3 hours at 60° C. The mixture was quenched with NH$_4$Cl (300 mL), extracted with EtOAc (200 mL*2). The combined organic phase was washed with brine (200 mL*2), dried over Na$_2$SO$_4$, filtered and concentrated under vacuum to give the crude product, which was purified by column chromatography on silica gel eluted with PE:EtOAc (2:1) to give the product 103-C (2-ethoxy-1-d$_3$-methoxy-4-(2-(methylsulfonyl) vinyl)benzene) as yellow solid (6.5 g, 42%).

$^1$H NMR (300 MHz, CDCl$_3$) δ 7.55 (d, J=15.3 Hz, 1H), 7.12 (d, J=2.8 Hz, 1H), 7.10 (d, J=1.8 Hz, 1H), 6.88-7.02 (m, 1H), 6.76 (d, J=15.3 Hz, 1H), 4.13 (q, J=6.9 Hz, 2H), 2.99 (s, 3H), 1.50 (t, J=6.9 Hz, 3H).

Step 3. Synthesis of Compound 103-D

A solution of H$_3$BO$_3$ (0.775 g, 12.5 mmol) in H$_2$O (25 mL) was stirred at 60° C. for 30 minutes. Then 103-C (6.5 g, 25 mmol) and NH$_4$OH (250 mL) was added. The mixture was stirred at 80° C. in a sealed tube for 3 days. The mixture was extracted with DCM (150 mL*3), the combined organic phase was washed with 2 N HCl (150 mL*2). The combined water phase was adjusted with NaOH to pH=10 then was extracted with DCM (150 mL*2). The combined organic solution was dried, filtered and concentrated under vacuum to get the product 103-D (1-(3-ethoxy-4-d$_3$-methoxyphenyl)-2-(methylsulfonyl)ethanamine) (3.5 g, 51%).

$^1$H NMR (300 MHz, CDCl$_3$) δ 6.83-6.93 (m, 3H), 4.60 (dd, J=9.3, 3.3 Hz, 1H), 4.11 (q, J=6.9 Hz, 2H), 3.20-3.37 (m, 2H), 2.91 (s, 3H), 1.83 (s, 2H), 1.47 (t, J=6.9 Hz, 3H).

Step 4. Synthesis of Compound 103-E

Compound 103-D (3.5 g, 12.68 mmol) was chiral separated to give the compound 103-E ((S)-1-(3-ethoxy-4-d$_3$-methoxyphenyl)-2-(methylsulfonyl)ethanamine) (0.9 g, ee:95.2%).

Separation Method:
Column: chiralpak IA, 5 μm, 4.6*250 mm.
Mobile phase: Hex:IPA:DEA=70:30:0.2
Flow Rate (F): 1.0 mL/min
Wave Length (W): 230 nm
Temperature (T): ambient Step 5. Synthesis of Compound 103

A mixture of compound 101-E (161 mg, 0.72 mmol) and 103-E (200 mg, 0.72 mmol) in HOAc (5 mL) reacted at 110° C. for overnight. The mixture was concentrated to dryness under reduced pressure, then the residue was purified by Prep-HPLC to afford compound 103 ((S)—N-(2-(1-(3-ethoxy-4-d$_3$-methoxyphenyl)-2-(methylsulfonyl)ethyl)-7-fluoro-1,3-dioxoiso indolin-4-yl)acetamide)) (160 mg, 46%).

$^1$H NMR (400 MHz, DMSO-d$_6$) δ 9.74 (s, 1H), 8.42 (dd, J=9.6, 4.0 Hz, 1H), 7.65 (t, J=9.2 Hz, 1H), 7.06 (d, J=1.6 Hz, 1H), 6.92-7.01 (m, 2H), 5.76 (dd, J=10.4, 4.4 Hz, 1H), 4.31 (dd, J=14.4, 10.8 Hz, 1H), 4.16 (dd, J=14.4, 4.4 Hz, 1H), 4.02 (q, J=7.2 Hz, 2H), 3.02 (s, 3H), 2.18 (s, 3H), 1.32 (t, J=6.8 Hz, 3H). LCMS: [(M+18)]$^+$=499.0.

Example 4 Synthesis of Compound 104, 105, 106

Compounds 104, 105 and 106 were synthesized according to the synthesis method of compound 103 in example 3, with using corresponding substrates.

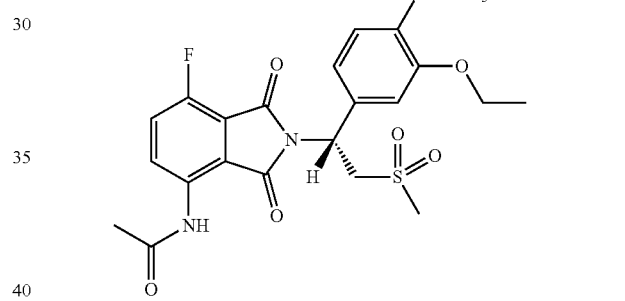

104

(R)—N-(2-(1-(3-ethoxy-4-d$_3$-methoxyphenyl)-2-(methylsulfonyl)ethyl)-7-fluoro-1,3-dioxoisoindolin-4-yl)acetamide $^1$H NMR (400 MHz, DMSO-d$_6$) δ 9.76 (s, 1H), 8.42 (dd, J=9.2, 4.0 Hz, 1H), 7.66 (t, J=9.2 Hz, 1H), 7.06 (d, J=2.0 Hz, 1H), 6.93-7.01 (m, 2H), 5.76 (dd, J=10.8, 4.4 Hz, 1H), 4.15-4.34 (m, 2H), 4.02 (q, J=6.8 Hz, 2H), 3.02 (s, 3H), 2.18 (s, 3H), 1.33 (t, J=6.8 Hz, 3H). LCMS: [(M+18)]$^+$=499.0.

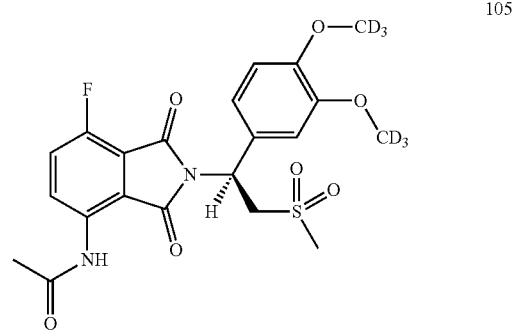 [SMILES: [2H]C([2H])([2H])Oc1ccc([C@@H](CS(C)(=O)=O)N2C(=O)c3c(F)ccc(NC(C)=O)c3C2=O)cc1OC([2H])([2H])[2H]]

105

(S)—N-(2-(1-(3,4-d₆-dimethoxyphenyl)-2-(methyl-sulfonyl)ethyl)-7-fluoro-1,3-dioxoisoindolin-4-yl)acetamide ¹H NMR (400 MHz, DMSO-d₆) δ 9.76 (s, 1H), 8.40-8.43 (m, 1H), 7.66 (t, J=9.2 Hz, 1H), 7.06 (d, J=2.0 Hz, 1H), 6.93-7.01 (m, 2H), 5.77 (dd, J=10.8, 4.4 Hz, 1H), 4.28-4.35 (m, 1H), 4.15-4.19 (m, 1H), 3.03 (s, 3H), 2.18 (s, 3H). LCMS: [(M+18)]⁺=488.0.

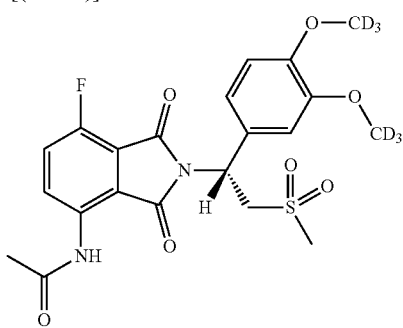

106

(R)—N-(2-(1-(3,4-d₆-dimethoxyphenyl)-2-(methyl-sulfonyl)ethyl)-7-fluoro-1,3-dioxoisoindolin-4-yl)acetamide ¹H NMR (400 MHz, DMSO-d₆) δ 9.77 (s, 1H), 8.42 (dd, J=9.6, 4.0 Hz, 1H), 7.66 (t, J=9.2 Hz, 1H), 7.06 (d, J=1.6 Hz, 1H), 6.93-7.02 (m, 2H), 5.75-5.79 (m, 1H), 4.28-4.37 (m, 1H), 4.15-4.20 (m, 1H), 3.03 (s, 3H), 2.17 (s, 3H). LCMS: [(M+18)]⁺=488.0.

Compounds 108 and 109 can be prepared according to the synthesis method of compound 103 in example 3.

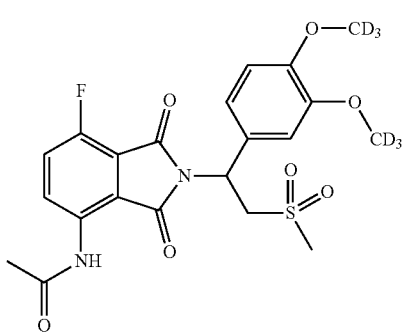

109

N-(2-(1-(3,4-d₆-dimethoxyphenyl)-2-(methylsulfo-nyl)ethyl)-7-fluoro-1,3-dioxoisoindolin-4-yl)acet-amide

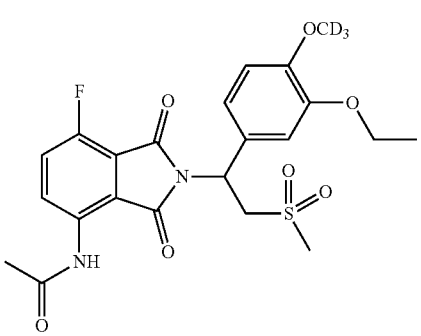

108

N-(2-(1-(3-ethoxy-4-d₃-methoxyphenyl)-2-(methyl-sulfonyl)ethyl)-7-fluoro-1,3-dioxoisoindolin-4-yl)acetamide Example 5. Synthesis of Compound 107

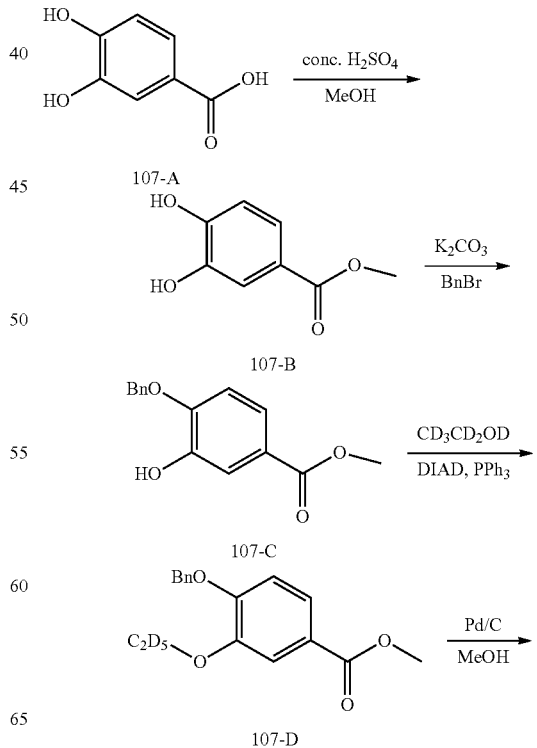

107

The compound 107 ((S)—N-(2-(1-(3-d₅-ethoxy-4-d₃-methoxyphenyl)-2-(methylsulfonyl) ethyl)-7-fluoro-1,3-di-oxoisoindolin-4-yl)acetamide) was synthesized according to the method of compound 103 in Example 3, except the following intermediate compound 107-H was used instead of compound 103-B.

¹H NMR (400 MHz, DMSO) δ 9.76 (s, 1H), 8.42 (dd, J=9.2, 3.8 Hz, 1H), 7.66 (t, J=9.0 Hz, 1H), 7.06 (d, J=2.1 Hz, 1H), 7.00-6.92 (m, 2H), 5.76 (dd, J=10.3, 4.4 Hz, 1H), 4.34-4.14 (m, 2H), 3.02 (s, 3H), 2.18 (s, 3H). LCMS: [(M+18)]⁺=504.0.

Synthesis of Intermediate Compound 107-H:

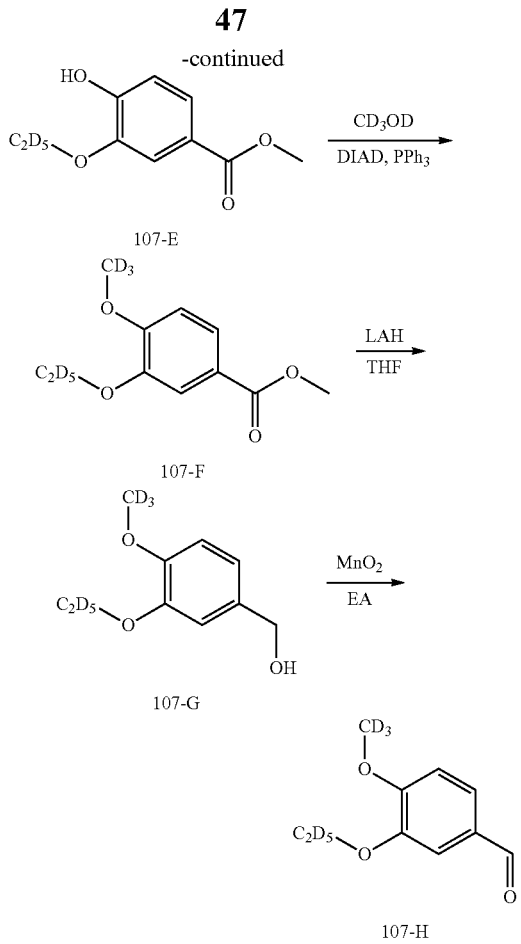

Step 1. Synthesis of Compound 107-B

To a solution of compound 107-A (CAS No. 99-50-3) (50 g, 0.325 mol) in MeOH (300 mL) was added conc. $H_2SO_4$ (50 mL) slowly. Then, the mixture was heated to reflux for overnight. The solvent was removed. The residue was diluted with water (500 mL), extracted with EA (300 mL*2), washed with brine (300 mL*2), dried and concentrated to give the product 107-B as white solid (54.5 g, 100%).

$^1$H NMR (300 MHz, DMSO) δ 9.77 (s, 1H), 9.34 (s, 1H), 7.35-7.29 (m, 2H), 6.80 (d, J=8.2 Hz, 1H), 3.76 (s, 3H).

Step 2. Synthesis of Compound 107-C

To a solution of compound 107-B (54.5 g, 0.32 mol) in MeCN (1.2 L) was added $K_2CO_3$ (63 g, 0.455 mol). Then, the mixture was stirred at 30° C. for 0.5 hour. BnBr (78 g, 0.455 mol) in MeCN (0.3 L) was added slowly. The mixture was stirred at 30° C. for overnight. The solid was removed. The solvent was removed. The residue was diluted with EA (Ethyl Acetate, 50 mL) and PE (Petroleum Ether, 100 mL), stirred at 30° C. for 15 minute, filtered. The cake was purified by triturate with EA (50 mL) and PE (100 mL) for overnight to give the product 107-C as white solid (28.8 g, 35%).

$^1$H NMR (300 MHz, CDCl$_3$) δ 7.63-7.59 (m, 2H), 7.42-7.38 (m, 5H), 6.95 (d, J=8.3 Hz, 1H), 5.76 (s, 1H), 5.18 (s, 2H), 3.89 (s, 3H).

Step 3. Synthesis of Compound 107-D

To a solution of compound 107-C (18 g, 69.8 mmol), $CD_3CD_2OD$ (4.4 g, 83.8 mmol) and Ph$_3$P (23.8 g, 90.7 mmol) in THF (300 mL) at 0° C. was added DIAD (Diisopropyl azodicarboxylate, 18.34 g, 90.7 mmol) slowly. Then, the mixture was stirred at 30° C. for overnight. The solvent was removed. The residue was purified by silica gel chromatography eluted with PE:EA=50:1 to give the product 107-D as white solid (16.7 g, 82%).

$^1$H NMR (300 MHz, CDCl$_3$) δ 7.62-7.59 (m, 2H), 7.46-7.30 (m, 5H), 6.92 (d, J=8.3 Hz, 1H), 5.22 (s, 2H), 3.89 (s, 3H).

Step 4. Synthesis of Compound 107-E

To a solution of compound 107-D (16.7 g, 57.3 mmol) in MeOH (300 mL) was added Pd/C (1.67 g, 10%). Then, the mixture was stirred at 30° C. for overnight under $H_2$ atmosphere (50 psi). The mixture was filtered. The solvent was removed to give the product 107-E as white solid (11.52 g, 100%).

$^1$H NMR (400 MHz, CDCl$_3$) δ 7.62 (dd, J=8.3, 1.8 Hz, 1H), 7.53 (d, J=1.8 Hz, 1H), 6.94 (d, J=8 Hz, 1H), 6.11 (s, 1H), 3.88 (s, 3H).

Step 5. Synthesis of Compound 107-F

To a solution of compound 107-E (11.52 g, 57.3 mmol), CD$_3$OD (2.5 g, 69.6 mmol) and Ph$_3$P (19.8 g, 75.4 mmol) in THF (300 mL) at 0° C. was added DIAD (15.3 g, 75.4 mmol) slowly. Then, the mixture was stirred at 30° C. for overnight. The solvent was removed. The residue was purified by silica gel chromatography eluted with PE:EA=10:1 to give the product 107-F as white solid (12.5 g, 100%).

$^1$H NMR (300 MHz, CDCl$_3$) δ 7.67 (dd, J=8.4, 0.9 Hz, 1H), 7.54 (s, 1H), 6.88 (d, J=8.4 Hz, 1H), 3.89 (s, 3H).

Step 6. Synthesis of Compound 107-G

To a solution of compound 107-F (12.5 g, 57.3 mmol) in THF (200 mL) at 0° C. was added LAH (3.3 g, 86 mmol) slowly. Then, the mixture was stirred at 30° C. for 2 hour. Water (4 mL) was added slowly to quench the reaction. Then NaOH aqueous solution (8 mL, 20%) was added slowly, stirred for 0.5 hour. The mixture was filtered, concentrated to give the residue which was purified by silica gel chromatography eluted with PE:EA=2:1 to give the product as colorless oil 107-G (10.6 g, 97%).

$^1$H NMR (300 MHz, CDCl$_3$) δ 6.91-6.81 (m, 3H), 4.59 (s, 2H).

Step 7. Synthesis of Compound 107-H

To a solution of compound 107-G (10.6 g, 55.7 mmol) in EA (200 mL) was added MnO$_2$ (48.5 g, 557 mmol). Then, the mixture was stirred at 25° C. for overnight. The mixture was filtered, concentrated to dryness to give the residue which was purified by triturate with PE:EA=5:1 (18 mL) at 0° C. for 0.25 hour to give the product 107-H (7.08 g, 67%) as white solid.

$^1$H NMR (300 MHz, CDCl$_3$) δ 9.83 (s, 1H), 7.45-7.39 (m, 2H), 6.96 (d, J=8.2 Hz, 1H).

Compound 110 can be prepared according to the synthesis method of compound 107.

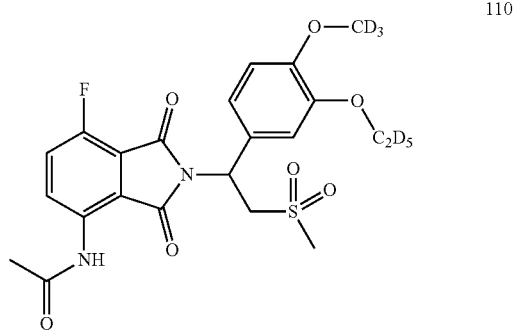

110

N-(2-(1-(3-d₅-ethoxy-4-d₃-methoxyphenyl)-2-(methylsulfonyl)ethyl)-7-fluoro-1,3-dioxoisoindolin-4-yl)acetamide Example 6. Synthesis of Compound 201

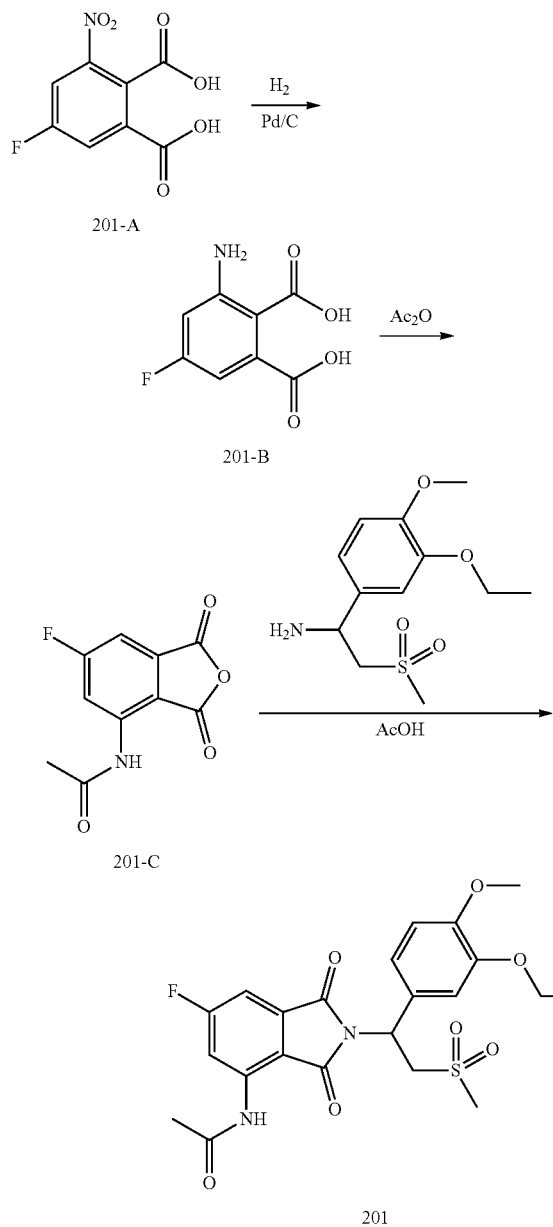

The compound 201-A (5-fluoro-3-nitrophthalic acid) was synthesized according to the method of compound 301-E in Example 10, except the corresponding starting material methyl 5-fluoro-2-methyl-3-nitrobenzoate was used instead of compound 301-A. Methyl 5-fluoro-2-methyl-3-nitrobenzoate was synthesized according to the method of the starting material 301-A, except compound 5-fluoro-2-methylbenzoic acid (CAS number 33184-16-6) was used instead of 301-A1 (4-fluoro-2-methylbenzoic acid).

Step 1. Synthesis of Compound 201-B

To a solution of 201-A (900 mg) in MeOH (15 mL) was added 10% Pd/C (180 mg, 50% wet.) under nitrogen atmosphere. The mixture was stirred under H₂ (50 psi) atmosphere for overnight. The mixture was filtered and concentrated under reduced pressure to afford 201-B (3-amino-5-fluorophthalic acid, 774 mg) as a yellow solid.

¹H NMR (DMSO-d₆, 400 MHz): δ 6.58-6.62 (m, 1H), 6.41-6.44 (m, 1H).

Step 2. Synthesis of Compound 201-C

A solution of 201-B (100 mg, 0.5 mmol) in Ac₂O (4 mL) was stirred at 25° C. overnight.

The reaction mixture was evaporated to dryness under reduced pressure to give compound 201-C (N-(6-fluoro-1,3-dioxo-1,3-dihydroisobenzofuran-4-yl)acetamide, 70 mg, yield: 63%) as a yellow solid.

¹H NMR (300 MHz, DMSO-d₆) δ 9.87-9.92 (m, 1H), 8.27-8.35 (m, 1H), 7.72-7.74 (m, 1H), 2.24 (s, 3H).

Step 3. Synthesis of Compound 201

A solution of compound 201-C (70 mg, 0.3 mmol) and compound 1-(3-ethoxy-4-methoxyphenyl)-2-(methylsulfonyl)ethanamine (CAS number 253168-94-4, 86 mg, 0.3 mmol) in AcOH (6 mL) was stirred overnight at 70° C. The reaction mixture was evaporated to dryness, then purified by prep-HPLC (NH₄HCO₃/Acetonitrile system), then freeze-dried to afford compound 201 (N-(2-(1-(3-ethoxy-4-methoxyphenyl)-2-(methylsulfonyl) ethyl)-6-fluoro-1,3-dioxoisoindolin-4-yl)acetamide, 42 mg, yield: 30%) as a white solid.

¹H NMR (300 MHz, DMSO-d₆) δ 9.77 (s, 1H), 8.24 (dd, J=12.0, 1.8 Hz, 1H), 7.48 (dd, J=6.9, 1.8 Hz, 1H), 7.04 (d, J=0.9 Hz, 1H), 6.90-6.98 (m, 2H), 5.73-5.77 (m, 1H), 4.29-4.34 (m, 1H), 4.10-4.17 (m, 1H), 3.96-4.03 (m, 2H), 3.72 (s, 3H), 3.00 (s, 3H), 2.20 (s, 3H), 1.30 (t, J=7.2 Hz, 3H). MS: 477 ([M−1]⁺).

Example 7. Synthesis of Compound 202

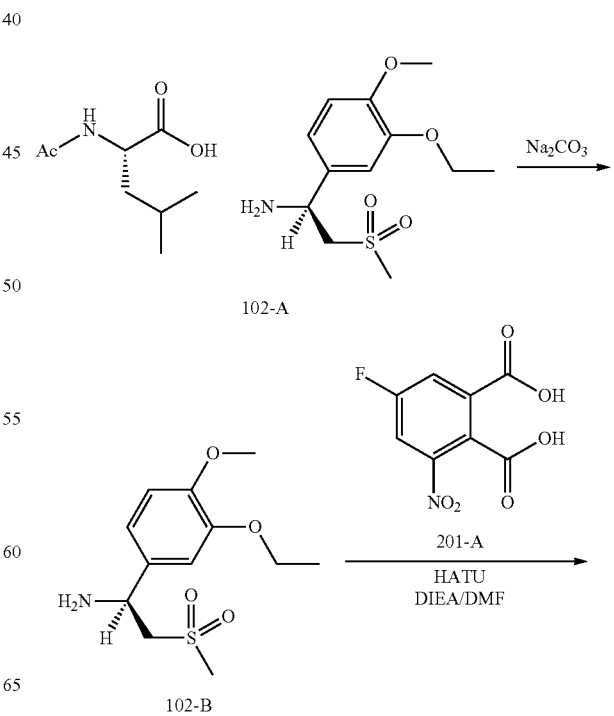

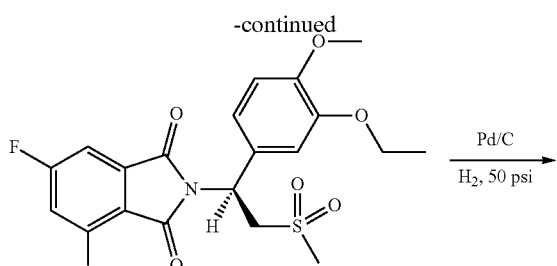

202-C

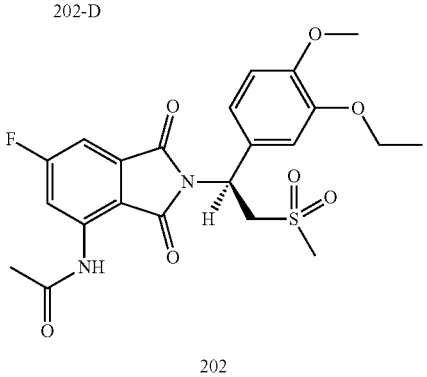

202-D

202

Step 1. Synthesis of Compound 102-B

To a solution of 102-A ((S)-1-(3-ethoxy-4-methoxyphenyl)-2-(methylsulfonyl) ethanamine (S)-2-acetamido-4-methylpentanoate, 800 mg, 1.79 mmol) in $H_2O$ (10 mL) was added saturated aqueous solution of $Na_2CO_3$ to pH=10, then the mixture was extracted with EtOAc (30 mL*2). The combined EtOAc solution was dried, filtered and concentrated to give compound 102-B ((S)-1-(3-ethoxy-4-methoxyphenyl)-2-(methylsulfonyl) ethanamine, 460 mg, yield: 94%) as yellow solid.

$^1$H NMR (300 MHz, DMSO-$d_6$) δ 7.02 (s, 1H), 6.89 (s, 2H), 4.27 (dd, J=9.3, 3.6 Hz, 1H), 3.99-4.06 (m, 2H), 3.73 (s, 3H), 3.20-3.45 (m, 2H), 2.95 (s, 3H), 2.16 (s, 2H), 1.27-1.35 (m, 3H).

Step 2. Synthesis of Compound 202-C

To a solution of 102-B in DMF (15 mL) was added compound 201-A (3-nitro-5-fluorine phthalic acid, 386 mg, 1.68 mmol) and HATU (1-[Bis(dimethylamino)methylene]-1H-1,2,3-triazolo[4,5-b]pyridinium 3-oxid hexafluorophosphate, 1.4 g, 3.7 mmol) and DIEA (N,N-Diisopropylethylamine, 760 mg, 5.88 mmol), then the mixture was stirred at 25° C. for overnight. To the reaction mixture was added $H_2O$ (10 mL) and then stirred for 15 minutes, extracted with EtOAc (100 mL). The EtOAc solution was washed with brine (20 mL*2), then dried, filtered and concentrated under vacuum to give the crude product. The residue was purified by column chromatography on silica gel with PE:EtOAc (3:1~1:1) to give 202-C ((S)-2-(1-(3-ethoxy-4-methoxyphenyl)-2-(methylsulfonyl)ethyl)-6-fluoro-4-nitroisoindndoline-1,3-dione, 330 mg, yield: 42%) as yellow solid.

$^1$H NMR (400 MHz, DMSO-$d_6$) δ 8.36 (dd, J=8.8, 2.4 Hz, 1H), 8.20 (dd, J=10.8, 2.2 Hz, 1H), 7.09 (d, J=1.6 Hz, 1H), 7.01 (dd, J=8.4, 2.0 Hz, 1H), 6.94 (d, J=8.8 Hz, 1H), 5.79 (dd, J=9.6, 5.6 Hz, 1H), 4.18-4.31 (m, 2H), 3.99-4.06 (m, 2H), 3.74 (s, 3H), 2.98 (s, 3H), 1.32 (t, J=6.8 Hz, 3H).

Step 3. Synthesis of Compound 202-D

To a mixture of 202-C (330 mg, 0.704 mmol) in EtOAc (20 mL) was added Pd/C (10%, 50% $H_2O$, 40 mg), and then stirred under $H_2$ (50 psi) atmosphere for 4 hours at 25° C. The mixture was filtered and concentrated to give 202-D ((S)-4-amino-2-(1-(3-ethoxy-4-methoxyphenyl)-2-(methylsulfonyl)ethyl)-6-fluoroisoindoline-1,3-dione, 289 mg, yield: 94%) as yellow solid.

$^1$H NMR (400 MHz, DMSO-$d_6$) δ 7.06 (s, 1H), 6.93 (d, J=0.4 Hz, 2H), 6.80 (dd, J=7.2, 2.0 Hz, 1H), 6.70-6.73 (m, 3H), 5.71 (dd, J=10.8, 4.4 Hz, 1H), 4.33 (dd, J=14.4, 10.4 Hz, 1H), 3.99-4.10 (m, 3H), 3.73 (s, 3H), 3.00 (s, 3H), 1.32 (t, J=7.2 Hz, 3H).

Step 4. Synthesis of Compound 202

To a solution of 202-D (289 mg, 0.66 mmol) in pyridine (30 mL) was added $AC_2O$ (5 mL), the mixture was heated to 70° C. and stirred for overnight. The mixture was concentrated. Then $CH_3CN$ (10 mL*2) was added and the mixture was concentrated for two more times to give the residue, which was purified with column chromatography on silica gel eluted with (PE:EtOAc=1:1) to give the crude product (200 mg), which was further purified by prep-HPLC to afford product 202 ((S)—N-(2-(1-(3-ethoxy-4-methoxyphenyl)-2-(methylsulfonyl)ethyl)-6-fluoro-1,3-dioxoisoindolin-4-yl)acetamide, 84 mg, yield: 26%) as yellow solid.

$^1$H NMR (400 MHz, DMSO-$d_6$) δ 9.77 (s, 1H), 8.26 (dd, J=12.4, 2.4 Hz, 1H), 7.48 (dd, J=6.8, 2.0 Hz, 1H), 7.07 (d, J=2.0 Hz, 1H), 6.93-7.00 (m, 2H), 5.77 (dd, J=10.4, 4.0 Hz, 1H), 4.32 (dd, J=14.4, 10.8 Hz, 1H), 4.15 (dd, J=14.4, 4.4 Hz, 1H), 4.02 (q, J=7.2 Hz, 2H), 3.74 (s, 3H), 3.01 (s, 3H), 2.22 (s, 3H), 1.32 (t, J=7.2 Hz, 3H). LCMS: 496.0 ([M+18]$^+$).

Example 8. Synthesis of Compound 203

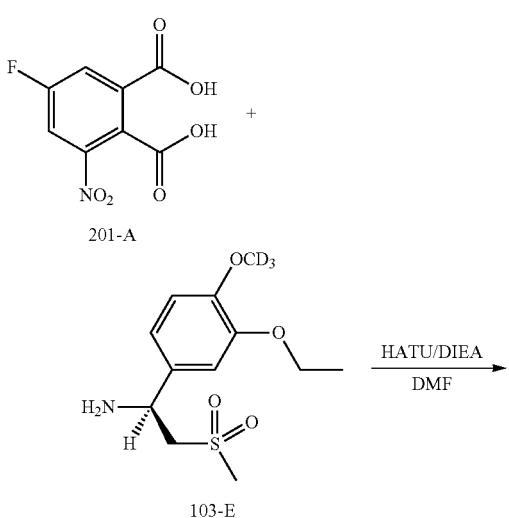

201-A

103-E

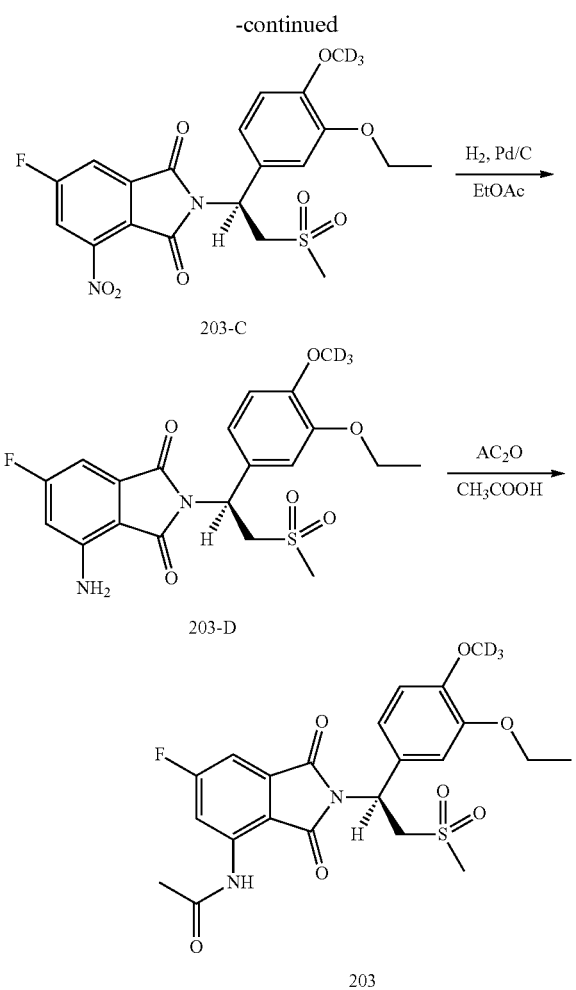

203-C

203-D

203

Step 1. Synthesis of Compound 203-C

To a mixture of 103-E ((S)-1-(3-ethoxy-4-d₃-methoxyphenyl)-2-(methylsulfonyl) ethanamine) (680 mg, 2.46 mmol) in DMF (30 mL) was added 201-A (3-nitro-5-fluorine phthalic acid, 564 mg, 2.46 mmol), HATU (2.06 g, 5.41 mmol) and DIEA (1.1 g, 9.61 mmol) at 25° C., then the mixture was stirred at 25° C. for overnight. The reaction mixture was added H₂O (15 mL) and stirred for 15 minute, then extracted with EtOAc (150 mL). The organic phase was washed with brine (50 mL*3), dried, filtered and concentrated to give the crude product. The crude product was purified by column chromatography on silica gel with PE:EtOAc (3:1~1:1) to give 203-C ((S)-2-(1-(3-ethoxy-4-d₃-methoxyphenyl)-2-(methylsulfonyl) ethyl)-6-fluoro-4-nitroisoindoline-1,3-dione, 605 mg, yield: 52%) as yellow solid.

¹H NMR (300 MHz, DMSO-d₆): δ 8.34-8.38 (m, 1H), 8.19-8.22 (m, 1H), 7.09 (s, 1H), 6.92-7.02 (m, 2H), 5.76-5.79 (m, 1H), 4.21-4.27 (m, 2H), 3.98-4.04 (m, 2H), 2.98 (s, 3H), 1.29-1.34 (m, 3H).

Step 2. Synthesis of Compound 203-D

To a mixture of 203-C (605 mg, 1.29 mmol) in EtOAc (20 mL) was added Pd/C (10%, 50% H₂O, 60 mg), reacted for 4 hours at 25° C. under H₂ atmosphere (50 psi). The mixture was filtered and concentrated to give 203-D ((S)-4-amino-2-(1-(3-ethoxy-4-d₃-methoxyphenyl)-2-(methylsulfonyl) ethyl)-6-fluoroisoindoline-1,3-dione, 518 mg, yield: 91%) as yellow solid.

¹H NMR (400 MHz, DMSO-d₆) δ 7.06 (s, 1H), 6.78-6.93 (m, 2H), 6.70-6.74 (m, 4H), 5.71 (dd, J=10.48, 4.4 Hz, 1H), 4.30-4.33 (m 1H), 3.98-4.10 (m, 3H), 3.00 (s, 3H), 1.32 (t, J=6.8 Hz, 3H).

Step 3. Synthesis of Compound 203

To a solution of 203-D (247 mg, 0.56 mmol) in CH₃COOH (6 mL) was added Ac₂O (3 mL). The mixture was heated to 85° C. and reacted for 5 hours, then concentrated and purified by prep-HPLC to afford a product. hexane (5 mL) was added to the product and the mixture was stirred for 2 hours, then filtered to afford compound 203 ((S)—N-(2-(1-(3-ethoxy-4-d₃-methoxyphenyl)-2-(methylsulfonyl)ethyl)-6-fluoro-1,3-dioxoisoindolin-4-yl)acetamide, 123 mg, yield: 46%) as yellow solid.

¹H NMR (400 MHz, DMSO-d₆) δ 9.77 (s, 1H), 8.26 (dd, J=12.0, 2.0 Hz, 1H), 7.49 (dd, J=6.8, 2.0 Hz, 1H), 7.07 (d, J=1.6 Hz, 1H), 6.92-7.00 (m, 2H), 5.77 (dd, J=10.4, 4.4 Hz, 1H), 4.32 (dd, J=14.4, 10.4 Hz, 1H), 4.15 (dd, J=14.4, 4.4 Hz, 1H), 4.02 (q, J=6.8 Hz, 2H), 3.02 (s, 3H), 2.22 (s, 3H), 1.32 (t, J=6.8 Hz, 3H). LCMS: 499.0 ([M+18]⁺).

Example 9. Synthesis of Compounds 204, 205, 206 and 207

Compounds 204, 205, 206 and 207 were synthesized according to the synthesis method of compound 203 in Example 8, with corresponding substrates to replace compound 103-E.

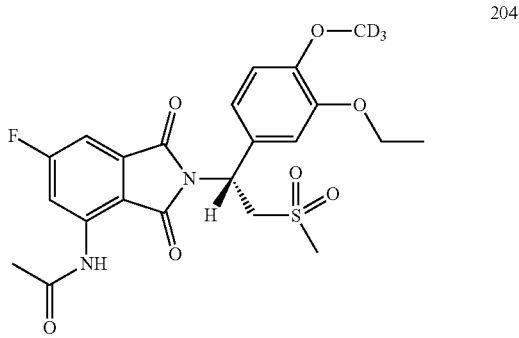 [SMILES: [2H]C([2H])([2H])Oc1ccc([C@H](CS(C)(=O)=O)N2C(=O)c3cc(F)cc(NC(C)=O)c3C2=O)cc1OCC]

204

(R)—N-(2-(1-(3-ethoxy-4-d₃-methoxyphenyl)-2-(methylsulfonyl)ethyl)-6-fluoro-1,3-dioxoisoindolin-4-yl)acetamide ¹H NMR (400 MHz, DMSO-d₆) δ 9.79 (s, 1H), 8.26 (dd, J=12.0, 2.4 Hz, 1H), 7.50 (dd, J=6.8, 2.4 Hz, 1H), 7.07 (d, J=2.0 Hz, 1H), 6.92-7.00 (m, 2H), 5.77 (dd, J=10.4, 4.4 Hz, 1H), 4.14-4.35 (m, 2H), 4.02 (q, J=6.8 Hz, 2H), 3.02 (s, 3H), 2.22 (s, 3H), 1.32 (t, J=6.8 Hz, 3H). LCMS: 499.0 ([M+18]⁺)

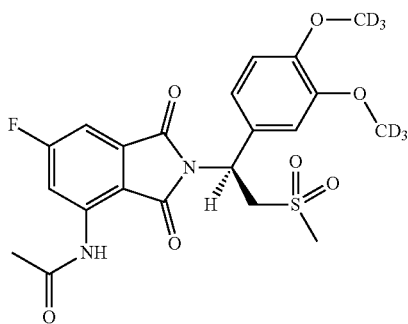

205

(S)—N-(2-(1-(3,4-d$_6$-dimethoxyphenyl)-2-(methylsulfonyl)ethyl)-6-fluoro-1,3-dioxoisoindolin-4-yl)acetamide $^1$H NMR (400 MHz, DMSO-d$_6$) δ 9.80 (s, 1H), 8.26 (dd, J=12.0, 2.0 Hz, 1H), 7.51 (dd, J=7.2, 2.4 Hz, 1H), 7.07 (d, J=2.0 Hz, 1H), 6.92-7.01 (m, 2H), 5.78 (dd, J=10.8, 4.4 Hz, 1H), 4.33 (dd, J=14.8, 10.8 Hz, 1H), 4.16 ((dd, J=10.8, 4.4 Hz, 1H), 3.02 (s, 3H), 2.22 (s, 3H). LCMS: 488.0 ([M+18]$^+$)

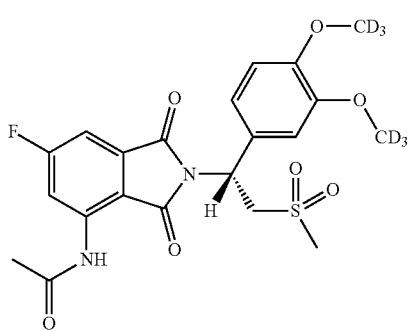

206

(R)—N-(2-(1-(3,4-d$_6$-dimethoxyphenyl)-2-(methylsulfonyl)ethyl)-6-fluoro-1,3-dioxoisoindolin-4-yl)acetamide $^1$H NMR (400 MHz, DMSO-d$_6$) δ 9.79 (s, 1H), 8.26 (dd, J=12.0, 2.4 Hz, 1H), 7.50 (dd, J=6.8, 2.0 Hz, 1H), 7.07 (d, J=2.0, 1H), 6.92-7.00 (m, 2H), 5.78 (dd, J=10.8, 4.4 Hz, 1H), 4.30-4.36 (m, 1H), 4.14-4.19 (m, 1H), 3.02 (s, 3H), 2.22 (s, 3H). LCMS: 488.0 ([M+18]$^+$)

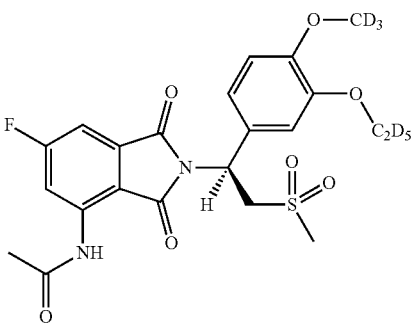

207

(S)—N-(2-(1-(3-d$_5$-ethoxy-4-d$_3$-methoxyphenyl)-2-(methylsulfonyl)ethyl)-6-fluoro-1,3-dioxoisoindolin-4-yl)acetamide $^1$H NMR (400 MHz, DMSO-d$_6$) δ 9.79 (s, 1H), 8.26 (dd, J=12.0, 2.4 Hz, 1H), 7.50 (dd, J=6.8, 2.4 Hz, 1H), 7.06 (d, J=2.0 Hz, 1H), 6.92-6.99 (m, 2H), 5.77 (dd, J=10.4, 4.4 Hz, 1H), 4.14-4.35 (m, 2H), 3.02 (s, 3H), 2.22 (s, 3H). LCMS: 504.0 ([M+18]$^+$)

Compounds 208, 209 and 210 can be synthesized according to the synthesis method of compound 203 in Example 8, with corresponding substrates to replace compound 103-E.

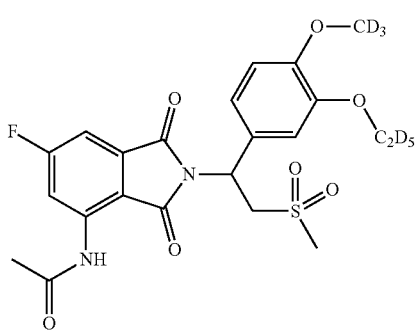

208

N-(2-(1-(3-d$_5$-ethoxy-4-d$_3$-methoxyphenyl)-2-(methylsulfonyl)ethyl)-6-fluoro-1,3-dioxoisoindolin-4-yl)acetamide

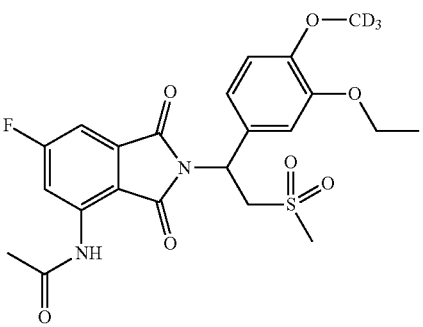

209

N-(2-(1-(3-ethoxy-4-d$_3$-methoxyphenyl)-2-(methylsulfonyl)ethyl)-6-fluoro-1,3-dioxoisoindolin-4-yl)acetamide

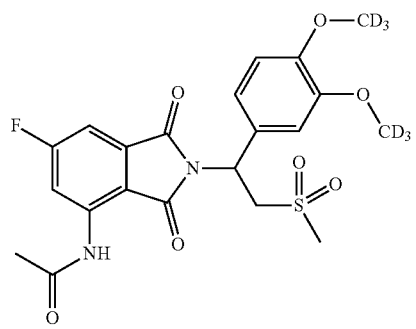

210

N-(2-(1-(3,4-d₆-dimethoxyphenyl)-2-(methylsulfonyl)ethyl)-6-fluoro-1,3-dioxoisoindolin-4-yl)acetamide

Example 10. Synthesis of Compound 301

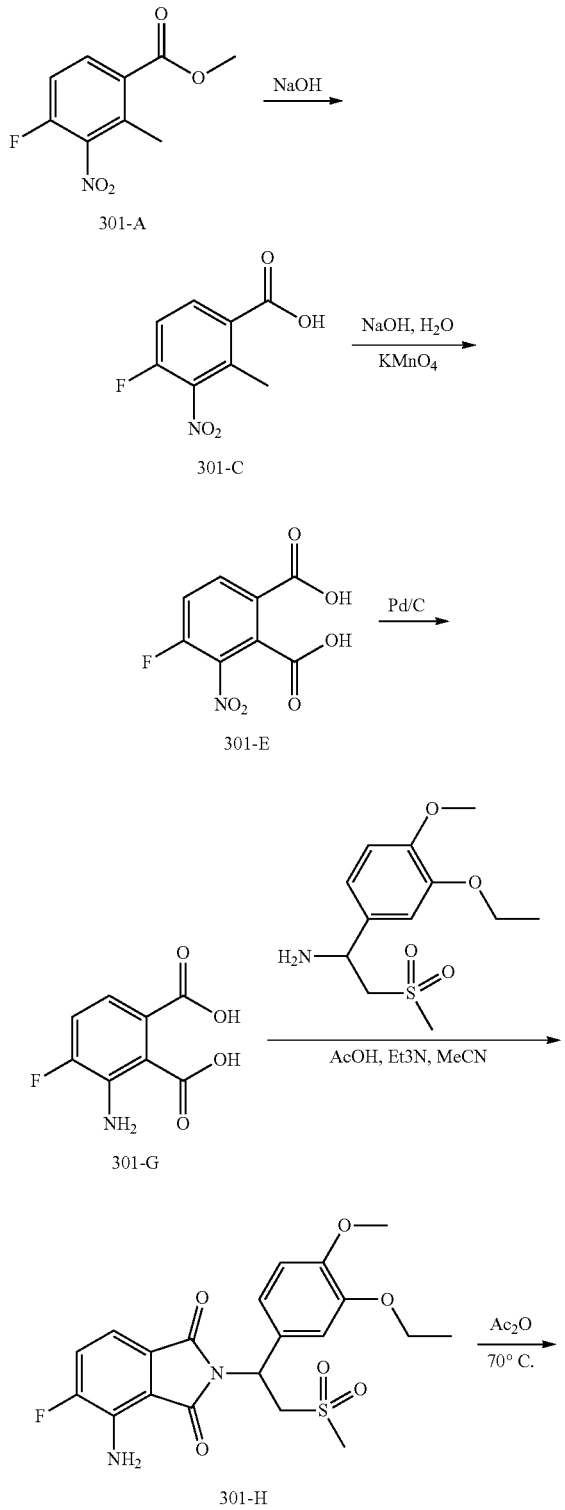

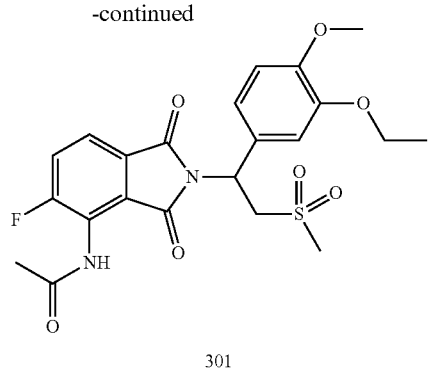

Step 1. Synthesis of Compound 301-C

A solution of compound 301-A (methyl 4-fluoro-2-methyl-3-nitrobenzoate, 3.0 g, 14.1 mmol), NaOH (1.6 g, 42.3 mmol) in H₂O/MeOH (30 mL/30 mL) was stirred at 25° C. for overnight. Then the mixture was adjusted pH=5, extracted by EtOAc (100 mL×3), washed by brine (100 mL×2), dried, filtered and concentrated to give compound 301-C (4-fluoro-2-methyl-3-nitrobenzoic acid, 2.8 g, yield: 100%) as a white solid.

¹H NMR (300 MHz, DMSO-d₆) δ 8.06-8.11 (m, 1H), 8.18 (t, J=9.0 Hz, 1H), 2.47 (s, 3H).

Step 2. Synthesis of Compound 301-E

To a solution of 301-C (2.8 g, 14.1 mmol), NaOH (1.6 g, 42 mmol) in H₂O (30 mL) was added KMnO₄ (17.7 g, 112 mmol) portion-wise during 3 hours at 85° C. and then the mixture was stirred for 3 hours at 85° C. Then the mixture was filtered and the cake was washed with H₂O (50 mL×3). The filtrate was adjusted pH=1, extracted by EtOAc (100 mL×3), washed by brine (100 mL×2), dried, filtered and concentrated to give 301-E (4-fluoro-3-nitrophthalic acid, 900 mg, yield: 28%) as a white solid.

¹H NMR (300 MHz, DMSO-d₆) δ 8.12-8.17 (m, 1H), 7.75-7.81 (m, 1H).

Step 3. Synthesis of Compound 301-G

To a solution of 301-E (900 mg, 3.9 mmol) in MeOH (30 ml) was added Pd/C (180 mg, 10%, 50% water). The mixture was stirred at 25° C. for overnight under H₂ (50 psi) atmosphere. After completed, the mixture was filtered through a Celite pad, and the filtrate was concentrated to afford 301-G (3-amino-4-fluorophthalic acid, 700 mg, crude) as a yellow solid.

¹H NMR (300 MHz, DMSO-d₆) δ 7.13-7.20 (m, 1H), 6.76-6.80 (m, 1H).

Step 4. Synthesis of Compound 301-H

A solution of 301-G (300 mg, 1.5 mmol), 1-(3-ethoxy-4-methoxyphenyl)-2-(methylsulfonyl)ethanamine (356 mg, 1.5 mmol), AcOH (660 mg, 15 mmol), Et₃N (758 mg, 7.5 mmol) in CH₃CN (20 mL) was stirred at 80° C. for overnight under N₂ atmosphere. Then the solvent was removed, the residue was purified by chromatography column on silica gel (PE/EtOAc=2/1) to afford compound 301-H (4-amino-2-(1-(3-ethoxy-4-methoxyphenyl)-2-(methylsulfonyl)ethyl)-5-fluoroisoindoline-1,3-dione, 150 mg, yield: 23%) as a yellow solid.

¹H NMR (300 MHz, DMSO-d₆) δ 7.37-7.44 (m, 1H), 7.07 (s, 1H), 6.99-7.03 (m, 1H), 6.94 (s, 2H), 6.55 (d, J=5.7 Hz, 1H), 5.70-5.75 (m, 1H), 4.30-4.38 (m, 1H), 4.12-4.13 (m, 1H), 3.97-4.08 (m, 2H), 3.74 (s, 3H), 3.01 (s, 3H), 1.33 (t, J=7.2 Hz, 3H).

Step 5. Synthesis of Compound 301

A solution of 301-H (100 mg, 0.23 mmol) in Ac$_2$O (6 mL) was stirred at 70° C. for overnight. The reaction mixture was evaporated to dryness and purified by prep-HPLC (NH$_4$HCO$_3$/Acetonitrile system) then freeze-dried to give compound 301 (N-(2-(1-(3-ethoxy-4-methoxyphenyl)-2-(methylsulfonyl)ethyl)-5-fluoro-1,3-dioxoisoindolin-4-yl)acetamide, 37 mg, yield: 34%) as a white solid.

$^1$H NMR (300 MHz, DMSO-d$_6$) δ 10.16 (s, 1H), 7.69-7.82 (m, 1H), 7.07 (s, 1H), 6.91-6.94 (m, 2H), 5.72-5.77 (m, 1H), 4.31-4.36 (m, 1H), 4.10-4.16 (m, 1H), 3.97-4.05 (m, 2H), 3.73 (s, 3H), 2.99 (s, 3H), 2.09 (s, 3H), 1.32 (t, J=7.2 Hz, 3H). MS: 477 ([M–1]$^+$).

Synthesis of Starting Material 301-A

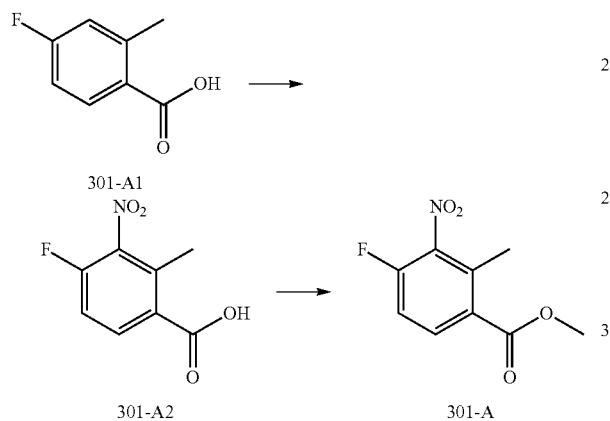

Compound 301-A1 (4-fluoro-2-methylbenzoic acid, CAS number 321-21-1, 100 g, 649 mmol) was added to 660 mL of fuming HNO$_3$, dropwise to keep the temperature below 10° C. The mixture was stirred for 1~2 hours. The mixture was poured into ice-water (2.4 L) and stirred for 30 minutes. The result solid was filtered and washed with cold water and then dissolved in 1.5 L of EtOAc. The EtOAc phase was washed with water and brine, dried over Na$_2$SO$_4$, and then filtered. The Na$_2$SO$_4$ solid was washed with EtOAc (200 mL*3). The combined EtOAc phase was concentrated to give crude product 301-A2 which was directly used in next step without purification.

To a solution of 301-A2 (110 g, 502 mmol) in 1.5 L of methanol was added 20 mL of conc. H$_2$SO$_4$. The mixture was heated to reflux for overnight. The mixture was cooled to room temperature, then concentrated to about 100 mL and then diluted with 500 mL of cold water. The mixture was extracted with EtOAc (500 mL*3). The combined organic phase was washed with sat.NaHCO$_3$, water and brine, dried over Na$_2$SO$_4$, filtered and washed with EtOAc, the EtOAc phase was concentrated to dry to give crude product. The crude was recrystallized from PE/EtOAc (10:1, 400 mL) to removed most major by-products, the residue was purified by column chromatography on silica gel (PE/EtOAc: 100:1) to give product 301-A (methyl 4-fluoro-2-methyl-3-nitrobenzoate, 20 g, two steps yield: 19%).

$^1$H NMR (DMSO-d$_6$, 300 MHz): 8.08 (dd, J=5.7, 9.0 Hz, 1H), 7.58 (t, J=9.0 Hz, 1H), 3.85 (s, 3H), δ 2.45 (s, 3H)

Example 11. Synthesis of Compound 302

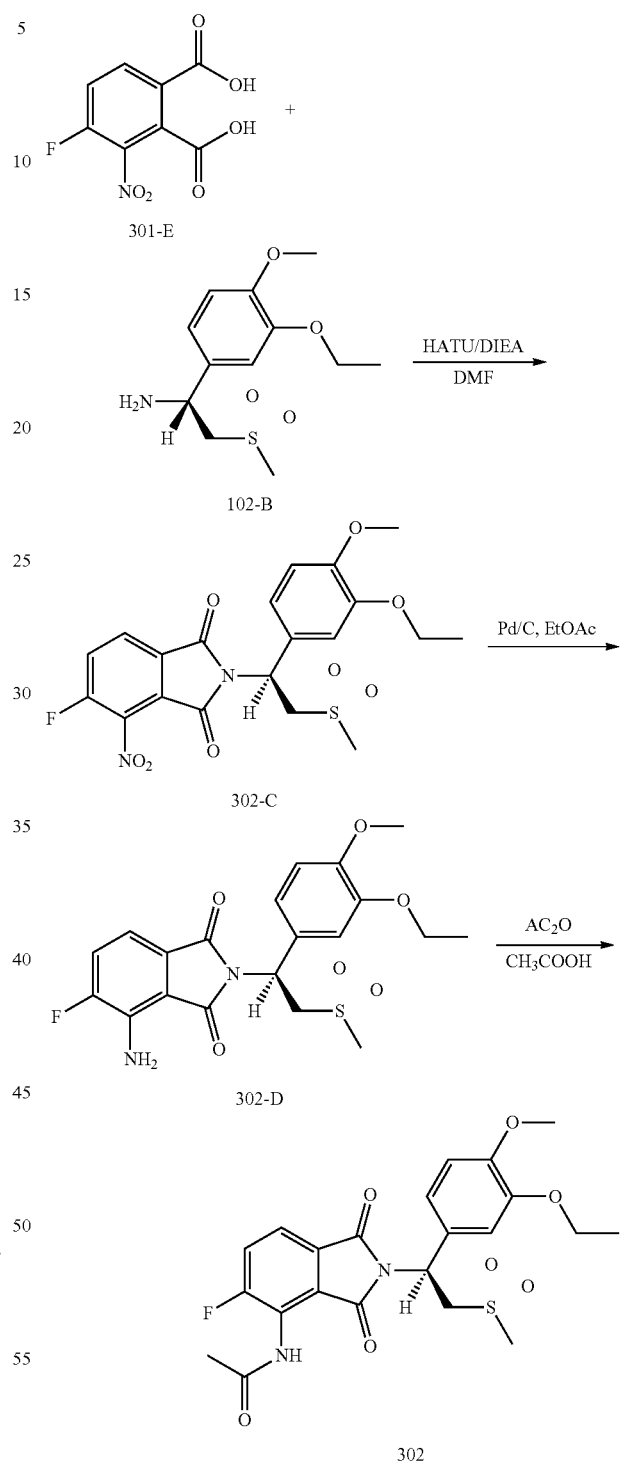

Step 1. Synthesis of Compound 302-C

To a mixture of 102-B ((S)-1-(3-ethoxy-4-methoxyphenyl)-2-(methylsulfonyl)ethanamine, 954 mg, 3.49 mmol) in DMF (60 mL) was added 301-E (3-nitro-4-fluorine phthalic acid, 800 mg, 3.49 mmol), HATU (CAS No. 148893-10-1, 2.08 g, 5.478 mmol) and DIEA (CAS No. 7087-68-5, 1.58 g, 12.2 mmol) at 5° C. The reaction mixture was stirred at 25° C. for overnight. To the reaction mixture was added H₂O (20 mL), stirred for 15 minutes, extracted with EtOAc (100 mL). The EtOAc solution was washed with brine (50 mL*3), dried, filtered and concentrated to give the crude product. The residue was purified by column chromatography on silica gel with PE:EtOAc (from 2:1 to 1:1) to give 302-C ((S)-2-(1-(3-ethoxy-4-methoxyphenyl)-2-(methylsulfonyl)ethyl)-5-fluoro-4-nitroisoindoline-1, 3-dione, 396 mg, yield: 25%) as yellow solid.

¹H NMR (400 MHz, DMSO-d₆) δ 8.24 (dd, J=8.4, 4.0 Hz, 1H), 8.09 (dd, J=10.0, 8.4 Hz, 1H), 7.09 (d, J=2.4 Hz, 1H), 7.01 (dd, J=8.4, 2.0 Hz, 1H), 6.94 (d, J=8.0 Hz, 1H), 5.78 (dd, J=9.6, 5.6 Hz, 1H), 4.22-4.26 (m, 2H), 4.00-4.06 (m, 2H), 3.74 (s, 3H), 2.99 (s, 3H), 1.32 (t, J=7.2 Hz, 3H).

Step 2. Synthesis of Compound 302-D

To a mixture of 302-C (396 mg, 0.85 mmol) in EtOAc (15 mL) was added Pd/C (50 mg, 10%, 50% H₂O), the reaction mixture was stirred under H₂ (50 Psi) atmosphere for 4 hours at 25° C. The mixture was filtered and concentrated to give 302-D ((S)-4-amino-2-(1-(3-ethoxy-4-methoxyphenyl)-2-(methylsulfonyl)ethyl)-5-fluoroisoindoline-1,3-dione, 327 mg, yield: 88%) as yellow solid.

¹H NMR (300 MHz, DMSO-d₆): δ 7.37-7.43 (m, 1H), 6.93-7.06 (m, 4H), 6.52 (s, 2H), 5.70-5.73 (m, 1H), 4.29-4.37 (m, 1H), 3.99-4.04 (m, 3H), 3.73 (s, 3H), 3.00 (s, 3H), 1.29-1.34 (m, 3H).

Step 3. Synthesis of Compound 302

To a solution of 302-D (132 mg, 0.302 mmol) in HOAc (4 mL) was added AC₂O (2 mL), the mixture was heated to 85° C. and reacted at 85° C. for 5 hours. This mixture was concentrated and diluted with EtOAc (30 ml). The EtOAc solution was washed with sat aqueous NaHCO₃ (15 mL), dried over Na₂SO₄, then concentrated to give crude product which was purified by prep-HPLC to afford compound 302 ((S)—N-(2-(1-(3-ethoxy-4-methoxyphenyl)-2-(methylsulfonyl)ethyl)-5-fluoro-1,3-dioxoisoindolin-4-yl)acetamide, 31 mg, yield: 21%) as white solid.

¹H NMR (400 MHz, DMSO-d₆) δ 10.13 (s, 1H), 7.79 (dd, J=8.0, 4.4 Hz, 1H), 7.72 (dd, J=10.4, 8.4 Hz, 1H), 7.07 (d, J=2.0 Hz, 1H), 6.92-6.95 (m, 2H), 5.75 (dd, J=10.4, 4.8 Hz, 1H), 4.11-4.32 (m, 2H), 4.01 (q, J=7.2 Hz, 2H), 3.73 (s, 3H), 2.99 (s, 3H), 2.09 (s, 3H), 1.32 (t, J=7.2 Hz, 3H). LCMS: 476.9 ([M−1]⁻).

Example 12. Synthesis of Compound 401

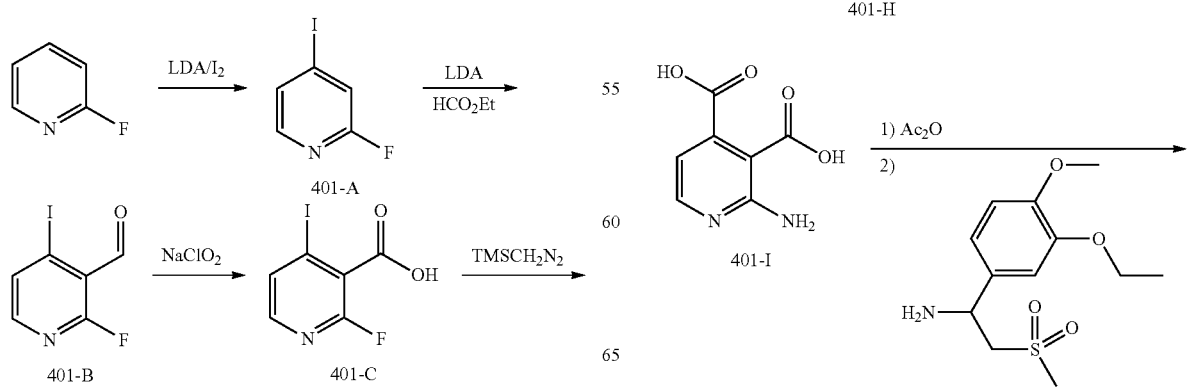

-continued

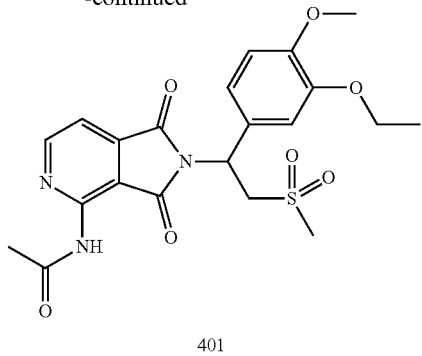

401

Step 1. Synthesis of Compound 401-A

Preparation of LDA (Lithium Diisopropylamide) Solution:

To a solution of diisopropylamine (35 mL, 0.25 mol) in 100 mL of dry THF was added n-BuLi (2.5 N, 96 mL, 0.24 mol) dropwise at −30° C. under $N_2$ atmosphere, the temperature was kept below −30° C. The reaction solution was stirred at −30° C. for 15 minutes and then at 0° C. for 30 minutes.

A solution of 2-fluoropyridine (CAS No. 372-48-5, 19.42 g, 0.2 mol) in 100 mL of dry THF was cooled to −70° C. under $N_2$ atmosphere. The above LDA solution was added dropwise to the solution while the temperature was kept below −70° C. Then the solution was stirred at −70° C. for 1 hour. To the reaction mixture was added a solution of $I_2$ (61 g, 0.24 mol) in 50 mL of dry THF dropwise and then the reaction was stirred at −75° C. for 1 hour. The reaction was quenched with sat. $NH_4Cl$ and stirred at 25° C. for 30 minutes. THF was removed by evaporation. The residue was extracted with EtOAc (500 mL*2). The combined EtOAc solution was washed with water and brine, dried over $Na_2SO_4$. Filtered and concentrated to dry to give crude product 401-A (2-fluoro-4-iodopyridine, 30 g, yield: 67%).

$^1$H NMR (300 MHz, DMSO-$d_6$): δ 8.37-8.43 (m, 1H), 8.21-8.22 (m, 1H), 7.13-7.18 (m, 1H).

Step 2. Synthesis of Compound 401-B

Preparation of LDA Solution:

To a solution of diisopropylamine (17 mL, 96.9 mmoL) in 300 mL of dry THF was added n-BuLi (46.5 mL, 116 mmol) dropwise at −30° C. under $N_2$ atmosphere, the temperature was kept below −30° C. The solution was stirred at −30° C. for 15 minute and then at 0° C. for 30 minute.

A solution of 401-A (21.6 g, 96.9 mmol) in 100 mL of dry THF was cooled to −70° C. The above LDA solution was added dropwise to the solution while the temperature was kept below −70° C. Then the solution was stirred at −70° C. for 1 hour. Ethyl formate (10 mL, 121 mmol) was added dropwise to the solution and slowly warmed to −50° C. during 1 hour. The reaction mixture was quenched with sat. $NH_4Cl$ and stirred at 25° C. for 30 minute. THF was removed by evaporation and the reaction solution was extracted with EtOAc (300 mL*2). The combined organic phase was washed with water and brine, dried over $Na_2SO_4$. $Na_2SO_4$ was filtered and the organic phase was concentrated to dry and the residue was purified by column chromatography on silica gel (PE/EtOAc: 50:1 to 10:1) to give the product 401-B (2-fluoro-4-iodonicotinaldehyde, 13.0 g, yield: 53%).

$^1$H NMR (300 MHz, DMSO-$d_6$): δ 10.15 (s, 1H), 7.97 (d, J=5.1 Hz, 1H), 7.87 (d, J=5.1 Hz, 1H).

Step 3. Synthesis of Compound 401-C

To a solution of 401-B (13.3 g, 53 mmol) in 466 mL of t-BuOH and 133 mL of water cooled with ice-eater was added 2-Methyl-2-butene (13.3 g, 53 mmol), $Na_2HPO_4$ (70 g, 583 mmol), followed by $NaClO_2$ (24 g, 265 mmol) portionwise. The reaction mixture was stirred at 25° C. for 1.5 hours, then diluted with 800 mL of DCM and acidified with 6 N/HCl to pH=2. The organic phase was separated and the water phase was extracted with DCM/MeOH (20:1, 1000 mL*2). The combined organic phase was washed with brine, dried over $Na_2SO_4$. Filtered and concentrated to dry. The residue was crystallized from DCM/PE (1:1) to give product 401-C (2-fluoro-4-iodonicotinic acid, 11.5 g, yield: 81%).

$^1$H NMR (300 MHz, DMSO-$d_6$): δ 14.26 (br s, 1H), 8.02 (d, J=4.2 Hz, 1H), 7.94 (dd, J=3.9, 0.6 Hz, 1H).

Step 4. Synthesis of 401-D

To a solution of 401-C (10.3 g, 38.6 mmol) in 40 mL of MeOH and $Et_2O$ (40 mL) cooled with ice-water, $TMSCH_2N_2$ (29 mL, 57.9 mmol) was added dropwise. The mixture was stirred at 25° C. for overnight. Then ice water was added to quench the reaction. The solvent was removed by evaporation and Sat. $NaHCO_3$ was added and the mixture was stirred for 30 minutes. The mixture was extracted with EtOAc (100 mL*3). The combined organic phase was washed with brine, dried over $Na_2SO_4$, filtered and concentrated to dry to give product 401-D (methyl 2-fluoro-4-iodonicotinate, 9.6 g, yield: 88%).

$^1$H NMR (300 MHz, DMSO-$d_6$): δ 8.06 (d, J=5.4 Hz, 1H), 7.97 (d, J=5.1 Hz, 1H), 3.93 (s, 3H).

Step 5. Synthesis of Compound 401-E

To a solution of 401-D (9.6 g, 34.1 mmol) and 2,4-dimethoxybenzylamine (7.41 g, 44.3 mmol) in 50 mL of DMSO was added $K_2CO_3$ (11.8 g, 68.2 mmol). The mixture was stirred at 25° C. for 5 hours, then diluted with 500 mL of EtOAc. The mixture was washed with water and brine, dried over $Na_2SO_4$, filtered and concentrated to dry and the residue was purified by column chromatography on silica gel (PE/EtOAc: 50:1 to 10:1) to give the product 401-E (methyl 2-((2,4-dimethoxybenzyl)amino)-4-iodonicotinate, 10.66 g, yield: 73%).

$^1$H NMR (400 MHz, DMSO-$d_6$): δ 7.69 (d, J=5.2 Hz, 1H), 7.07 (d, J=5.2 Hz, 1H), 7.00-7.03 (m, 2H), 6.55 (d, J=2.4 Hz, 1H), 6.44 (dd, J=8.4, 2.4 Hz, 1H), 4.44 (d, J=6.0 Hz, 2H), 3.87 (s, 3H), 3.81 (s, 3H), 3.72 (s, 3H).

Step 6. Synthesis of Compound 401-F

To a solution of 401-E (10.66 g, 24.9 mmol) in 80 mL of DCM cooled with ice-water was added 30 mL of TFA. The mixture was stirred at 25° C. for 3 hours, concentrated to dry. The mixture was basified with sat. $NaHCO_3$. The solid was filtered and washed with ice-water and dried to give the product 401-F (methyl 2-amino-4-iodonicotinate, 5.54 g, yield: 80%).

$^1$H NMR (300 MHz, DMSO-$d_6$): δ 7.65 (d, J=5.1 Hz, 1H), 7.07 (d, J=5.4 Hz, 1H), 6.43 (s, 2H), 3.83 (s, 3H).

Step 7. Synthesis of Compound 401-G

A solution of 401-F (5.54 g, 0.02 mmol) in 100 mL of HOAc and 50 mL of $Ac_2O$ was stirred at 80° C. for overnight. The mixture was concentrated to dry and purified by column chromatography on silica gel (PE/EtOAc: 1:1 to 1:2) to give product 401-G (methyl 2-acetamido-4-iodonicotinate, 2.7 g, 42%).

$^1$H NMR (300 MHz, DMSO-$d_6$): δ 10.56 (s, 1H), 8.08 (d, J=5.1 Hz, 1H), 7.82 (d, J=5.4 Hz, 1H), 3.74 (s, 3H), 2.01 (s, 3H).

Step 8. Synthesis of Compound 401-H

To a solution of 401-G (3.2 g, 10 mmol) in 50 mL of MeOH was added DIEA (3.3 mL, 20 mmol) and $PdCl_2$ (PPh$_3$)$_2$ (702 mg, 1 mmol). The mixture was stirred under 50 Mpa CO atmosphere at 100° C. for overnight. Cooled to 25° C. and concentrated to dry and purified by column chromatography on silica gel (PE/EtOAc: 5:1-2:1) to give product 401-H (dimethyl 2-aminopyridine-3,4-dicarboxylate, 1.8 g, yield: 86%).

$^1$H NMR (300 MHz, DMSO-d$_6$): δ 8.24 (d, J=4.8 Hz, 1H), 6.97 (s, 2H), 6.67 (d, J=4.8 Hz, 1H), 3.80 (s, 3H), 3.78 (s, 3H).

Step 9. Synthesis of Compound 401-I

A solution of 401-H (400 mg, 1.9 mmol) in 20 mL of 20% KOH solution and 20 mL of THF was stirred at 25° C. for overnight. Extracted with TMBE (50 mL), the organic phase was separated and water phase was acidified with 2N HCl to pH=2. The resulted solid was filtered and washed with ice-water and dried to give product 401-I (2-aminopyridine-3,4-dicarboxylic acid, 285 mg, yield: 82%)

$^1$H NMR (300 MHz, DMSO-d$_6$): δ 8.15 (d, J=4.8 Hz, 1H), 6.59 (d, J=4.8 Hz, 1H),

Step 10. Synthesis of Compound 401

A solution of 401-I (500 mg, 2.75 mmol) in 20 mL of Ac$_2$O was heated to reflux for 3 hours. Then the mixture cooled to room temperature and concentrated to dry, the residue was dissolved in 20 mL of HOAc, followed by addition of 1-(3-ethoxy-4-methoxyphenyl)-2-(methylsulfonyl)ethanamine (750 mg, 2.75 mmol). The reaction mixture was refluxed for overnight and then cooled to 25° C. and added 20 mL of Ac$_2$O and stirred at 85° C. for another 5 hours. The mixture was cooled to 25° C. and concentrated to dry and purified by prep-HPLC to give product 401 (N-(2-(1-(3-ethoxy-4-methoxyphenyl)-2-(methylsulfonyl)ethyl)-1,3-dioxo-2,3-dihydro-1H-pyrrolo[3,4-c]pyridin-4-yl)acetamide, 735 mg, yield: 58%).

$^1$H NMR (300 MHz, DMSO-d$_6$): δ 10.51 (s, 1H), 8.88 (d, J=4.8 Hz, 1H), 7.67 (s, 1H), 7.09 (s, 1H), 6.92-7.00 (m, 2H), 5.73-5.78 (m, 1H), 4.25-4.33 (m, 1H), 4.10-4.17 (m, 1H), 3.98-4.06 (m, 2H), 3.73 (s, 3H), 2.97 (s, 3H), 2.17 (s, 3H), 1.32 (t, J=7.2 Hz, 3H). LCMS: [(M+1)]$^+$=461.9.

Example 13. Synthesis of Compound 601

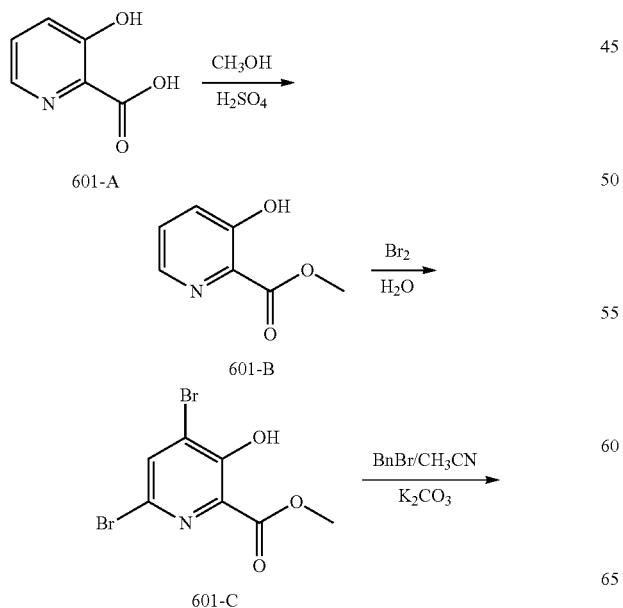

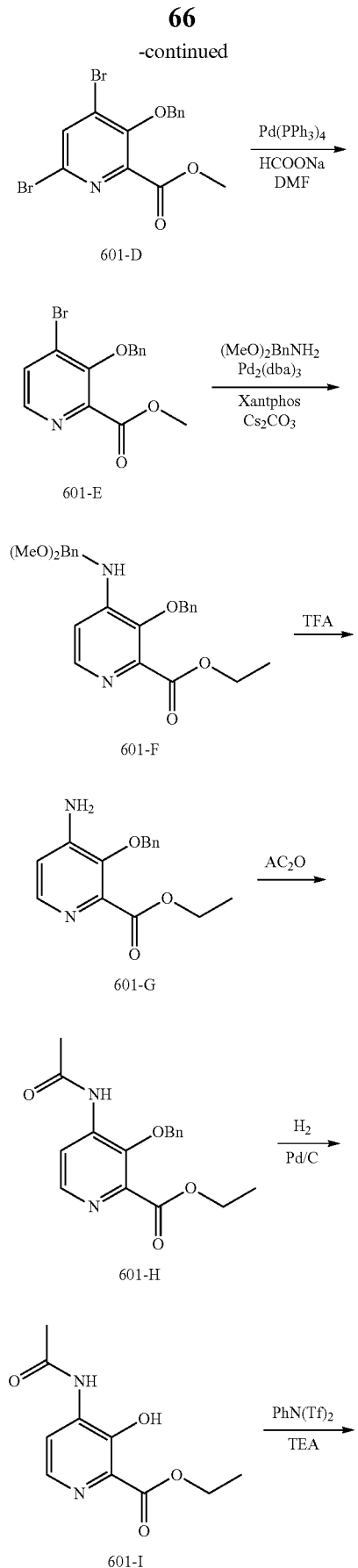

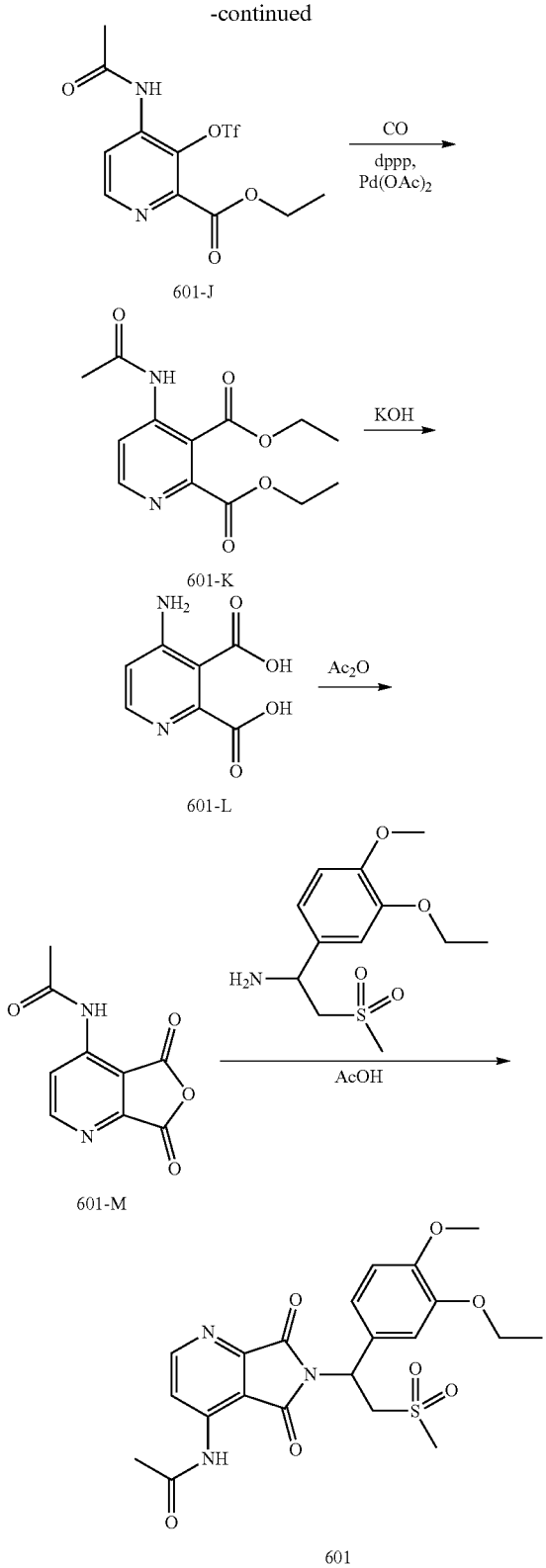

Step 1. Synthesis of Compound 601-B

To a solution of 601-A (3-hydroxypicolinic acid, CAS No. 874-24-8, 60 g, 430 mmol) in MeOH (600 mL) was added conc. $H_2SO_4$ (60 mL) slowly. Then, the mixture was heated to 80° C. for overnight. Adjusted the pH=7 with solid $Na_2CO_3$, the mixture was filtered and the cake was washed with EtOAc (500 mL). The filtrate was concentrated to give 601-B (methyl 3-hydroxypicolinate, 40 g, yield: 61%) as a white solid.

$^1$H NMR (300 MHz, $CDCl_3$) δ 10.60 (s, 1H), 8.27 (d, J=3.7 Hz, 1H), 7.35-7.44 (m, 2H), 4.05 (s, 3H).

Step 2. Synthesis of Compound 601-C

To a solution of compound 601-B (30 g, 196 mmol) in $H_2O$ (1500 mL) was added $Br_2$ (94 g, 590 mmol) slowly. The mixture was stirred at 30° C. for overnight. Then the mixture was extracted with DCM (500 mL*2), washed with brine (500 mL), dried, filtered and concentrated to afford 601-C (methyl 4,6-dibromo-3-hydroxypicolinate, 49 g, yield: 81%) as a white solid.

$^1$H NMR (300 MHz, $CDCl_3$) δ 11.35 (s, 1H), 7.87 (s, 1H), 4.07 (s, 3H).

Step 3. Synthesis of Compound 601-D

A solution of compound 601-C (49 g, 157 mmol), BnBr (80.5 g, 472 mmol) and $K_2CO_3$ (98 g, 710 mmol) in $CH_3CN$ (1 L) was heated to reflux for overnight. The mixture was cooled to 25° C. The solid was removed by filtration and the filtrate was evaporated to give the residue which was purified by triturated with PE:EtOAc=10:1 (100 mL) at 30° C. for 1 hour to give 601-D (methyl 3-(benzyloxy)-4,6-dibromopicolinate, 43 g, yield: 68%) as yellow solid.

$^1$H NMR (300 MHz, $CDCl_3$): δ 7.89 (s, 1H), 7.39-7.54 (m, 5H), 5.15 (s, 2H), 3.94 (s, 3H).

Step 4. Synthesis of 601-E

To a solution of 601-D (43 g, 107 mmol), HCOONa (8.7 g, 128 mmol) in DMF (1 L) was added Pd($PPh_3$)$_4$ (6.2 g, 5.35 mmol). The mixture was stirred at 80° C. for overnight. $H_2O$ (5 L) was added and the mixture was extracted with EtOAc (1 L*2). The combined EtOAc solution was washed with brine (1 L*2), dried and concentrated to give the crude product which was purified by column chromatography on silica gel eluted with PE:EtOAc=10:1 to give the product 601-E (methyl 3-(benzyloxy)-4-bromopicolinate, 14.8 g, 43%) as yellow solid.

$^1$H NMR (300 MHz, $CDCl_3$) δ 8.27 (dd, J=4.8, 0.6 Hz, 1H), 7.71 (dd, J=4.8, 0.6 Hz, 1H), 7.55 (d, J=6.9 Hz, 2H), 7.37-7.45 (m, 3H), 5.17 (s, 2H), 3.95 (s, 3H).

Step 5. Synthesis of Compound 601-F

To a solution of 601-E (14.7 g, 45.63 mmol), 2,4-Dimethoxy-benzylamine (9.92 g, 59.32 mmol), xantphos (1.58 g, 2.74 mmol), $Cs_2CO_3$ (22.3 g, 68.5 mmol) in toluene (350 mL) was added $Pd_2(dba)_3$ (0.84 g, 0.913 mmol) under $N_2$ atmosphere. Then, the mixture was heated to 100° C. for 2 days. The reaction solution was concentrated to get the crude product which was purified by column chromatography on silica gel eluted with PE:EtOAc (1:1) to give the product 601-F (ethyl 3-(benzyloxy)-4-((2,4-dimethoxybenzyl)amino)picolinate, 8.4 g, 58%) as orange oil.

$^1$H NMR (300 MHz, $CDCl_3$) δ 8.12 (d, J=5.7 Hz, 1H), 7.35-7.44 (m, 5H), 7.00 (d, J=8.4 Hz, 1H), 6.64 (d, J=5.1 Hz, 1H), 6.40-6.45 (m, 2H), 5.26-5.31 (m, 1H), 4.99 (s, 2H), 4.40-4.48 (m, 2H), 4.24 (d, J=6.0 Hz, 2H), 3.80 (s, 3H), 3.75 (s, 3H), 1.41 (t, J=7.2 Hz, 3H).

Step 6. Synthesis of Compound 601-G

To a solution of 601-F (7.33 g, 17.4 mmol) in DCM (dichloromethane, 60 mL) and TFA (trifluoroacetic acid, 30 mL) was stirred at 30° C. for 4 hours. $H_2O$ (50 mL) was added, extracted with DCM (50 mL*2). The combined DCM solution was dried and concentrated to get the crude product which was purified by column chromatography on silica gel eluted with PE:EtOAc (1:1) to give the product 601-G (ethyl 4-amino-3-(benzyloxy)picolinate, 4.0 g, 85%) as brown oil.

¹H NMR (300 MHz, CDCl₃) δ 8.08 (d, J=5.1 Hz, 1H), 7.36-7.48 (m, 5H), 6.71 (d, J=5.1 Hz, 1H), 5.02 (s, 2H), 4.40-4.48 (m, 4H), 1.41 (t, J=7.2 Hz, 3H).

Step 7. Synthesis of Compound 601-H

A solution of 601-G (4.0 g, 15.5 mmol) in Ac₂O (40 mL) was stirred at 100° C. for overnight. The mixture was concentrated to get the crude product, which was purified by column chromatography on silica gel eluted with PE:EtOAc (1:1) to give the product 601-H (ethyl 4-acetamido-3-(benzyloxy)picolinate, 3.17 g, 69%) as yellow oil.

¹H NMR (300 MHz, CDCl₃) δ 0.38-8.438 (m, 2H), 7.66 (s, 1H), 7.43 (s, 5H), 5.10 (s, 2H), 4.51 (q, J=7.2 Hz, 2H), 1.86 (s, 3H), 1.47 (t, J=7.2 Hz, 3H).

Step 8. Synthesis of Compound 601-I

To a mixture of compound 601-H (3.17 g, 10.01 mmol) in MeOH (30 mL) and EtOAc (30 mL) was added Pd/C (10%, 50% H₂O, 0.32 g). Then, the mixture was stirred at 30° C. under H₂ (50 psi) atmosphere for overnight. The mixture was filtered, the filtrate was concentrated to afford the crude product 601-I (ethyl 4-acetamido-3-hydroxypicolinate, 1.67 g, 74%) as a brown solid.

¹H NMR (400 MHz, DMSO-d₆) δ 10.99 (br s, 1H), 9.78 (s, 1H), 8.27 (d, J=5.6 Hz, 1H), 8.07 (s, 1H), 4.40 (q, J=7.2 Hz, 2H), 2.19 (s, 3H), 1.35 (t, J=7.2 Hz, 3H).

Step 9. Synthesis of Compound 601-J

To a mixture of compound 601-I (1.53 g, 6.8 mmol) in DMF (30 mL) was added Et₃N (1.44 g, 14.28 mmol) and N,N-Bis(trifluoromethylsulfonyl)aniline (3.83 g, 10.7 mmol), the mixture was stirred at 25° C. for 3 hours. Water (500 mL) was added and the mixture was extracted with EtOAc (200 mL*2). The combined EtOAc solution was washed with brine (200 mL*2), dried and concentrated to get the crude product which was purified by column chromatography on silica gel eluted with PE:EtOAc (2:1) to give the product 601-J (ethyl 4-acetamido-3-(((trifluoromethyl)sulfonyl)oxy)picolinate, 2.0 g, 83%) as colorless oil.

¹H NMR (300 MHz, CDCl₃) δ 8.56-8.61 (m, 2H), 7.87 (s, 1H), 4.49 (q, J=7.2 Hz, 2H), 2.29 (s, 3H), 1.44 (t, J=7.2 Hz, 3H).

Step 10. Synthesis of Compound 601-K

A mixture of compound 601-J (1.85 g, 5.2 mmol), Pd(OAc)₂ (233 mg, 1.04 mmol), DPPP (1,3-bis(diphenylphosphino) propane, 429 mg, 1.04 mmol) and Et₃N (1.16 g, 11.5 mmol) in DMSO (1.84 mL) and EtOH (50 mL) was heated to 70° C. for overnight. The mixture was filtered, the filtrate was concentrated to get the crude product which was purified by column chromatography on silica gel eluted with PE:EtOAc (1:1) to give the product 601-K (diethyl 4-acetamidopyridine-2,3-dicarboxylate, 1.0 g, 69%) as colorless oil.

¹H NMR (300 MHz, CDCl₃): δ 10.50 (s, 1H), 8.56-8.66 (m, 2H), 4.35-4.46 (m, 4H), 2.26 (s, 3H), 1.35-1.44 (m, 6H).

Step 11. Synthesis of Compound 601-L

A mixture of 601-K (1.0 g, 3.6 mmol) in KOH (20%, 50 mL, aq) and THF (50 mL) was stirred at 25° C. for 3 hours. The solvent was removed and the residue was diluted with MeOH (100 mL), stirred at 50° C. for 1 hour, filtered. The filtrate was concentrated to get the product 601-L (4-aminopyridine-2,3-dicarboxylic acid, 0.9 g, crude) as white solid.

¹H NMR (400 MHz, DMSO-d₆) δ 8.52-9.26 (m, 2H), 8.11 (d, J=6.8 Hz, 1H), 7.19 (d, J=6.8 Hz, 1H).

Step 12. Synthesis of Compound 601-M

A mixture of compound 601-L (0.9 g) in Ac₂O (30 mL) was heated to 80° C. for overnight. Then the solvent was removed to get the product 601-M (N-(5,7-dioxo-5,7-dihydrofuro[3,4-b]pyridin-4-yl)acetamide, 0.6 g) as brown oil.

Step 13. Synthesis of Compound 601

A mixture of compound 601-M (0.6 g) and [1-(3-ethoxy-4-methoxyphenyl)-2-(methylsulfonyl)ethanamine] (0.8 g, 2.9 mmol) in AcOH (20 mL) was heated to 120° C. for 3 hours. The solvent was removed to get the crude product which was purified by prep-HPLC to give the target product 601 (N-(6-(1-(3-ethoxy-4-methoxyphenyl)-2-(methylsulfonyl)ethyl)-5,7-dioxo-6,7-dihydro-5H-pyrrolo[3,4-b]pyridin-4-yl)acetamide, 71 mg, yield for 3 steps 4%).

¹H NMR (400 MHz, DMSO-d₆) δ 9.79 (s, 1H), 8.80 (d, J=5.6 Hz, 1H), 8.36 (d, J=6.0 Hz, 1H), 7.08 (d, J=2.0 Hz, 1H), 7.02 (dd, J=8.4, 2.0 Hz, 1H), 6.94 (d, J=8.4 Hz, 1H), 5.82 (dd, J=10.4, 4.8 Hz, 1H), 4.17-4.33 (m, 2H), 4.03 (q, J=7.2 Hz, 2H), 3.74 (s, 3H), 3.02 (s, 3H), 2.26 (s, 3H), 1.32 (t, J=7.2 Hz, 3H). LCMS [(M+1)]⁺=462.0.

Example 14. Synthesis of Compound 701

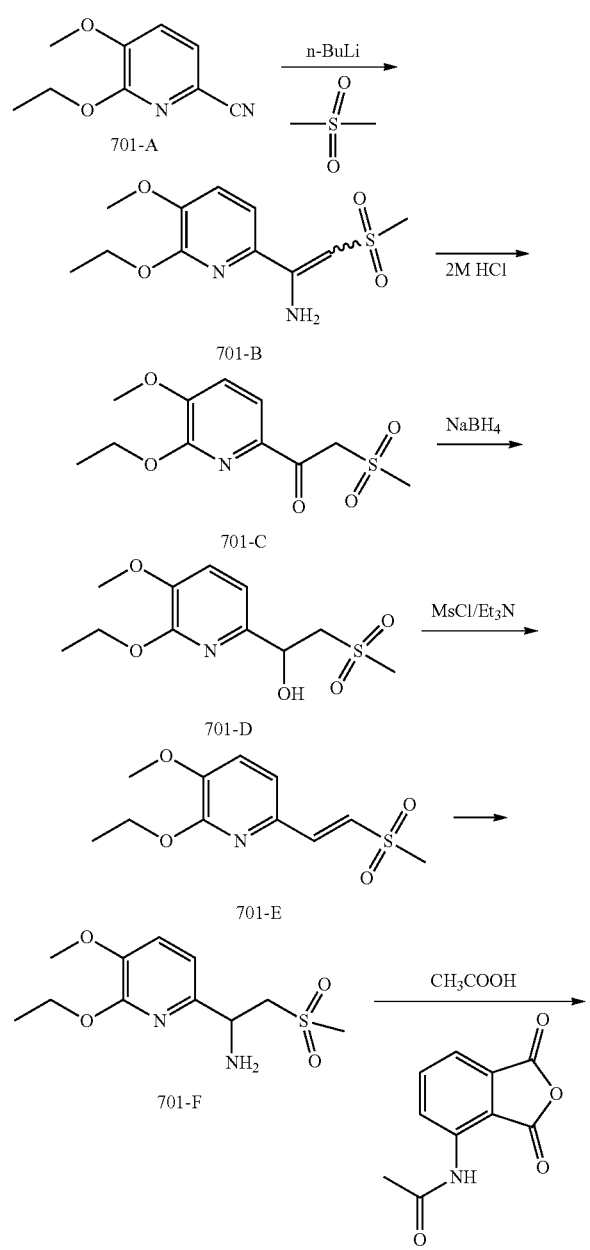

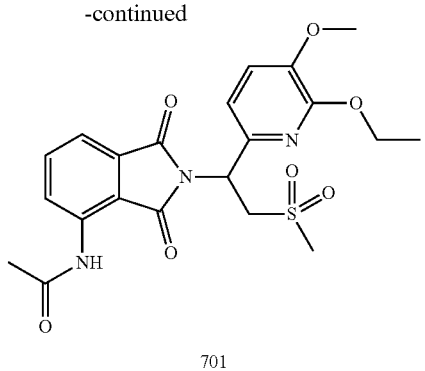

701

Step 1. Synthesis of Compound 701-B

To a solution of DMSO (3.79 g, 40.3 mmol) in 150 mL of dry THF cooled to 0° C. with ice-water was added dropwise n-BuLi (2.5 M, 16.1 mL, 40.3 mmol) slowly under $N_2$ atmosphere. Then the reaction mixture was stirred in ice-water bath for 2 hours. A solution of 701-A (6-ethoxy-5-methoxypicolinonitrile, 2.87 g, 16.1 mmol) in 30 mL of dry THF was added dropwise to the solution. Then the mixture was stirred at 0° C. in ice-water bath for 2 hours. The mixture was quenched with ice-water and THF was removed by evaporation. The mixture was extracted with EtOAc (500 mL*3). The combined organic phase was washed with water and brine, dried over $Na_2SO_4$, concentrated to dry and crystallized from PE/EtOAc (2:1) to give product 701-B (1-(6-ethoxy-5-methoxypyridin-2-yl)-2-(methylsulfonyl)ethenamine, 3.5 g, yield: 80%).

$^1$H NMR (300 MHz, DMSO-$d_6$): δ 7.52 (d, J=8.1 Hz, 1H), 7.35 (d, J=8.4 Hz, 1H), 6.80 (s, 2H), 5.55 (s, 1H), 4.40 (q, J=6.9 Hz, 2H), 3.83 (s, 3H), 3.00 (s, 3H), 1.34 (t, J=6.9 Hz, 3H).

Step 2: synthesis of compound 701-C

To a solution of 701-B (4.2 g, 15.4 mmol) in 100 mL THF cooled with ice-water was added 2N HCl (50 mL). The mixture was stirred at 25° C. for overnight. THF was evaporated and the mixture was basified with sat. NaHCO$_3$, then extracted with EtOAc (200 mL*3). The combined organic phase was washed with brine, dried over $Na_2SO_4$ and concentrated to dry to give product 701-C (1-(6-ethoxy-5-methoxypyridin-2-yl)-2-(methylsulfonyl)ethenone, 4.0 g, yield: 95%)

$^1$H NMR (300 MHz, DMSO-$d_6$): δ 7.73 (d, J=8.1 Hz, 1H), 7.46 (d, J=8.1 Hz, 1H), 5.07 (s, 2H), 4.45 (q, J=7.2 Hz, 2H), 3.89 (s, 3H), 3.15 (s, 3H), 1.38 (t, J=7.2 Hz, 3H).

Step 3. Synthesis of 701-D

To a solution of 701-C (4.0 g, 14.6 mmol) in 100 mL of MeOH cooled with ice-water was added NaBH$_4$ (1.11 g, 29.3 mmol) portion wise and stirred at 25° C. for 2 hours. Then the mixture was quenched with 2 N HCl (20 mL) and stirred for 30 minutes, concentrated to dry and basified with sat. NaHCO$_3$, then extracted with DCM/MeOH (20:1, 400 mL*2). The combined organic phase was washed with brine, dried over $Na_2SO_4$, concentrated to dry to give crude product 701-D (1-(6-ethoxy-5-methoxypyridin-2-yl)-2-(methylsulfonyl)ethanol, 4.0 g, yield: 100%) which was directly used in the next step.

Step 4. Synthesis of Compound 701-E

To a solution of 701-D (4.0 g, 14.53 mmol) in 100 mL of DCM cooled with ice-water was added Et$_3$N (4.0 mL, 29.0 mmol), followed by MsCl (1.7 mL, 21.8 mmol) dropwise. The mixture was stirred at 25° C. for overnight and then quenched with ice-water and stirred for 30 minutes, then extracted with DCM. The combined organic phase was washed with water and brine, dried over $Na_2SO_4$ and concentrated to dry and crystallized from PE/EtOAc (1:1) to give product 701-E (2-ethoxy-3-methoxy-6-(2-(methylsulfonyl)vinyl)pyridine, 1.8 g, yield: 48%).

$^1$H NMR (300 MHz, DMSO-$d_6$): δ 7.37 (d, J=6.3 Hz, 2H), 7.31 (s, 2H), 4.40 (q, J=6.9 Hz, 2H), 3.83 (s, 3H), 3.11 (s, 3H), 1.35 (t, J=6.9 Hz, 3H).

Step 5. Synthesis of Compound 701-F

A solution of B(OH)$_3$ (70 mg, 0.81 mmol) in 5 mL of water was heated to 50° C. and stirred for 15 minutes. 701-E (140 mg, 0.54 mmol) was added and stirred for 30 minute and then 20 mL of NH$_3$.H$_2$O was added. The mixture was stirred at 80° C. in a sealed tube for 3 days. Then the mixture was cooled to 25° C. and concentrated to dry and basified with sat. NaHCO$_3$, and stirred for 30 minutes, then extracted with DCM/MeOH (50 mL*3), the combined organic phase was washed with brine, dried over $Na_2SO_4$, concentrated to dry to give crude product 701-F (1-(6-ethoxy-5-methoxypyridin-2-yl)-2-(methylsulfonyl)ethanamine, 110 mg).

$^1$H NMR (400 MHz, DMSO-$d_6$): δ 7.24 (d, J=8.0 Hz, 1H), 6.98 (d, J=8.0 Hz, 1H), 4.31-4.39 (m, 2H), 4.21-4.25 (m, 1H), 3.76 (s, 3H), 3.36-3.43 (m, 2H), 3.02 (s, 3H), 2.32 (s, 2H), 1.32 (t, J=7.2 Hz, 3H).

Step 6. Synthesis of Compound 701

To a solution of 701-F (110 mg, 0.4 mmol) in 20 mL of HOAc was added (N-(1,3-dioxo-1,3-dihydroisobenzofuran-4-yl)acetamide, CAS number 6296-53-3, 82 mg, 0.4 mmol). The mixture was heated to reflux for overnight, then cooled to 25° C. and concentrated to dry and purified by prep-HPLC to give product 701 (N-(2-(1-(6-ethoxy-5-methoxypyridin-2-yl)-2-(methylsulfonyl)ethyl)-1,3-dioxoisoindolin-4-yl)acetamide, 123 mg, yield for 2 steps: 49%).

$^1$H NMR (400 MHz, DMSO-$d_6$): δ 9.71 (s, 1H), 8.47 (d, J=8.4 Hz, 1H), 7.80-7.84 (m, 1H), 7.60 (d, J=7.2 Hz, 1H), 7.27 (d, J=8.0 Hz, 1H), 7.02 (d, J=8.0 Hz, 1H), 5.81 (dd, J=10.8, 4.0 Hz, 1H), 4.30-4.34 (m, 1H), 4.15-4.22 (m, 0.3H), 3.76 (s, 3H), 3.09 (s, 3H), 2.18 (s, 3H), 1.17 (dd, J=7.2 Hz, 3H). LCMS: [(M+1)]$^+$=462.0.

Synthesis of Starting Material 701-A:

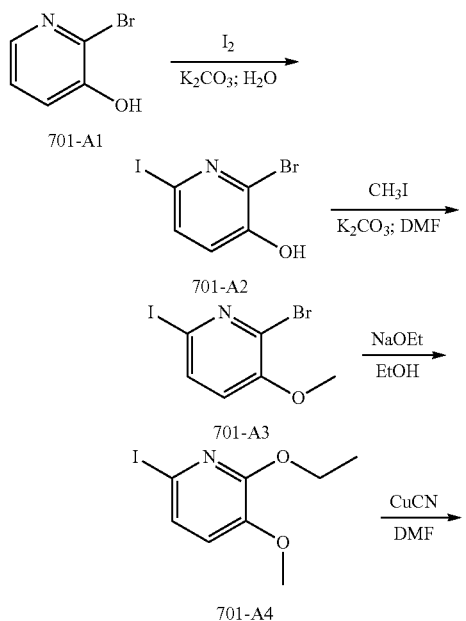

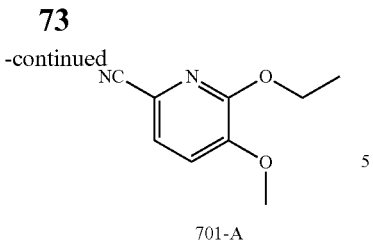

701-A

Synthesis of Compound 701-A2:

To a solution of 701-A1 (2-bromo-pyridin-3-ol, CAS number 6602-32-0, 60 g, 0.35 mol) in H₂O (600 mL) was added K₂CO₃ (96.7 g, 0.7 mol), 12 (90.7 g, 0.357 mol). The reaction mixture was stirred at 15° C. for overnight. The mixture was adjusted the pH to 5 with 3N HCl. The resulting solid was collected by filtration, washed with water (200 mL*3), dried to give 701-A2 (2-bromo-6-iodopyridin-3-ol, 101 g, yield: 97%) as a yellow solid.

$^1$H NMR (300 MHz, DMSO-d$_6$) δ 11.11 (s, 1H), 7.62 (d, J=8.4 Hz, 1H), 7.03 (d, J=8.1 Hz, 1H).

Synthesis of Compound 701-A3:

A solution of 701-A2 (2-bromo-6-iodopyridin-3-ol, 101 g, 0.337 mol) in 200 mL of DMF was added K₂CO₃ (70 g, 0.506 mol) and the mixture was stirred for 30 minutes. CH₃I (57.4 g, 0.404 mol) was added, then the mixture was stirred at 100° C. for 2 hours. The reaction mixture was poured into 2 L of H₂O, stirred for 1 hour, filtered, washed with water (500 mL*2), collected the solid which was slurried with PE:EtOAc=2:1 (300 mL) at 15° C. for 1 hour to give product 701-A3 (2-bromo-6-iodo-3-methoxypyridine, 74 g, yield: 70%) as brown solid. $^1$H NMR (300 MHz, DMSO-d$_6$) δ 7.79 (d, J=8.4 Hz, 1H), 7.28 (d, J=8.1 Hz, 1H), 3.87 (s, 3H).

Synthesis of Compound 701-A4:

A solution of EtOH (1.5 L) was added 27.6 g of Na then the mixture was stirred at 15° C. until the solid was disappeared. Compound 701-A3 (2-bromo-6-iodo-3-methoxypyridine, 37.7 g, 0.12 mol) was added and the mixture was heated to 100° C. for overnight. The solvent was removed. The residue was diluted with EtOAc (1 L) and the solution was washed with water (1 L*2), dried over Na₂SO₄, concentrated to dry to give product 701-A4 (2-ethoxy-6-iodo-3-methoxypyridine, 31.6 g, yield: 94%) as brown solid.

$^1$H NMR (400 MHz, DMSO-d$_6$) δ 7.32 (d, J=8.0 Hz, 1H), 7.05 (d, J=8.0 Hz, 1H), 4.26 (q, J=7.2 Hz, 2H), 3.76 (s, 3H), 1.31 (t, J=7.2 Hz, 3H).

Synthesis of Compound 701-A

To a solution of 701-A4 [2-ethoxy-6-iodo-3-methoxypyridine] (31.6 g, 0.113 mol) in 300 mL of DMF was added CuCN (12.2 g, 0.136 mol). The mixture was heated to 150° C. for 2 hours and then diluted with water (1 L) and extracted with EtOAc (500 mL*2). The organic phase was washed with brine (500 mL*3), dried over Na₂SO₄, concentrated to dryness to give 701-A (6-ethoxy-5-methoxypicolinonitrile, 20 g, yield: 99%) as yellow solid.

$^1$H NMR (300 MHz, DMSO-d$_6$) δ 7.63 (d, J=8.1 Hz, 1H), 7.39 (d, J=7.8 Hz, 1H), 4.31 (q, J=7.2 Hz, 2H), 3.86 (s, 3H), 1.32 (t, J=7.2 Hz, 3H).

Example 15. Synthesis of Compound 801

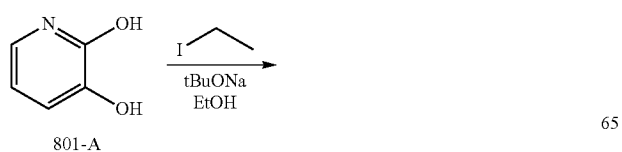

801-A

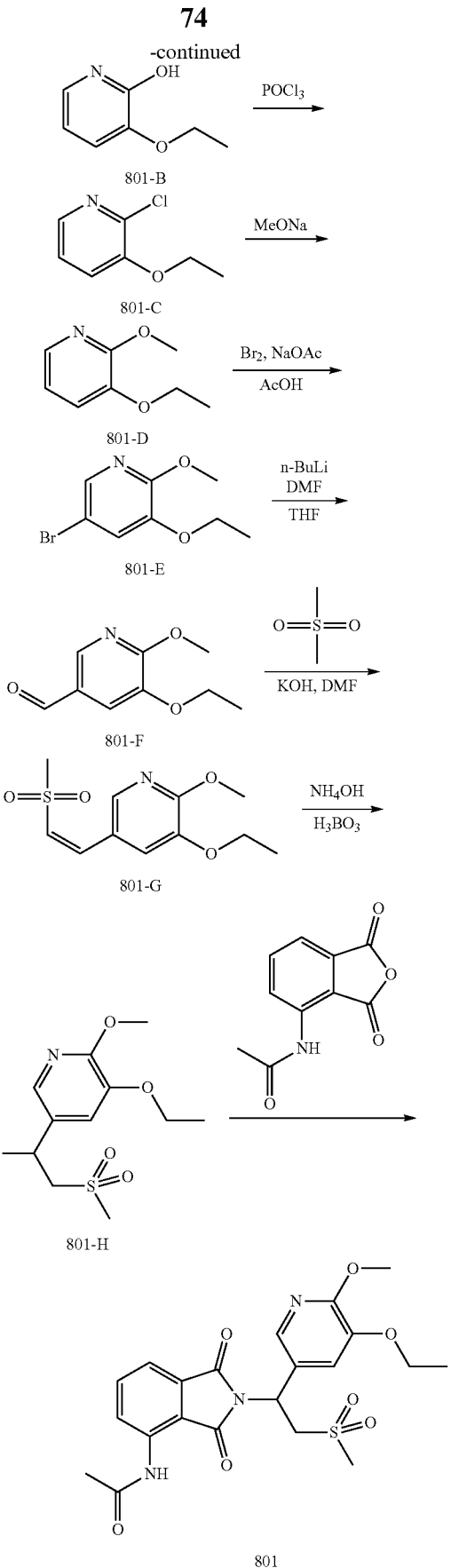

Step 1. Synthesis of Compound 801-B

To a solution of compound 801-A (pyridine-2,3-diol, CAS number 16867-04-2, 24 g, 216 mmol) and NaOBu$^t$ (20.75 g, 216 mmol) in EtOH (200 mL) was added Iodo-ethane (37 g, 237.6 mmol). The mixture was stirred at 85° C. for overnight. The solvent was removed by evaporation. The residue was purified by column chromatography on silica gel eluted with DCM:MeOH (50:1) to give the product 801-B (3-ethoxypyridin-2-ol, 12.2 g, 40%) as brown solid.

$^1$H NMR (400 MHz, DMSO-d$_6$) δ 11.52 (s, 1H), 6.90-6.92 (m, 1H), 6.77 (d, J=7.2 Hz, 1H), 6.06 (dd, J=14.0, 6.8 Hz, 1H), 3.91 (q, J=6.8 Hz, 2H), 1.30 (t, J=6.8 Hz, 3H).

Step 2. Synthesis of Compound 801-C

A solution of compound 801-B (12.2 g, 87.7 mmol) in POCl$_3$ (160 mL) was stirred at 80° C. for overnight. The solvent was removed by evaporation. The residue was diluted with water (200 mL) and the mixture was adjusted to pH=8 with NaHCO$_3$, then extracted with DCM (200 mL*2). The combined organic solution was dried over NaSO$_4$, filtered and concentrated to give the crude which was purified by column chromatography on silica gel eluted with PE:EtOAc (4:1) to give the product 801-C (2-chloro-3-ethoxypyridine, 12.1 g, 87%) as yellow oil.

$^1$H NMR (300 MHz, CDCl$_3$) δ 7.93 (t, J=3.0 Hz, 1H), 7.15-7.18 (m, 2H), 4.09 (q, J=7.2 Hz, 2H), 1.46 (t, J=7.2 Hz, 3H).

Step 3. Synthesis of Compound 801-D

Na (13.1 g, 571 mmol) was carefully added to MeOH (250 mL) and stirred at 30° C. until Na was disappeared. Then, compound 801-C (9.0 g, 57.14 mmol) was added to the mixture and the mixture was heated to reflux for 2 days. The solvent was removed. The residue was diluted with DCM (300 mL), washed with water (200 mL*2), dried and concentrated to give product 801-D (3-ethoxy-2-methoxypyridine, 7.2 g, yield: 83%) as yellow oil.

$^1$H NMR (300 MHz, CDCl$_3$) δ 7.71 (dd, J=5.1, 1.5 Hz, 1H), 7.02 (dd, J=7.8, 1.2 Hz, 1H), 6.80 (dd, J=7.8, 5.1 Hz, 1H), 4.03-4.12 (m, 5H), 1.46 (t, J=6.9 Hz, 3H).

Step 4. Synthesis of Compound 801-E

To a solution of compound 801-D (7.2 g, 47 mmol) and NaOAc (4.6 g, 56.4 mmol) in AcOH (120 mL) was added Br$_2$ (9.0 g, 56.4 mmol) in AcOH (20 mL) slowly at 10° C. The mixture was stirred at 30° C. for overnight. The reaction mixture was poured into ice (300 g), extracted with MTBE (methyl tert-butyl ether, 100 mL*2). The combined organic layer was dried over Na$_2$SO$_4$, filtered and concentrated to give the crude product which was purified by column chromatography on silica gel eluted with PE:EtOAc (20:1) to give the product 801-E (5-bromo-3-ethoxy-2-methoxypyridine, 8.4 g, 77%) as yellow oil.

$^1$H NMR (300 MHz, CDCl$_3$) δ 7.77 (d, J=2.1 Hz, 1H), 7.13 (d, J=1.8 Hz, 1H), 4.05-4.11 (m, 2H), 3.98 (s, 3H), 1.44-1.51 (m, 3H).

Step 5. Synthesis of Compound 801-F

To a solution of 801-E (8.4 g, 36.2 mmol) in THF (150 mL) was added n-BuLi (17.4 mL, 2.5 M) slowly at −70° C. The mixture was stirred at −70° C. for 1.5 hours. DMF (7 mL, 90.5 mmol) was added to the reaction mixture and stirred at −70° C. for 0.5 hour. The mixture was quenched with NH$_4$Cl (100 mL), extracted with EtOAc (100 mL*2). The combined EtOAc solution was washed with brine (100 mL), dried over NaSO$_4$, filtered and concentrated to get crude product 801-F (5-ethoxy-6-methoxynicotinaldehyde, 6.5 g) as red solid.

$^1$H NMR (400 MHz, CDCl$_3$) δ 9.85 (s, 1H), 8.11 (d, J=2.0 Hz, 1H), 7.38 (d, J=2.0 Hz, 1H), 4.07-4.13 (m, 2H), 4.04 (s, 3H), 1.41-1.47 (m, 3H).

Step 6. Synthesis of Compound 801-G

To a solution of dimethyl sulfone (30.8 g, 328 mmol), KOH (1.84 g, 32.8 mmol) in DMF (400 mL) was added 801-F (5.94 g, 32.8 mmol) in DMF (100 mL) slowly. The mixture was stirred at 30° C. for 3 hours. The mixture was quenched with NH$_4$Cl (500 mL), extracted with EtOAc (500 mL*2). The combined organic phase was washed with brine (500 mL*2), dried over Na$_2$SO$_4$ then filtered and concentrated to get the crude product which was purified by column chromatography on silica gel eluted with PE:EtOAc (2:1) to give the product 801-G (3-ethoxy-2-methoxy-5-(2-(methylsulfonyl)vinyl)pyridine, 0.71 g, 8.5%) as brown solid.

$^1$H NMR (300 MHz, CDCl$_3$) δ 7.87 (d, J=1.8 Hz, 1H), 7.58 (d, J=15.3 Hz, 1H), 7.13 (d, J=1.8 Hz, 1H), 6.80 (d, J=15.3 Hz, 1H), 4.09-4.16 (m, 2H), 4.06 (s, 3H), 3.05 (s, 3H), 1.52 (t, J=6.9 Hz, 3H).

Step 7. Synthesis of Compound 801-H

A solution of H$_3$BO$_3$ (0.368 g, 5.95 mmol) in H$_2$O (6 mL) was stirred at 50° C. for 15 minutes. Compound 801-G (1.1 g, 4.3 mmol) was added and stirred at 50° C. for 15 minutes. Then, NH$_4$OH (60 mL) was added, the reaction mixture was stirred at 80° C. in sealed tube for 3 days. The mixture was extracted with DCM (50 mL*3), the combined organic phase was extracted with 2 N HCl (50 mL*2). The water phase was adjusted the pH=10 with NaOH, extracted with DCM (100 mL*2). The combined DCM solution was dried and concentrated to get the product 801-H (1-(5-ethoxy-6-methoxypyridin-3-yl)-2-(methylsulfonyl)ethanamine, 0.71 g, 66%).

$^1$H NMR (300 MHz, CDCl$_3$) δ 7.71 (s, 1H), 7.12 (s, 1H), 4.67 (d, J=9.6 Hz, 1H), 4.11 (q, J=6.9 Hz, 2H), 4.01 (s, 3H), 3.09-3.40 (m, 2H), 2.99 (s, 3H), 1.88 (s, 2H), 1.49 (t, J=6.9 Hz, 3H).

Step 8. Synthesis of Compound 801

A mixture of compound (N-(1,3-dioxo-1,3-dihydroisobenzofuran-4-yl)acetamide, 112 mg, 0.55 mmol) and 801-H (150 mg, 0.55 mmol) in HOAc (5 mL) was heated to 110° C. for overnight. Concentrated to dry under reduced pressure, the residue was purified by Prep-HPLC to afford 801 (N-(2-(1-(5-ethoxy-6-methoxypyridin-3-yl)-2-(methylsulfonyl)ethyl)-1,3-dioxoisoindolin-4-yl)acetamide, 66 mg, 26%) as a white solid.

$^1$H NMR (400 MHz, DMSO-d$_6$) δ 9.70 (s, 1H), 8.44 (d, J=8.4 Hz, 1H), 7.78-7.81 (m, 2H), 7.57 (d, J=6.8 Hz, 1H), 7.39 (s, 1H), 5.83 (dd, J=10.4, 4.4 Hz, 1H), 4.32-4.38 (m, 1H), 4.15-4.20 (m, 1H), 4.05-4.10 (m, 2H), 3.85 (s, 3H), 3.04 (s, 3H), 2.19 (s, 3H), 1.34 (t, J=6.8 Hz, 3H). LCMS: [(M+1)]$^+$=462.0.

Example 16. Synthesis of Compound 901

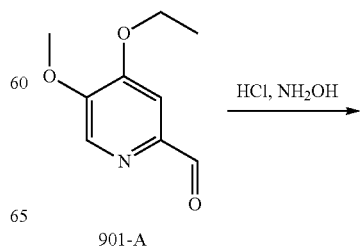

901-A

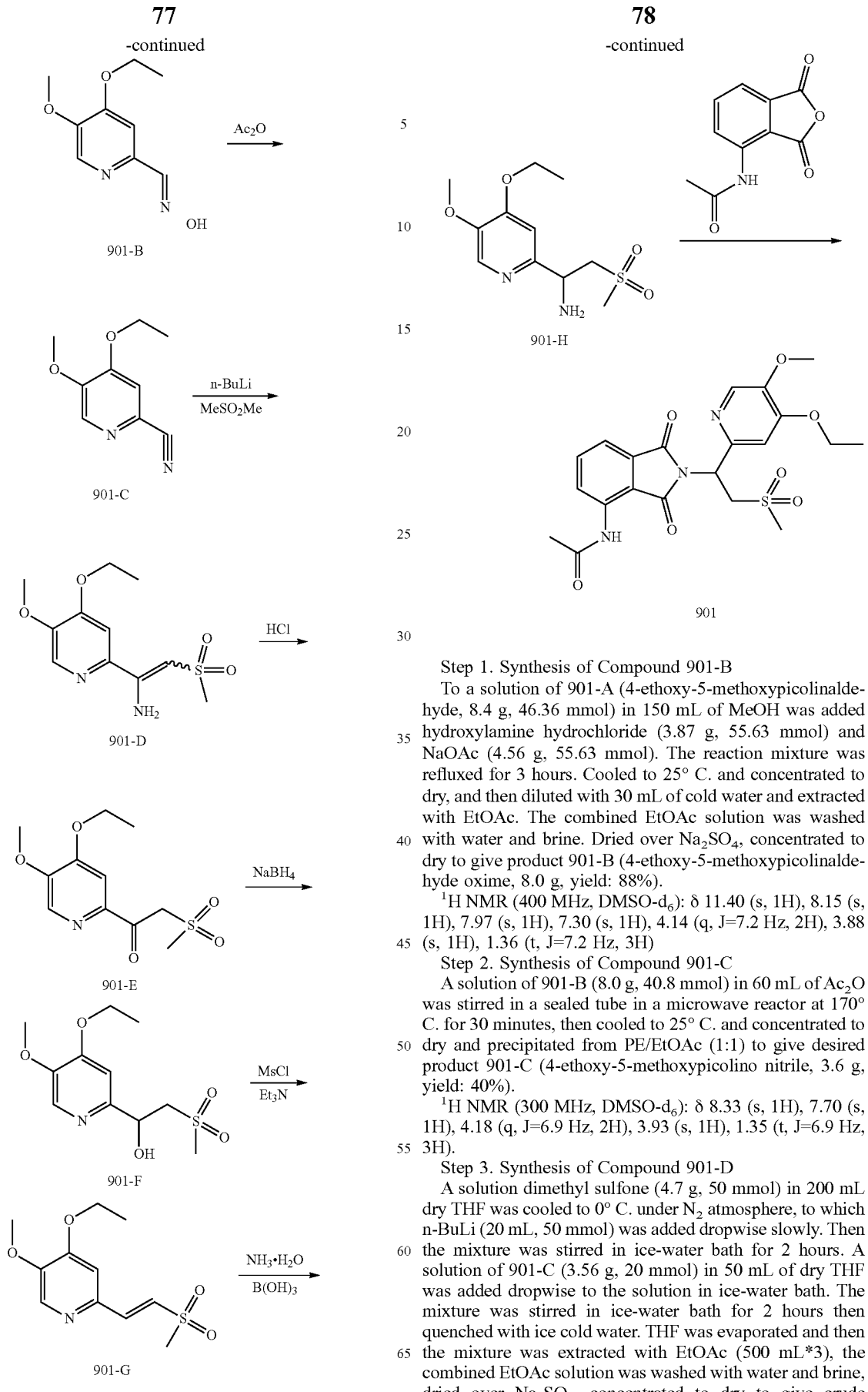

Step 1. Synthesis of Compound 901-B

To a solution of 901-A (4-ethoxy-5-methoxypicolinaldehyde, 8.4 g, 46.36 mmol) in 150 mL of MeOH was added hydroxylamine hydrochloride (3.87 g, 55.63 mmol) and NaOAc (4.56 g, 55.63 mmol). The reaction mixture was refluxed for 3 hours. Cooled to 25° C. and concentrated to dry, and then diluted with 30 mL of cold water and extracted with EtOAc. The combined EtOAc solution was washed with water and brine. Dried over $Na_2SO_4$, concentrated to dry to give product 901-B (4-ethoxy-5-methoxypicolinaldehyde oxime, 8.0 g, yield: 88%).

$^1$H NMR (400 MHz, DMSO-$d_6$): δ 11.40 (s, 1H), 8.15 (s, 1H), 7.97 (s, 1H), 7.30 (s, 1H), 4.14 (q, J=7.2 Hz, 2H), 3.88 (s, 1H), 1.36 (t, J=7.2 Hz, 3H)

Step 2. Synthesis of Compound 901-C

A solution of 901-B (8.0 g, 40.8 mmol) in 60 mL of $Ac_2O$ was stirred in a sealed tube in a microwave reactor at 170° C. for 30 minutes, then cooled to 25° C. and concentrated to dry and precipitated from PE/EtOAc (1:1) to give desired product 901-C (4-ethoxy-5-methoxypicolino nitrile, 3.6 g, yield: 40%).

$^1$H NMR (300 MHz, DMSO-$d_6$): δ 8.33 (s, 1H), 7.70 (s, 1H), 4.18 (q, J=6.9 Hz, 2H), 3.93 (s, 1H), 1.35 (t, J=6.9 Hz, 3H).

Step 3. Synthesis of Compound 901-D

A solution dimethyl sulfone (4.7 g, 50 mmol) in 200 mL dry THF was cooled to 0° C. under $N_2$ atmosphere, to which n-BuLi (20 mL, 50 mmol) was added dropwise slowly. Then the mixture was stirred in ice-water bath for 2 hours. A solution of 901-C (3.56 g, 20 mmol) in 50 mL of dry THF was added dropwise to the solution in ice-water bath. The mixture was stirred in ice-water bath for 2 hours then quenched with ice cold water. THF was evaporated and then the mixture was extracted with EtOAc (500 mL*3), the combined EtOAc solution was washed with water and brine, dried over $Na_2SO_4$, concentrated to dry to give crude product 901-D (1-(4-ethoxy-5-methoxypyridin-2-yl)-2-(methylsulfonyl)ethenamine, 5.5 g) which was directly used in the next step without purification.

Step 4. Synthesis of Compound 901-E

To a solution of 901-D (5.0 g, 18.4 mmol) in 140 mL THF cooled with ice-water was added 2N HCl (60 mL). The mixture was stirred at 25° C. for overnight. THF was evaporated and the residue was basified with sat. NaHCO$_3$. The mixture was extracted with EtOAc (200 mL*3). The combined EtOAc solution was washed with brine, dried over Na$_2$SO$_4$. Concentrated to dry to give the product 901-E (1-(4-ethoxy-5-methoxypyridin-2-yl)-2-(methylsulfonyl)ethenone, 6.5 g).

$^1$H NMR (400 MHz, DMSO-d$_6$): δ 8.38 (s, 1H), 7.60 (s, 1H), 5.15 (s, 2H), 4.22 (q, J=6.8 Hz, 2H), 3.99 (s, 3H), 3.17 (s, 3H), 1.37 (t, J=6.8 Hz, 3H).

Step 5. Synthesis of Compound 901-F

To a solution of 901-E (6.5 g crude, 23.8 mmol) in 100 mL of MeOH cooled with ice-water was added NaBH$_4$ (1.8 g, 47.6 mmol) portion wise. The mixture was stirred at 25° C. for 2 hours then quenched with 2 N HCl (30 mL) and stirred for 30 minutes. The mixture was concentrated to dry and basified with sat. NaHCO$_3$ and extracted with DCM/MeOH (20:1, 400 mL*2). The combined organic phase was washed with brine. Dried over Na$_2$SO$_4$, concentrated to dry to give crude product 901-F (1-(4-ethoxy-5-methoxypyridin-2-yl)-2-(methylsulfonyl) ethanol, 5.5 g).

Step 6. Synthesis of Compound 901-G

To a solution of 901-F (5.5 g, 20 mmol) in 100 mL of DCM cooled with ice-water was added Et$_3$N (5.6 mL, 40 mmol), followed by added MsCl (2.3 mL, 30 mmol) dropwise. The mixture was stirred at 25° C. for overnight then quenched with ice-water and stirred for 30 minutes. Extracted with DCM (100 mL*2), the combined organic phase was washed with water and brine. Dried over Na$_2$SO$_4$. Concentrated to dry and crystallized from PE/EtOAc (1:1) to give product 901-G (4-ethoxy-5-methoxy-2-(2-(methylsulfonyl)vinyl)pyridine, 4.0 g, yield: 34% for 4 steps).

$^1$H NMR (300 MHz, DMSO-d$_6$): δ 8.26 (s, 1H), 7.39-7.59 (m, 3H), 4.12-4.18 (m, 2H), 3.90 (s, 3H), 3.12 (s, 3H), 1.36 (t, J=6.9 Hz, 3H).

Step 7. Synthesis of Compound 901-H

A solution of B(OH)$_3$ (93 mg, 1.5 mmol) in 5 mL of water was heated to 50° C. for 15 minutes. 901-G (515 mg, 2.0 mmol) was added and the mixture was stirred for 30 minutes. Then 30 mL of NH$_3$.H$_2$O was added. The mixture was stirred at 80° C. in a sealed tube for 3 days. Cooled to 25° C. and concentrated to dry and basified with sat. NaHCO$_3$, and stirred at 25° C. for 30 minutes. The mixture was extracted with DCM/MeOH (50 mL*3), the combined organic phase was washed with brine, dried over Na$_2$SO$_4$, concentrated to dry to give crude product 901-H (1-(4-ethoxy-5-methoxypyridin-2-yl)-2-(methylsulfonyl)ethanamine, 470 mg, yield: 86%).

$^1$H NMR (400 MHz, DMSO-d$_6$): δ 8.07 (s, 1H), 7.17 (s, 1H), 4.29-4.32 (m, 1H), 4.13 (q, J=7.2 Hz, 2H), 3.82 (s, 3H), 3.37-3.46 (m, 2H), 3.05 (s, 3H), 1.36 (t, J=7.2 Hz, 3H).

Step 8. Synthesis of Compound 901

To a solution of 901-H (220 mg, 0.8 mmol) in 20 mL of HOAc was added N-(1,3-dioxo-1,3-dihydroisobenzofuran-4-yl)acetamide (164 mg, 0.8 mmol) then the mixture was refluxed for overnight. Then the mixture was cooled to 25° C. and concentrated to dry and purified by prep-HPLC to give product 901 (N-(2-(1-(4-ethoxy-5-methoxypyridin-2-yl)-2-(methylsulfonyl)ethyl)-1,3-dioxoisoindolin-4-yl)acetamide, 100 mg, yield: 27%).

$^1$H NMR (400 MHz, DMSO-d$_6$): δ 9.71 (s, 1H), 8.48 (d, J=8.4 Hz, 1H), 8.08 (s, 1H), 7.79-7.83 (m, 1H), 7.59 (d, J=6.8 Hz, 1H), 7.10 (s, 1H), 5.86 (dd, J=10.8, 3.6 Hz, 1H), 5.86 (dd, J=3.6, 7.2 Hz, 1H), 4.40 (dd, J=14.8, 3.6 Hz, 1H), 4.16-4.19 (m, 1H), 4.10 (q, J=7.2 Hz, 2H), 3.82 (s, 3H), 3.09 (s, 3H), 2.19 (s, 3H), 1.32 (t, J=7.2 Hz, 3H). LCMS: [(M+1)]$^+$=461.9.

Synthesis of Starting Material 901-A

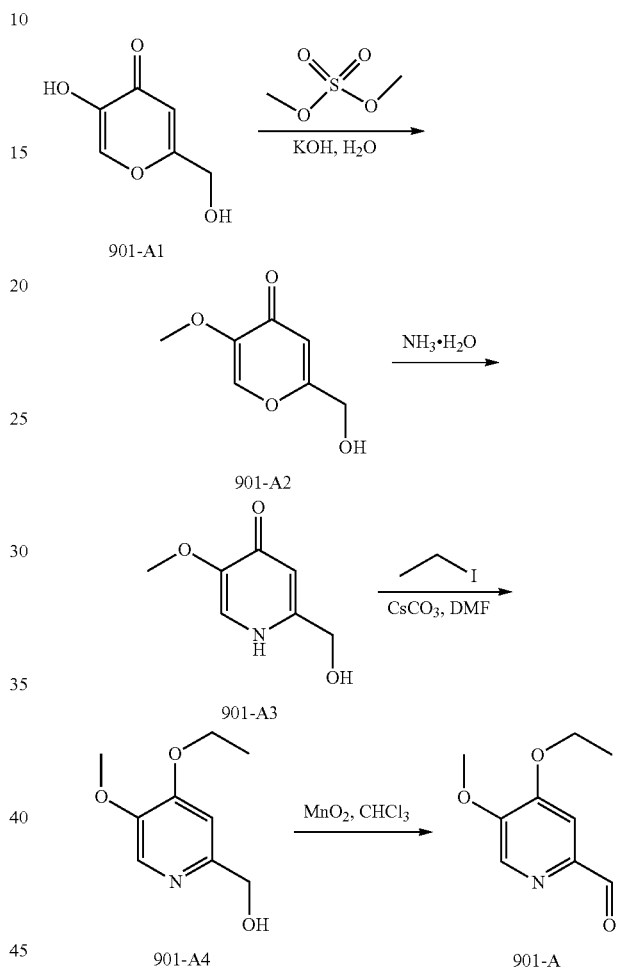

Synthesis of Compound 901-A2

A solution of 901-A1 (5-hydroxy-2-(hydroxymethyl)-4H-pyran-4-one, CAS number 501-30-4, 60 g, 422 mmol) in 300 mL of H$_2$O and KOH (30 g) was cooled to 10° C. The Sulfuric acid dimethyl ester (53.2 g, 422 mmol) was added by dropwise at 10° C. The mixture was stirred at 10° C. for 1 hour, then filtrated, collected the solid, washed with acetone (40 mL), dried to give the product 901-A2 (2-(hydroxymethyl)-5-methoxy-4H-pyran-4-one, 17.5 g, yield: 26.6%) as yellow solid.

$^1$H NMR (400 MHz, DMSO) δ 8.08 (s, 1H), 6.30 (s, 1H), 5.79 (br s, 1H), 4.30 (s, 2H), 3.65 (s, 3H).

Synthesis of Compound 901-A3

To a sealable tube was added 901-A2 (2-(hydroxymethyl)-5-methoxy-4H-pyran-4-one, 32 g, 205 mmol) and NH$_4$OH (160 mL). The tube was sealed and heated to 90° C. for 3 hour. The mixture was concentrated, then MeOH (200 mL) and activated carbon (15 g) were added. The mixture was heated to reflux for 0.5 hour. The mixture was filtrated through a Celite pad and concentrated to dryness to give the product 901-A3 (2-(hydroxymethyl)-5-methoxypyridin-4(1H)-one, 27.8 g, yield: 87%) as yellow solid.

$^1$H NMR (400 MHz, DMSO) δ 7.38 (s, 1H), 6.22 (s, 1H), 4.36 (s, 2H), 3.67 (s, 3H).

Synthesis of Compound 901-A4

To a solution of 901-A3 [2-(hydroxymethyl)-5-methoxypyridin-4(1H)-one, 27.8 g, 179 mmol) in DMF (280 mL) was added Cs$_2$CO$_3$ (64.2 g, 197 mmol). The mixture was heated to 85° C. and then the Iodo-ethane (29.3 g, 188 mmol) was added. The mixture was stirred at 85° C. for 2 hours. The mixture was filtrated. The filtrate was diluted with water (300 mL), extracted with DCM:MeOH=10:1 (300 mL*4), the organic phase was dried and concentrated to give crude product which was purified by column chromatography on silica gel eluted with EtOAc to give the product 901-A4 ((4-ethoxy-5-methoxypyridin-2-yl)methanol, 17.5 g, yield: 53%) as yellow solid.

$^1$H NMR (400 MHz, DMSO-d$_6$) δ 8.04 (s, 1H), 7.04 (s, 1H), 5.29 (t, J=6.0 Hz, 1H), 4.44 (d, J=5.6 Hz, 2H), 4.10 (q, J=7.2 Hz, 2H), 3.81 (s, 3H), 1.36 (t, J=7.2 Hz, 3H).

Synthesis of Compound 901-A

To a solution of 901-A4 ((4-ethoxy-5-methoxypyridin-2-yl)methanol, 10 g, 54.6 mmol) in CHCl$_3$ (400 mL) was added MnO$_2$ (47 g, 546 mmol). The mixture was heated to 65° C. and reacted for 2 hours. The mixture was filtrated, concentrated to give the product 901-A (4-ethoxy-5-methoxypicolinaldehyde, 9 g, yield: 91%) as gray solid.

$^1$H NMR (300 MHz, DMSO-d$_6$) δ 9.82 (s, 1H), 8.40 (s, 1H), 7.45 (s, 1H), 4.23-4.16 (m, 2H), 3.97 (s, 3H), 1.36 (t, J=6.9 Hz, 3H).

Example 17. Synthesis of Compound 702 and 703

Synthesis of Intermediate Compounds 701-F1 and 701-F2

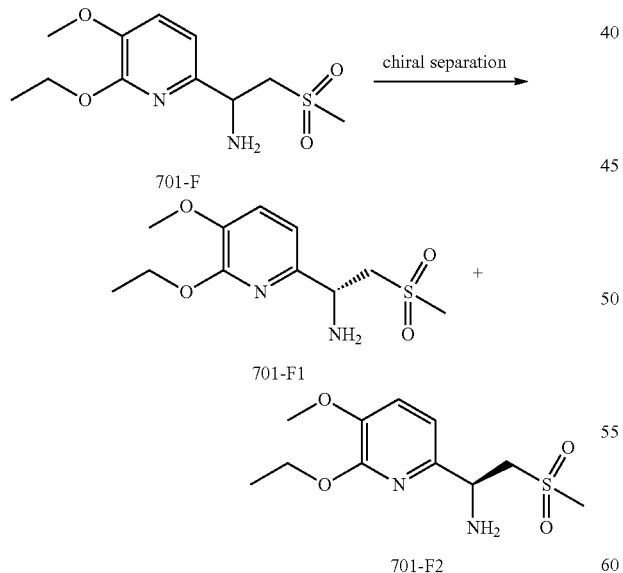

Compound 701-F (6.6 g, 24 mmol) was chiral separated to give the product 701-F1 ((R)-1-(6-ethoxy-5-methoxypyridin-2-yl)-2-(methylsulfonyl)ethanamine, 2.5 g, ee: 98.42%) and 701-F2 ((S)-1-(6-ethoxy-5-methoxypyridin-2-yl)-2-(methylsulfonyl)ethanamine, 1.7 g, ee: 98.29%).

Separation Method:
Column: chiralpak IA 5 μm 4.6*250 mm
Mobile phase: Hex:EtOH:DEA=70:30:0.2
Flow Rate (F): 1.0 mL/min
Wave Length (W): 230 nm
Temperature (T): 30° C.

Synthesis of Compound 702

Compound 702 was synthesized according to the method of compound 701 in Example 14, except the intermediate compound 701-F2 was used instead of compound 701-F.

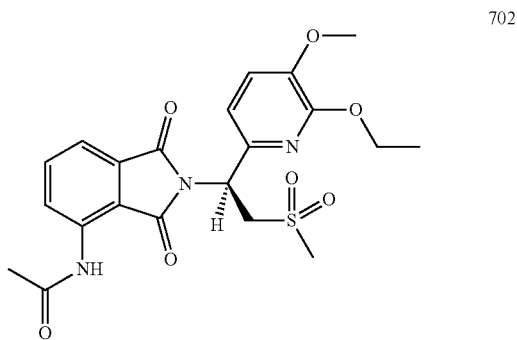 [SMILES: CCOc1nc([C@@H](CS(C)(=O)=O)N2C(=O)c3cccc(NC(C)=O)c3C2=O)ccc1OC]

(S)—N-(2-(1-(6-ethoxy-5-methoxypyridin-2-yl)-2-(methylsulfonyl)ethyl)-1,3-dioxoisoindolin-4-yl)acetamide $^1$H NMR (400 MHz, DMSO-d$_6$) δ 9.73 (s, 1H), 8.47 (d, J=8.4 Hz, 1H), 7.82 (t, J=8.0 Hz, 1H), 7.60 (d, J=7.2 Hz, 1H), 7.27 (d, J=8.0 Hz, 1H), 7.02 (d, J=8.0 Hz, 1H), 5.81 (dd, J=10.8, 3.2 Hz, 1H), 4.15-4.35 (m, 4H), 3.76 (s, 3H), 3.10 (s, 3H), 2.18 (s, 3H), 1.17 (t, J=7.2 Hz, 3H). LC-MS: 462.2 ([M+1]$^+$).

Synthesis of Compound 703

Compound 703 was synthesized according to the method of compound 701 in Example 14, except the intermediate compound 701-F1 was used instead of compound 701-F.

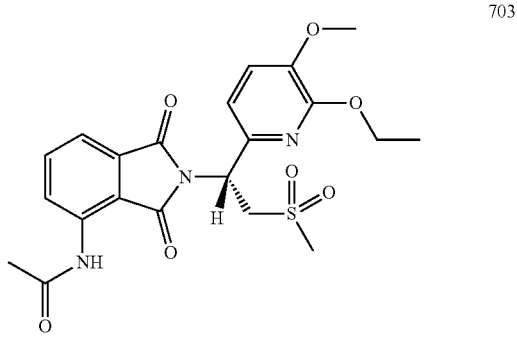 [SMILES: CCOc1nc([C@H](CS(C)(=O)=O)N2C(=O)c3cccc(NC(C)=O)c3C2=O)ccc1OC]

(R)—N-(2-(1-(6-ethoxy-5-methoxypyridin-2-yl)-2-(methylsulfonyl)ethyl)-1,3-dioxoisoindolin-4-yl)acetamide $^1$H NMR (400 MHz, DMSO-d$_6$) δ 9.73 (s, 1H), 8.47 (d, J=8.4 Hz, 1H), 7.82 (t, J=8.0 Hz, 1H), 7.60 (d, J=7.6 Hz, 1H), 7.27 (d, J=8.4 Hz, 1H), 7.02 (d, J=7.6 Hz, 1H), 5.81 (dd, J=10.8, 3.6 Hz, 1H), 4.15-4.35 (m, 4H), 3.76 (s, 3H), 3.10 (s, 3H), 2.18 (s, 3H), 1.17 (t, J=7.2 Hz, 3H). LC-MS: 462.1 ([M+1]$^+$).

Example 18. Synthesis of Compound 704, 705 and 706

Compound 705 and 706 were synthesized according to the method of compound 701 in Example 14, except the intermediate compound 701-F2 ((S)-1-(6-ethoxy-5-methoxypyridin-2-yl)-2-(methylsulfonyl)ethanamine) or 701-F1 ((R)-1-(6-ethoxy-5-methoxypyridin-2-yl)-2-(methylsulfonyl)ethanamine) was used respectively instead of compound 701-F and intermediate compound 101-E (N-(7-fluoro-1,3-dioxo-1,3-dihydroisobenzofuran-4-yl) acetamide) was used instead of compound N-(1,3-dioxo-1,3-dihydroisobenzofuran-4-yl) acetamide.

Compound 704 can be synthesized according to the method of compound 701 in Example 14, except the intermediate compound 101-E was used instead of compound N-(1,3-dioxo-1,3-dihydroisobenzofuran-4-yl) acetamide.

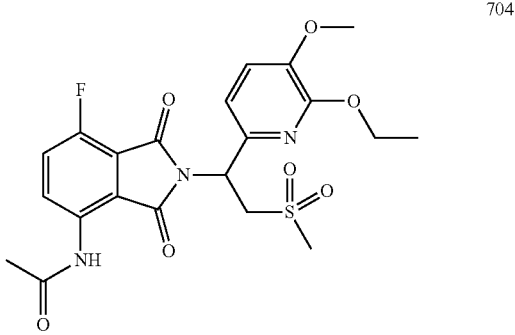 [SMILES: CCOc1nc(C(CS(C)(=O)=O)N2C(=O)c3c(F)ccc(NC(C)=O)c3C2=O)ccc1OC]

704

N-(2-(1-(6-ethoxy-5-methoxypyridin-2-yl)-2-(methylsulfonyl)ethyl)-7-fluoro-1,3-dioxoisoindolin-4-yl) acetamide

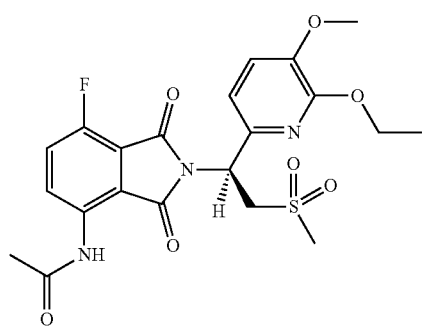

705

(S)—N-(2-(1-(6-ethoxy-5-methoxypyridin-2-yl)-2-(methylsulfonyl)ethyl)-7-fluoro-1,3-dioxoisoindolin-4-yl)acetamide $^1$H NMR (400 MHz, DMSO-d$_6$) δ 9.77 (s, 1H), 8.45 (dd, J=9.2, 3.6 Hz, 1H), 7.69 (t, J=9.2 Hz, 1H), 7.28 (d, J=8.4 Hz, 1H), 7.05 (d, J=8.4 Hz, 1H), 5.78-5.81 (m, 1H), 4.12-4.36 (m, 4H), 3.77 (s, 3H), 3.10 (s, 3H), 2.16 (s, 3H), 1.20 (t, J=6.8 Hz, 3H). LCMS: [(M+1)]$^+$=480.2

Example 19. Synthesis of Compound 707, 708 and 709

Compound 708 and 709 were synthesized according to the method of compound 701 in Example 14, except the intermediate compound 701-F2 ((S)-1-(6-ethoxy-5-methoxypyridin-2-yl)-2-(methylsulfonyl)ethanamine) or 701-F1 ((R)-1-(6-ethoxy-5-methoxypyridin-2-yl)-2-(methylsulfonyl)ethanamine) was used respectively instead of compound 701-F and intermediate compound 201-C (N-(6-fluoro-1,3-dioxo-1,3-dihydroisobenzofuran-4-yl) acetamide) was used instead of compound N-(1,3-dioxo-1,3-dihydroisobenzofuran-4-yl) acetamide.

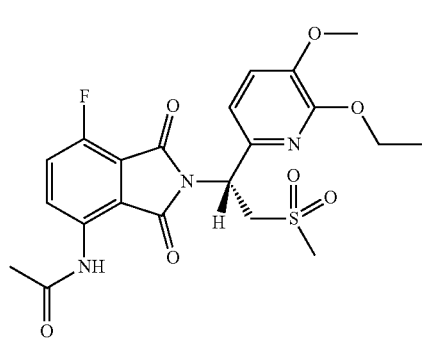

706

(R)—N-(2-(1-(6-ethoxy-5-methoxypyridin-2-yl)-2-(methylsulfonyl)ethyl)-7-fluoro-1,3-dioxoisoindolin-4-yl)acetamide $^1$H NMR (400 MHz, DMSO-d$_6$) δ 9.78 (s, 1H), 8.44-8.46 (m, 1H), 7.69 (t, J=8.8 Hz, 1H), 7.28 (d, J=8.0 Hz, 1H), 7.06 (d, J=8.0 Hz, 1H), 5.80 (d, J=8.0 Hz, 1H), 4.12-4.35 (m, 4H), 3.77 (s, 3H), 3.10 (s, 3H), 2.17 (s, 3H), 1.20 (t, J=6.8 Hz, 3H). LCMS: [(M+1)]$^+$=480.0

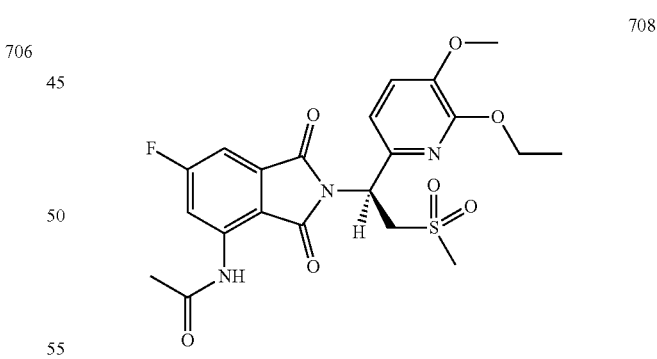

708

(S)—N-(2-(1-(6-ethoxy-5-methoxypyridin-2-yl)-2-(methylsulfonyl)ethyl)-6-fluoro-1,3-dioxoisoindolin-4-yl)acetamide $^1$H NMR (400 MHz, DMSO-d$_6$) δ 9.81 (s, 1H), 8.29 (dd, J=12.0, 1.6 Hz, 1H), 7.54 (dd, J=6.8, 1.6 Hz, 1H), 7.28 (d, J=8.4 Hz, 1H), 7.04 (d, J=8.0 Hz, 1H), 5.80 (dd, J=10.8, 3.2 Hz, 1H), 4.13-4.36 (m, 4H), 3.76 (s, 3H), 3.10 (s, 3H), 2.21 (s, 3H), 1.18 (t, J=7.2 Hz, 3H). LC-MS: 479.9 ([M+1]$^+$).

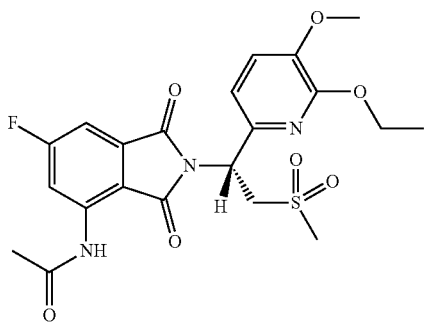

(R)—N-(2-(1-(6-ethoxy-5-methoxypyridin-2-yl)-2-(methylsulfonyl)ethyl)-6-fluoro-1,3-dioxoisoindolin-4-yl)acetamide $^1$H NMR (400 MHz, DMSO-d$_6$) δ 9.80 (s, 1H), 8.29 (dd, J=12.0, 2.0 Hz, 1H), 7.54 (dd, J=6.4, 2.0 Hz, 1H), 7.28 (d, J=8.0 Hz, 1H), 7.04 (d, J=8.0 Hz, 1H), 5.81 (dd, J=10.4, 3.2 Hz, 1H), 4.16-4.32 (m, 4H), 3.76 (s, 3H), 3.10 (s, 3H), 2.21 (s, 3H), 1.19 (t, J=7.2 Hz, 3H). LC-MS: 480.2 ([M+1]$^+$).

Compound 707 can be synthesized according to the method of compound 701 in Example 14, except the intermediate compound 201-C (N-(6-fluoro-1,3-dioxo-1,3-dihydroisobenzofuran-4-yl)acetamide) was used instead of compound N-(1,3-dioxo-1,3-dihydroisobenzofuran-4-yl) acetamide.

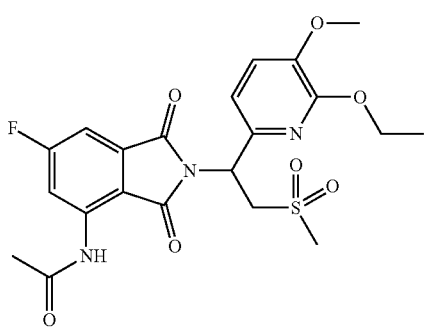

N-(2-(1-(6-ethoxy-5-methoxypyridin-2-yl)-2-(methylsulfonyl)ethyl)-6-fluoro-1,3-dioxoisoindolin-4-yl) acetamide Example 20. Synthesis of Compound 712

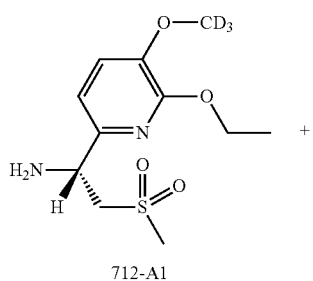

712-A1

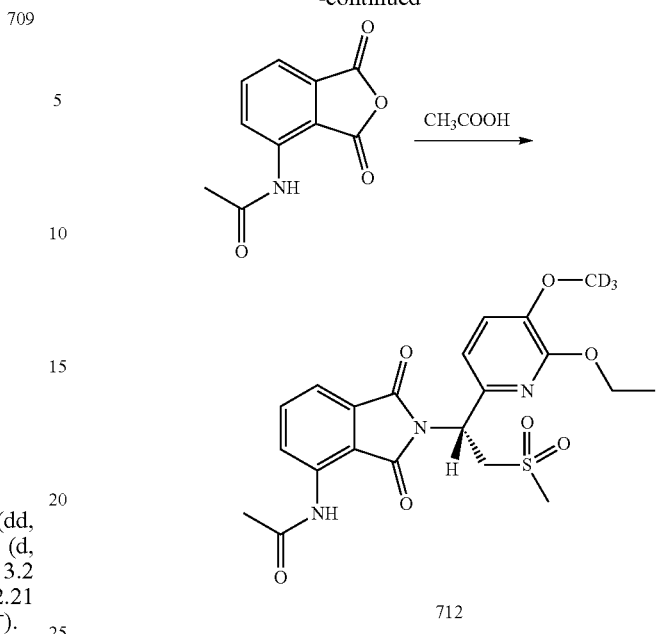

To a solution of N-(1,3-dioxo-1,3-dihydroisobenzofuran-4-yl) acetamide (117 mg, 0.568 mmol) in AcOH (5 mL) was added compound 712-A1 (150 mg, 0.54 mmol), the mixture was stirred at 80° C. for overnight. The reaction solution was concentrated by Rotary evaporator to dryness and purified by Prep-HPLC and freeze-dried to obtain compound 712 ((R)—N-(2-(1-(6-ethoxy-5-d$_3$-methoxypyridin-2-yl)-2-(methylsulfonyl)ethyl)-1,3-dioxoisoindolin-4-yl)acetamide, 185 mg).

$^1$H NMR (400 MHz, DMSO-d$_6$) δ 9.72 (s, 1H), 8.478 (d, J=8.4 Hz, 1H), 7.82 (t, J=8.0 Hz, 1H), 7.60 (d, J=7.2 Hz, 1H), 7.27 (d, J=8.0 Hz, 1H), 7.01 (d, J=8.4 Hz, 1H), 5.81 (dd, J=10.8, 3.2 Hz, 1H), 4.35-4.30 (m, 1H), 4.22-4.15 (m, 3H), 3.09 (s, 3H), 2.18 (s, 3H), 1.17 (t, J=7.2 Hz, 3H). LCMS: ([M+H]$^+$). 465.0. ee %=100%.

Synthesis of Intermediate Compound 712-A

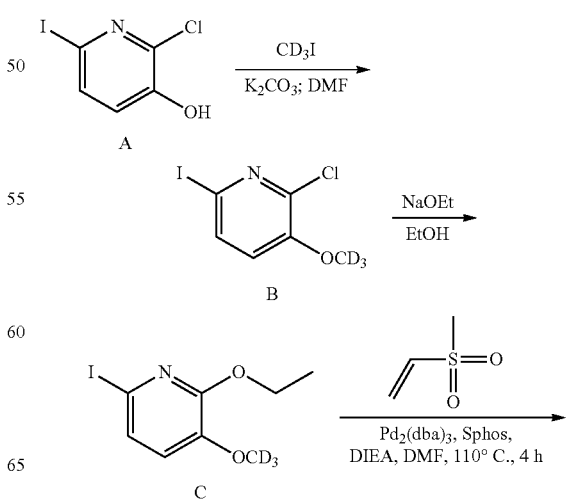

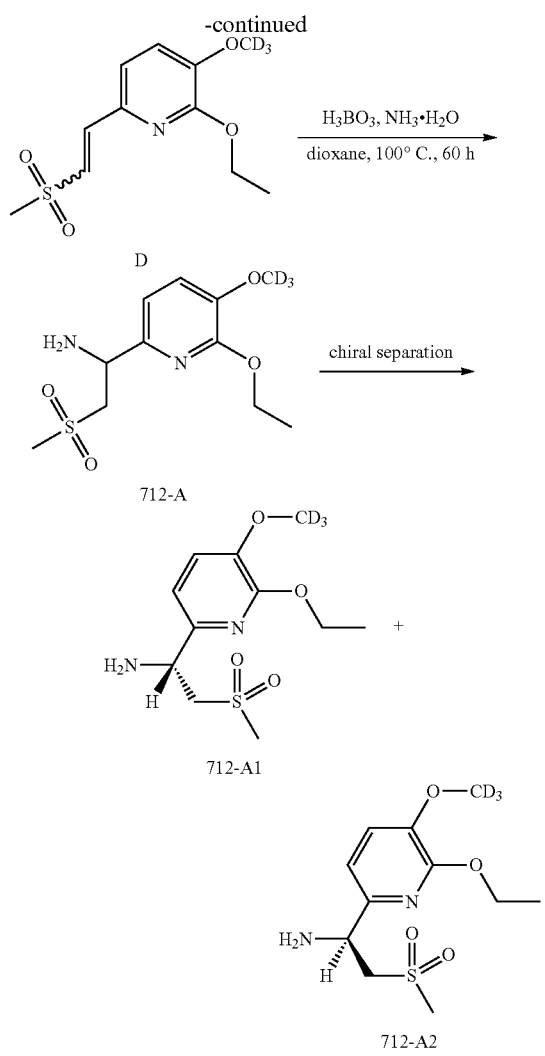

Step 1. Synthesis of Compound B

To a solution of A (2-chloro-6-iodopyridin-3-ol, CAS number 185220-68-2, 5 g, 19.6 mmol) in 14 mL of DMF was added $K_2CO_3$ (4.06 g, 29.4 mmol). The mixture was stirred for 30 minutes. $CD_3I$ (3.41 g, 23.5 mmol) was added. The mixture was stirred at 100° C. for 2 hours. The mixture was cooled and poured into 100 mL of water, stirred for 0.5 hour, filtrated, washed with water (200 mL×2), collected the solid, dried in vacuo to give compound B (2-chloro-6-iodo-3-$d_3$-methoxypyridine, 4.87 g, yield: 91%) as yellow solid.

$^1$H NMR (300 MHz, DMSO-$d_6$) δ 7.81 (d, J=8.4 Hz, 1H), 7.36 (d, J=8.4 Hz, 1H).

Step 2. Synthesis of Compound C

NaOEt (8.53 g, 125.3 mmol) was added in portions slowly to anhydrous EtOH (100 mL) at 10° C. The inner temperature was raised to 35° C. when the addition completed. Then B (2-chloro-6-iodo-3-$d_3$-methoxypyridine, 4.87 g, 17.9 mmol) was added and the mixture was heated to 100° C. and stirred for 2 hours. Cooled and the solvent was removed. The residue was diluted with EtOAc (100 mL) and ice water (100 mL), then stirred and stratified. The organic phase was washed with water (100 mL) and brine (100 mL), then dried over $Na_2SO_4$, filtered and concentrated to dry to give compound C (2-ethoxy-6-iodo-3-d3-methoxypyridine, 4.86 g, yield: 96%) as brown solid.

$^1$H NMR (300 MHz, DMSO-$d_6$) δ 7.30 (dd, J=8.1, 1.2 Hz, 1H), 7.03 (dd, J=8.1, 1.2 Hz, 1H), 4.28-4.21 (m, 2H), 1.32-1.27 (m, 3H).

Step 3. Synthesis of Compound D

To a solution of C (2-ethoxy-6-iodo-3-$d_3$-methoxypyridine, 4.86 g, 17.2 mmol) in DMF (50 mL, $N_2$ bubbled for 0.5 hour) were added DIEA (3.33 g, 25.8 mmol), Methanesulfonyl-ethene (2.19 g, 20.6 mmol), S-Phos (2-dicyclohexylphosphine-2', 6'-dimethoxy-biphenyl, 1.09 g, 2.58 mmol), and $Pd_2(dba)_3$ (1.06 g, 1.5 mmol). The mixture was purged with $N_2$ for 4 times, and stirred at 110° C. for 4 hours under $N_2$ protection. Then the mixture was cooled, filtered and the filtrate was concentrated through Rotary evaporator to give crude product, which was purified by column chromatography on silica gel (PE:EtOAc=4:1 to 1:1). to give D (2-ethoxy-3-d3-methoxy-6-(2-(methylsulfonyl)vinyl)pyridine, 3.6 g, 80%) as off white solid.

$^1$H NMR (300 MHz, DMSO-$d_6$): δ 7.43-7.31 (m, 4H), 4.43-4.36 (m, 2H), 3.11 (s, 3H), 1.34 (t, J=7.2 Hz, 3H).

Step 4. Synthesis of Compound 712-A $B(OH)_3$ (2.49 g, 40.3 mmol), dioxane (40 mL), D (2-ethoxy-3-d3-methoxy-6-(2-(methylsulfonyl)vinyl)pyridine, 7.0 g, 26.9 mmol) and $NH_3.H_2O$ (200 mL) was added to sealed tube and the mixture was stirred at 100° C. for 60 hours. Then the sealed tube was cooled, deflated and opened. The reaction solution was concentrated to 50 mL, then the precipitated solid was filtered and washed with $H_2O$. The filtration was concentrated to dryness through rotary evaporator to give a crude which was slurried with PE/EtOAc (3:1, 40 mL) to give 712-A (1-(6-ethoxy-5-$d_3$-methoxypyridin-2-yl)-2-(methylsulfonyl)ethanamine, 5.3 g, yield: 71%) as white solid.

$^1$H NMR (400 MHz, DMSO-$d_6$): δ 7.23 (d, J=7.8 Hz, 1H), 6.97 (d, J=8.1 Hz, 1H), 4.33 (q, J=6.9 Hz, 2H), 4.23-4.19 (m, 1H), 3.76 (s, 3H), 3.38-3.36 (m, 2H), 3.02 (s, 3H), 2.21 (br s, 2H), 1.31 (t, J=6.9 Hz, 3H).

Step 5. Chiral Separation

712-A (1-(6-ethoxy-5-$d_3$-methoxypyridin-2-yl)-2-(methylsulfonyl)ethanamine) was purified by chiral Prep-HPLC to afford 712-A1 ((R)-1-(6-ethoxy-5-$d_3$-methoxypyridin-2-yl)-2-(methylsulfonyl)ethanamine) and 712-A2 ((S)-1-(6-ethoxy-5-$d_3$-methoxypyridin-2-yl)-2-(methylsulfonyl) ethanamine).

Chiral Separation conditions: Column: CHIRALPAK IA, Particle size: 5 μm; Wave Length: 230 nm; Mobile Phase: Hexane/EtOH/(0.2% TEA)=70/30[V/V (0.2% TEA)]; Temperature: 30° C.

Example 21. Synthesis of Compound 710 and 711

Compound 711 was synthesized according to the method of compound 712 in Example 20, except the corresponding substrate 712-A2 was used instead of compound 712-A1.

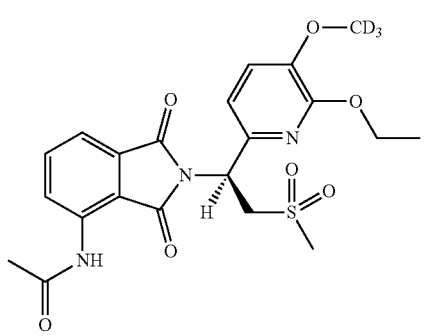

(S)—N-(2-(1-(6-ethoxy-5-d₃-methoxypyridin-2-yl)-2-(methylsulfonyl)ethyl)-1,3-dioxoisoindolin-4-yl)acetamide ¹H NMR (400 MHz, DMSO-d₆) δ 9.72 (s, 1H), 8.47 (d, J=8.4 Hz, 1H), 7.82 (t, J=8.4 Hz, 1H), 7.60 (d, J=7.2 Hz, 1H), 7.27 (d, J=8.0 Hz, 1H), 7.02 (d, J=8.4 Hz, 1H), 5.81 (dd, J=10.4, 3.6 Hz, 1H), 4.32 (dd, J=14.4, 3.6 Hz, 1H), 4.22-4.15 (m, 3H), 3.09 (s, 3H), 2.18 (s, 3H), 1.17 (t, J=7.2 Hz, 3H). LCMS: ([M+H]⁺).=465.0. ee %=98.3%

Compound 710 can be synthesized according to the method of compound 712 in Example 20, except the corresponding substrate 712-A was used instead of compound 712-A1.

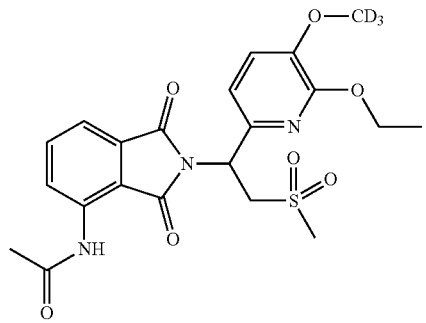

N-(2-(1-(6-ethoxy-5-d₃-methoxypyridin-2-yl)-2-(methylsulfonyl)ethyl)-1,3-dioxoisoindolin-4-yl)acetamide)

Example 22. Synthesis of Compound 716, 718 and 719

Compound 719 was synthesized according to the method of compound 712 in Example 20, except the corresponding substrate 101-E (N-(7-fluoro-1,3-dioxo-1,3-dihydroisobenzofuran-4-yl)acetamide) was used instead of N-(1,3-dioxo-1,3-dihydroisobenzofuran-4-yl)acetamide.

Compound 718 was synthesized according to the method of compound 712 in Example 20, except the corresponding substrate 101-E was used instead of N-(1,3-dioxo-1,3-dihydroisobenzofuran-4-yl)acetamide and the corresponding substrate 712-A2 ((S)-1-(6-ethoxy-5-d₃-methoxypyridin-2-yl)-2-(methylsulfonyl)ethanamine) was used instead of 712-A1 ((R)-1-(6-ethoxy-5-d₃-methoxypyridin-2-yl)-2-(methylsulfonyl) ethanamine)).

(R)—N-(2-(1-(6-ethoxy-5-d₃-methoxypyridin-2-yl)-2-(methylsulfonyl)ethyl)-7-fluoro-1,3-dioxoisoindolin-4-yl)acetamide)

¹H NMR (400 MHz, DMSO-d₆) δ 9.76 (s, 1H), 8.45 (dd, J=9.2, 3.6 Hz, 1H), 7.69 (t, J=9.2 Hz, 1H), 7.27 (d, J=7.6 Hz, 1H), 7.05 (d, J=8.0 Hz, 1H), 5.79 (dd, J=10.8, 3.6 Hz, 1H), 4.35-4.31 (m, 1H), 4.23-4.12 (m, 3H), 3.10 (s, 3H), 2.16 (s, 3H), 1.20 (t, J=7.2 Hz, 3H).

LCMS: ([M+H]⁺)=483.0. ee %=99.6%

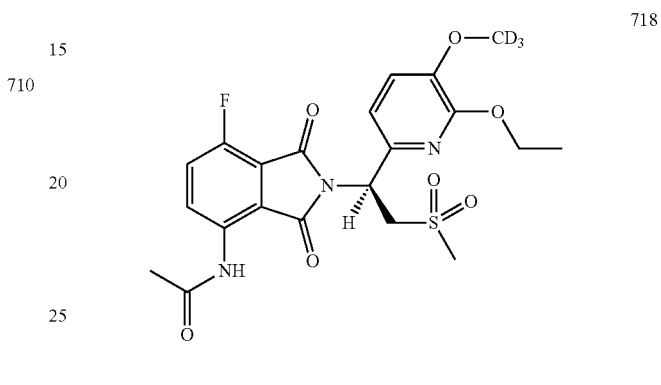

(S)—N-(2-(1-(6-ethoxy-5-d₃-methoxypyridin-2-yl)-2-(methylsulfonyl)ethyl)-7-fluoro-1,3-dioxoisoindolin-4-yl)acetamide)

¹H NMR (400 MHz, DMSO-d₆) δ 9.76 (s, 1H), 8.45 (dd, J=9.2, 3.6 Hz, 1H), 7.69 (t, J=9.2 Hz, 1H), 7.27 (d, J=8.0 Hz, 1H), 7.05 (d, J=8.0 Hz, 1H), 5.79 (dd, J=10.8, 4.0 Hz, 1H), 4.33 (dd, J=14.8, 4.0 Hz, 1H), 4.23-4.13 (m, 3H), 3.10 (s, 3H), 2.16 (s, 3H), 1.20 (t, J=6.8 Hz, 3H). LCMS: ([M+H]⁺)=482.9. ee %=98.5%

Compound 716 can be synthesized according to the method of compound 712 in Example 20, except the corresponding substrate 101-E (N-(7-fluoro-1,3-dioxo-1,3-dihydroisobenzofuran-4-yl)acetamide) was used instead of N-(1,3-dioxo-1,3-dihydroisobenzofuran-4-yl)acetamide and the corresponding substrate 712-A (1-(6-ethoxy-5-d₃-methoxypyridin-2-yl)-2-(methyl sulfonyl)ethanamine) was used instead of 712-A1 ((R)-1-(6-ethoxy-5-d₃-methoxypyridin-2-yl)-2-(methylsulfonyl) ethanamine)).

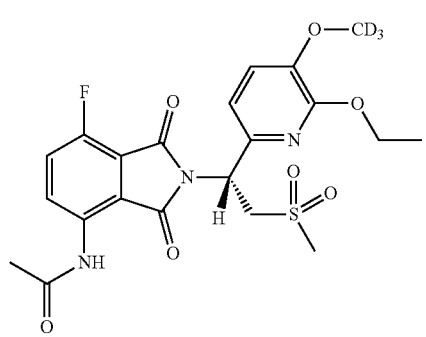

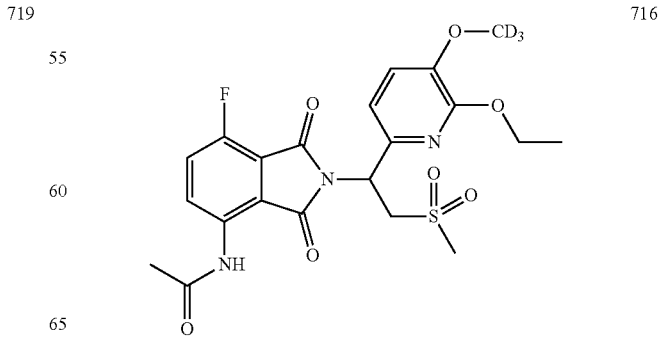

N-(2-(1-(6-ethoxy-5-d$_3$-methoxypyridin-2-yl)-2-(methylsulfonyl)ethyl)-7-fluoro-1,3-dioxoisoindolin-4-yl)acetamide)

Example 23. Synthesis of Compound 722, 724 and 725

Compound 725 was synthesized according to the method of compound 712 in Example 20, except the corresponding substrate 201-C (N-(6-fluoro-1,3-dioxo-1,3-dihydroisobenzofuran-4-yl)acetamide) was used instead of N-(1,3-dioxo-1,3-dihydroisobenzofuran-4-yl) acetamide.

Compound 724 was synthesized according to the method of compound 712 in Example 20, except the corresponding substrate 201-C (N-(6-fluoro-1,3-dioxo-1,3-dihydroisobenzofuran-4-yl)acetamide) was used instead of N-(1,3-dioxo-1,3-dihydroisobenzofuran-4-yl) acetamide and the corresponding substrate 712-A2 ((S)-1-(6-ethoxy-5-d$_3$-methoxypyridin-2-yl)-2-(methylsulfonyl)ethanamine) was used instead of 712-A1 ((R)-1-(6-ethoxy-5-d$_3$-methoxy pyridin-2-yl)-2-(methylsulfonyl) ethanamine).

(S)—N-(2-(1-(6-ethoxy-5-d$_3$-methoxypyridin-2-yl)-2-(methylsulfonyl)ethyl)-6-fluoro-1,3-dioxoisoindolin-4-yl)acetamide $^1$H NMR (400 MHz, DMSO-d$_6$) δ 9.79 (s, 1H), 8.31-8.27 (m, 1H), 7.53 (dd, J=6.8, 2.4 Hz, 1H), 7.27 (d, J=8.4 Hz, 1H), 7.03 (d, J=8.0 Hz, 1H), 5.80 (dd, J=10.8, 3.6 Hz, 1H), 4.33 (dd, J=14.4, 3.6 Hz, 1H), 4.21-4.14 (m, 3H), 3.10 (s, 3H), 2.21 (s, 3H), 1.19 (t, J=7.2 Hz, 3H). LCMS: ([M+H]$^+$)= 483.2. ee %=98.4%

Compound 722 can be synthesized according to the method of compound 712 in Example 20, except the corresponding substrate 201-C (N-(6-fluoro-1,3-dioxo-1,3-dihydroisobenzofuran-4-yl)acetamide) was used instead of N-(1,3-dioxo-1,3-dihydroisobenzofuran-4-yl) acetamide and the corresponding substrate 712-A (1-(6-ethoxy-5-d$_3$-methoxypyridin-2-yl)-2-(methylsulfonyl)ethanamine) was used instead of 712-A1 ((R)-1-(6-ethoxy-5-d$_3$-methoxy pyridin-2-yl)-2-(methylsulfonyl) ethanamine).

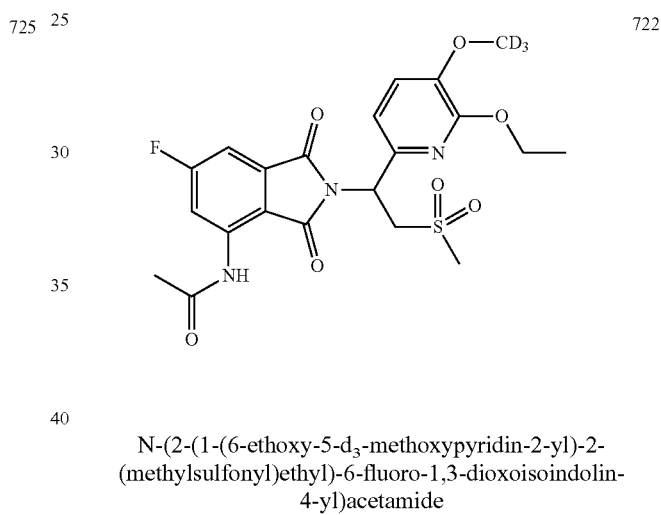

725

722

(R)—N-(2-(1-(6-ethoxy-5-d$_3$-methoxypyridin-2-yl)-2-(methylsulfonyl)ethyl)-6-fluoro-1,3-dioxoisoindolin-4-yl)acetamide $^1$H NMR (400 MHz, DMSO-d$_6$) δ 9.79 (s, 1H), 8.29 (dd, J=12.0, 2.0 Hz, 1H), 7.53 (dd, J=6.8, 2.4 Hz, 1H), 7.27 (d, J=8.0 Hz, 1H), 7.03 (d, J=8.4 Hz, 1H), 5.80 (dd, J=10.8, 3.6 Hz, 1H), 4.33 (dd, J=14.8, 4.0 Hz, 1H), 4.21-4.14 (m, 3H), 3.09 (s, 3H), 2.21 (s, 3H), 1.19 (t, J=7.2 Hz, 3H). LCMS: ([M+H]$^+$)=483.0. ee %=100%

N-(2-(1-(6-ethoxy-5-d$_3$-methoxypyridin-2-yl)-2-(methylsulfonyl)ethyl)-6-fluoro-1,3-dioxoisoindolin-4-yl)acetamide Example 24. Synthesis of Compound 111

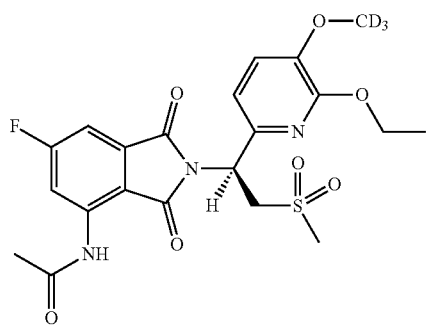

724

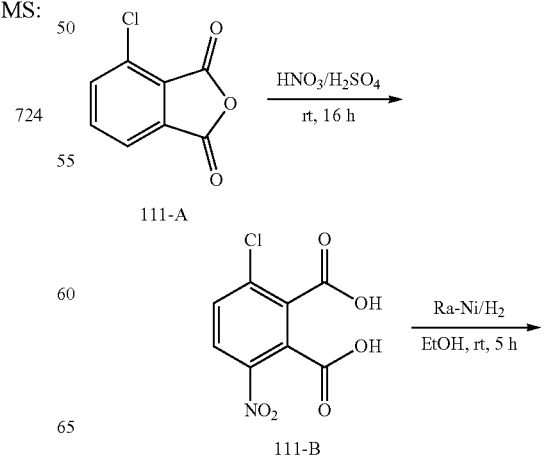

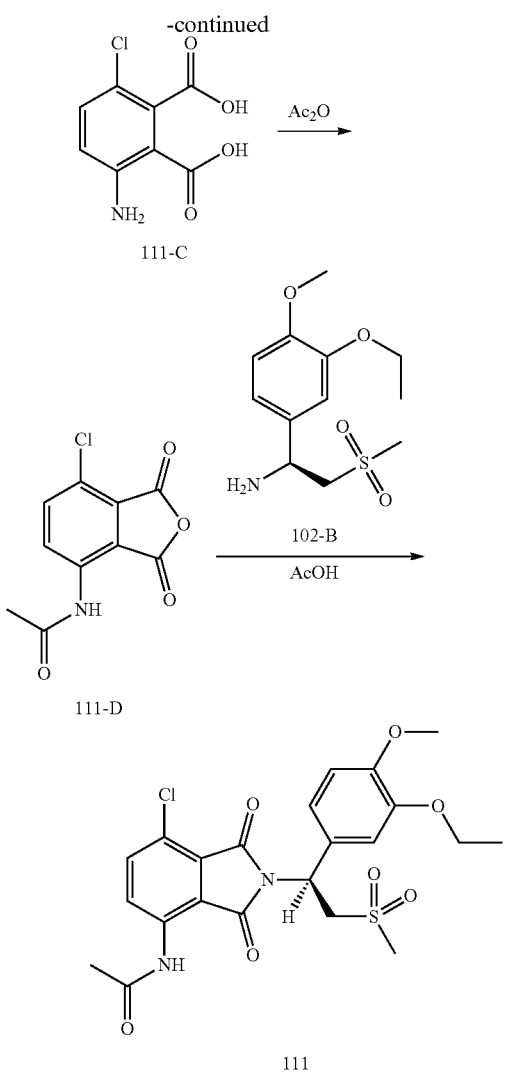

Step 3. Synthesis of Compound 111-D

A mixture of 111-C (3-amino-6-chlorophthalic acid, 0.75 g, 3.49 mmol) in Ac$_2$O (10 mL) was stirred at 120° C. for overnight. The reaction solution was concentrated through rotary evaporator then the precipitated solid was filtered and washed with Petrol Ether to give the product 111-D (N-(7-chloro-1,3-dioxo-1,3-dihydroisobenzofuran-4-yl)acetamide) as pale yellow solid.

$^1$H NMR (300 MHz, DMSO-d$_6$) δ 9.86 (s, 1H), 8.38 (d, J=8.7 Hz, 1H), 7.93 (d, J=9.0 Hz, 1H).

Step 4. Synthesis of Compound 111

A mixture of 111-D (N-(7-chloro-1,3-dioxo-1,3-dihydroisobenzofuran-4-yl)acetamide, 100 mg, 0.418 mmol) and 102-B ((S)-1-(3-ethoxy-4-methoxyphenyl)-2-(methylsulfonyl) ethanamine, 115 mg, 0.418 mmol) in AcOH (2 mL) was stirred at 80° C. for 16 hours. The mixture was cooled then a solid precipitated. The solid was filtered and washed with EtOAc, n-hexane, dried in vacuo to give compound 111 ((S)—N-(7-chloro-2-(1-(3-ethoxy-4-methoxyphenyl)-2-(methylsulfonyl)ethyl)-1,3-dioxoisoindolin-4-yl)acetamide, 155 mg, 75% yield).

$^1$H NMR (400 MHz, DMSO-d$_6$) δ 9.77 (s, 1H), 8.46 (d, J=9.2 Hz, 1H), 7.80 (d, J=9.2 Hz, 1H), 7.07 (d, J=1.2 Hz, 1H), 7.01-6.93 (m, 2H), 5.78 (dd, J=10.0, 4.4 Hz, 1H), 4.35-4.29 (m, 1H), 4.20-4.16 (m, 1H), 4.03 (q, J=6.8 Hz, 2H), 3.74 (s, 3H), 3.03 (s, 3H), 2.20 (s, 3H), 1.33 (t, J=6.8 Hz, 3H). LCMS: [(M−H)]$^-$=493.1. ee %=100%.

Example 25. Synthesis of Compound 112, 113 and 114

Compound 112 can be prepared according to the method of compound 111, except the corresponding substrate 1-(3-ethoxy-4-methoxyphenyl)-2-(methylsulfonyl) ethanamine was used instead of 102-B ((S)-1-(3-ethoxy-4-methoxyphenyl)-2-(methylsulfonyl)ethanamine).

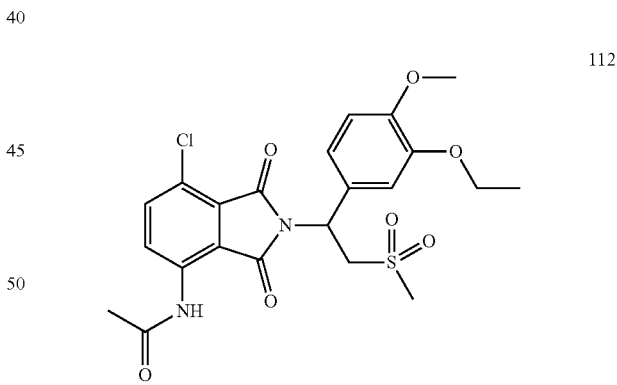

N-(7-chloro-2-(1-(3-ethoxy-4-methoxyphenyl)-2-(methylsulfonyl)ethyl)-1,3-dioxoisoindolin-4-yl) acetamide Step 1. Synthesis of Compound 111-B To a mixture of HNO$_3$ and H$_2$SO$_4$ (20 mL:50 mL) was added compound 111-A (3-chloro phthalic anhydride, CAS number 117-21-5, 25.0 g, 137 mmol) in small portions at 0° C. The mixture was stirred at 25° C. for 12 hours, then cooled to 0° C., followed by the addition of crushed ice. The solid was filtered and dried to afford compound 111-B (3-chloro-6-nitro phthalic acid, 21.0 g, 63% yield) as a white solid.

$^1$H NMR (400 MHz, DMSO-d$_6$): δ 14.34 (br s, 2H), 8.17 (d, J=8.8 Hz, 1H), 7.93 (d, J=8.8 Hz, 1H).

Step 2. Synthesis of Compound 111-C

To a solution of 111-B (3-chloro-6-nitrophthalic acid, 1.0 g, 4.08 mmol) in EtOH (130 mL) was added Raney Ni (1 g) under N$_2$ protection. The mixture was purged with H$_2$ and stirred under H$_2$ balloon pressure for 5 hours at 25° C. The reaction mixture was filtered through a celite pad under N$_2$ protection and the cake was washed with EtOH and the filtrate was concentrated to afford compound 111-C (3-amino-6-chlorophthalic acid, 0.75 g, 85%) as a pale green solid.

$^1$H NMR (400 MHz, DMSO-d$_6$): δ 7.35-7.14 (m, 1H), 6.86-6.67 (m, 1H).

Synthesis of Compound 113

Compound 113 can be prepared according to the method of compound 111, except the corresponding substrate 103-E ((S)-1-(3-ethoxy-4-d$_3$-methoxyphenyl)-2-(methylsulfonyl) ethanamine) was used instead of 102-B ((S)-1-(3-ethoxy-4-methoxyphenyl)-2-(methylsulfonyl) ethanamine).

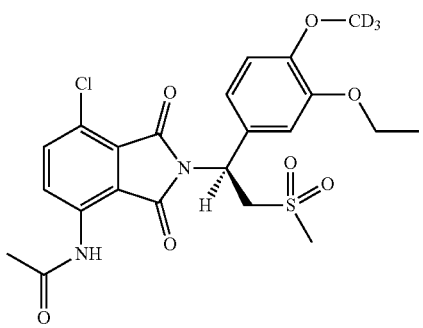

113

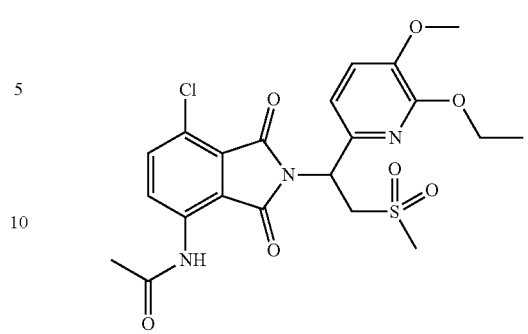

728

N-(7-chloro-2-(1-(6-ethoxy-5-methoxypyridin-2-yl)-2-(methylsulfonyl)ethyl)-1,3-dioxoisoindolin-4-yl)acetamide $^1$H NMR (400 MHz, DMSO-d$_6$) δ 9.79 (s, 1H), 8.49 (d, J=9.2 Hz, 1H), 7.84 (d, J=8.8 Hz, 1H), 7.28 (d, J=8.0 Hz, 1H), 7.06 (d, J=8.0 Hz, 1H), 5.81 (dd, J=10.4, 3.2 Hz, 1H), 4.36-4.32 (m, 1H), 4.23-4.17 (m, 3H), 3.77 (s, 3H), 3.10 (s, 3H), 2.19 (s, 3H), 1.19 (t, J=6.8 Hz, 3H). LCMS: [(M–H)]$^-$= 496.2.

(S)—N-(7-chloro-2-(1-(3-ethoxy-4-d$_3$-methoxyphenyl)-2-(methylsulfonyl)ethyl)-1,3-dioxoisoindolin-4-yl)acetamide $^1$H NMR (400 MHz, DMSO-d$_6$) δ 9.77 (s, 1H), 8.46 (d, J=9.2 Hz, 1H), 7.80 (d, J=9.2 Hz, 1H), 7.06 (s, 1H), 7.01-6.93 (m, 2H), 5.78 (dd, J=10.0 Hz, 4.4 Hz, 1H), 4.32-4.28 (m, 1H), 4.20-4.15 (m, 1H), 4.02 (q, J=6.8 Hz, 2H), 3.02 (s, 3H), 2.20 (s, 3H), 1.32 (t, J=6.8 Hz, 3H). LCMS: [(M–H)]$^-$=496.1. ee %=99.5%.

Compound 114 can be prepared according to the method of compound 111, except the corresponding substrate 103-D (1-(3-ethoxy-4-d$_3$-methoxyphenyl)-2-(methylsulfonyl)ethanamine) was used instead of 102-B ((S)-1-(3-ethoxy-4-methoxyphenyl)-2-(methylsulfonyl) ethanamine).

Compound 729 and 730 were synthesized according to the method of compound 111 in example 24, except the corresponding substrate 701-F2 ((S)-1-(6-ethoxy-5-methoxypyridin-2-yl)-2-(methylsulfonyl)ethanamine) or 701-F1 ((R)-1-(6-ethoxy-5-methoxypyridin-2-yl)-2-(methylsulfonyl)ethanamine) was used instead of 102-B ((S)-1-(3-ethoxy-4-methoxyphenyl)-2-(methylsulfonyl) ethanamine) respectively.

114

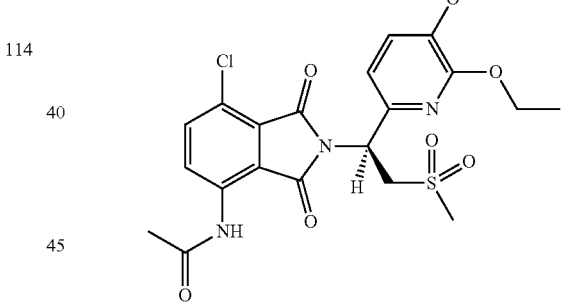

729

(N-(7-chloro-2-(1-(3-ethoxy-4-d$_3$-methoxyphenyl)-2-(methylsulfonyl)ethyl)-1,3-dioxoisoindolin-4-yl)acetamide)

Example 26. Synthesis of Compound 728, 729 and 730

Compound 728 was synthesized according to the method of compound 111 in example 24, except the corresponding substrate 701-F (1-(6-ethoxy-5-methoxypyridin-2-yl)-2-(methylsulfonyl)ethanamine) was used instead of 102-B ((S)-1-(3-ethoxy-4-methoxyphenyl)-2-(methylsulfonyl) ethanamine).

(S)—N-(7-chloro-2-(1-(6-ethoxy-5-methoxypyridin-2-yl)-2-(methylsulfonyl)ethyl)-1,3-dioxoisoindolin-4-yl)acetamide

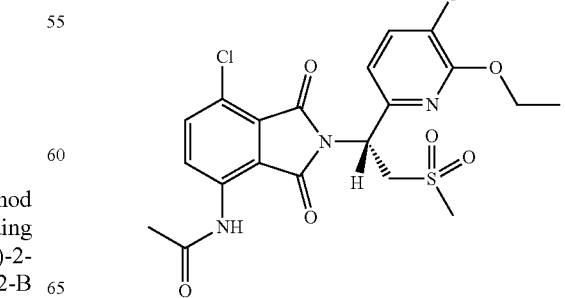

730

(R)—N-(7-chloro-2-(1-(6-ethoxy-5-methoxypyridin-2-yl)-2-(methylsulfonyl)ethyl)-1,3-dioxoisoindolin-4-yl)acetamide Example 27. Synthesis of Compound 731

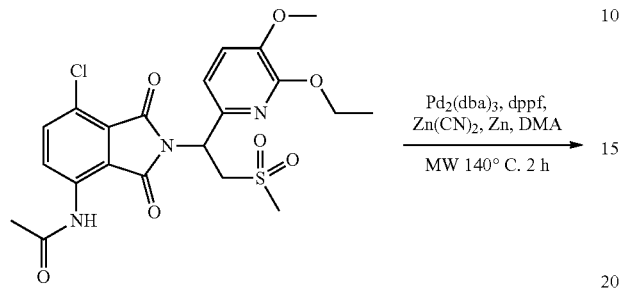

728

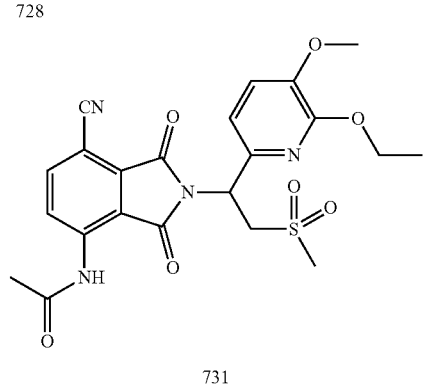

731

To a mixture of 728 (N-(7-chloro-2-(1-(6-ethoxy-5-methoxypyridin-2-yl)-2-(methyl sulfonyl)ethyl)-1,3-dioxoisoindolin-4-yl)acetamide, 150 mg, 0.303 mmol), $Zn(CN)_2$ (222 mg, 1.90 mmol), Zn powder (100 mg, 1.54 mmol), and dppf (76 mg, 0.137 mmol) in DMA (3 mL) was added $Pd_2(dba)_3$ (105 mg, 0.115 mmol). The mixture was purged with $N_2$ and stirred at 140° C. for 2 hours under microwave irradiation then cooled and filtered. The filtrate was concentrated to gave crude product, which was purified by column chromatography on silica gel (EtOAc:petroleum ether=2/1) to afford the crude compound which was further purified by prep-HPLC to give compound 731 (N-(7-cyano-2-(1-(6-ethoxy-5-methoxypyridin-2-yl)-2-(methylsulfonyl)ethyl)-1,3-dioxoisoindolin-4-yl)acetamide, 62.0 mg, 42% yield).

$^1$H NMR (400 MHz, DMSO-$d_6$) δ 9.93 (s, 1H), 8.64 (d, J=8.8 Hz, 1H), 8.23 (d, J=8.8 Hz, 1H), 7.28 (d, J=8.0 Hz, 1H), 7.09 (d, J=8.0 Hz, 1H), 5.83 (dd, J=10.4, 3.6 Hz, 1H), 4.38-4.34 (m, 1H), 4.25-4.16 (m, 3H), 3.77 (s, 3H), 3.11 (s, 3H), 2.24 (s, 3H), 1.21 (t, J=7.2 Hz, 3H). LCMS: [(M+H)]$^+$= 487.2

Example 28. Synthesis of Compound 732 and 733

Compound 729 was converted into compound 732 according to the method of compound 731 in Example 27.

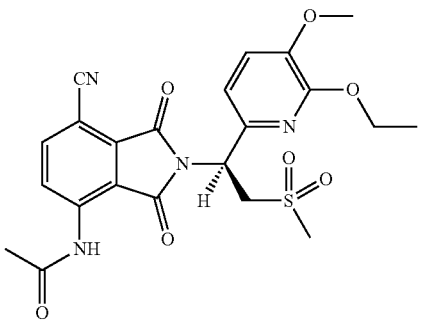

732

(S)—N-(7-cyano-2-(1-(6-ethoxy-5-methoxypyridin-2-yl)-2-(methylsulfonyl)ethyl)-1,3-dioxoisoindolin-4-yl)acetamide $^1$H NMR (400 MHz, DMSO-$d_6$) δ 9.93 (s, 1H), 8.65 (d, J=8.8 Hz, 1H), 8.23 (d, J=8.8 Hz, 1H), 7.28 (d, J=8.0 Hz, 1H), 7.09 (d, J=8.0 Hz, 1H), 5.83 (dd, J=10.8 Hz, 4.0 Hz, 1H), 4.35-4.34 (m, 1H), 4.25-4.17 (m, 3H), 3.77 (s, 3H), 3.11 (s, 3H), 2.24 (s, 3H), 1.21 (t, J=6.8 Hz, 3H). LCMS: [(M+H)]$^+$=487.2. ee %: 100%.

Compound 733 was converted from compound 730 according to the method of compound 731 in Example 27.

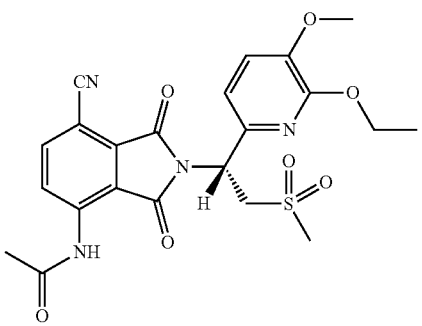

733

(R)—N-(7-cyano-2-(1-(6-ethoxy-5-methoxypyridin-2-yl)-2-(methylsulfonyl)ethyl)-1,3-dioxoisoindolin-4-yl)acetamide Example 29. Synthesis of Compound 115 and 116

Compound 111 was converted into compound 115 according to the method of compound 731 in Example 27.

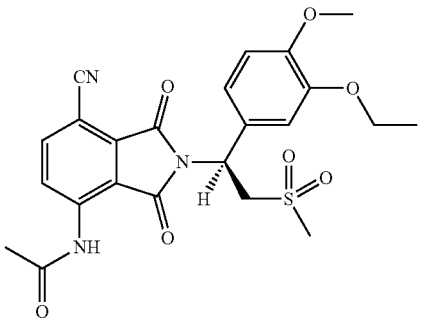

115

(S)—N-(7-cyano-2-(1 1-(3-ethoxy-4-methoxyphe-nyl)-2-(methylsulfonyl)ethyl)-1,3-dioxoisoindolin-4-yl)acetamide $^1$H NMR (400 MHz, DMSO-d$_6$) δ 9.91 (s, 1H), 8.62 (dd, J=8.8, 3.2 Hz, 1H), 8.19 (d, J=8.4 Hz, 1H), 7.08 (d, J=1.6 Hz, 1H), 7.03 (dd, J=8.4, 1.6 Hz, 1H), 6.95 (d, J=8.8 Hz, 1H), 5.79 (dd, J=10.0, 4.8 Hz, 1H), 4.33-4.18 (m, 2H), 4.03 (q, J=6.8 Hz, 2H), 3.74 (s, 3H), 3.02 (s, 3H), 2.25 (s, 3H), 1.33 (t, J=7.2 Hz, 3H). LCMS: [M+NH$_4^+$]=503.0. ee %: 100%.

Compound 116 was converted from compound 112 according to the method of compound 731 in Example 27.

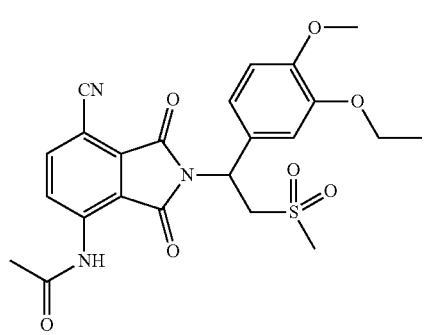

116

N-(7-cyano-2-(1-(3-ethoxy-4-methoxyphenyl)-2-(methylsulfonyl)ethyl)-1,3-dioxoisoindolin-4-yl)acetamide Example 30. Synthesis of Compound 734

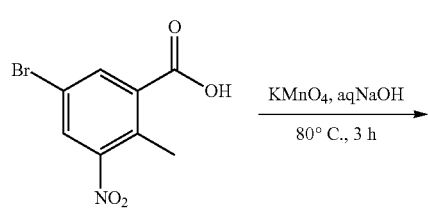

734-A

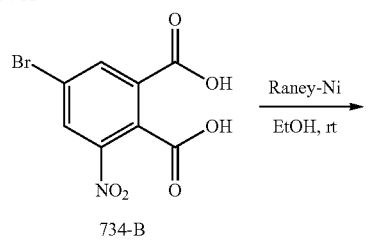

734-B

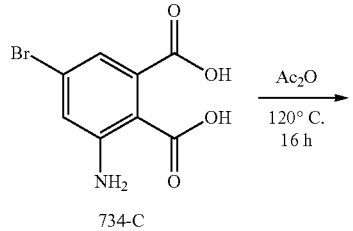

734-C

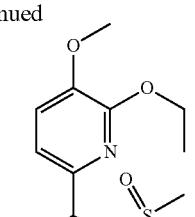

701-F2

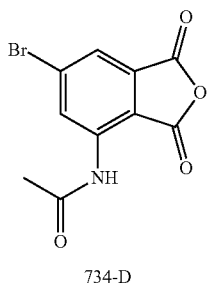

734-D

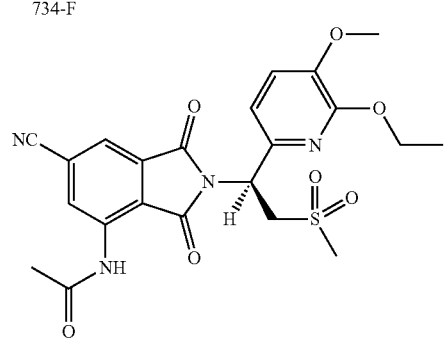

734-F

734

Step 1. Synthesis of Compound 734-B

To a mixture of compound 734-A (5-bromo-2-methyl-3-nitrobenzoic acid, CAS number 107650-20-4, 16.0 g, 0.062 mol) in H$_2$O (240 mL) was added NaOH (4.92 g, 0.122 mol). The mixture was heated to 80° C. then KMnO4 (39 g, 0.123 mol) was added in portions during 3 hours. Then the mixture was stirred for 30 minutes. The reaction solution was filtered and the cake was washed with hot water (200 mL). The filtrate was adjusted with 2N HCl to pH=1, extracted with EtOAc (300 mL×3), the combined organic layers was dried over Na$_2$SO$_4$ and concentrated in vacuum to give compound 734-B (5-bromo-3-nitrophthalic acid, 9.0 g, yield: 51%) as yellow solid.

$^1$H NMR (300 MHz, DMSO) δ 14.0 (br s, 1H), 8.52 (s, 1H), 8.33 (s, 1H).

Step 2. Synthesis of Compound 734-C

To a solution of 734-B (5-bromo-3-nitrophthalic acid, 5.0 g, 17.24 mmol) in EtOH (150 mL) was added Raney Ni (5 g) under N$_2$ atmosphere. The mixture was purged with H$_2$ and stirred under H$_2$ balloon pressure for 7 hours at 25° C. The reaction mixture was filtered through a celite pad and the cake was washed with EtOH. The filtrate was concentrated to dryness to afford compound 734-C (3-amino-5-bromophthalic acid, 5.0 g, crude) as a pale green solid.

1H NMR (300 MHz, DMSO-d$_6$): δ 7.02-7.01 (m, 1H), 6.79-6.77 (m, 1H), 1.03 (br s, 2H).

Step 3. Synthesis of Compound 734-D

A mixture of 734-C (3-amino-5-bromophthalic acid, 5.0 g) in Ac$_2$O (50 mL) was stirred at 120° C. for overnight. The reaction solution was concentrated through rotary evaporator and the solid precipitated then filtered and washed the solid with EtOAc to give the product 734-D (N-(6-bromo-1,3-dioxo-1,3-dihydroisobenzofuran-4-yl)acetamide, 2.1 g, yield: 38%) as pale yellow solid.

$^1$H NMR (300 MHz, DMSO-d$_6$) δ 9.90 (s, 1H), 8.63 (s, 1H), 8.00 (s, 1H), 2.98 (s, 3H), 2.22 (s, 3H).

Step 4. Synthesis of Compound 734-F

A mixture of compound 734-D (N-(6-fluoro-1,3-dioxo-1,3-dihydroisobenzofuran-4-yl) acetamide, 500 mg, 1.767 mmol) and 701-F2 ((S)-1-(6-ethoxy-5-methoxypyridin-2-yl)-2-(methylsulfonyl)ethanamine, 484 mg, 1.767 mmol) in AcOH (5 mL) was stirred at 80° C. for 2 hours. Then H$_2$O (30 mL) was added and the mixture was extracted with EtOAc (30 mL×2).

The organic layers was washed with brine, dried over Na$_2$SO$_4$ and concentrated to give a crude product, which was purified by column chromatography on silica gel (PE:EtOAc=1:1) to afford 734-F ((S)—N-(6-bromo-2-(1-(6-ethoxy-5-methoxypyridin-2-yl)-2-(methylsulfonyl)ethyl)-1,3-dioxoisoindolin-4-yl)acetamide, 0.9 g, yield: 95%) as a white solid.

1H NMR (400 MHz, DMSO-d$_6$) δ 9.77 (s, 1H), 8.69 (d, J=1.2 Hz, 1H), 7.81 (d, J=1.2 Hz, 1H), 7.27 (d, J=8.4 Hz, 1H), 7.03 (d, J=8.0 Hz, 1H), 5.79 (m, 1H), 4.31-4.30 (m, 1H), 4.20-4.16 (m, 3H), 3.76 (s, 3H), 3.09 (s, 3H), 2.20 (s, 3H), 1.19 (t, J=7.2 Hz, 3H).

Step 5. Synthesis of Compound 734

To a degassed mixture of 734-F ((S)—N-(6-bromo-2-(1-(6-ethoxy-5-methoxypyridin-2-yl)-2-(methylsulfonyl)ethyl)-1,3-dioxoisoindolin-4-yl)acetamide, 450 mg, 0.833 mmol), Zn(CN)$_2$ (292 mg, 2.50 mmol), and dppf (185 mg, 0.333 mmol) in DMA (8 mL) was added Pd$_2$(dba)$_3$ (305 mg, 0.333 mmol). The mixture was purged with N$_2$ and stirred at 110° C. for 1 hour under microwave irradiation. The reaction mixture was cooled, filtered and the filtrate was concentrated to give crude product, which was purified by column chromatography on silica gel (EtOAc:petroleum ether=1:1) to afford the crude compound which was further purified by Prep-HPLC to give 734 ((S)—N-(6-cyano-2-(1-(6-ethoxy-5-methoxypyridin-2-yl)-2-(methylsulfonyl)ethyl)-1,3-dioxoisoindolin-4-yl)acetamide, 220.0 mg, 54% yield) as yellow solid.

$^1$H NMR (400 MHz, DMSO-d$_6$) δ 9.94 (d, J=0.8 Hz, 1H), 8.14 (d, J=1.2 Hz, 1H), 7.27 (d, J=8.0 Hz, 1H), 7.06 (d, J=8.0 Hz, 1H), 5.83 (dd, J=10.8, 3.6 Hz, 1H), 4.35 (dd, J=14.4, 3.6 Hz, 1H), 4.22-4.16 (m, 3H), 3.77 (s, 3H), 3.10 (s, 3H), 2.22 (s, 3H), 1.20 (t, J=7.2 Hz, 3H). LCMS (ESI) [M+H]$^+$=486.9.

Compounds 735 and 736 can be synthesized according to the method compound 734, except the corresponding substrate 701-F1 ((R)-1-(6-ethoxy-5-methoxypyridin-2-yl)-2-(methyl sulfonyl)ethanamine) and 701-F (1-(6-ethoxy-5-methoxypyridin-2-yl)-2-(methylsulfonyl) ethanamine) were used instead of 701-F2 respectively.

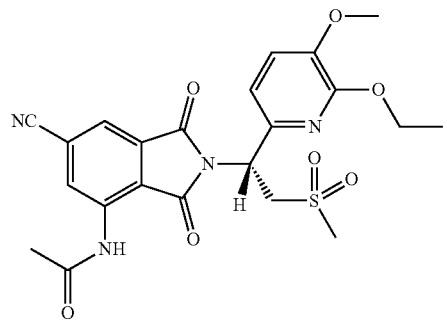

735

(R)—N-(6-cyano-2-(1-(6-ethoxy-5-methoxypyridin-2-yl)-2-(methylsulfonyl)ethyl)-1,3-dioxoisoindolin-4-yl)acetamide

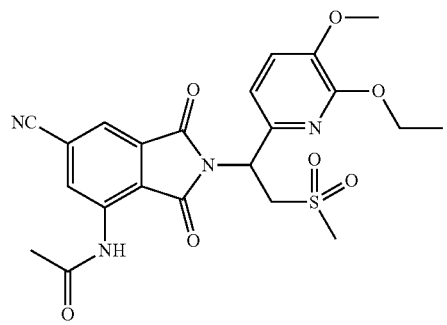

736

N-(6-cyano-2-(1-(6-ethoxy-5-methoxypyridin-2-yl)-2-(methylsulfonyl)ethyl)-1,3-dioxoisoindolin-4-yl)acetamide Example 31. Synthesis of Compound 737

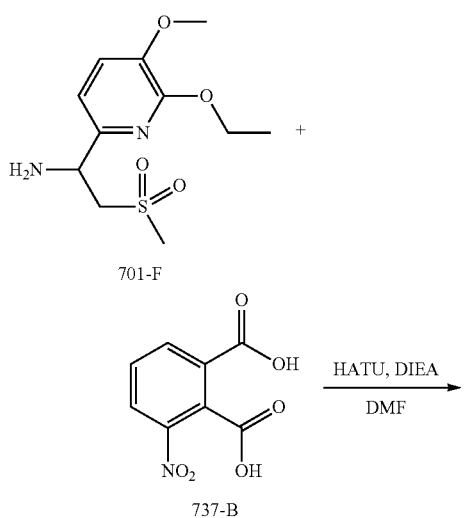

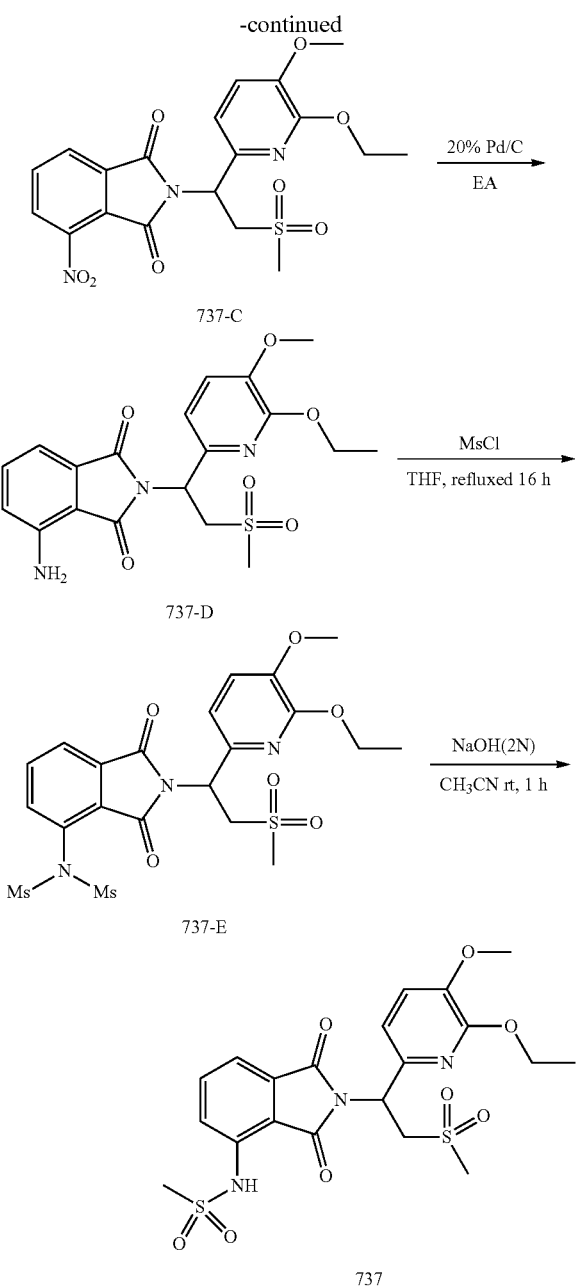

737-C

737-D

737-E

737

Step 1. Synthesis of Compound 737-C

To the mixture of 701-F (5 g, 18.2 mmol) in DMF (300 mL) was added 737-B (3-nitro phthalic acid, CAS number 603-11-2, 3.85 g, 18.2 mmol), HATU (15.2 g, 40 mmol) and DIEA (8.23 g, 63.7 mmol) and the mixture was stirred at room temperature for overnight. The reaction was added H₂O (150 ml) and stirred for 15 minutes, then extracted with EtOAc (400 mL) and the organic phase was washed with brine (300 mL*2), dried over Na₂SO₄, filtered and concentrated to give the crude product which was purified by column chromatography with PE:EA (2:1~1:1) to give 737-C (4.5 g, yield: 55%) as yellow solid.

¹H NMR (300 MHz, DMSO) δ 8.35 (d, J=8.4 Hz, 1H), 8.24 (d, J=7.8 Hz, 1H), 8.11 (t, J=8.1 Hz, 1H), 7.27 (d, J=7.5 Hz, 1H), 7.08 (d, J=7.5 Hz, 1H), 5.89-5.80 (m, 1H), 4.39-4.31 (m, 1H), 4.22-4.12 (m, 3H), 3.76 (s, 3H), 3.09 (s, 3H), 1.18 (t, J=7.2 Hz, 3H).

Step 2. Synthesis of Compound 737-D

A mixture of 737-C (4.5 g, 0.01 mmol) in Ethyl Acetate (200 ml) was added 20% Pd/C (800 mg) and stirred at room temperature for 7 hours under H₂ (50 psi) atmosphere. The mixture was filtered and concentrated to give 737-D (4.09 g, yield: 97%) as yellow solid.

¹H NMR (300 MHz, DMSO) δ 7.45 (t, J=7.5 Hz, 1H), 7.26 (d, J=8.1 Hz, 1H), 7.04-6.90 (m, 3H), 6.49 (s, 2H), 5.79-5.71 (m, 1H), 4.25-4.16 (m, 4H), 3.76 (s, 3H), 3.08 (s, 3H), 1.20 (t, J=6.9 Hz, 3H).

Step 3. Synthesis of Compound 737-E

To a solution of 737-D (4-amino-2-(1-(6-ethoxy-5-methoxypyridin-2-yl)-2-(methyl sulfonyl)ethyl)isoindoline-1,3-dione, 500 mg, 1.19 mmol) in THF (15 mL) was added Et₃N (606 mg, 6 mmol), MsCl (187 mg, 1.79 mmol) and DMAP (290 mg, 2.38 mmol). The mixture was stirred at 75° C. for 16 hours. The mixture was concentrated and extracted with EtOAc (30 mL), washed with 1N HCl, brine, dried over Na₂SO₄, concentrated to give crude, then purified by column chromatography on silica gel (PE:EtOAc 1:1) and Pre-HPLC to afford 350 mg of a mixture of 737-E (N-(2-(1-(6-ethoxy-5-methoxypyridin-2-yl)-2-(methylsulfonyl)ethyl)-1,3-dioxoisoindolin-4-yl)-N-(methylsulfonyl)methanesulfonamide) and (N-(2-(1-(6-ethoxy-5-methoxypyridin-2-yl)-2-(methylsulfonyl)ethyl)-1,3-dioxoisoindolin-4-yl)methanesulfonamide) as yellow solid.

Step 4. Synthesis of Compound 737

A solution of 737-E (300 mg) in CH₃CN was added NaOH solution (2N, 0.6 mL), the mixture was stirred at 25° C. for 1 hour. Then the mixture was adjusted to pH=8 with HCl (1N), extracted with EtOAc, dried over Na₂SO₄, and the filtration was concentrated to give crude which was purified by Prep-HPLC to afford compound 737 (N-(2-(1-(6-ethoxy-5-methoxypyridin-2-yl)-2-(methylsulfonyl)ethyl)-1,3-dioxoisoindolin-4-yl)methanesulfonamide, 103 mg, 20% for 2 steps).

¹H NMR (400 MHz, DMSO-d₆) δ 9.33 (s, 1H), 7.86-7.78 (m, 2H), 7.63 (d, J=6.8 Hz, 1H), 7.27 (d, J=8.0 Hz, 1H), 7.02 (d, J=8.4 Hz, 1H), 5.80 (dd, J=10.0, 3.6 Hz, 1H), 4.34-4.29 (m, 1H), 4.22-4.16 (m, 3H), 3.76 (s, 3H), 3.28 (s, 3H), 3.09 (s, 3H), 1.18 (t, J=7.2 Hz, 3H), LCMS (ESI) [M+H]⁺=498.1.

Compound 737-D2 was synthesized according to the method of compound 737-D, except compound 701-F2 ((S)-1-(6-ethoxy-5-methoxypyridin-2-yl)-2-(methylsulfonyl)ethanamine) was used instead of 701-F.

737-D2

(S)-4-amino-2-(1-(6-ethoxy-5-methoxypyridin-2-yl)-2-(methylsulfonyl)ethyl)isoindoline-1,3-dione ¹H NMR (300 MHz, DMSO-d₆) δ 7.48-7.43 (m, 1H), 7.27-7.24 (m, 1H), 7.02-6.92 (m, 3H), 6.49 (s, 2H), 5.77-5.73 (m, 1H), 4.24-4.19 (m, 4H), 3.76 (s, 3H), 3.07 (s, 3H), 1.23-1.17 (m, 3H).

Compound 737-D1 can be synthesized according to the method of compound 737-D, except compound 701-F1 ((R)-1-(6-ethoxy-5-methoxypyridin-2-yl)-2-(methylsulfonyl) ethanamine) was used instead of 701-F.

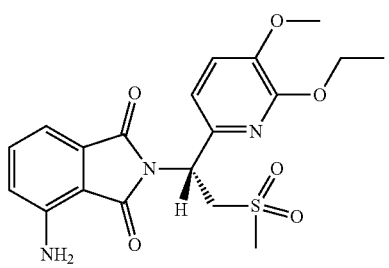

737-D1

(R)-4-amino-2-(1-(6-ethoxy-5-methoxypyridin-2-yl)-2-(methylsulfonyl)ethyl)isoindoline-1,3-dione Compound 738 can be synthesized according to the method of compound 737, except compound 737-D2 was used instead of 737-D.

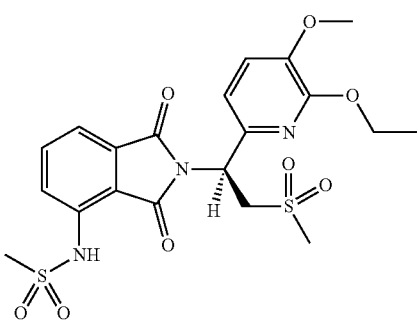

738

(S)—N-(2-(1-(6-ethoxy-5-methoxypyridin-2-yl)-2-(methylsulfonyl)ethyl)-1,3-dioxoisoindolin-4-yl)methanesulfonamide)

Example 32. Synthesis of Compound 742

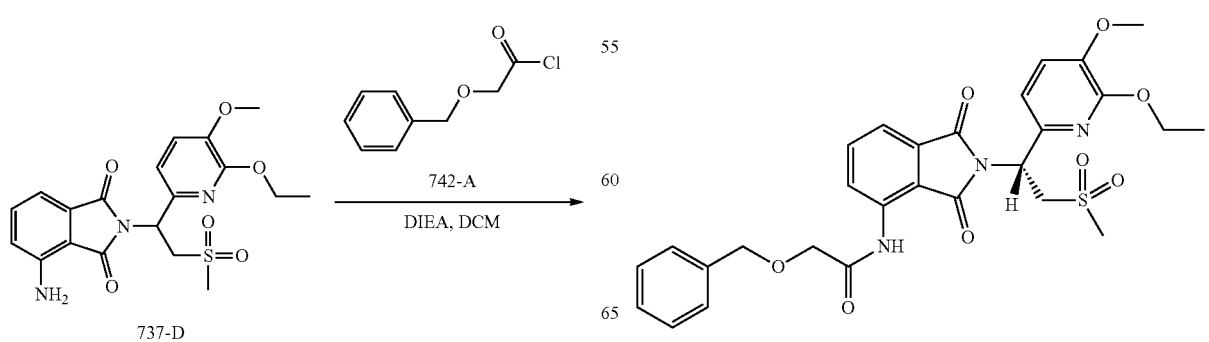

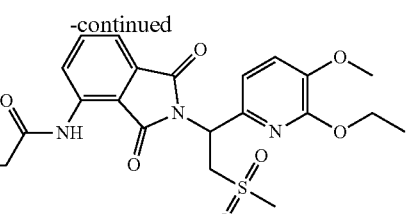

742

A solution of 737-D (4-amino-2-(1-(6-ethoxy-5-methoxypyridin-2-yl)-2-(methylsulfonyl) ethyl)isoindoline-1,3-dione, 479 mg, 1.143 mmol) in DCM (20 mL) cooled to 0° C. was added 742-A (2-(benzyloxy)acetyl chloride, CAS number 19810-31-2, 1.26 g, 6.86 mmol) and DIEA (1.28 g, 9.94 mmol), then the mixture was stirred at 0° C. for 1 hour. Then the mixture was concentrated and purified with column chromatography on silica gel (PE:EtOAc=3:1-2:1) to give the product (625 mg, yield: 96%) as yellow solid. 125 mg of the product was purified by prep-HPLC to afford 742 (2-(benzyloxy)-N-(2-(1-(6-ethoxy-5-methoxypyridin-2-yl)-2-(methyl sulfonyl)ethyl)-1,3-dioxoisoindolin-4-yl)acetamide, 53 mg).

$^1$H NMR (400 MHz, DMSO-$d_6$) δ 10.42 (s, 1H), 8.71 (d, J=8.4 Hz, 1H), 7.86 (t, J=8.0 Hz, 1H), 7.62 (d, J=7.2 Hz, 1H), 7.46 (d, J=6.4 Hz, 2H), 7.35-7.27 (m, 3H), 7.05 (d, J=8.0 Hz, 1H), 5.83 (dd, J=10.8, 3.6 Hz, 1H), 4.69 (s, 2H), 4.36-4.32 (m, 1H), 4.20-4.16 (m, 5H), 3.76 (s, 3H), 3.10 (s, 3H), 1.17 (t, J=7.2 Hz, 3H). LCMS: [M+H]$^+$=568.0.

Compounds 743 and 744 can be synthesized according to the method of compound 742, except compounds 737-D2 and 737-D1 were used instead of 737-D respectively.

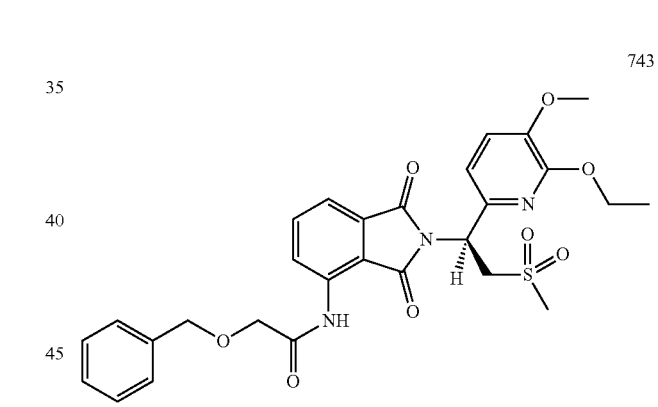

743

(S)-2-(benzyloxy)-N-(2-(1-(6-ethoxy-5-methoxypyridin-2-yl)-2-(methylsulfonyl)ethyl)-1,3-dioxoisoindolin-4-yl)acetamide

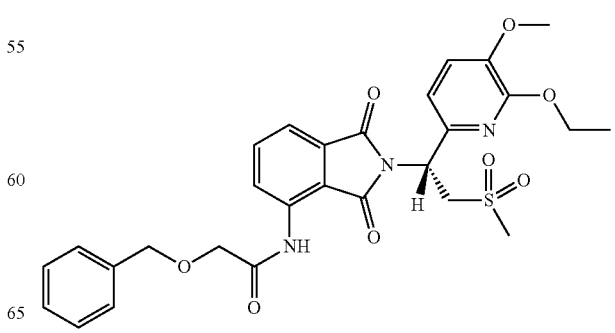

744

107

(R)-2-(benzyloxy)-N-(2-(1-(6-ethoxy-5-methoxy-pyridin-2-yl)-2-(methylsulfonyl)ethyl)-1,3-dioxoisoindolin-4-yl)acetamide Example 33. Synthesis of Compound 739

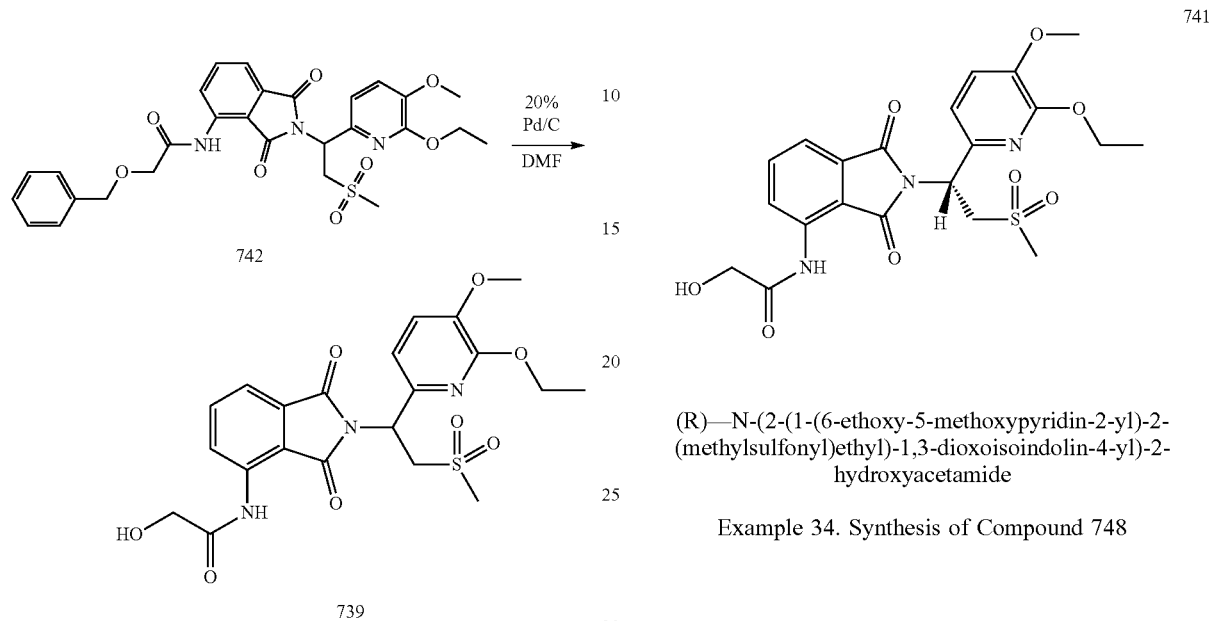

A mixture of 742 (2-(benzyloxy)-N-(2-(1-(6-ethoxy-5-methoxypyridin-2-yl)-2-(methyl sulfonyl)ethyl)-1,3-dioxoisoindolin-4-yl)acetamide, 500 mg, 0.88 mmol) in DMF (50 mL) was added Pd/C (20%, 50% wet, 50 mg) and stirred at 25° C. for 12 hours under H$_2$ (50 psi). The mixture was filtered and concentrated and purified by Prep-HPLC to give 739 (N-(2-(1-(6-ethoxy-5-methoxypyridin-2-yl)-2-(methylsulfonyl)ethyl)-1,3-dioxoisoindolin-4-yl)-2-hydroxyacetamide, 160 mg, yield: 32%).

$^1$H NMR (400 MHz, DMSO-d$_6$) δ 10.63 (s, 1H), 8.78 (d, J=8.4 Hz, 1H), 7.86 (t, J=8.4 Hz, 1H), 7.61 (d, J=7.2 Hz, 1H), 7.27 (d, J=8.4 Hz, 1H), 7.04 (d, J=8.0 Hz, 1H), 6.34 (t, J=5.6 Hz, 1H), 5.82 (dd, J=10.8, 3.6 Hz, 1H), 4.35-4.31 (m, 1H), 4.22-4.16 (m, 3H), 4.07 (d, J=5.6 Hz, 2H), 3.76 (s, 3H), 3.10 (s, 3H), 1.17 (t, J=7.2 Hz, 3H). LCMS: [M+H]$^+$=478.2.

Compounds 740 and 741 can be prepared from compounds 743 and 744 respectively according to the method of compound 739.

108

(S)—N-(2-(1-(6-ethoxy-5-methoxypyridin-2-yl)-2-(methylsulfonyl)ethyl)-1,3-dioxoisoindolin-4-yl)-2-hydroxyacetamide (R)—N-(2-(1-(6-ethoxy-5-methoxypyridin-2-yl)-2-(methylsulfonyl)ethyl)-1,3-dioxoisoindolin-4-yl)-2-hydroxyacetamide Example 34. Synthesis of Compound 748

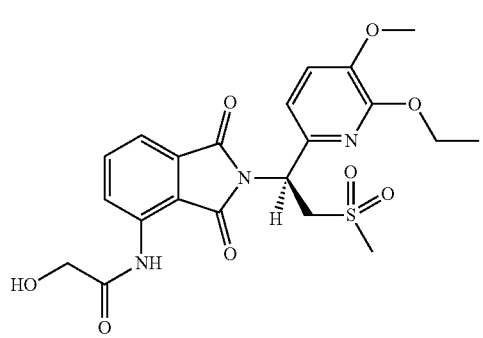

A solution of 737-D (4-amino-2-(1-(6-ethoxy-5-methoxy-pyridin-2-yl)-2-(methylsulfonyl) ethyl)isoindoline-1,3-dione, 100 mg, 0.238 mmol) in DMF (10 mL) cooled to 0° C. was added 2-methoxyacetyl chloride (CAS number 38870-89-2, 148 mg, 1.367 mmol) and DMAP (45.8 mg, 0.357 mmol), and the mixture was stirred at 0° C. for 2 hours. Then the reaction mixture was quenched with HCl (1M, 20 mL) and extracted with EtOAc (20 mL). The organic phase was concentrated and purified by Prep-HPLC to afford 748 (N-(2-(1-(6-ethoxy-5-methoxy pyridin-2-yl)-2-(methylsulfonyl)ethyl)-1,3-dioxoisoindolin-4-yl)-2-methoxyacetamide, 30 mg, yield: 26%).

$^1$H NMR (400 MHz, DMSO-d$_6$) δ 10.29 (s, 1H), 8.72 (d, J=8.4 Hz, 1H), 7.86 (t, J=8.4 Hz, 1H), 7.62 (d, J=6.8 Hz, 1H), 7.27 (d, J=8.0 Hz, 1H), 7.04 (d, J=8.0 Hz, 1H), 5.81 (dd, J=10.8, 3.6 Hz, 1H), 4.34-4.30 (m, 1H), 4.23-4.15 (m, 3H), 4.10 (s, 2H), 3.76 (s, 3H), 3.45 (s, 3H), 3.10 (s, 3H), 1.17 (t, J=7.2 Hz, 3H). LCMS: [M+H]+=492.2.

Compounds 749 and 750 can be synthesized according to the method of compound 748, except compounds 737-D2 and 737-D1 were used instead of compound 737-D respectively.

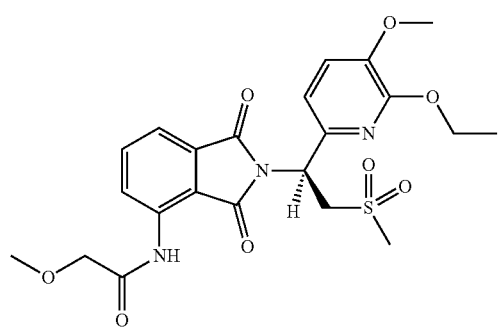

749

(S)—N-(2-(1-(6-ethoxy-5-methoxypyridin-2-yl)-2-(methylsulfonyl)ethyl)-1,3-dioxoisoindolin-4-yl)-2-methoxyacetamide

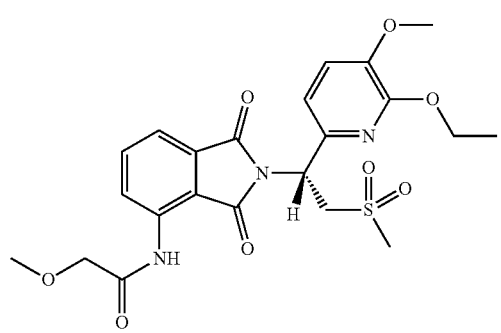

750

(R)—N-(2-(1-(6-ethoxy-5-methoxypyridin-2-yl)-2-(methylsulfonyl)ethyl)-1,3-dioxoisoindolin-4-yl)-2-methoxyacetamide Example 35. Synthesis of Compound 745

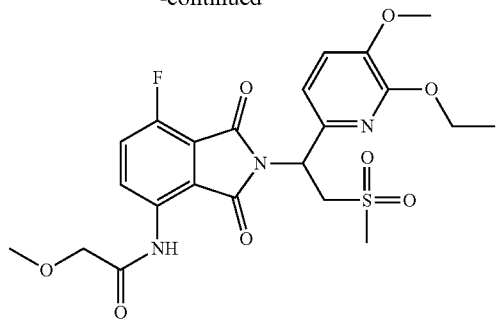

745

Compound 745 (N-(2-(1-(6-ethoxy-5-methoxypyridin-2-yl)-2-(methylsulfonyl)ethyl)-7-fluoro-1,3-dioxoisoindolin-4-yl)-2-methoxyacetamide) was synthesized according to the method of 748 in Example 34, except the appropriate compound 745-D was used instead of 737-D (4-amino-2-(1-(6-ethoxy-5-methoxypyridin-2-yl)-2-(methylsulfonyl) ethyl)isoindoline-1,3-dione).

$^1$H NMR (400 MHz, DMSO-d$_6$) δ 10.28 (s, 1H), 8.74 (dd, J=9.6, 4.0 Hz, 1H), 7.73 (t, J=9.2 Hz, 1H), 7.27 (d, J=8.0 Hz, 1H), 7.07 (d, J=8.4 Hz, 1H), 5.80 (dd, J=10.8, =3.6 Hz, 1H), 4.35-4.14 (m, 4H), 4.10 (s, 2H), 3.77 (s, 3H), 3.45 (s, 3H), 3.10 (s, 3H), 1.21 (t, J=7.2 Hz, 3H). LCMS: [M+H]$^+$=510.2.

Synthesis of Compound 745-D

The compound 745-D (4-amino-2-(1-(6-ethoxy-5-methoxypyridin-2-yl)-2-(methyl sulfonyl)ethyl)-7-fluoroisoindoline-1,3-dione) was synthesized according to the method of compound 737-D in Example 31, except the corresponding starting material 101-A (3-fluoro-6-nitrophthalic acid) was used instead of compound 737-B (3-nitro phthalic acid).

$^1$H NMR (300 MHz, DMSO-d$_6$) δ 7.35 (t, J=9.0 Hz, 1H), 7.26 (d, J=8.1 Hz, 1H), 7.07-6.95 (m, 2H), 6.46 (br s, 2H), 5.75-5.70 (m, 1H), 4.28-4.16 (m, 4H), 3.75 (s, 3H), 3.08 (s, 3H), 2.68 (s, 3H), 1.35-1.17 (m, 3H).

Compounds 745-D2 and 745-D1 were synthesized according to the method of compound 737-D in example 31, except the corresponding starting material 101-A (3-fluoro-6-nitrophthalic acid) was used instead of compound 737-B (3-nitro phthalic acid), and compounds 701-F2 ((S)-1-(6-ethoxy-5-methoxypyridin-2-yl)-2-(methylsulfonyl)ethan amine) or 701-F1 ((R)-1-(6-ethoxy-5-methoxypyridin-2-yl)-2-(methylsulfonyl)ethanamine) was used instead of 701-F (1-(6-ethoxy-5-methoxypyridin-2-yl)-2-(methylsulfonyl) ethanamine) respectively.

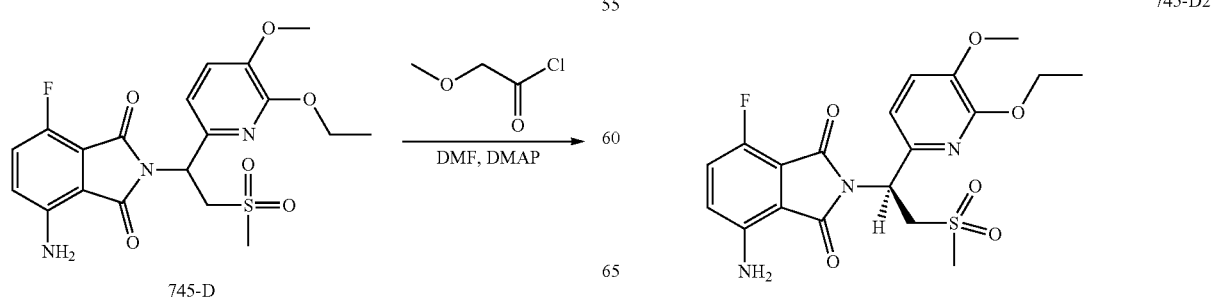

745-D

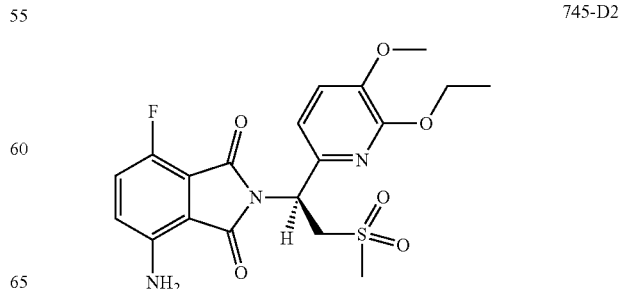

745-D2

111

(S)-4-amino-2-(1-(6-ethoxy-5-methoxypyridin-2-yl)-2-(methylsulfonyl)ethyl)-7-fluoroisoindoline-1,3-dione ¹H NMR (300 MHz, DMSO-d₆) δ 7.35-7.25 (m, 2H), 7.07-7.04 (m, 2H), 6.46-6.44 (m, 2H), 5.77-5.72 (m, 1H), 4.25-4.17 (m, 4H), 4.04-4.02 (m, 1H), 3.76 (s, 3H), 3.08 (s, 3H), 1.23-1.15 (m, 3H).

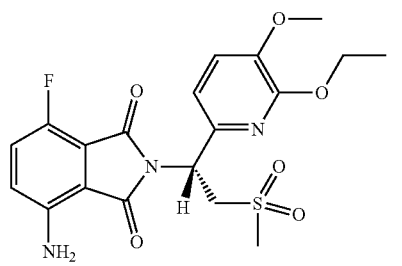

745-D1

(R)-4-amino-2-(1-(6-ethoxy-5-methoxypyridin-2-yl)-2-(methylsulfonyl)ethyl)-7-fluoroisoindoline-1,3-dione Synthesis of Compounds 746 and 747

Compounds 746 and 747 can be synthesized according to the method of compound 745, except compound 745-D2 or 745-D1 was used instead of compound 745-D.

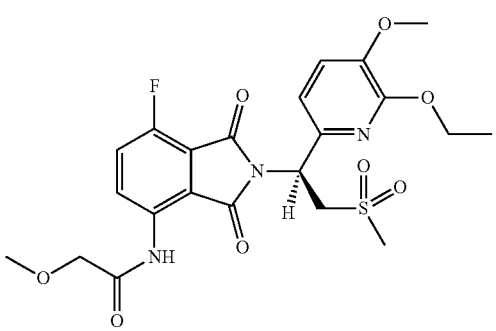

746

(S)—N-(2-(1-(6-ethoxy-5-methoxypyridin-2-yl)-2-(methylsulfonyl)ethyl)-7-fluoro-1,3-dioxoisoindolin-4-yl)-2-methoxyacetamide

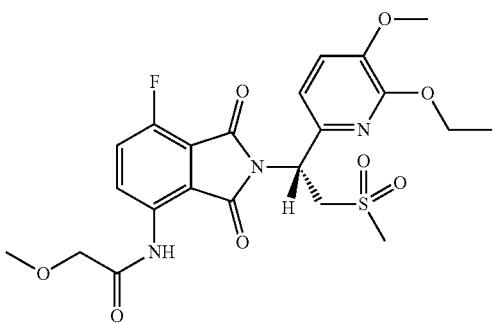

747

112

(R)—N-(2-(1-(6-ethoxy-5-methoxypyridin-2-yl)-2-(methylsulfonyl)ethyl)-7-fluoro-1,3-dioxoisoindolin-4-yl)-2-methoxyacetamide)

Example 36. Synthesis of Compound 751

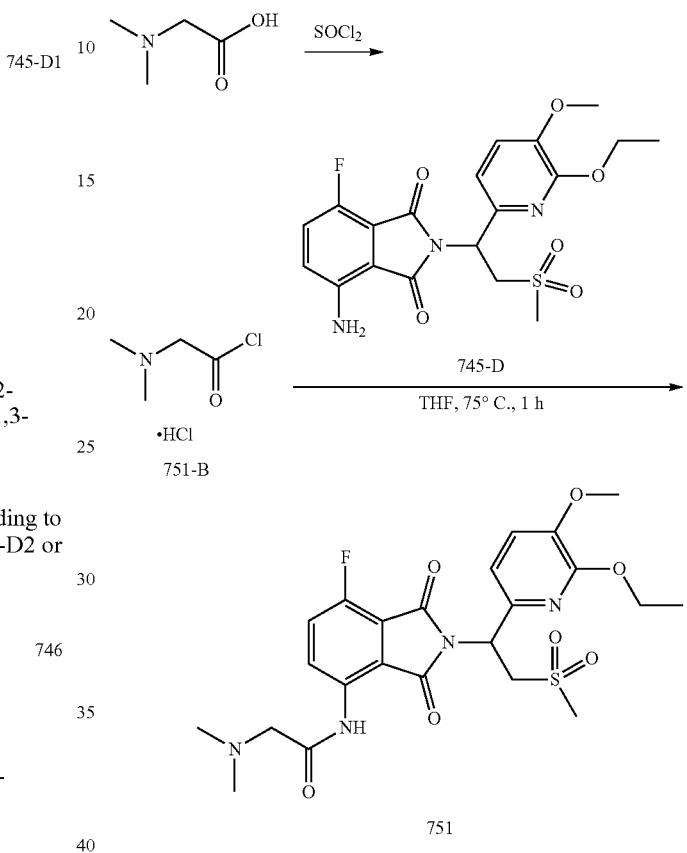

Step 1. Synthesis of Compound 751-B 2-(dimethylamino)acetic acid (CAS number 1118-68-9, 1.50 g, 14.56 mol) in SOCl₂ (15 mL) was stirred at 75° C. for 2 hours. The reaction mixture was concentrated to give compound 751-B (2-(dimethylamino)acetyl chloride, 1.90 g, crude), which was used to the next step without further purification.

Step 2. Synthesis of Compound 751

A solution of 745-D (4-amino-2-(1-(6-ethoxy-5-methoxypyridin-2-yl)-2-(methylsulfonyl) ethyl)-7-fluoroisoindoline-1,3-dione, 300 mg, 0.68 mmol) in THF (10 mL) was added 751-B (2-(dimethylamino)acetyl chloride, 432 mg, 2.74 mmol). The mixture was stirred at 75° C. for 1 hour then cooled to 25° C. NaHCO₃ aqueous solution (30 mL) was added and the mixture was extracted with EtOAc (50 mL×2). The organic layers was washed with brine, dried over Na₂SO₄, filtered and the filtration was concentrated to give a crude product, which was purified by Prep-HPLC to afford 751 (2-(dimethylamino)-N-(2-(1-(6-ethoxy-5-methoxypyridin-2-yl)-2-(methylsulfonyl)ethyl)-7-fluoro-1,3-dioxoisoindolin-4-yl)acetamide, 120 mg, yield: 34%).

¹H NMR (300 MHz, DMSO-d₆) δ 10.84 (s, 1H), 8.80-8.77 (m, 1H), 7.71 (t, J=8.7 Hz, 1H), 7.28 (d, J=6.9 Hz, 1H), 7.08 (d, J=6.9 Hz, 1H), 5.83-5.79 (m, 1H), 4.31-4.20 (m, 4H), 3.77 (s, 3H), 3.18-3.11 (m, 5H), 2.32 (s, 6H), 1.20 (t, J=6.3 Hz, 3H). LCMS: [M+H]⁺=523.2.

Compounds 752 and 753 can be synthesized according to the method of compound 751, except compound 745-D2 or 745-D1 was used respectively instead of compound 745-D.

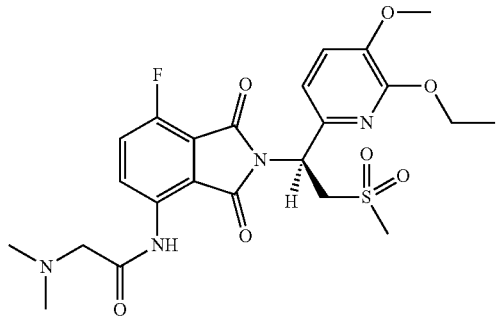

(S)-2-(dimethylamino)-N-(2-(1-(6-ethoxy-5-methoxypyridin-2-yl)-2-(methylsulfonyl)ethyl)-7-fluoro-1,3-dioxoisoindolin-4-yl)acetamide

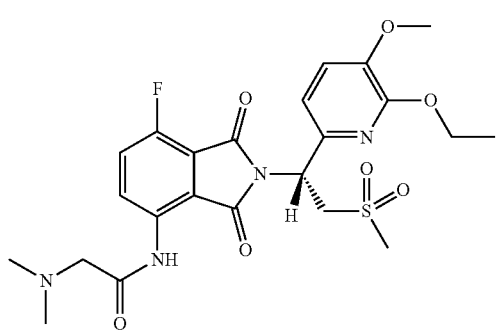

(R)-2-(dimethylamino)-N-(2-(1-(6-ethoxy-5-methoxypyridin-2-yl)-2-(methylsulfonyl)ethyl)-7-fluoro-1,3-dioxoisoindolin-4-yl)acetamide Example 37. Synthesis of Compound 754

Compound 754 was synthesized according to the method of compound 751 in example 36, except corresponding substrate 737-D (4-amino-2-(1-(6-ethoxy-5-methoxypyridin-2-yl)-2-(methylsulfonyl)ethyl)isoindoline-1,3-dione) was used instead of compound 745-D.

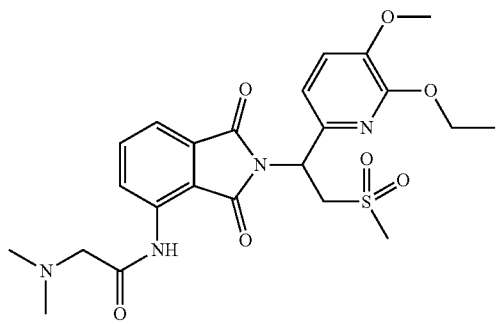

2-(dimethylamino)-N-(2-(1-(6-ethoxy-5-methoxy-pyridin-2-yl)-2-(methylsulfonyl)ethyl)-1,3-dioxoisoindolin-4-yl)acetamide)

$^1$H NMR (300 MHz, DMSO-$d_6$) δ 10.84 (s, 1H), 8.75 (d, J=8.4 Hz, 1H), 7.86-7.82 (m, 1H), 7.59 (d, J=6.4 Hz, 1H), 7.28 (d, J=8.4 Hz, 1H), 7.04 (d, J=8.4 Hz, 1H), 5.81-5.70 (m, 1H), 4.31-4.16 (m, 4H), 3.76 (s, 3H), 3.16 (s, 2H), 3.10 (s, 3H), 2.32 (s, 6H), 1.16 (t, J=7.2 Hz, 3H). LCMS: [M+H]$^+$= 505.2.

Compounds 755 and 756 can be synthesized according to the method of compound 751 in example 36, except corresponding substrate 737-D2 ((S)-4-amino-2-(1-(6-ethoxy-5-methoxy pyridin-2-yl)-2-(methylsulfonyl)ethyl)isoindoline-1,3-dione) or 737-D1 ((R)-4-amino-2-(1-(6-ethoxy-5-methoxypyridin-2-yl)-2-(methylsulfonyl)ethyl)isoindoline-1,3-dione) was used respectively instead of compound 745-D.

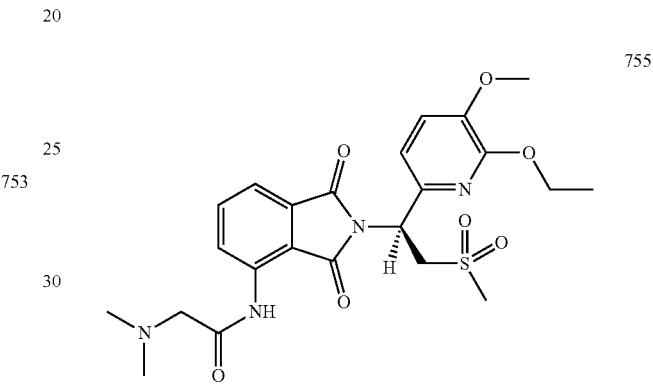

(S)-2-(dimethylamino)-N-(2-(1-(6-ethoxy-5-methoxypyridin-2-yl)-2-(methylsulfonyl)ethyl)-1,3-dioxoisoindolin-4-yl)acetamide)

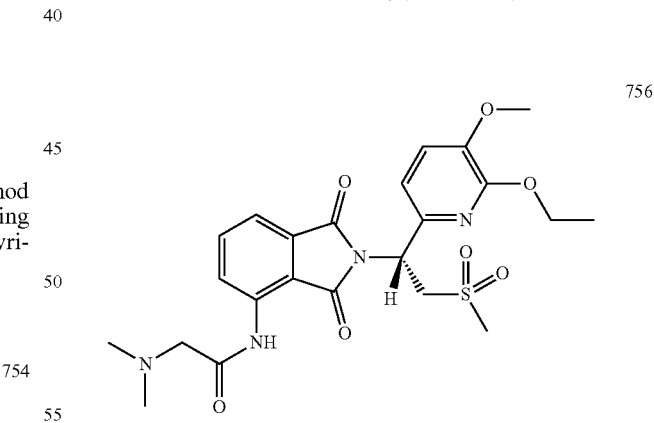

(R)-2-(dimethylamino)-N-(2-(1-(6-ethoxy-5-methoxypyridin-2-yl)-2-(methylsulfonyl)ethyl)-1,3-dioxoisoindolin-4-yl)acetamide Example 38. Synthesis of Compound 757

Compound 757 was synthesized according to the method of compound 751 in example 36, except isovaleryl chloride (CAS number 108-12-3) was used instead of compound 751-B (2-(dimethylamino)acetyl chloride).

(R)—N-(2-(1-(6-ethoxy-5-methoxypyridin-2-yl)-2-(methylsulfonyl)ethyl)-7-fluoro-1,3-dioxoisoindolin-4-yl)-3-methylbutanamide Example 39. Synthesis of Compound 760

Compound 760 was synthesized according to the method of compound 751 in example 36, except isovaleryl chloride was used instead of compound 751-B (2-(dimethylamino)acetyl chloride) and compound 737-D (4-amino-2-(1-(6-ethoxy-5-methoxypyridin-2-yl)-2-(methyl sulfonyl)ethyl)isoindoline-1,3-dione) was used instead of 745-D (4-amino-2-(1-(6-ethoxy-5-methoxypyridin-2-yl)-2-(methylsulfonyl)ethyl)-7-fluoroisoindoline-1,3-dione).

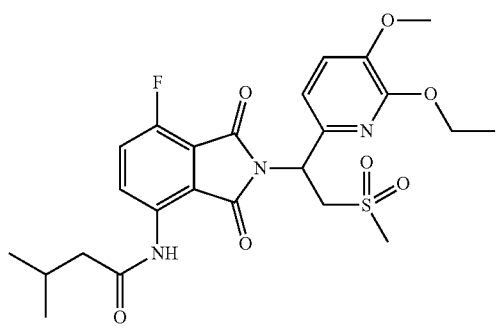

757

N-(2-(1-(6-ethoxy-5-methoxypyridin-2-yl)-2-(methylsulfonyl)ethyl)-7-fluoro-1,3-dioxoisoindolin-4-yl)-3-methylbutanamide $^1$H NMR (400 MHz, DMSO-d$_6$) δ 9.71 (s, 1H), 8.47 (dd, J=9.2, 3.2 Hz, 1H), 7.69 (t, J=9.2 Hz, 1H), 7.27 (d, J=8.0 Hz, 1H), 7.05 (d, J=8.0 Hz, 1H), 5.79 (dd, J=10.8, 3.6 Hz, 1H), 4.33 (dd, =14.4, 2.8 Hz, 1H), 4.22-4.13 (m, 3H), 3.77 (s, 3H), 3.10 (s, 3H), 2.33 (d, J=6.8 Hz, 2H), 2.09-2.06 (m, 1H), 1.19 (t, J=7.2 Hz, 3H), 0.94 (d, J=6.8 Hz, 6H). LCMS: [M+H]$^+$=522.2

Compounds 758 and 759 can be synthesized according to the method of compound 751 in example 36, except isovaleryl chloride was used instead of compound 751-B (2-(dimethylamino)acetyl chloride) and 745-D2 ((S)-4-amino-2-(1-(6-ethoxy-5-methoxy pyridin-2-yl)-2-(methylsulfonyl)ethyl)-7-fluoroisoindoline-1,3-dione)) or 745-D1 ((R)-4-amino-2-(1-(6-ethoxy-5-methoxypyridin-2-yl)-2-(methylsulfonyl)ethyl)-7-fluoroisoindoline-1,3-dion e) was used respectively instead of compound 745-D.

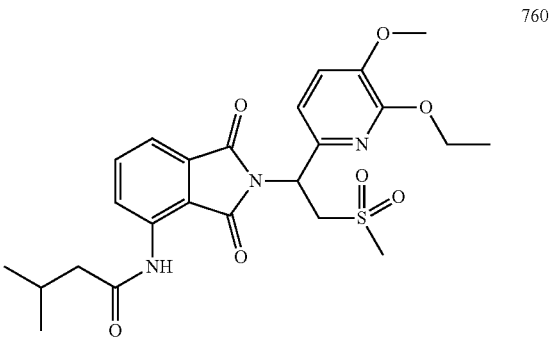

760

N-(2-(1-(6-ethoxy-5-methoxypyridin-2-yl)-2-(methylsulfonyl)ethyl)-1,3-dioxoisoindolin-4-yl)-3-methylbutanamide $^1$H NMR (400 MHz, DMSO-d$_6$) δ 9.68 (s, 1H), 8.49 (d, J=8.4 Hz, 1H), 7.82 (t, J=8.0 Hz, 1H), 7.60 (d, J=7.2 Hz, 1H), 7.28 (d, J=8.0 Hz, 1H), 7.03 (d, J=8.4 Hz, 1H), 5.81 (dd, J=10.8, 3.6 Hz, 1H), 4.32 (dd, J=14.4, 3.6 Hz, 1H), 4.23-4.15 (m, 3H), 3.76 (s, 3H), 3.10 (s, 3H), 2.34 (d, J=6.8 Hz, 2H), 2.10-2.07 (m, 1H), 1.16 (t, J=7.2 Hz, 3H), 0.95 (d, J=6.8 Hz, 6H). LCMS: [M+H]$^+$=504.0.

Compounds 761 and 762 can be synthesized according to the method of compound 751 in example 36, except isovaleryl chloride was used instead of compound 751-B (2-(dimethylamino)acetyl chloride) and compound 737-D2 ((S)-4-amino-2-(1-(6-ethoxy-5-methoxypyridin-2-yl)-2-(methylsulfonyl)ethyl)isoindoline-1,3-dione) or 737-D1 ((R)-4-amino-2-(1-(6-ethoxy-5-methoxypyridin-2-yl)-2-(methylsulfonyl) ethyl)isoindoline-1,3-dione) was used respectively instead of 745-D.

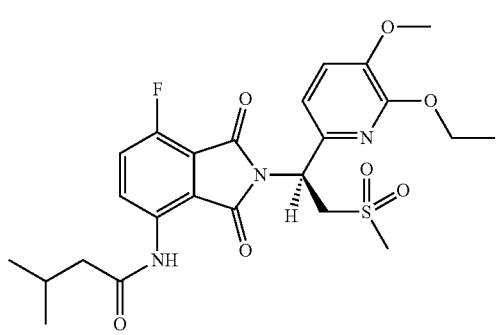

758

(S)—N-(2-(1-(6-ethoxy-5-methoxypyridin-2-yl)-2-(methylsulfonyl)ethyl)-7-fluoro-1,3-dioxoisoindolin-4-yl)-3-methylbutanamide

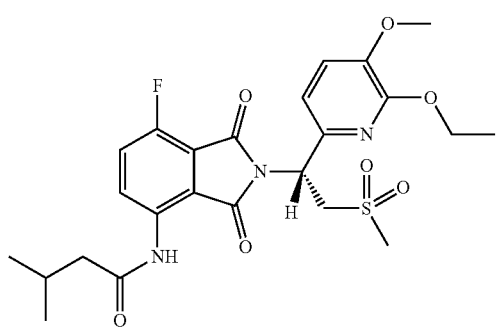

759

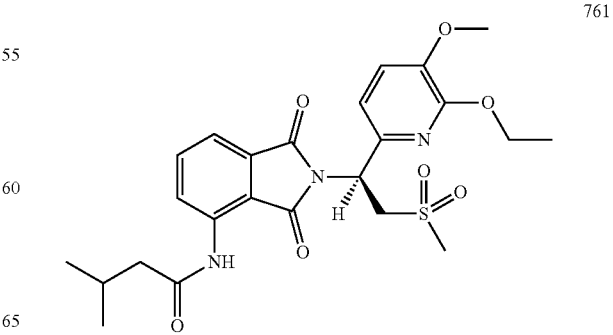

761

(S)—N-(2-(1-(6-ethoxy-5-methoxypyridin-2-yl)-2-(methylsulfonyl)ethyl)-1,3-dioxoisoindolin-4-yl)-3-methylbutanamide

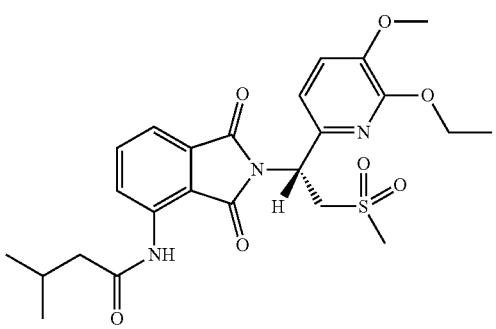

762

(R)—N-(2-(1-(6-ethoxy-5-methoxypyridin-2-yl)-2-(methylsulfonyl)ethyl)-1,3-dioxoisoindolin-4-yl)-3-methylbutanamide Example 40. Synthesis of Compound 763

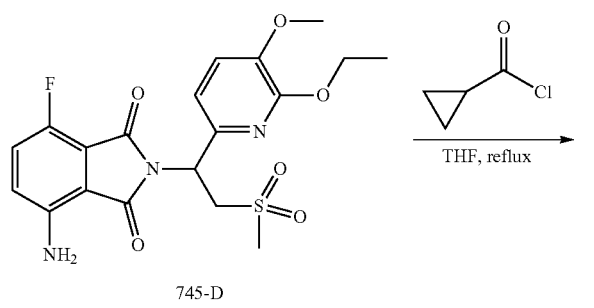

745-D

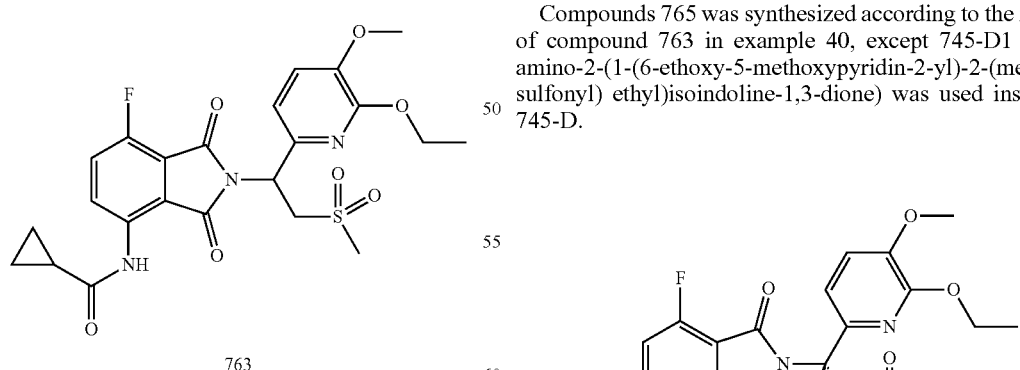

763

A solution of 745-D (4-amino-2-(1-(6-ethoxy-5-methoxypyridin-2-yl)-2-(methyl sulfonyl)ethyl)-7-fluoroisoindoline-1,3-dione, 260 mg, 0.59 mmol) in THF (3 mL) was added cyclopropanecarbonyl chloride (CAS number 4023-34-1, 124 mg, 1.19 mmol) and stirred at 75° C. for 1.5 hours. The mixture was concentrated and purified by Prep-HPLC to afford product 763 (119 mg, yield: 40%).

$^1$H NMR (400 MHz, DMSO-d$_6$) δ 10.03 (s, 1H), 8.43-8.40 (m, 1H), 7.68 (t, J=9.2 Hz, 1H), 7.27 (d, J=8.4 Hz, 1H), 7.06 (d, J=8.4 Hz, 1H), 5.80 (dd, J=10.4, 3.6 Hz, 1H), 4.36-4.31 (m, 1H), 4.24-4.13 (m, 3H), 3.77 (s, 3H), 3.10 (s, 3H), 2.00-1.97 (m, 1H), 1.20 (t, J=7.2 Hz, 3H), 0.87 (d, J=5.2 Hz, 4H). LCMS: [M+H]$^+$=506.2.

Compounds 764 was synthesized according to the method of compound 763 in example 40, except 745-D2 ((S)-4-amino-2-(1-(6-ethoxy-5-methoxypyridin-2-yl)-2-(methylsulfonyl) ethyl)-7-fluoroisoindoline-1,3-dione) was used instead of 745-D.

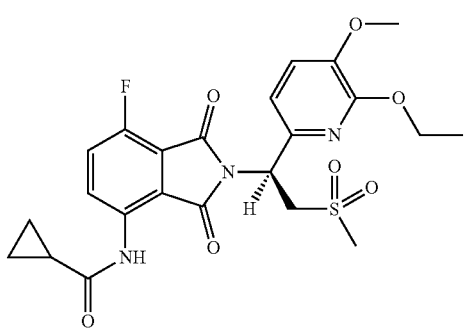

764

(S)—N-(2-(1-(6-ethoxy-5-methoxypyridin-2-yl)-2-(methylsulfonyl)ethyl)-7-fluoro-1,3-dioxoisoindolin-4-yl)cyclopropanecarboxamide)

$^1$H NMR (400 MHz, DMSO-d$_6$) δ 10.02 (s, 1H), 8.42 (dd, J=9.2, 4.0 Hz, 1H), 7.67 (t, J=9.2 Hz, 1H), 7.27 (d, J=8.0 Hz, 1H), 7.07 (d, J=7.6 Hz, 1H), 5.82-5.80 (m, 1H), 4.32-4.31 (m, 1H), 4.24-4.18 (m, 3H), 3.77 (s, 3H), 3.10 (s, 3H), 2.07-1.96 (m, 1H), 1.20 (t, J=7.2 Hz, 3H), 0.88-0.86 (m, 4H). LCMS: [M+H]$^+$=506.2.

Compounds 765 was synthesized according to the method of compound 763 in example 40, except 745-D1 ((R)-4-amino-2-(1-(6-ethoxy-5-methoxypyridin-2-yl)-2-(methylsulfonyl) ethyl)isoindoline-1,3-dione) was used instead of 745-D.

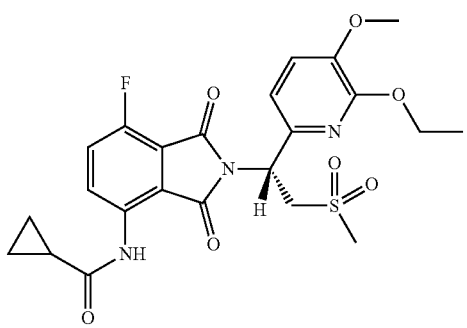

765

(R)—N-(2-(1-(6-ethoxy-5-methoxypyridin-2-yl)-2-(methylsufonyl)ethyl)-7-1,3-dioxoisoindolin-4-yl)cyclopropanecarboxamide Example 41. Synthesis of Compound 767

Synthesis of Intermediate Compound 767-D2

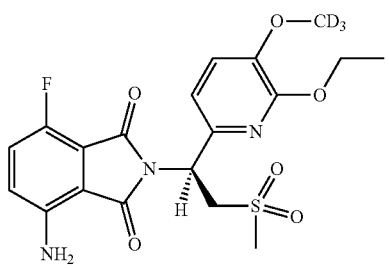

767-D2

Compound 767-D2 ((S)-4-amino-2-(1-(6-ethoxy-5-d$_3$-methoxypyridin-2-yl)-2-(methylsulfonyl)ethyl)-7-fluoroisoindoline-1,3-dione)) was synthesized according to the method of compound 737-D in example 31, except 712-A2 ((S)-1-(6-ethoxy-5-d$_3$-methoxypyridin-2-yl)-2-(methylsulfonyl) ethanamine) was used instead of compound 701-F (1-(6-ethoxy-5-methoxypyridin-2-yl)-2-(methylsulfonyl) ethanamine) and 101-A (3-fluoro-6-nitrophthalic acid) was used instead of 737-B (3-nitro phthalic acid).

$^1$H NMR (300 MHz, DMSO-d$_6$) δ 7.38-7.33 (m, 1H), 7.26 (d, J=10.5 Hz, 1H), 7.09-7.03 (m, 1H), 6.98-6.95 (m, 1H), 6.46 (s, 2H), 5.77-5.71 (m, 1H), 4.31-4.16 (m, 4H), 3.08 (s, 3H), 1.23-1.15 (m, 3H).

Synthesis of Compounds 767-D and 767-D1

Compounds 767-D and 767-D1 can be synthesized according to the method of compound 737-D in example 31, except 101-A (3-fluoro-6-nitrophthalic acid) was used instead of 737-B (3-nitro phthalic acid) and 712-A (1-(6-ethoxy-5-d$_3$-methoxypyridin-2-yl)-2-(methylsulfonyl) ethanamine) or 712-A1 ((R)-1-(6-ethoxy-5-d$_3$-methoxypyridin-2-yl)-2-(methylsulfonyl)ethan amine) was used respectively instead of compound 701-F (1-(6-ethoxy-5-methoxypyridin-2-yl)-2-(methylsulfonyl)ethanamine).

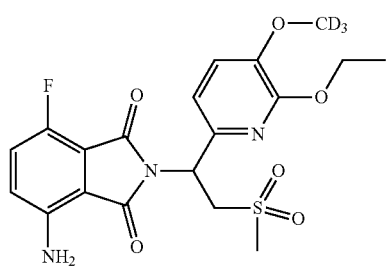

767-D 4-amino-2-(1-(6-ethoxy-5-d$_3$-methoxypyridin-2-yl)-2-(methylsulfonyl)ethyl)-7-fluoroisoindoline-1,3-dione

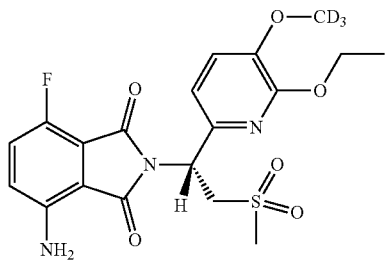

767-D1

(R)-4-amino-2-(1-(6-ethoxy-5-d$_3$-methoxypyridin-2-yl)-2-(methylsulfonyl)ethyl)-7-fluoroisoindoline-1,3-dione

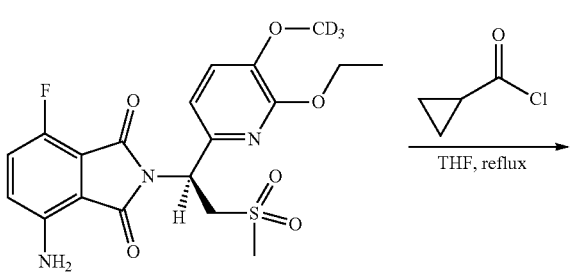

767-D2

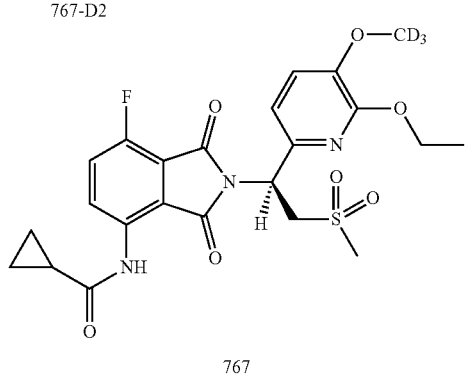

767

Compound 767 ((S)—N-(2-(1-(6-ethoxy-5-d$_3$-methoxypyridin-2-yl)-2-(methylsulfonyl) ethyl)-7-fluoro-1,3-dioxoisoindolin-4-yl)cyclopropanecarboxamide) was synthesized according to the method of compound 763 in example 40, except compound 767-D2 was used instead of 745-D.

$^1$H NMR (400 MHz, DMSO-d$_6$) δ 10.02 (s, 1H), 8.43-8.40 (m, 1H), 7.67 (t, J=9.2 Hz, 1H), 7.27 (d, J=8.0 Hz, 1H), 7.06 (d, J=8.0 Hz, 1H), 5.82-5.78 (m, 1H), 4.33 (dd, J=14.4, 3.6 Hz, 1H), 4.22-4.13 (m, 3H), 3.10 (s, 3H), 2.01-1.95 (m, 1H), 1.20 (t, J=7.2 Hz, 3H), 0.90-0.86 (m, 4H). LCMS: 509.2 ([M+H]$^+$). ee %=98.9%

Compound 766 can be synthesized according to the method of compound 763 in example 40, except compound 767-D was used instead of 745-D.

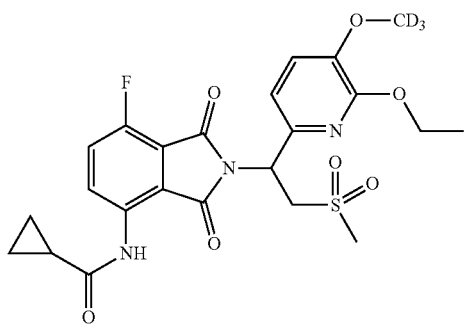

N-(2-(1-(6-ethoxy-5-d₃-methoxypyridin-2-yl)-2-(methylsulfonyl)ethyl)-7-fluoro-1,3-dioxoisoindolin-4-yl)cyclopropanecarboxamide Compound 768 can be synthesized according to the method of compound 763 in example 40, except compound 767-D1 was used instead of 745-D.

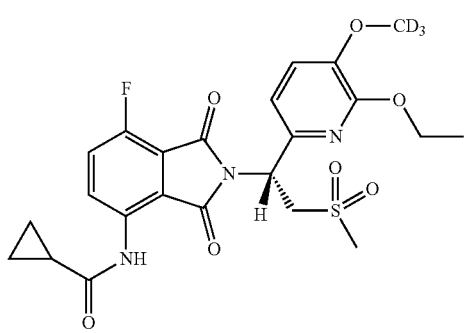

(R)—N-(2-(1-(6-ethoxy-5-d₃-methoxypyridin-2-yl)-2-(methylsulfonyl)ethyl)-7-fluoro-1,3-dioxoisoindolin-4-yl)cyclopropanecarboxamide Example 42. Synthesis of Compound 770

Compound 770 was synthesized according to the method of compound 763 in example 40, except compound 737-D2 ((S)-4-amino-2-(1-(6-ethoxy-5-methoxypyridin-2-yl)-2-(methyl sulfonyl)ethyl)isoindoline-1,3-dione) was used instead of 745-D.

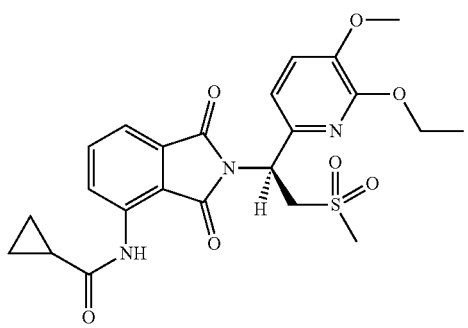

(S)—N-(2-(1-(6-ethoxy-5-methoxypyridin-2-yl)-2-(methylsulfonyl)ethyl)-1,3-dioxoisoindolin-4-yl)cyclopropanecarboxamide ¹H NMR (400 MHz, DMSO-d₆) δ 9.98 (s, 1H), 8.43 (d, J=8.4 Hz, 1H), 7.80 (t, J=8.0 Hz, 1H), 7.59 (d, J=7.6 Hz, 1H), 7.27 (d, J=8.4 Hz, 1H), 7.03 (d, J=8.0 Hz, 1H), 5.82 (dd, J=10.8 Hz, 3.6 Hz, 1H), 4.31-4.30 (m, 1H), 4.23-4.16 (m, 3H), 3.76 (s, 3H), 3.10 (s, 3H), 2.00-1.97 (m, 1H), 1.17 (t, J=7.2 Hz, 3H), 0.88-0.87 (m, 4H). LCMS: 487.9 ([M+H]⁺).

Compounds 769 and 771 can be synthesized according to the method of compound 763 in example 40, except compound 737-D (4-amino-2-(1-(6-ethoxy-5-methoxypyridin-2-yl)-2-(methylsulfonyl)ethyl)isoindoline-1,3-dione) or 737-D1 ((R)-4-amino-2-(1-(6-ethoxy-5-methoxypyridin-2-yl)-2-(methylsulfonyl) ethyl)isoindoline-1,3-dione) was used respectively instead of 745-D.

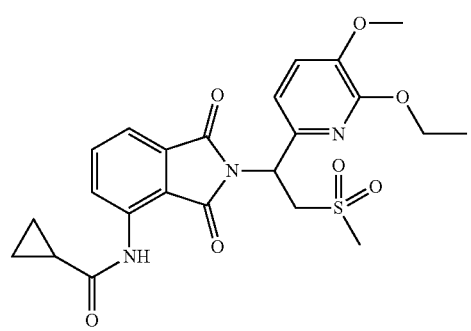

N-(2-(1-(6-ethoxy-5-methoxypyridin-2-yl)-2-(methylsulfonyl)ethyl)-1,3-dioxoisoindolin-4-yl)cyclopropanecarboxamide

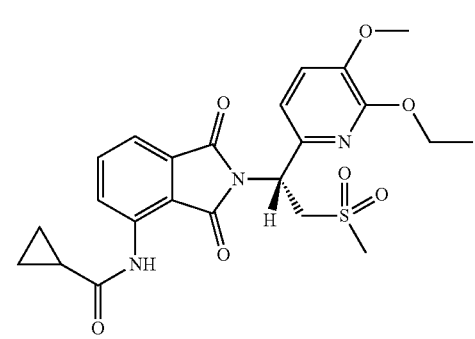

(R)—N-(2-(1-(6-ethoxy-5-methoxypyridin-2-yl)-2-(methylsulfonyl)ethyl)-1,3-dioxoisoindolin-4-yl)cyclopropanecarboxamide Example 43. Synthesis of Compound 773

Synthesis of Intermediate Compound 773-D2

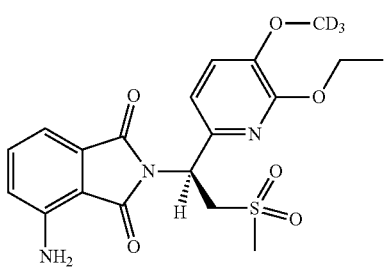
773-D2

Compound 773-D2 ((S)-4-amino-2-(1-(6-ethoxy-5-methoxypyridin-2-yl)-2-(methyl sulfonyl)ethyl)isoindoline-1,3-dione) was synthesized according to the method of compound 737-D in example 31, except compound 712-A2 ((S)-1-(6-ethoxy-5-d₃-methoxypyridin-2-yl)-2-(methylsulfonyl) ethanamine) was used instead of 701-F (1-(6-ethoxy-5-methoxypyridin-2-yl)-2-(methylsulfonyl) ethanamine).

$^1$H NMR (300 MHz, DMSO-$d_6$) δ 7.48-7.43 (m, 1H), 7.25 (d, J=8.4 Hz, 1H), 7.01-6.91 (m, 3H), 6.49 (s, 2H), 5.78-5.72 (m, 1H), 4.30-4.19 (m, 4H), 3.07 (s, 3H), 1.22-1.15 (m, 3H).

Synthesis of Compounds 773-D and 773-D1

Compounds 773-D and 773-D1 can be synthesized according to the method of compound 737-D in example 31, except compound 712-A (1-(6-ethoxy-5-d₃-methoxypyridin-2-yl)-2-(methylsulfonyl)ethanamine) or 712-A1 ((R)-1-(6-ethoxy-5-d₃-methoxypyridin-2-yl)-2-(methyl sulfonyl)ethanamine) was used respectively instead of 701-F.

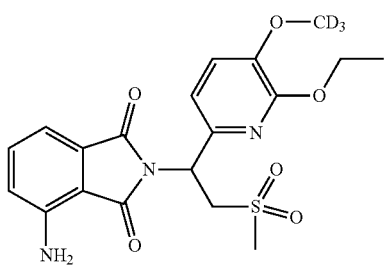
773-D 4-amino-2-(1-(6-ethoxy-5-d₃-methoxypyridin-2-yl)-2-(methylsulfonyl)ethyl)isoindoline-1,3-dione

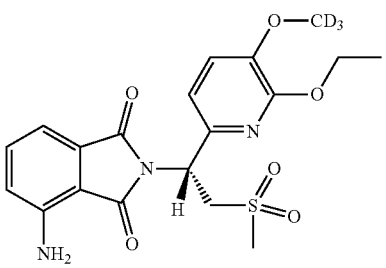
773-D1

(R)-4-amino-2-(1-(6-ethoxy-5-d₃-methoxypyridin-2-yl)-2-(methylsulfonyl)ethyl)isoindoline-1,3-dione Compound 773 was synthesized according to the method of 763 in example 40, except compound 773-D2 was used instead of 745-D.

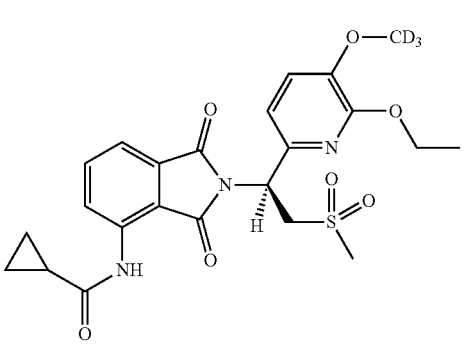
773

(S)—N-(2-(1-(6-ethoxy-5-d₃-methoxypyridin-2-yl)-2-(methylsulfonyl)ethyl)-1,3-dioxoisoindolin-4-yl)cyclopropanecarboxamide)

$^1$H NMR (400 MHz, DMSO-$d_6$) δ 9.99 (s, 1H), 8.43 (d, J=8.4 Hz, 1H), 7.80 (t, J=8.0 Hz, 1H), 7.59 (d, J=6.8 Hz, 1H), 7.27 (d, J=7.6 Hz, 1H), 7.04-7.02 (m, 1H), 5.83-5.80 (m, 1H), 4.36-4.29 (m, 1H), 4.23-4.16 (m, 3H), 3.10 (s, 3H), 2.02-1.96 (m, 1H), 1.17 (t, J=7.2 Hz, 3H), 0.88 (d, J=6.0 Hz, 4H). LCMS: ([M+H]$^+$)=491.2 ee %=99.0%

Compounds 772 and 774 can be synthesized according to the method of 763 in example 40, except compound 773-D or 773-D1 was used respectively instead of 745-D.

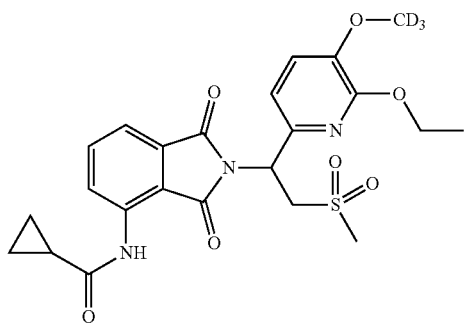

N-(2-(1-(6-ethoxy-5-d₃-methoxypyridin-2-yl)-2-(methylsulfonyl)ethyl)-1,3-dioxoisoindolin-4-yl)cyclopropanecarboxamide

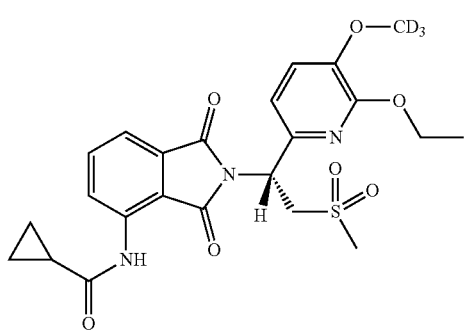

(R)—N-(2-(1-(6-ethoxy-5-d₃-methoxypyridin-2-yl)-2-(methylsulfonyl)ethyl)-1,3-dioxoisoindolin-4-yl)cyclopropanecarboxamide Example 44. Synthesis of Compound 118

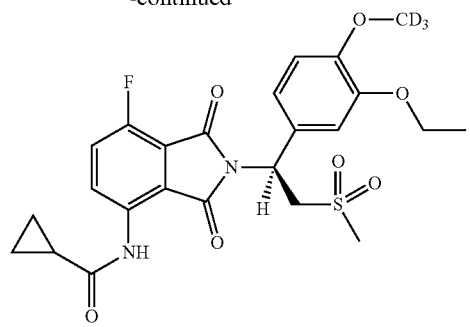

118

Compound 118 ((S)—N-(2-(1-(3-ethoxy-4-d₃-methoxyphenyl)-2-(methylsulfonyl)ethyl)-7-fluoro-1,3-dioxoisoindolin-4-yl)cyclopropanecarboxamide) was synthesized according to the method of 763 in example 40, except compound 118-D2 was used instead of 745-D.

$^1$H NMR (400 MHz, DMSO-d$_6$) δ 10.01 (s, 1H), 8.38 (dd, J=9.2, 3.6 Hz, 1H), 7.64 (t, J=9.2 Hz, 1H), 7.07 (s, 1H), 7.01-6.93 (m, 2H), 5.77 (dd, J$_1$=10.4, 4.4 Hz, 1H), 4.31 (dd, J$_1$=14.4, 10.8 Hz, 1H), 4.18-4.14 (m, 1H), 4.03 (q, J=6.8 Hz, 2H), 3.02 (s, 3H), 2.00-1.97 (m, 1H), 1.33 (t, J=6.8 Hz, 3H), 0.89-0.87 (m, 4H). LCMS: ([M+H]$^+$)=507.9.

Synthesis of Compound 118-D2

Compound 118-D2 ((S)-4-amino-2-(1-(3-ethoxy-4-d₃-methoxyphenyl)-2-(methylsulfonyl) ethyl)-7-fluoroisoindoline-1,3-dione) was synthesized according to the method of 737-D in example 31, except compound 103-E ((S)-1-(3-ethoxy-4-d₃-methoxyphenyl)-2-(methyl sulfonyl) ethanamine) was used instead of 701-F (1-(6-ethoxy-5-methoxypyridin-2-yl)-2-(methylsulfonyl)ethanamine) and 101-A (3-fluoro-6-nitrophthalic acid) was used instead of 737-B (3-nitro phthalic acid).

$^1$H NMR (300 MHz, DMSO-d$_6$) δ 7.33 (t, J=9.0 Hz, 1H), 7.06-7.01 (m, 2H), 6.95-6.93 (m, 2H), 6.46 (s, 2H), 5.73-5.69 (m, 1H), 4.37-4.29 (m, 1H), 4.12-3.98 (m, 3H), 3.01 (s, 3H), 1.36-1.30 (m, 3H).

Example 45. Synthesis of Compound 120

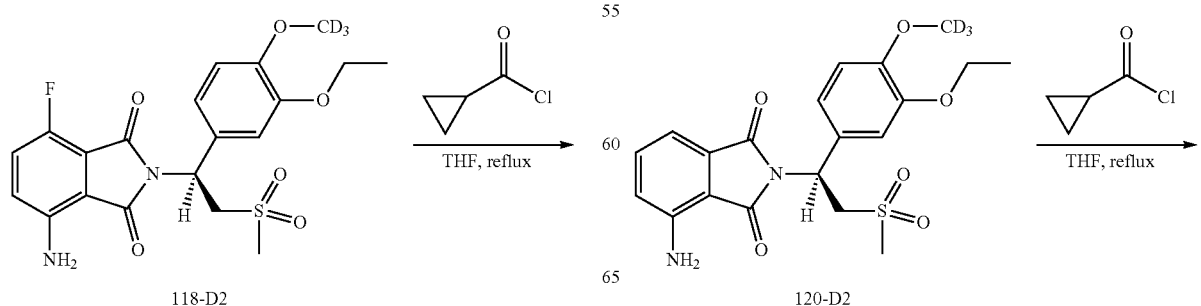

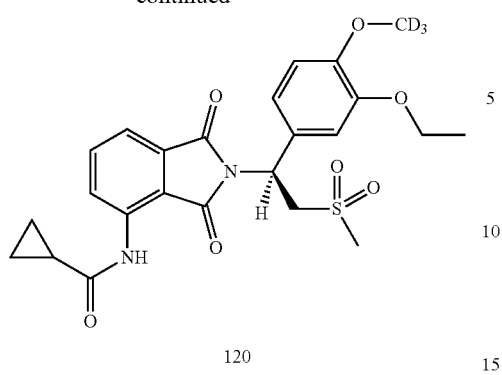

120

Compound 120 ((S)—N-(2-(1-(3-ethoxy-4-d₃-methoxyphenyl)-2-(methylsulfonyl)ethyl)-1,3-dioxoisoindolin-4-yl)cyclopropanecarboxamide) was synthesized according to the method of compound 763 in example 40, except compound 120-D2 was used instead of 745-D.

¹H NMR (400 MHz, DMSO-d₆) δ 9.98 (s, 1H), 8.40 (d, J=8.4 Hz, 1H), 7.78 (t, J=8.0 Hz, 1H), 7.56 (d, J=7.2 Hz, 1H), 7.08 (d, J=2.0 Hz, 1H), 7.01-6.92 (m, 2H), 5.79 (dd, J=10.4, 4.4 Hz, 1H), 4.35 (dd, J=14.4, 10.8 Hz, 1H), 4.15 (dd, J=14.4, 4.4 Hz, 1H), 4.02 (q, J=7.2 Hz, 2H), 3.02 (s, 3H), 2.00-1.94 (m, 1H), 1.32 (t, J=7.2 Hz, 3H), 0.90-0.88 (m, 4H). LCMS: ([M+H]⁺)=490.0.

Synthesis of Compound 120-D2

Compound 120-D2

((S)-4-amino-2-(1-(3-ethoxy-4-d₃-methoxyphenyl)-2-(methylsulfonyl)ethyl)isoindoline-1,3-dione) was synthesized according to the method of compound 737-D in example 31, except compound 103-E ((S)-1-(3-ethoxy-4-d₃-methoxyphenyl)-2-(methyl sulfonyl)ethanamine) was used instead of 701-F (1-(6-ethoxy-5-methoxypyridin-2-yl)-2-(methylsulfonyl)ethanamine).

¹H NMR (300 MHz, DMSO-d₆) δ 7.46-7.41 (m, 1H), 7.06 (s, 1H), 6.99-6.93 (m, 4H), 6.52-6.50 (m, 2H), 6.46 (s, 2H), 5.74-5.69 (m, 1H), 4.35-4.31 (m, 1H), 4.11-3.97 (m, 3H), 3.00 (s, 3H), 1.32 (t, J=6.9 Hz, 3H).

Example 46. Synthesis of Compound 502

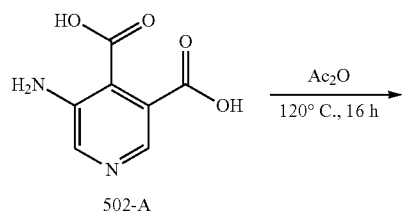

502-A

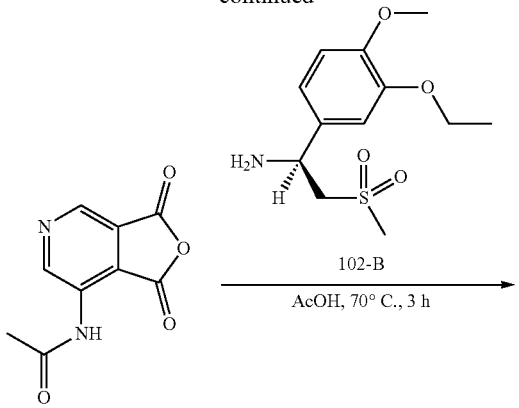

502-B

502

Step 1. Synthesis of Compound 502-B

A mixture of compound 502-A (5-aminopyridine-3,4-dicarboxylic acid, 0.3 g, 1.32 mmol) in Ac₂O (8 mL) was stirred at 120° C. for overnight. The solvent was removed to give the crude product 502-B (N-(1,3-dioxo-1,3-dihydrofuro[3,4-c]pyridin-7-yl)acetamide, 0.35 g).

¹H NMR (300 MHz, DMSO-d₆) δ 10.47 (s, 1H), 9.45 (s, 1H), 9.03 (s, 1H), 2.22 (s, 3H).

Step 2. Synthesis of Compound 502

A mixture of compound 502-B (N-(1,3-dioxo-1,3-dihydrofuro[3,4-c]pyridin-7-yl) acetamide, 0.3 g crude) and 102-B ((S)-1-(3-ethoxy-4-methoxyphenyl)-2-(methylsulfonyl) ethanamine, 0.30 g, 1.10 mmol) in AcOH (6 mL) was stirred at 70° C. for 3 hours. The solvent was removed to get the crude product which was purified by prep-HPLC to give compound 502 ((S)—N-(2-(1-(3-ethoxy-4-methoxyphenyl)-2-(methylsulfonyl)ethyl)-1,3-dioxo-2,3-dihydro-1H-pyrrolo[3,4-c]pyridin-7-yl)acetamide, 144 mg, yield: 28%).

¹H NMR (400 MHz, DMSO-d₆) δ 9.98 (s, 1H), 9.52 (s, 1H), 8.83 (s, 1H), 7.08 (d, J=2.0 Hz, 1H), 7.01 (dd, J=8.4, 2.0 Hz, 1H), 6.94 (d, J=8.4 Hz, 1H), 5.79 (dd, J=10.4, 4.8 Hz, 1H), 4.30-4.17 (m, 2H), 4.02 (q, J=6.8 Hz, 2H), 3.74 (s, 3H), 3.01 (s, 3H), 2.21 (s, 3H), 1.32 (t, J=6.8 Hz, 3H). LCMS: [M+H]+=461.9.

Synthesis of the Starting Material 502-A

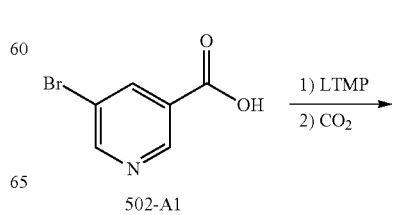

502-A1

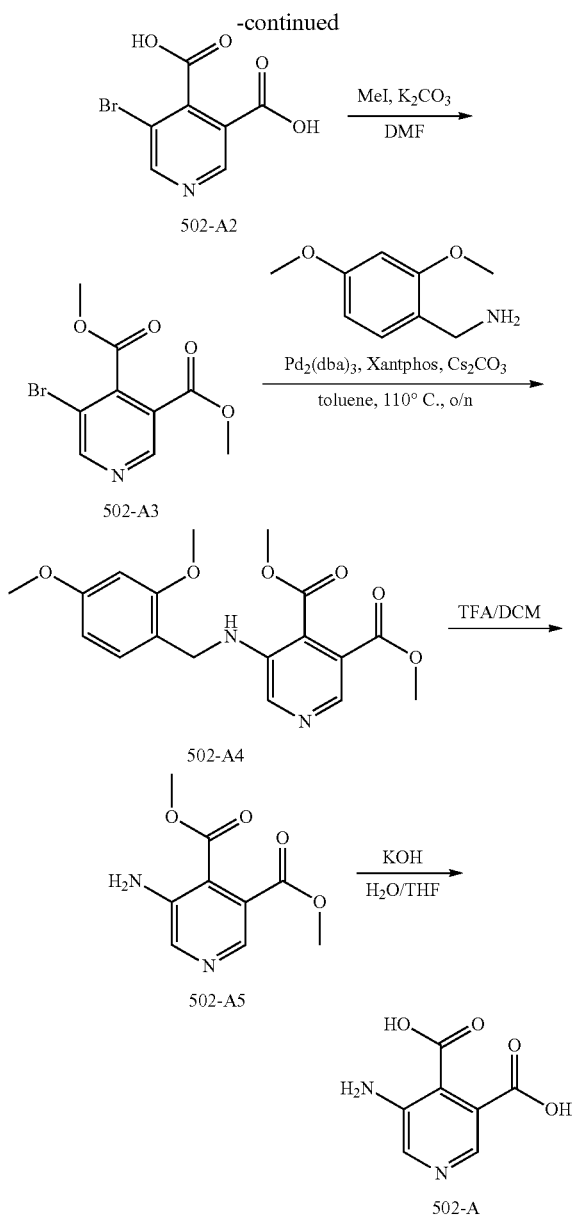

Synthesis of Compound 502-A2

At −60° C., a solution of 2,2,6,6-Tetramethyl-piperidine (16.8 g, 118.8 mmol) in 200 mL of THF was added n-BuLi (2.5 M, 44 mL, 108.9 mmol) by dropwise slowly and stirred for 15 minutes. Then 502-A1 (5-bromonicotinic acid, 10 g, 49.5 mmol) was added and stirred at −60° C. for 0.5 hour. Then, dry $CO_2$ was bubbled into the reaction mixture at 25° C. for 3 hours. Water (150 mL) was added to quench the reaction. The THF was removed. The water phase was adjusted to pH=3 with 1N HCl, concentrated and the resulting precipitate solid was collected by filtration and dried to give compound 502-A2 (5-bromopyridine-3,4-dicarboxylic acid, 12.5 g) as brown solid.

$^1$H NMR (300 MHz, DMSO-$d_6$) δ 9.02-9.03 (m, 2H), 8.73 (br s, 2H).

Synthesis of Compound 502-A3

A solution of 502-A2 (9.3 g, 37.8 mmol) in 100 mL of DMF was added $K_2CO_3$ (26.1 g, 189 mmol) and stirred at 25° C. for 0.5 hour. Then $CH_3I$ (5.9 mL, 94.5 mmol) was added to the mixture at 0° C. The mixture was stirred at 25° C. for 3 hours. The mixture was poured into water (600 mL), extracted with EtOAc (200 mL*2), washed with brine (200 mL*2), dried and concentrated to give the crude product which was purified by column chromatography on silica gel eluted with PE:EtOAc=6:1 to give product 502-A3 (dimethyl 5-bromopyridine-3,4-dicarboxylate, 1.59 g, 15%) as yellow solid.

$^1$H NMR (300 MHz, DMSO-$d_6$) δ 9.13 (s, 1H), 9.12 (s, 1H), 3.93 (s, 3H), 3.90 (s, 3H).

Synthesis of Compound 502-A4

A solution of 502-A3 (1.59 g, 5.8 mmol) in 70 mL of toluene was added 2,4-Dimethoxy-benzylamine (1.46 g, 8.75 mmol), $Pd_2(dba)_3$ (0.532 g, 0.58 mmol), Xantphos (1.0 g, 1.74 mmol), $Cs_2CO_3$ (3.8 g, 11.6 mmol). Then, the mixture was stirred at 105° C. for overnight. The mixture was cooled to 25° C., filtrated and concentrated to give the crude product which was purified by column chromatography on silica gel eluted with PE:EtOAc=10:1 to 3:1 to give the 502-A4 (dimethyl 5-((2,4-dimethoxybenzyl)amino)pyridine-3,4-dicarboxylate, 1.92 g, 92%) as brown oil.

$^1$H NMR (300 MHz, CDCl$_3$) δ 8.33 (s, 1H), 8.13 (s, 1H), 7.16 (d, J=8.1 Hz, 1H), 6.56-6.60 (m, 1H), 6.43-6.49 (m, 2H), 4.42 (d, J=6.0 Hz, 2H), 3.90-3.81 (m, 12H).

Synthesis of Compound 502-A5

A solution of compound 502-A4 (1.92 g, 5.33 mmol) in 30 mL of DCM was added TFA (9 mL) slowly by drop wise at 0° C. Then, the mixture was stirred at 25° C. for 2 hours. The solvent was removed. The residue was diluted with water (100 mL), adjusted to pH=8 with $Na_2CO_3$, extracted with DCM (100 mL*2), dried and concentrated to give product 502-A5 (dimethyl 5-aminopyridine-3,4-dicarboxylate, 1.15 g) as brown oil.

$^1$H NMR (300 MHz, DMSO-$d_6$) δ 8.32 (s, 1H), 7.99 (s, 1H), 6.18 (s, 2H), 3.81 (s, 6H).

Synthesis of Compound 502-A

A mixture of 502-A5 (0.8 g, 3.8 mmol) in 60 mL of THF was added KOH (20%, 60 mL). Then, the mixture was stirred at 25° C. for 3 hours. The solvent was removed. The residue was diluted with water (20 mL), extracted with EtOAc (20 mL*2). The water phase was adjusted the pH to 3 with 2 N HCl. The solvent was removed. The residue was diluted with EtOH (50 mL), stirred at 25° C. for 1 hour, filtrated, concentrated to give 502-A (5-aminopyridine-3,4-dicarboxylic acid, 1.2 g) as yellow solid.

Example 47. Synthesis of Compound 121

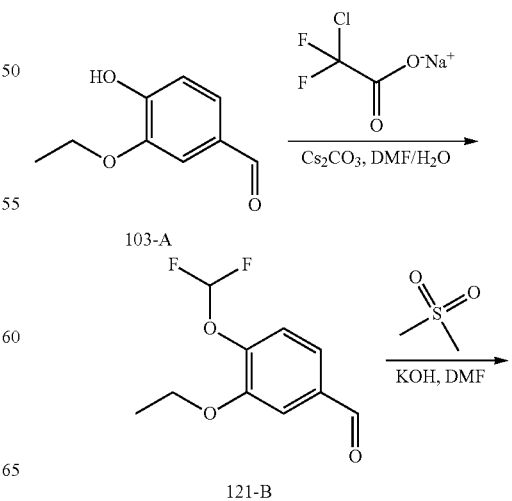

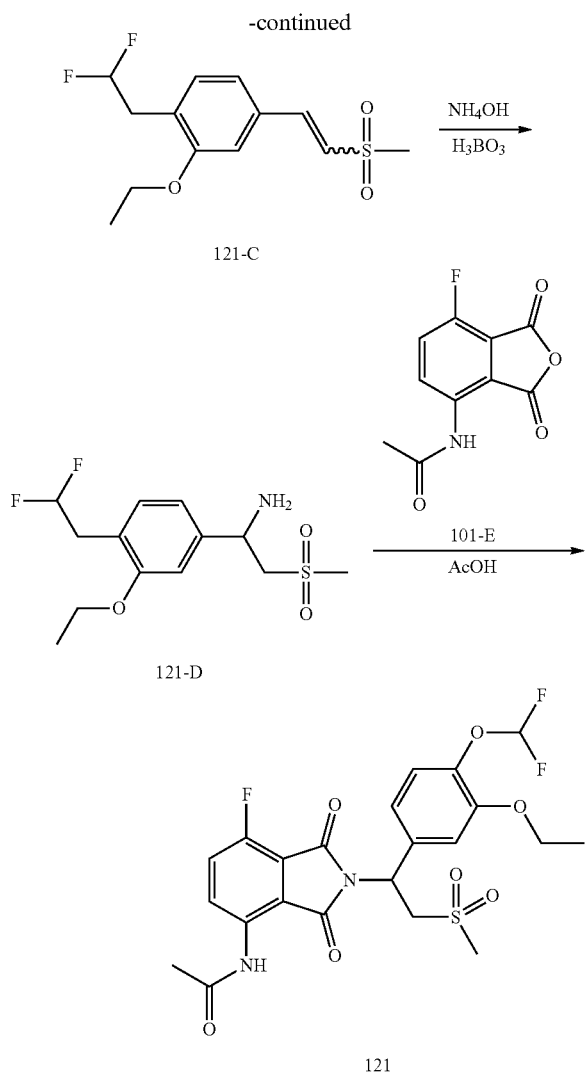

Step 1. Synthesis of Compound 121-B

A solution of 103-A (3-ethoxy-4-hydroxybenzaldehyde, 10 g, 60.2 mmol) and Cs$_2$CO$_3$ (29.43 g, 90.3 mmol) in DMF (70 mL) and H$_2$O (70 mL) was added sodium 2-chloro-2,2-difluoroacetate (23 g, 150.5 mmol). The mixture was stirred at 100° C. for overnight. Water (500 mL) was added and the mixture was extracted with EtOAc (100 mL×2). The organic phase was washed with brine (100 mL×2), dried and concentrated and purified by column chromatography on silica gel (PE:EtOAc=10:1) to give 121-B (4-(difluoromethoxy)-3-ethoxybenzaldehyde, 2.5 g, 19%) as yellow oil.

$^1$H NMR (300 MHz, CDCl$_3$) δ 9.92 (s, 1H), 7.48-7.43 (m, 2H), 7.30 (d, J=6.8 Hz, 1H), 6.70 (td, J=99.6, 0.9 Hz, 1H), 4.20-4.14 (m, 2H), 1.50-1.45 (m, 3H).

Step 2. Synthesis of Compound 121-C

A solution of DMSO (2.72 g, 29 mmol), KOH (0.97 g, 17.3 mmol) in DMF (50 mL) was stirred at 30° C. for 30 minutes. Compound 121-B (4-(difluoromethoxy)-3-ethoxy benzaldehyde, 2.5 g, 11.65 mmol) was added to the mixture slowly and stirred at 30° C. for 3 hours. The mixture was quenched with sat. NH$_4$Cl (50 mL), extracted with EtOAc (100 mL×3), washed with brine (100 mL×3), the combined organic phase was dried, filtered and concentrated to get the crude product which was purified by column chromatography on silica gel eluted with PE:EtOAc=5:1 to 1:1 to give 121-C (1-(difluoromethoxy)-2-ethoxy-4-(2-(methylsulfonyl)vinyl)benzene, 0.45 g, 13%) as yellow oil.

$^1$H NMR (300 MHz, CDCl$_3$) δ 7.57 (d, J=15.3 Hz, 1H), 7.27-6.39 (m, 5H), 44.14 (q, J=6.9 Hz, 2H), 3.05 (s, 3H), 1.49 (t, J=6.9 Hz, 3H).

Step 3. Synthesis of Compound 121-D

A solution of H$_3$BO$_3$ (0.19 g, 3.08 mmol) and compound 121-C (1-(difluoromethoxy)-2-ethoxy-4-(2-(methylsulfonyl)vinyl)benzene, 0.45 g, 1.54 mmol) in NH$_{40}$H (60 mL) and dioxane (10 mL) was stirred in a sealed tube for 3 days at 100° C. The mixture was extracted with EtOAc (50 mL×3), the organic layer was washed with 1 N HCl (50 mL×2), adjusted the pH to 12 with NaOH, extracted with EtOAc (50 mL×3), dried and concentrated to get product 121-D (1-(4-(difluoromethoxy)-3-ethoxyphenyl)-2-(methylsulfonyl)ethanamine, 0.29 g, 61%) as colorless oil.

$^1$H NMR (400 MHz, DMSO-d$_6$) δ 7.22-6.96 (m, 3H), 4.34-4.31 (m, 1H), 4.11 (q, J=7.2 Hz, 2H), 3.48-3.42 (m, 1H), 3.30-3.25 (m, 1H), 3.02 (s, 3H), 2.33 (br s, 2H), 1.35 (t, J=7.2 Hz, 3H).

Step 4. Synthesis of Compound 121

A mixture of 121-D (1-(4-(difluoromethoxy)-3-ethoxyphenyl)-2-(methylsulfonyl)ethanamine, 280 mg, 0.906 mmol) and 101-E (N-(7-fluoro-1,3-dioxo-1,3-dihydroisobenzofuran-4-yl) acetamide, 202 mg, 0.906 mmol) in HOAc (10 mL) was stirred at 80° C. for overnight. Then the mixture was concentrated to dryness under reduced pressure. The residue was purified by Prep-HPLC to afford 121 (N-(2-(1-(4-(difluoromethoxy)-3-ethoxyphenyl)-2-(methylsulfonyl) ethyl)-7-fluoro-1,3-dioxoisoindolin-4-yl)acetamide, 235 mg, 50%) as a white solid.

$^1$H NMR (400 MHz, DMSO-d$_6$) δ 9.76 (s, 1H), 8.44-8.41 (m, 1H), 7.67 (t, J=9.2 Hz, 1H), 7.25-6.88 (m, 4H), 5.83 (dd, J=10.4, 4.4 Hz, 1H), 4.34-4.19 (m, 2H), 4.12 (q, J=7.2 Hz, 2H), 3.06 (s, 3H), 2.17 (s, 3H), 1.35 (t, J=7.2 Hz, 3H). LCMS: [M+H]+=514.9.

Effect Example 1. PDE4 Activity Inhibition Assay

The IC$_{50}$ value of the inhibitory effect of the compound on PDE4A1A, PDE4B1 and PDE4D3 was tested.

Experiment Materials:

Enzyme: PDE4A1A (BPS, Cat No. 60040); PDE4B1 (BPS, Cat No. 60041); PDE4D3 (BPS, Cat No. 60046).

Positive compound: Trequinsin (Sigma, Cat. No. T2057).

Reaction plate: a 384-well plate (Perkin Elmer, Cat. No. 6007279).

Equipment: Wallac Victor Multi-label counter (Perkin Elmer).

Experiment Steps:

I. Preparing 1× reaction liquid and termination liquid;

II. PDE enzymatic reaction;

1) The PDE was dissolved in 1× reaction solution to form 2× enzyme solution.
2) FAM-cAMP was dissolved in 1× reaction solution to form 2× substrate solution.
3) Echo 550 was used to transfer the corresponding volume of the compound in DMSO solution to the reaction plate.
4) 2× enzyme solution was added into the corresponding well of the reaction plate and incubated with the compound solution at room temperature for 15 minutes.
5) 2× substrate solution was added into the corresponding well of the reaction plate to initiate the reaction.

6) Reaction plate was incubated at room temperature for 30 minutes and terminated by adding termination liquid, then incubated at room temperature for 60 minutes.

III. Read on Victor;

IV. Curve fitting;

The inhibition rate was calculated by Excel; $IC_{50}$ was calculated by GraphPad Prism.

The corresponding structures of the compound codes of the present invention are as described above, and the structures of the reference compounds are as follows:

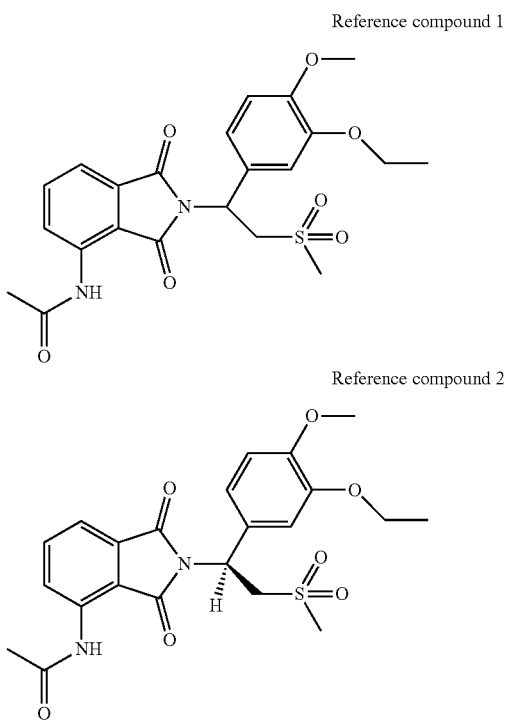

Reference compound 1

Reference compound 2

Experimental Results:

| Compound | IC$_{50}$ (nM) | | |
|---|---|---|---|
| | PDE4A1A | PDE4B1 | PDE4D3 |
| Reference compound 1 | 22 | 29 | 13 |
| Reference compound 2 | 9.85 | 14.5 | 6.4 |
| 101 | 17 | 27 | 12 |
| 201 | 39 | 41 | 25 |
| 301 | 102 | 116 | 65 |
| 401 | 182 | 211 | 110 |
| 601 | 273 | 390 | 201 |
| 701 | 2.5 | 3.5 | 2.1 |
| 801 | 295 | 364 | 202 |
| 901 | 411 | 484 | 248 |
| 102 | 11 | 14 | 7.4 |
| 202 | 11 | 11 | 5.4 |
| 302 | 33 | 41 | 22 |
| 103 | 7.25 | 12.75 | 3.7 |
| 203 | 22 | 31 | 18 |
| 105 | 61 | 97 | 41 |
| 106 | 340 | 493 | 300 |
| 107 | 8.3 | 12 | 4.6 |
| 205 | 123 | 165 | 79 |
| 206 | 1455 | 1347 | 997 |
| 207 | 20 | 20 | 12 |
| 104 | 53 | 70 | 31 |
| 204 | 133 | 157 | 83 |
| 703 | 30 | 55 | 20 |
| 702 | 2.2 | 4.7 | 4.0 |
| 706 | 6.5 | 18 | 4.0 |
| 705 | 0.58 | 1.6 | 0.53 |
| 709 | 17 | 32 | 11 |
| 708 | 3.1 | 5.1 | 1.6 |
| 712 | 32.6 | 82.8 | 29.0 |
| 711 | 1.1 | 5.1 | 2.0 |
| 719 | 15.3 | 57.8 | 15.4 |
| 718 | 0.9 | 3.0 | 0.7 |
| 725 | 32.1 | 93.0 | 33.5 |
| 724 | 2.3 | 5.7 | 3.1 |
| 113 | 2.1 | 5.1 | 1.3 |
| 111 | 1.3 | 4.3 | 1.9 |
| 728 | 0.6 | 1.6 | 0.4 |
| 115 | 6.0 | 17.3 | 5.7 |
| 732 | 0.8 | 2.4 | 1.1 |
| 734 | 5.6 | 17.8 | 13.0 |
| 737 | 51.8 | 136.0 | 35.9 |
| 739 | 14.5 | 36.3 | 10.9 |
| 742 | 2.4 | 6.2 | 2.6 |
| 745 | 1.1 | 2.6 | 1.2 |
| 748 | 2.8 | 7.9 | 3.3 |
| 757 | 2.5 | 4.5 | 1.8 |
| 760 | 3.1 | 4.7 | 1.3 |
| 121 | 3.4 | 7.0 | 0.9 |
| 751 | 5.0 | 9.9 | 3.1 |
| 754 | 10.6 | 21.9 | 8.0 |
| 502 | 205.6 | 512.7 | 107.2 |
| 764 | 1.6 | 1.9 | 1.0 |
| 767 | 1.3 | 2.2 | 1.0 |
| 770 | 1.6 | 1.8 | 1.5 |
| 773 | 1.7 | 1.7 | 1.2 |
| 118 | 5.1 | 8.7 | 2.5 |
| 120 | 7.6 | 11.0 | 4.9 |

Effect Example 2. TNF-α Activity Assay

I. PBMC Recovery and Cell Plating Steps:

(1) Cell Recovery:

1) Agitation was performed continuously in a 37° C. water bath to rapidly thaw cells.

2) The cells were gently added to a 15 ml centrifuge tube, to which was then added 10 ml of fresh, prewarmed recovery medium gently and then centrifugation was performed at 1000 rpm for 10 min.

3) The supernatant medium was discarded and resuspension was performed with 10 ml of fresh, prewarmed RPMI 1640 complete medium.

(2) 96-Well Plate Plating:

1) The total number of cells needed for the experiment was calculated and adjusted to the appropriate cell concentration per ml. 100 ul and $10^5$ cells per well.

2) The cell suspension was diluted with appropriate volume of cell culture medium.

3) The cell suspension was added to a disposable sterile sample well.

4) 100 ul of cell suspension was added to each well of a 96-well plate.

5) The plate was incubated in a 37° C., 5% $CO_2$ incubator for 2 hours.

(3) Compound Preparation Steps:

1) LPS: The 1 mg/mL stock solution was diluted with water, aliquoted, and stored at −80° C. Prior to each test, the working solution of LPS was diluted from the stock solution with serum-free RPMI 1640 medium.

2) Test Compound 20 mM stock solution was dissolved in DMSO and the compound was checked for solubility, aliquoted, and stored at −80° C.

(4) 8× Compound Gradient Preparation:

A series of compound concentration gradient was diluted with DMSO: 10 mM, 2 mM, 0.4 mM, 80 uM, 16 uM, 3.2 uM, 0.64 uM, 0.128 uM were obtained and then the compounds were diluted 125-fold with serum-free RPMI 1640 medium to the final 8×. The final concentration of DMSO in cell culture was 0.1%.

(5) Compound Processing Experimental Procedures and Collection of Supematants:

1) Cell Plating: Fresh cells were plated in 96-well cell culture plates according to the procedure above, 100 ul and $10^5$ cells per well, and then incubated in a 37° C., 5% $CO_2$ incubator for 2 hours.

2) Compound Preparation: Before test, compounds were added to the plates according to the above description. A dose of compound in 8× concentration was prepared with serum-free RPMI 1640 medium and all gradients of solution were added to the compound plate.

3) Compound addition: 16.7 ul of compound solution in working concentration was added to each well of the cell culture plate. The plate was incubated in a 37° C., 5% $CO_2$ incubator for 1 hour.

4) 16.7 ul of 8×LPS per well (final concentration of LPS is EC80, the amount of each PBMC needed to be determined) was added. The plate was incubated for 18 hours in 37° C., 5% $CO_2$ incubator.

5) 80 ul of supernatant per well was collected and then subjected to TNF-α ELISA assay. The collected supernatant can be stored at −80° C. The supernatant needed to be diluted in various ratios to ensure that the experimental dose would not exceed the linear range of the TNF-α standard curve, depending on the amount of TNF-α released in different donors. Typically, 20-100 ul of supernatant was diluted to 200 ul and then used for ELISA experiments.

(6) TNF-α ELISA Steps:

The TNF-α ELISA test procedure were referred to the BD human TNF-α ELISA kit experimental procedure.

Experimental Design:

Four compounds per plate. 5-fold dilution was performed, starting from 10 uM, by 8 gradients, and parallel wells were made. The TNF-α standard was added to each plate. ($1^{st}$ well, starting from 500 pg/ml, 2-fold dilution, 7 gradients)

ZPE (0% inhibition) used 15 pg/ml LPS+0.1% DMSO, while HPE (100% inhibition) used only 0.1% DMSO.

The inhibition rate statistics were calculated. The inhibition rate (%)=[1−(Max−Min)/(Test cpd−Min)]*100%. IC50 was used to evaluate the concentration of the test compound (nM) at 50% inhibition.

Effect Example 3. PK Parameter Test

1. Purpose of the Test

Test compounds were administered intravenously or intragastrically singly to SD rats.

Blood samples were collected at different time points. LC-MS/MS was used to determine the concentration of the test compounds in rat plasma after administration of tested compounds and calculate the relevant PK parameters.

2. Experimental Design 2.1. Preparation of Test Compounds

The test compounds are calculated based on free radicals and are converted only by purity.

2.1.1. Intravenous Injection Group

A suitable amount of the test compound was added 5% DMSO+95% HP-beta-CD (20%) to prepare a solution of 0.6 mg/mL for intravenous administration.

2.1.2. Oral Administration Group

A suitable amount of the test compound was added 5% DMSO+95% HP-beta-CD (20%) to prepare a solution of 1 mg/mL for intragastrical administration.

2.2. Dose and Route of Administration

Male Sprague-Dawley rats were purchased from Shanghai Xipuer-Bikai Laboratory Animal Co., Ltd. There were 3 rats in each group. One group was used as control to collect blank plasma. The other groups were given each test compound by intravenous injection (the dose was 3 mg/kg) or intragastrical administration (the dose was 10 mg/kg). Heparin sodium was used for anticoagulation. Analyze the concentration of the test compound in the blood sample.

Abrosia for 10-14 hours before oral administration of the test compounds and resume feeding 4 hours after oral administration of the test compounds.

2.3. Detailed Clinical Observation

Intravenous injection group: Before and after administration, no obvious abnormal conditions were observed at each time point of blood collection.

Oral administration group: soft stool was observed 4-8 hours after administration in every group and all were recovered the next day.

2.4. Sample Collection and Processing

The time points of blood sample collection were: intravenous injection: before administration and at 0.083 hour, 0.25 hour, 0.5 hour, 1 hour, 2 hour, 4 hour, 6 hour, 8 hour, 24 hour after administration; oral administration: before administration and at 0.25 hour, 0.5 hour, 1 hour, 2 hour, 4 hour, 6 hour, 8 hour, 24 hour after administration. Blood samples were collected through jugular vein puncture. About 0.25 mL blood was collected for each sample. Heparin sodium was used for anticoagulation and the samples were placed on ice after collection. Blood samples were placed on ice after collection, and plasma was separated by centrifugation (centrifugation condition: 8000 rpm, 6 min, 2-8° C.). The collected plasma was stored at −80° C. before analysis.

3. Analytical Methods 3.1. Drugs and Reagents

Test Compounds: Provided by Kangpu Biopharmaceuticals, Ltd.

Internal Standard Toluene Sulfonylurea: Provided by Test Institution.

Methanol (Burdick & Jackson, HPLC), acetonitrile (Burdick & Jackson, HPLC), formic acid (J&K), water is ultra-pure water.

3.2. Equipments

Ultra high performance liquid chromatography (Waters, ACQUITY UPLC), including binary solvent manager (AC-QUITY UPLC Binary Solvent Manager), Sample Manager (ACQUITY UPLC Autosampler Mod.), high throughput sample organizer (ACQUTIY UPLC Sample Organizer), high temperature column compartment (ACQUITY UPLC Column Heater HT). Mass spectrometer (API 4000, Bio System Inc, USA), electrospray ion source (ESI), series quadrupole mass analyzer. Data processing system is Analyst software (American Applied Biosystems Inc., version 1.5.1).

3.3. Analytical Methods

LC-MS/Ms Determination.

Sample Pretreatment

50 μL plasma sample was added into a 1.5 mL centrifugal tube, and 250 μL internal standard solution (the same volume of methanol was added to blank sample instead of internal standard) was added to the sample. The sample was mixed in a whirlpool and centrifuged for 5 minutes at 14000 rpm. The supernatant of 200 μL was added to 96-well plate for LC-MS/MS analysis.

4. Pharmacokinetic Results

The pharmacokinetic parameters of the test compounds were calculated using the non-compartment model of Win-Nonlin v5.2, a software for pharmacokinetic calculation, based on the data of plasma concentration. The experimental results are shown in the table below.

| Compound | Tmax(po) | T1/2 (IV) | T1/2(po) | AUC(iv) | AUC(po) | F |
|---|---|---|---|---|---|---|
| Reference compound 2 | 1 | 0.47 | 0.94 | 1048 | 785 | 22.5 |
| 103 | 2 | 1.05 | 3.83 | 1260 | 4125 | 98.2 |
| 203 | 0.5 | 0.95 | 0.87 | 1012 | 250 | 7.4 |
| 702 | 0.67 | 0.38 | 6.53 | 1328 | 1047 | 15.5 |
| 705 | 0.5 | 0.92 | 9.25 | 1343 | 3588 | 80.2 |
| 708 | 0.67 | 0.54 | 4.21 | 945 | 51 | 1.62 |

What is claimed is:

1. A compound of formula I, or a pharmaceutically acceptable salt, solvate, polymorph, co-crystal or stereoisomer thereof,

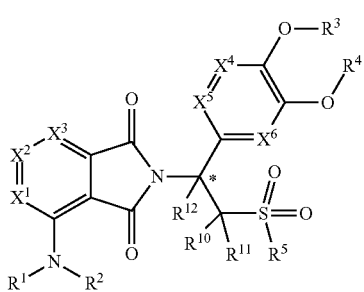

Formula I wherein, the carbon atom labelled by * is an asymmetric center;

$R^1$ and $R^2$ are independently H, D, substituted or unsubstituted $(C_1-C_6)$alkyl, substituted or unsubstituted $(C_3-C_6)$cycloalkyl, $R^6$—$S(O)_2$— or $R^6$—$C(O)$—;

$R^6$ is substituted or unsubstituted $(C_3-C_6)$cycloalkyl; or $(C_1-C_6)$alkyl, which is optionally substituted with one or more groups selected from D, halogen, hydroxyl, amino, $(C_1-C_6)$alkyl amino, $(C_1-C_6)$alkoxy and benzyloxy;

$X^1$, $X^2$, $X^3$, $X^4$, and $X^5$ are independently CH, CD, or $CR^7$;

$X^6$ is N;

$R^7$ is halogen or cyano;

$R^3$ and $R^4$ are independently H, substituted or unsubstituted $(C_1-C_6)$alkyl, substituted or unsubstituted $(C_3-C_6)$cycloalkyl, or, substituted or unsubstituted $(C_1-C_6)$alkyl-$(C_3-C_6)$cycloalkyl;

$R^5$ is substituted or unsubstituted $(C_1-C_6)$alkyl;

$R^{10}$, $R^{11}$ and $R^{12}$ are independently H or D;

the substituent in substituted $(C_1-C_6)$alkyl, substituted $(C_3-C_6)$cycloalkyl, or, substituted $(C_1-C_6)$alkyl-$(C_3-C_6)$cycloalkyl is one or more selected from the group consisting of: D, halogen, hydroxyl, amino, $(C_1-C_6)$alkyl amino, $(C_1-C_6)$alkoxy and benzyloxy; when there are a plurality of substituents, the substituents are the same or different.

2. The compound of formula I, or the pharmaceutically acceptable salt, solvate, polymorph, co-crystal or stereoisomer thereof according to claim 1, wherein, $X^6$ is N, $X^1$, $X^2$, $X^3$ are independently CH, CD or $CR^7$, $X^4$, $X^5$ are independently CH, CD; or $X^6$ is N, $X^1$ is $CR^7$, $X^2$, $X^3$, $X^4$ and $X^5$ are independently CH or CD; or $X^6$ is N, $X^2$ is $CR^7$, $X^1$, $X^3$, $X^4$ and $X^5$ are independently CH or CD; or $X^6$ is N, $X^3$ is $CR^7$, $X^1$, $X^2$, $X^4$ and $X^5$ are independently CH or CD.

3. The compound of formula I, or the pharmaceutically acceptable salt, solvate, polymorph, co-crystal or stereoisomer thereof according to claim 1, wherein, one of $R^1$ and $R^2$ is H or D, the other is $R^6$—$S(O)_2$— or $R^6$—$C(O)$—.

4. The compound of formula I, or the pharmaceutically acceptable salt, solvate, polymorph, co-crystal or stereoisomer thereof according to claim 1, wherein, $R^6$ is $(C_3-C_6)$cycloalkyl; or $(C_1-C_4)$alkyl, which is optionally substituted with one or more substituents selected from the group consisting of D, halogen, hydroxyl, amino, $(C_1-C_4)$alkyl amino, $(C_1-C_4)$alkoxy, and benzyloxy.

5. The compound of formula I, or the pharmaceutically acceptable salt, solvate, polymorph, co-crystal or stereoisomer thereof according to claim 1, wherein, $R^3$ and $R^4$ are independently H, or substituted or unsubstituted $(C_1-C_6)$alkyl.

6. The compound of formula I, or the pharmaceutically acceptable salt, solvate, polymorph, co-crystal or stereoisomer thereof according to claim 1, wherein, $R^5$ is methyl, ethyl, propyl, isopropyl, $CD_3$, $CH_2D$, $CHD_2$, $C_2D_5$ or $CH_2CD_3$.

7. The compound of formula I, or the pharmaceutically acceptable salt, solvate, polymorph, co-crystal or stereoisomer thereof according to claim 1, wherein, $R^7$ is fluorine, chlorine, bromine or cyano.

8. The compound of formula I, or the pharmaceutically acceptable salt, solvate, polymorph, co-crystal or stereoisomer thereof according to claim 1, wherein $X^1$, $X^2$, $X^3$, $X^4$ and $X^5$ are independently CH or $CR^7$.

9. The compound of formula I, or the pharmaceutically acceptable salt, solvate, polymorph, co-crystal or stereoisomer thereof according to claim 1, wherein, $R^{10}$ and $R^{11}$ are H.

10. The compound of formula I, or the pharmaceutically acceptable salt, solvate, polymorph, co-crystal or stereoisomer thereof according to claim 1, wherein, $R^{12}$ is H.

11. The compound of formula I, or the pharmaceutically acceptable salt, solvate, polymorph, co-crystal or stereoisomer thereof according to claim 1, wherein, the asymmetric center refers to (S)-configured carbon.

12. The compound of formula I, or the pharmaceutically acceptable salt, solvate, polymorph, co-crystal or stereoisomer thereof according to claim 1, wherein, the compound of formula I is any one of the following compounds:

701 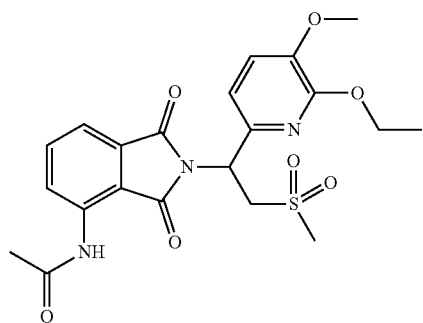
702 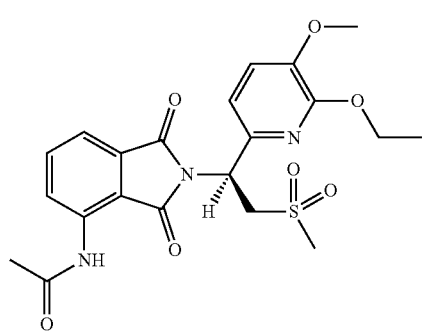
703 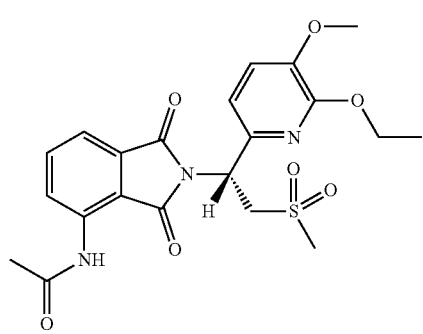
704 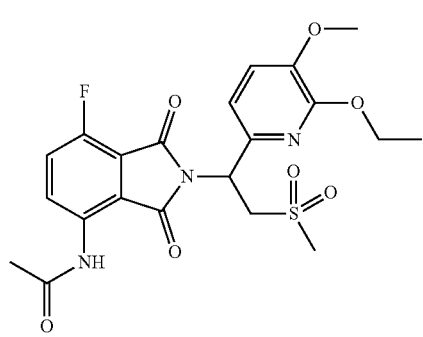
705 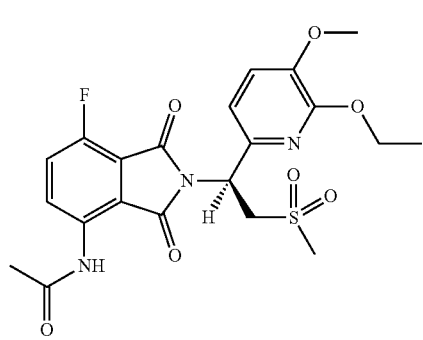
706 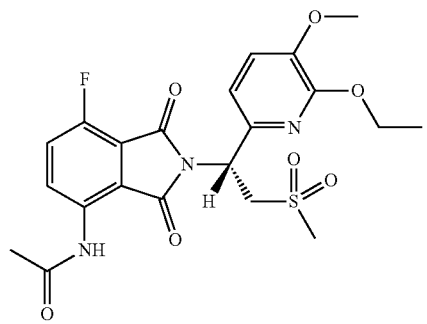
707 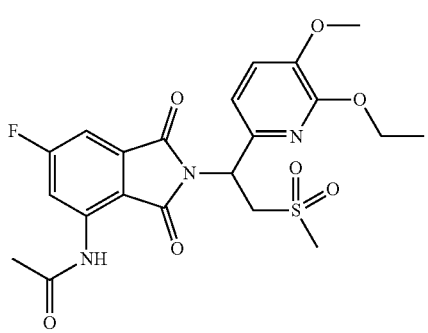
708 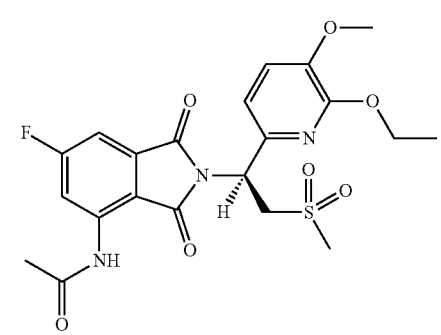
709 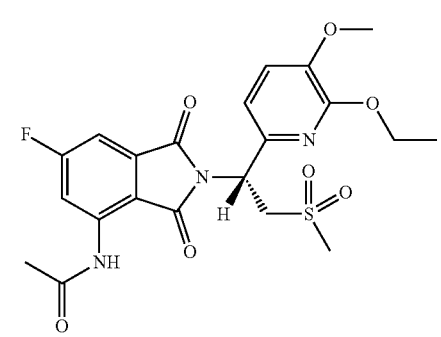
710 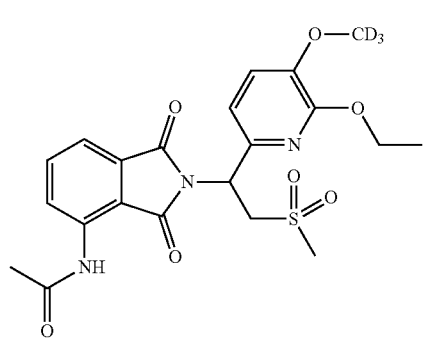

711 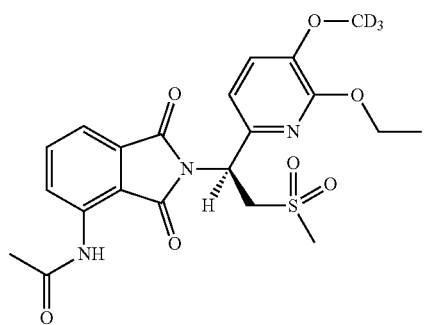
712 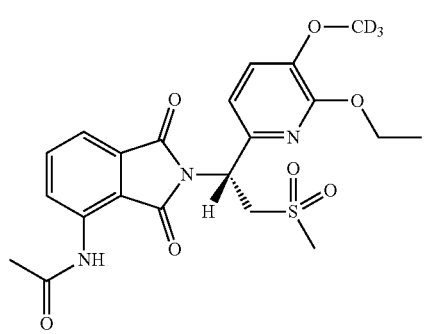
713 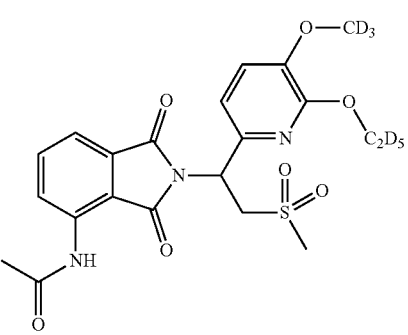
714 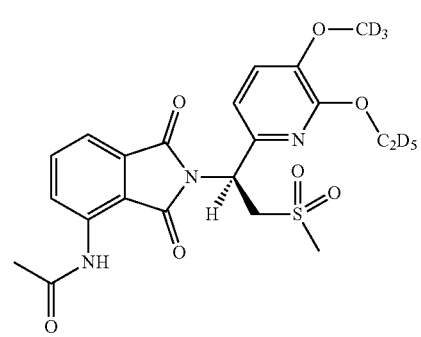
715 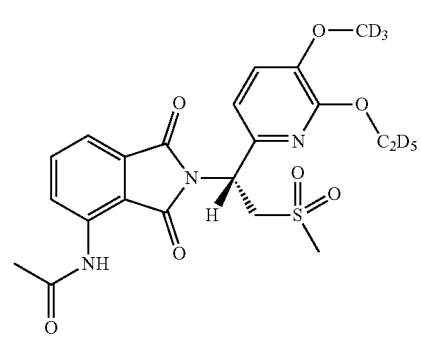
716 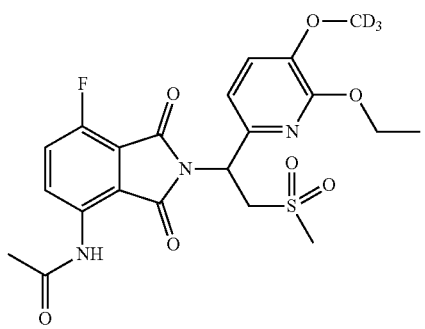
717 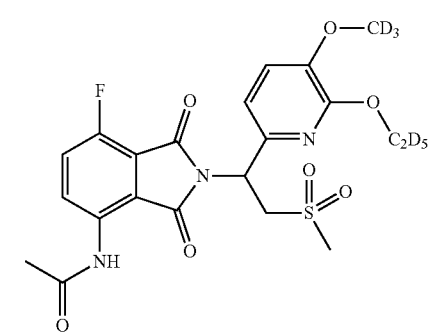
718 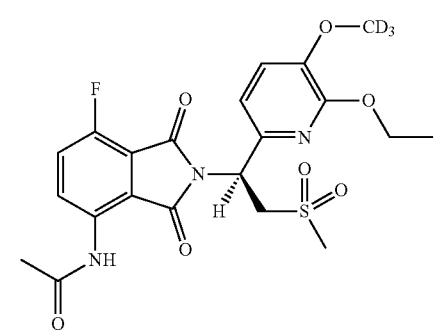
719 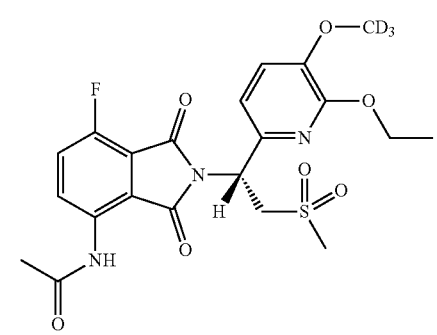
720 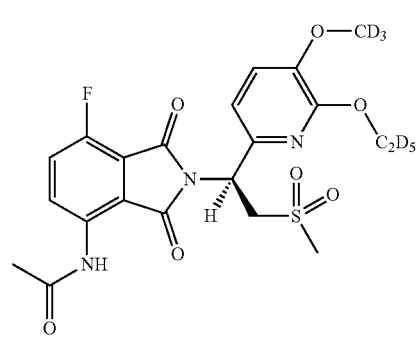

| 721 | 726 |
|---|---|
| 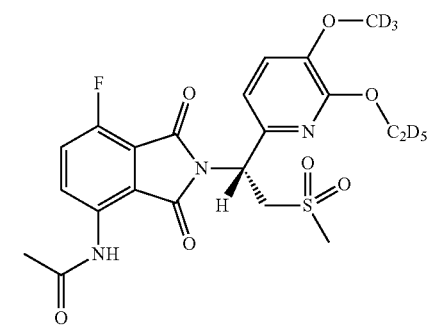 | 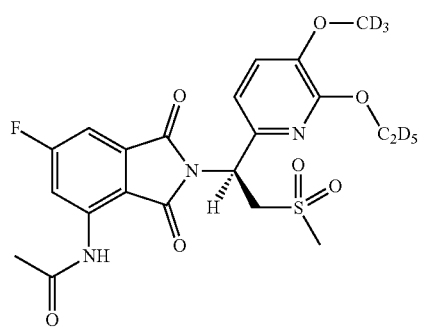 |
| 722 | 727 |
| 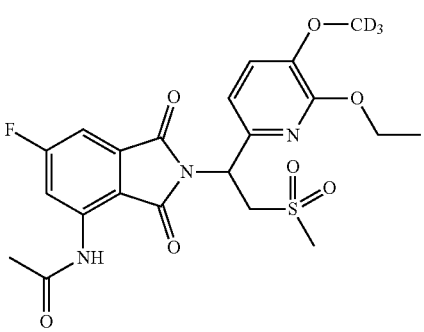 | 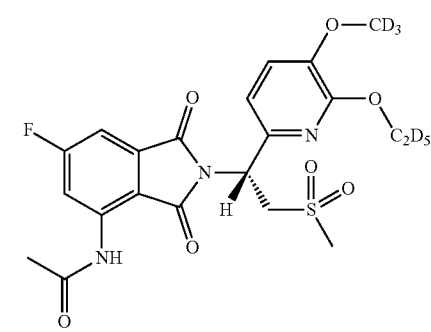 |
| 723 | 728 |
| 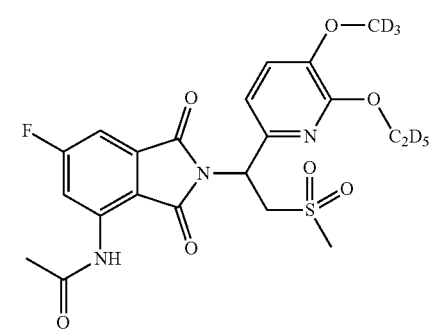 | 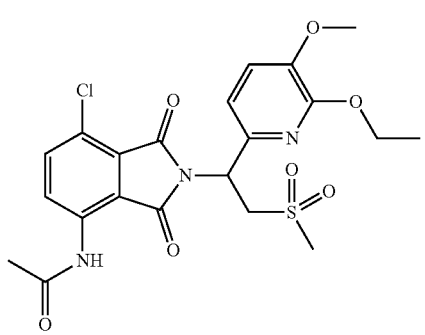 |
| 724 | 729 |
| 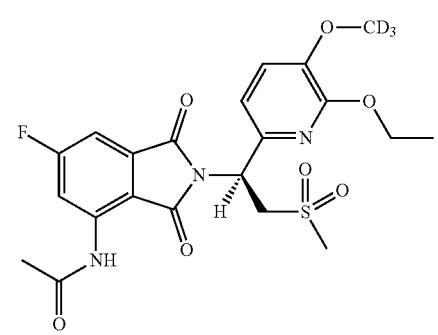 | 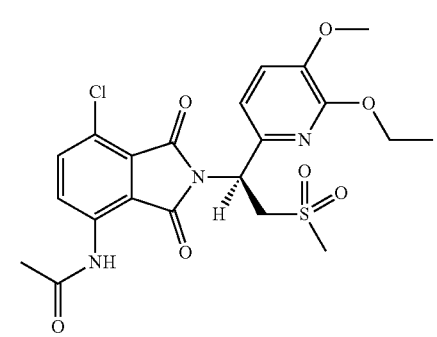 |
| 725 | 730 |
| 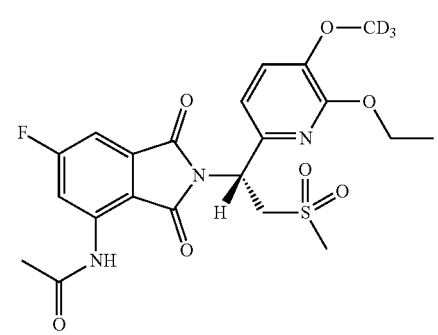 | 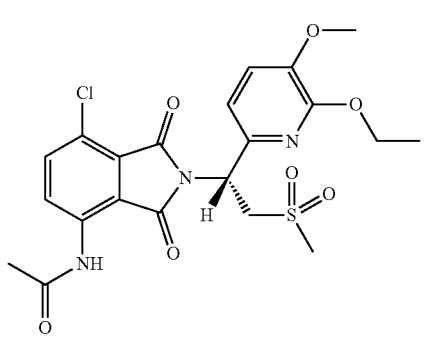 |

731 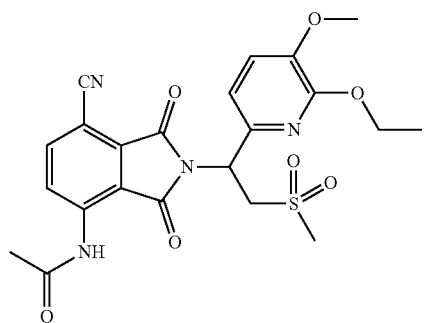
732 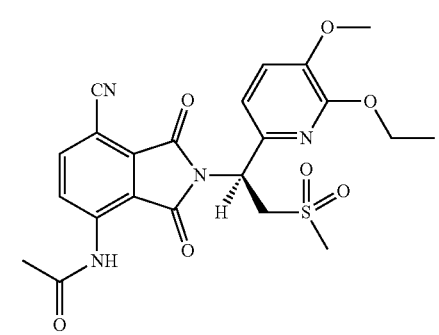
733 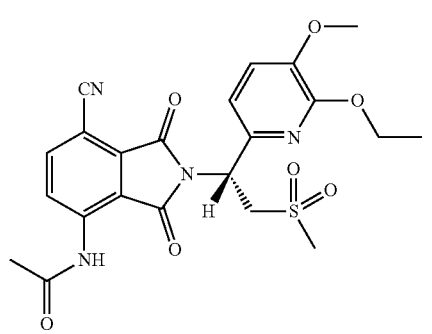
734 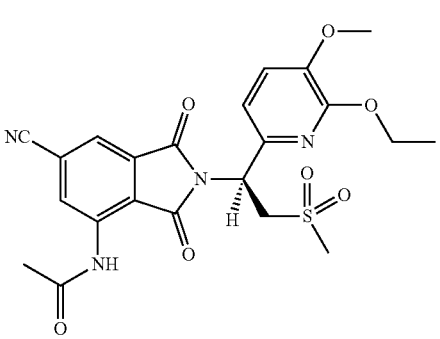
735 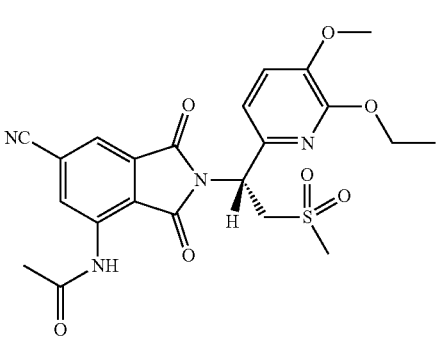
736 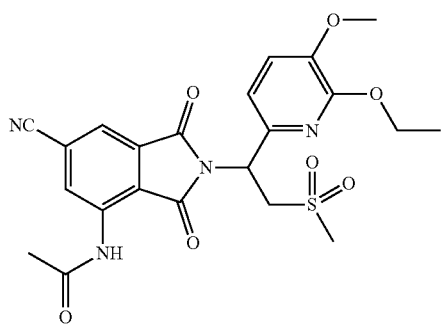
737 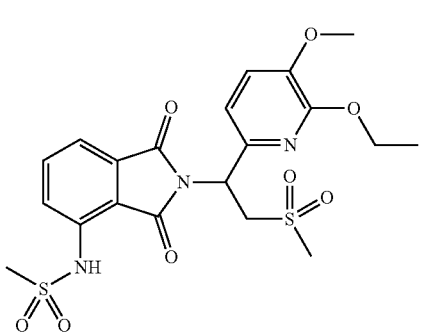
738 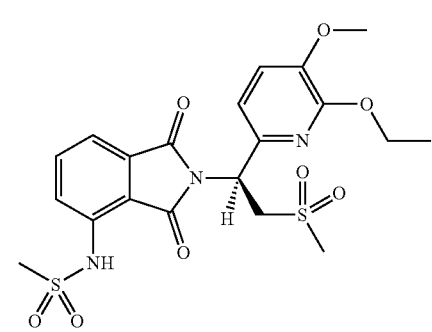
739 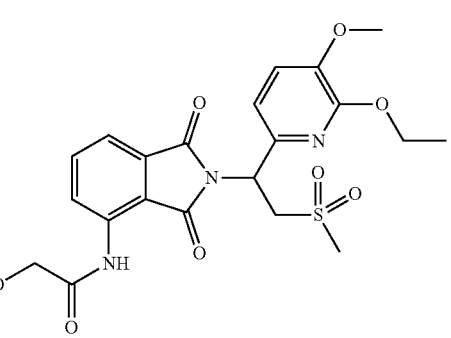
740 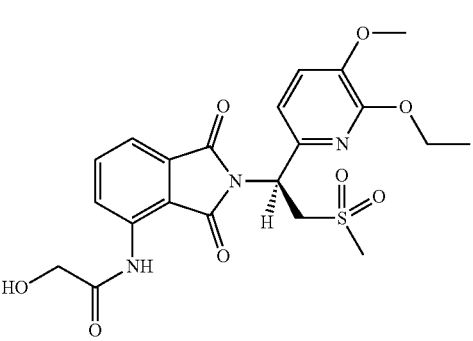

741
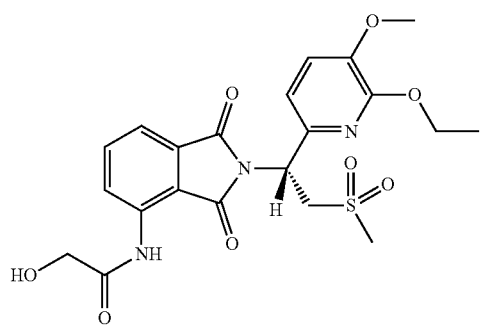
742
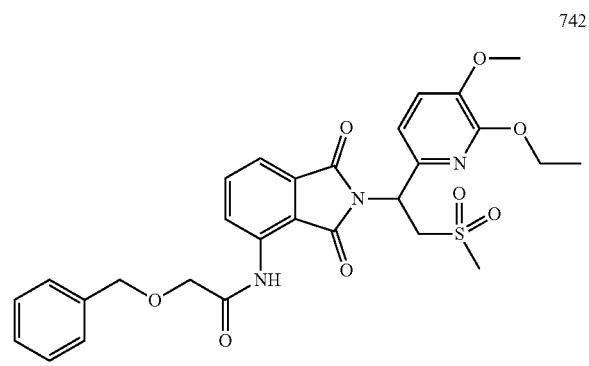 [SMILES: CCOc1nc([C@@H](CS(C)(=O)=O)N2C(=O)c3cccc(NC(=O)COCc4ccccc4)c3C2=O)ccc1OC]
743
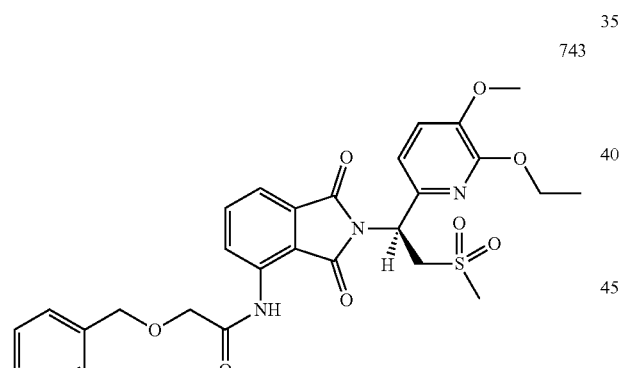
744
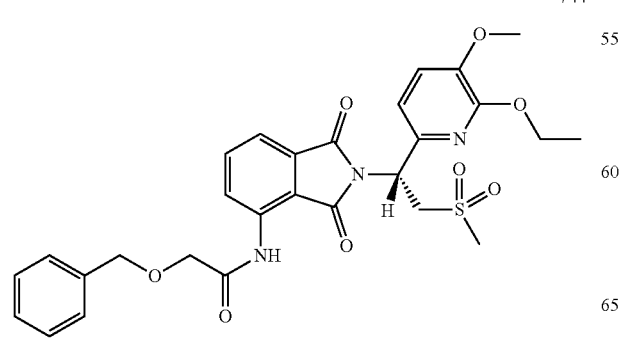
745
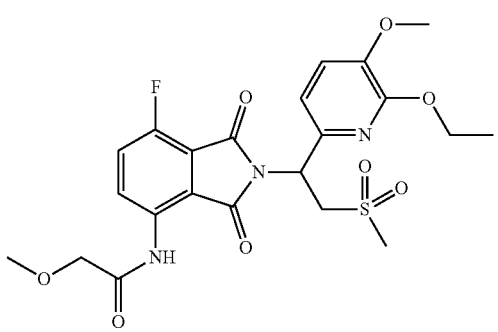
746
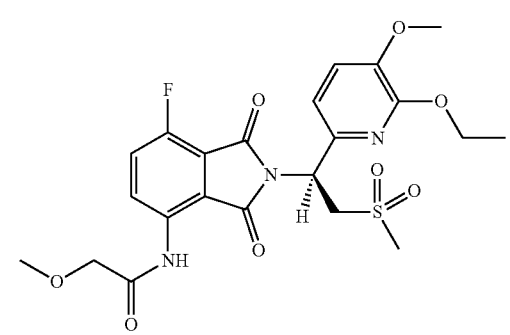
747
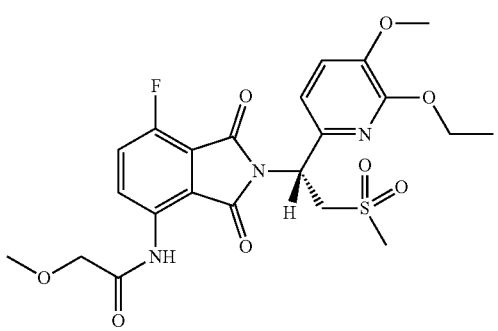
748
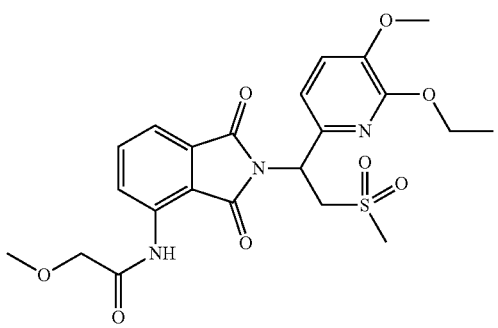

749
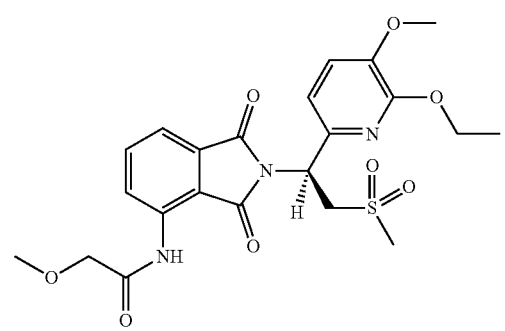
750
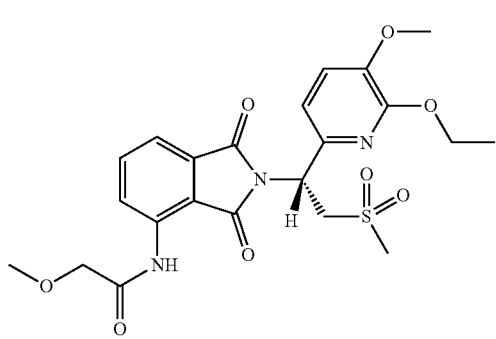
751
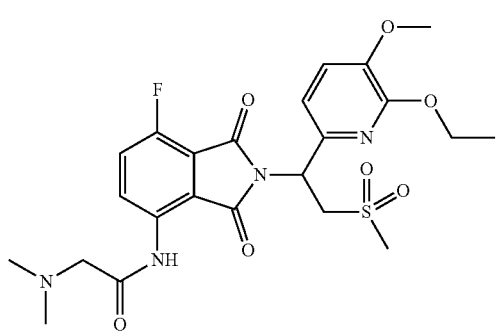
752
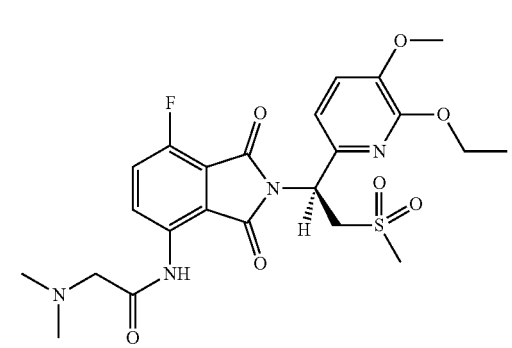
753
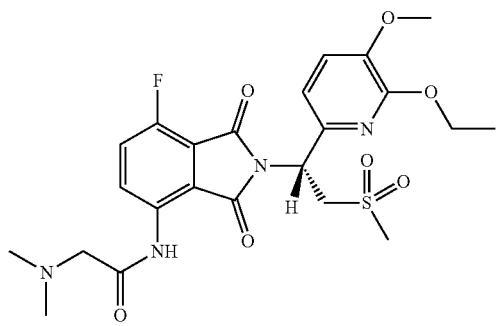
754
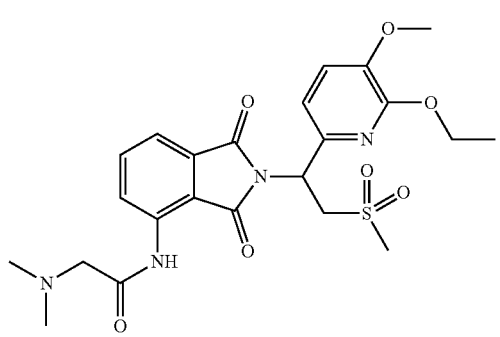
755
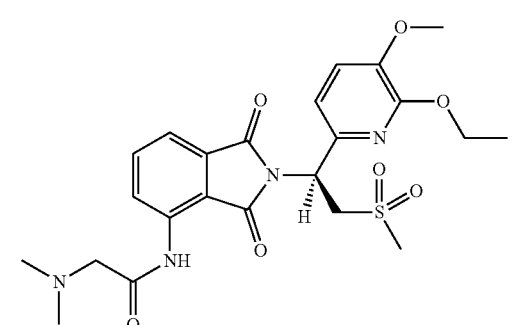
756
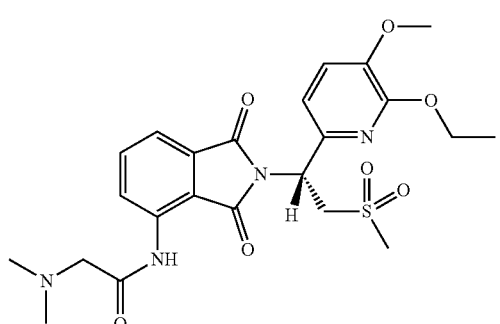
757
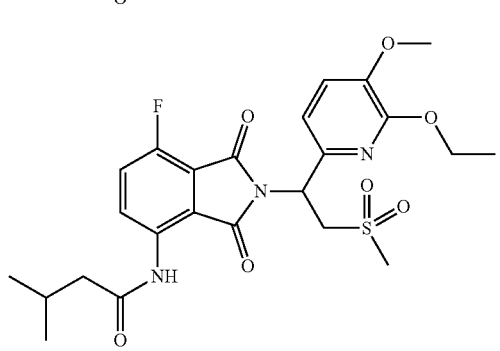

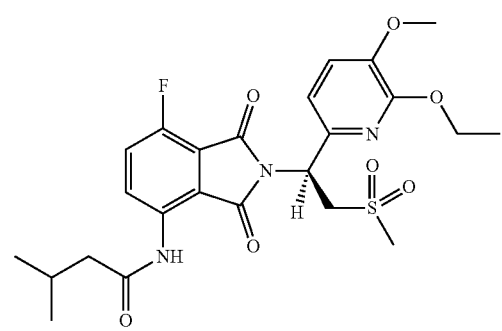
758
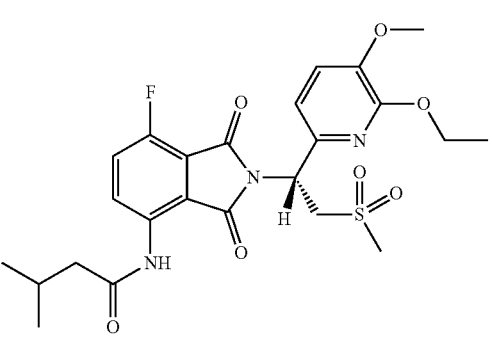
759
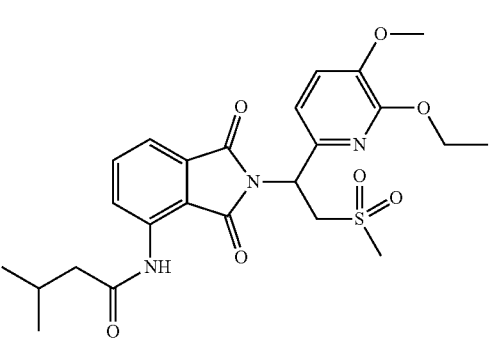
760
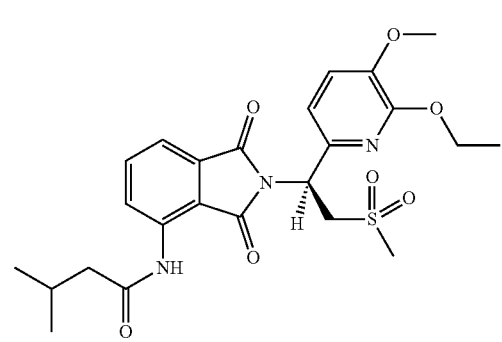
761
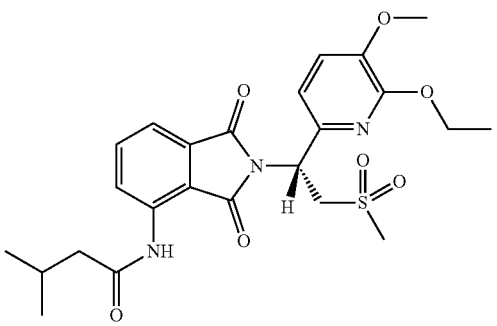
762
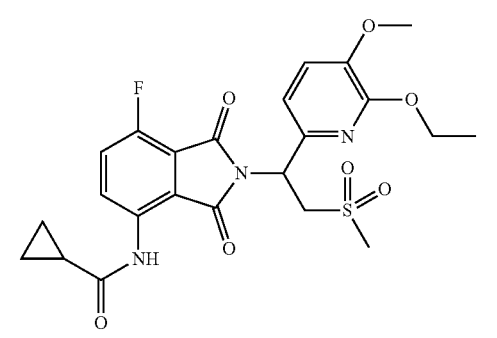
763
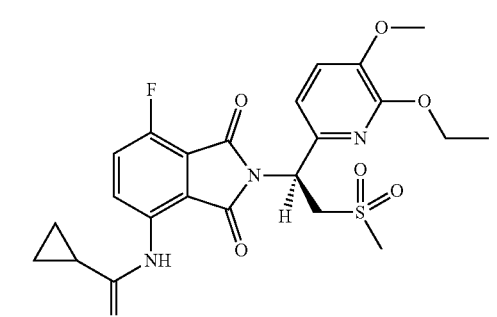
764
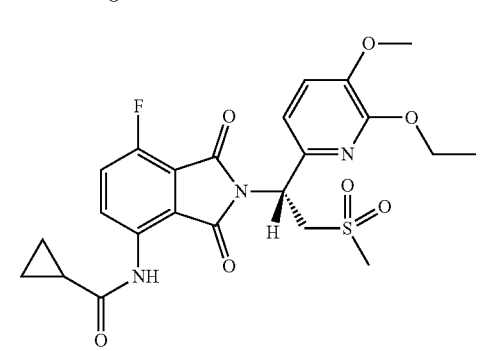
765
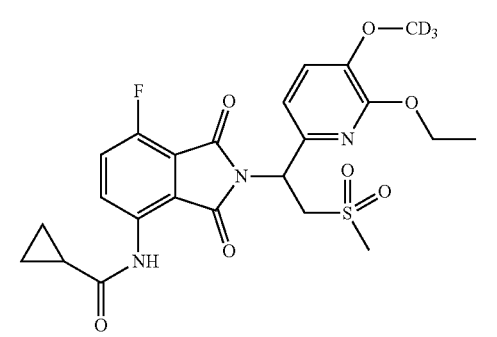
766

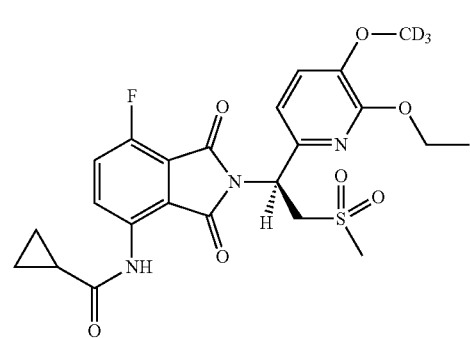
767

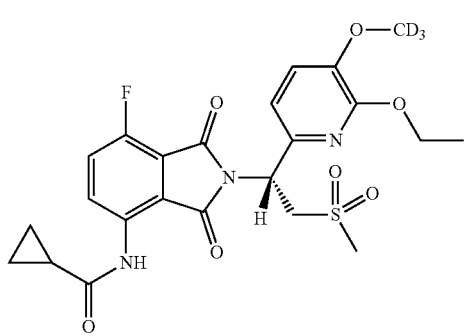
768

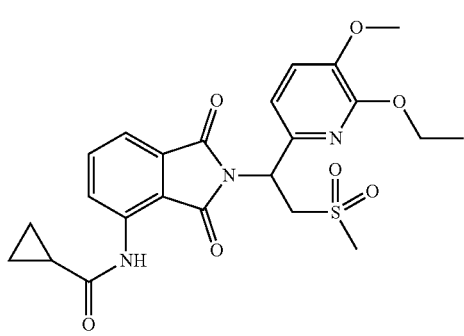
769

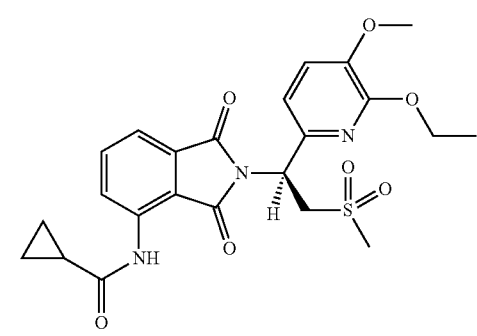
770

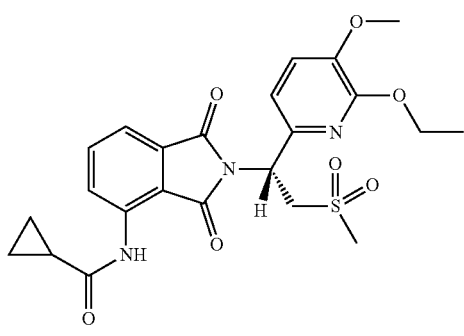
771

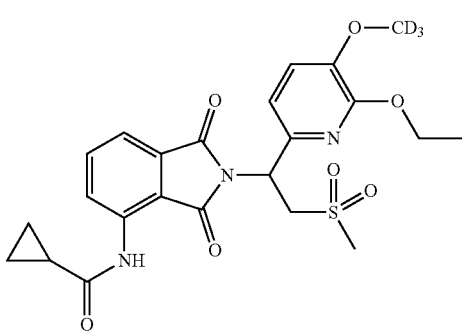
772

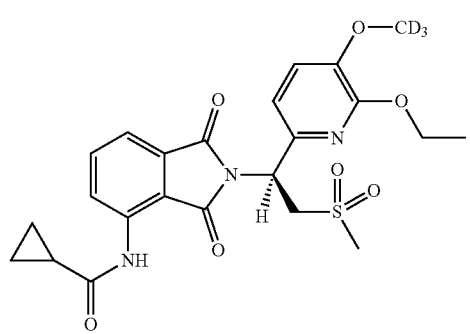
773

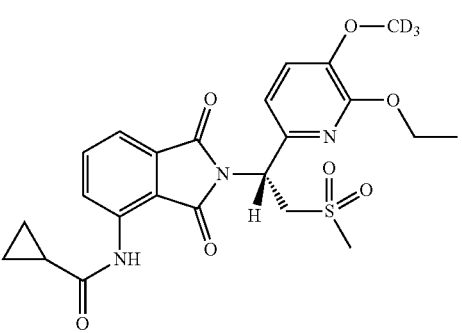
774

13. A compound of formula I-3:

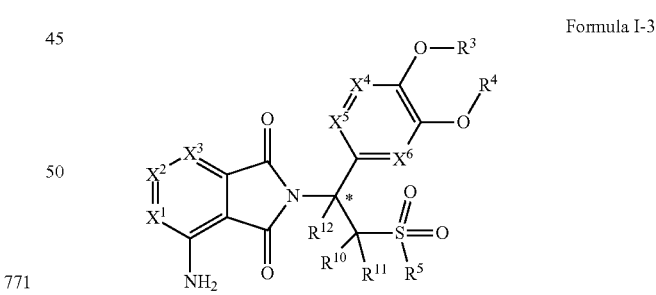

Formula I-3 wherein,
$X^1$, $X^2$, $X^3$, $X^4$, and $X^5$ are independently CH, CD, or $CR^7$;
$X^6$ is N;
$R^7$ is halogen or cyano;
$R^3$ and $R^4$ are independently H, substituted or unsubstituted $(C_1\text{-}C_6)$alkyl, substituted or unsubstituted $(C_3\text{-}C_6)$ cycloalkyl, or, substituted or unsubstituted $(C_1\text{-}C_6)$ alkyl-$(C_3\text{-}C_6)$cycloalkyl;
$R^5$ is substituted or unsubstituted $(C_1\text{-}C_6)$alkyl;
$R^{10}$, $R^{11}$ and $R^{12}$ are independently H or D;

the substituent in substituted $(C_1-C_6)$alkyl, substituted $(C_3-C_6)$cycloalkyl, or, substituted $(C_1-C_6)$alkyl-$(C_3-C_6)$cycloalkyl is one or more selected from the group consisting of: D, halogen, hydroxyl, amino, $(C_1-C_6)$alkyl amino, $(C_1-C_6)$alkoxy, and benzyloxy; when there are a plurality of substituents, the substituents are the same or different.

14. A pharmaceutical composition comprising one or more compounds of formula I or the pharmaceutically acceptable salt, solvate, polymorph, co-crystal or stereoisomer thereof according to claim 1, and one or more pharmaceutical excipients.

15. The compound of formula I, or the pharmaceutically acceptable salt, solvate, polymorph, co-crystal or stereoisomer thereof according to claim 1, wherein, $R^6$ is cyclopropyl, methyl, ethyl, hydroxymethyl, benzyloxymethyl, methoxymethyl, isobutyl, dimethylaminomethyl, isopropyl, $CD_3$, or $C_2D_5$.

16. The compound of formula I, or the pharmaceutically acceptable salt, solvate, polymorph, co-crystal or stereoisomer thereof according to claim 1, wherein, $R^3$ and $R^4$ are independently H, methyl, ethyl, propyl, isopropyl, $CD_3$, $CH_2D$, $CHD_2$, $C_2D_5$, $CH_2CD_3$ or $CHF_2$.

\* \* \* \* \*